(12) United States Patent
Yoshida et al.

(10) Patent No.: US 9,089,133 B2
(45) Date of Patent: Jul. 28, 2015

(54) INSECTICIDE FOR AGRICULTURAL OR HORTICULTURAL USE AND METHOD OF USE THEREOF

(75) Inventors: Kei Yoshida, Mobara (JP); Takeo Wakita, Mobara (JP); Hiroyuki Katsuta, Mobara (JP); Akiyoshi Kai, Mobara (JP); Yutaka Chiba, Mobara (JP); Kiyoshi Takahashi, Mobara (JP); Hiroko Kato, Mobara (JP); Nobuyuki Kawahara, Mobara (JP); Michikazu Nomura, Mobara (JP); Hidenori Daido, Mobara (JP); Junji Maki, Mobara (JP); Shinichi Banba, Mobara (JP); Atsuko Kawahara, Mobara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/419,063

(22) Filed: Mar. 13, 2012

(65) Prior Publication Data

US 2012/0220802 A1 Aug. 30, 2012

Related U.S. Application Data

(62) Division of application No. 10/570,013, filed as application No. PCT/JP2004/012416 on Aug. 23, 2004, now Pat. No. 8,158,814.

(30) Foreign Application Priority Data

Aug. 29, 2003 (JP) ................................ 2003-305816

(51) Int. Cl.
| | | |
|---|---|---|
| C07C 233/65 | (2006.01) |
| C07C 211/52 | (2006.01) |
| C07C 237/40 | (2006.01) |
| C07C 317/44 | (2006.01) |
| C07C 327/48 | (2006.01) |
| C07C 333/08 | (2006.01) |
| C07C 323/33 | (2006.01) |
| A01N 47/20 | (2006.01) |
| C07C 211/47 | (2006.01) |
| C07C 211/48 | (2006.01) |
| C07C 215/68 | (2006.01) |
| C07C 265/12 | (2006.01) |
| C07C 271/28 | (2006.01) |
| C07C 317/18 | (2006.01) |
| C07C 317/36 | (2006.01) |
| C07C 317/40 | (2006.01) |
| C07C 323/12 | (2006.01) |
| C07C 323/36 | (2006.01) |

(Continued)

(52) U.S. Cl.
CPC ............ A01N 47/20 (2013.01); C07C 211/47 (2013.01); C07C 211/48 (2013.01); C07C 215/68 (2013.01); C07C 237/40 (2013.01); C07C 265/12 (2013.01); C07C 271/28 (2013.01); C07C 317/18 (2013.01); C07C 317/36 (2013.01); C07C 317/40 (2013.01); C07C 323/12 (2013.01); C07C 323/36 (2013.01); C07C 323/42 (2013.01); C07C 327/48 (2013.01); C07C 333/08 (2013.01); C07D 213/81 (2013.01); C07C 2101/04 (2013.01); C07C 2101/08 (2013.01)

(58) Field of Classification Search
CPC .. C07C 211/52; C07C 317/44; C07C 323/33; C07C 233/66
USPC ............... 564/155, 166, 440, 442; 568/30, 36
See application file for complete search history.

(56) References Cited

U.S. PATENT DOCUMENTS

2,697,662 A 12/1954 McQueen et al.
3,254,094 A 5/1966 Ross (Continued)

FOREIGN PATENT DOCUMENTS

AU 199723913 10/1997
CN 1200725 12/1998

(Continued)

OTHER PUBLICATIONS

Welch et al, J. Med. Chem., 1969, 12, 957-959.*
Horowitz et al, Weed Research, 97-109, 1974.*
Orr, Plant Disease Reprter, 120-121, 1974.*
RN 20200-22-0, 1974(Only English abstract enclosed).*
RN 119658-39-9, 1916.*
RN 69127-75-9, 1978.*
Yagupolskii et al, Synthesis, 1978, 835-837.*

(Continued)

*Primary Examiner* — Shailendra Kumar
(74) *Attorney, Agent, or Firm* — Rankin, Hill & Clark LLP

(57) ABSTRACT

Aniline derivatives represented by formula (8) and formula (9):

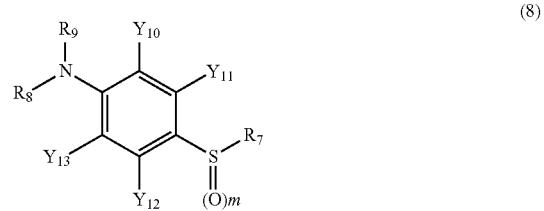

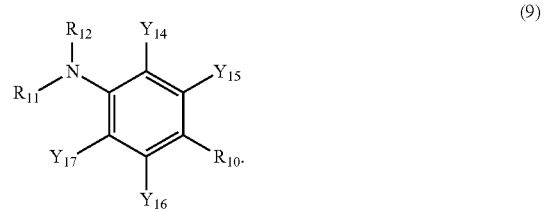

The aniline derivatives can be used as insecticides.

2 Claims, No Drawings

(51) Int. Cl.
*C07C 323/42* (2006.01)
*C07D 213/81* (2006.01)

(56) References Cited

U.S. PATENT DOCUMENTS

| | | |
|---|---|---|
| 3,257,190 A | 6/1966 | Soper |
| 3,631,019 A | 12/1971 | Herder et al. |
| 3,631,069 A | 12/1971 | Renner |
| 3,632,629 A | 1/1972 | Bulteau |
| 3,781,323 A | 12/1973 | Wagner |
| 3,790,681 A | 2/1974 | Bulteau |
| 3,849,107 A | 11/1974 | Fischer |
| 3,901,910 A | 8/1975 | Hunter et al. |
| 3,933,467 A | 1/1976 | Fischer |
| 3,989,508 A | 11/1976 | Fischer |
| 4,020,169 A | 4/1977 | Remy et al. |
| 4,199,597 A | 4/1980 | Neustadt et al. |
| 4,230,635 A | 10/1980 | Neustadt |
| 4,315,766 A | 2/1982 | Hamprecht et al. |
| 4,526,979 A | 7/1985 | Peet et al. |
| 4,638,014 A | 1/1987 | Clark |
| 4,753,941 A | 6/1988 | Cotrel et al. |
| 5,017,211 A | 5/1991 | Wenger et al. |
| 5,109,004 A | 4/1992 | Bettesworth et al. |
| 5,817,834 A | 10/1998 | Kameswaran |
| 5,849,709 A | 12/1998 | Fugedi et al. |
| 6,001,879 A | 12/1999 | Seitz et al. |
| 6,600,074 B2 | 7/2003 | Onishi et al. |
| 6,603,044 B1 * | 8/2003 | Tohnishi et al. ............... 564/154 |
| 2001/0041814 A1 | 11/2001 | Tohnishi et al. |
| 2002/0198399 A1 | 12/2002 | Onishi et al. |
| 2003/0055229 A1 | 3/2003 | Coppola |
| 2003/0055287 A1 | 3/2003 | Tohnishi et al. |
| 2003/0187233 A1 | 10/2003 | Onishi et al. |
| 2003/0204104 A1 | 10/2003 | Onishi et al. |
| 2004/0116744 A1 | 6/2004 | Furuya et al. |
| 2004/0152598 A1 * | 8/2004 | Goto et al. ............... 504/270 |
| 2004/0235959 A1 * | 11/2004 | Lahm et al. ............... 514/616 |
| 2005/0014700 A1 | 1/2005 | Boger |
| 2006/0128732 A1 | 6/2006 | Shimada et al. |
| 2008/0064708 A1 | 3/2008 | Furuya et al. |
| 2009/0105325 A1 | 4/2009 | Furuya et al. |

FOREIGN PATENT DOCUMENTS

| | | |
|---|---|---|
| CN | 1230539 | 10/1999 |
| CN | 1257861 | 6/2000 |
| CN | 1398249 | 2/2003 |
| CN | 101676260 | 3/2010 |
| DE | 26 06 982 | 2/1976 |
| DE | 28 14 860 | 6/1978 |
| DE | 920300 | 10/2006 |
| EP | 0425134 | 3/1998 |
| EP | 0572973 | 8/1998 |
| EP | 1006102 | 6/2000 |
| EP | 1714958 | 10/2006 |
| FR | 2099642 | 3/1972 |
| GB | 1535234 | 12/1978 |
| JP | 55-141476 | 11/1980 |
| JP | 07-043870 | 4/1989 |
| JP | 02-133067 | 5/1990 |
| JP | 02-510388 | 5/1990 |
| JP | 04-066579 | 3/1992 |
| JP | 10-062917 | 2/1995 |
| JP | 11-511442 | 10/1999 |
| JP | 11-302233 | 11/1999 |
| JP | 2001-122836 | 5/2001 |
| JP | 2002-166663 | 6/2002 |
| JP | 2002-249473 | 9/2002 |
| JP | 2003-34671 | 2/2003 |
| JP | 2003-048878 | 2/2003 |
| JP | 01-106055 | 4/2004 |
| JP | 2004189738 A2 | 7/2004 |
| WO | 9965880 | 3/1963 |
| WO | 9635700 | 11/1996 |
| WO | 97/08135 | 3/1997 |
| WO | 99/59968 | 11/1999 |
| WO | 04029055 | 12/1999 |
| WO | 00/29387 | 5/2000 |
| WO | 0034237 | 6/2000 |
| WO | 00/54759 | 9/2000 |
| WO | 02/094765 | 11/2002 |
| WO | 03011028 | 2/2003 |
| WO | 03/022806 | 3/2003 |
| WO | 03/026415 | 4/2003 |

OTHER PUBLICATIONS

Colombian Office Action dated May 23, 2012, four pages.
Everett E. Gilbert et al. "Perhalo Ketones. VI. Aromatic Amino Derivatives of the Perhaloacetones" General Chemical Research Laboratory, Allied Chemical Corporation, New Jersey, The Journal of Organic Chemistry, The American Chemical Society, 1965, vol. 30 (4), pp. 1001-1003.
Basil S. Farah et al. "Perhalo Ketones. VIII. Hydrolysis of Mono- and Bis(2-hydroxyhexahalo-2-propyl)arenes to Carboxylic Acids" General Chemical Research Laboratory, Allied Chemical Corporation, New Jersey, The Journal of Organic Chemistry, The American Chemical Society, 1965, vol. 30 (4), pp. 1006-1007.
Konstantinova, N. V. et al. "Acylation of bis(trifluoromethyl)phenylcarbinols substituted in the ring" Zhurnal Vsesoyuznogo Khimicheskogo Obshchestva im. D. I. Mendeleeva, 1981, vol. 26 (2), pp. 219-220.
Knunyants, I. L. et al. "Reaction of hexafluoroacetone with phenols and aniline" Zhurnal Vsesoyuznogo Khimicheskogo Obshchestva im. D. I. Mendeleeva, 1960, vol. 5, pp. 114-116.
Colombian Office Action dated Nov. 9, 2012 filed in corresponding Colombian patent application No. 6-30672-A-4.
US Office Action dated Mar. 22, 2013 filed in U.S. Appl. No. 13/614,287.
US Office Action dated Aug. 9, 2013 filed in related U.S. Appl. No. 13/614,287.
Zhurnal Organicheskoi Khimii, 1978, 14(3), 578-586.; Cited in US Office action dated Aug. 9, 2013.
Remy et al, J. Org. Chem, 1976, 41(9), 1644-1646.; Cited in US Office action dated Mar. 22, 2013.
Hulton et al, J. Physical Chemistry, 1996, 100(1), 85-94.; Cited in US Office action dated Mar. 22, 2013.
US Office Action dated Nov. 25, 2013 filed in related U.S. Appl. No. 13/614,287.
RN 4589-45-1, 1984.; Abstract ; Cited in US Office Action dated Nov. 25, 2013 filed in related U.S. Appl. No. 13/614,287.
RN 66476-53-7, 1984.; Abstract ; Cited in US Office Action dated Nov. 25, 2013 filed in related U.S. Appl. No. 13/614,287.
Chinese Office Action dated Oct. 15, 2013 filed in the corresponding Chinese application No. 201210199369.0.
Christalli, Cloria and Mills, David C.B. "Identification of a receptor for ADP on blood platelets by photoaffinity labelling," Biochemical Journal, 291, pp. 875-881,1993; Cited in Chinese Office Action.
Davidson, Robert B. and Williams, C. Richard. "Molecular Orbital Studies of Organic Substituent Effects. Semiempirical Calculations on Charge and Energy Perturbation through the Benzene Nucleus in a Model SN2 Reaction," Journal of the American Chemical Society, 100:1, pp. 73-79, Jan. 4, 1978; Cited in Chinese Office Action.
Japanese Office Action dated Feb. 25, 2014 filed in corresponding Japanese Patent application No. 2012-228273.
Chinese Office Action dated Jul. 25, 2014 issued in the corresponding Chinese patent application No. 201210431478.0.
Chinese Office Action dated Aug. 18, 2014 issued in the corresponding Chinese patent application No. 201210199369.0.
Paul T. Van Hutten et al. "Calculation of the Hyperpolarizabilities of Silicon-Based Donor-Acceptor Compounds for Nonlinear Optics," J, Phys. Chem., 1996, 100, pp. 85-94.; Cited in Chinese Office Action dated Jul. 25, 2014.
Frederick G. Bordwell et al. "Acidities of Anilines in Dimethyl Sulfoxide Solution," J. Am. Chem. Soc., 1988, 110, pp. 2964-2968.; Cited in Chinese Office Action dated Jul. 25, 2014.
Yagupol'skii et al. "Cyanine dyes containing fluorine. VII. Synthesis of cyanine dyes from 6-trifluoromethyl- and

(56) References Cited

OTHER PUBLICATIONS 6-trifluoromethylsulfonylbenzimidazole," Zhurnal Obshchei Khimii, 1959, 29, pp. 2409-2416.; English abstract thereof; Cited in Chinese Office Action dated Jul. 25, 2014.

Yagupol'skii et al. "Cyanine dyes containing fluorine. XII. Cyanine dyes from derivatives of 5-trifluoromethylthio-2-methylbenzimidazole," Zhurnal Obshchei Khimii, 1965, 35(9), pp. 1644-1650.; English abstract thereof; Cited in Chinese Office Action dated Jul. 25, 2014.

Argyle et al. "Constitution and Reactions of Thiocarbonyl Tetrachloride. Part IV. Reaction with secondary and tertiary amines," Journal of the Chemical Society, 1937, pp. 1629-1634.; Cited in Chinese Office Action dated Jul. 25, 2014.

Bzhezovskii et al. "Semiempirical quantum-chemical MNDO-PM3 study of the steric structure of methyl and trifluoromethyl sulfides," Ukrainskii Khimicheskii Zhurnal, 1997, pp. 43-46.; English abstract thereof; Cited in Chinese Office Action dated Jul. 25, 2014.

Malichenko et al. "Derivatives of nitro-and dinitrotrifluoromethylsulfonylbenzene," Ukrainskii Khimicheskii Zhurnal, 1968, 34(5), pp. 486-489.; English abstract thereof; Cited in Chinese Office Action dated Jul. 25, 2014.

Croft et al. "Fluoroalkylthio substituted aromatic derivatives," Phosphorus and Sulfur and the Related Elements, 1976, pp. 133-139.; English abstract thereof; Cited in Chinese Office Action dated Jul. 25, 2014.

STN Registry Database, RN 240490-01-1, Sep. 22, 1999; Cited in Chinese Office Action dated Jul. 25, 2014.

RN 160647-7607, 1997.

"Convergent Functional Groups, 13, High-Affinity Complexation of Adenoshine Derivatives within Induced Binding Pockets", M. Morgan Conn et al., vol. 155, No. 9, 3548p-3557p, 1993, Journal of the American Chemical Society.

Iwakura, et al., The Syntheses and Some Reactions of isocyanatoalkanecarboxylic Acid Chlorides and Isocyanatobenzoyl Chlorides, J. Org. Chem. vol. 31(1). p. 142, 1966.

Boger et al., Total Synthesis of Distamycin A and 2640 Analogues: A Solution-Phase Combinatorial Approach to the Discovery of New, Bioactive DNA Binding Agents and Development of a Rapid High-Throughput Screen for Determining Relative DNA . . . J. Am. Chem Coc. Vil. 122(27) p. 6382, 2000.

Endo et al, Synthesis of Novel Peptidomimetics, Cyclic Hexamers of Unnatural Amino Acids, 2,5-Disubstituted 3-Aminobenzoic Acids, 1999, hetercycles, vol. 51, No. 2.

Goswami et al. Molecular Recognition of Xanthine Alkaloids; First Synthetic Receptors for Thebromine and a Series of New Receptorsm for Caffiene, The Royal Society of Chemistry, 2001.

Database Crossfire Bellstein, Belstein Institut Zur Foerderdung Der Chemischen Wissenchaften, Frankfuyrt Am Main, XP002431155, J. Chem. Soc. 1950 pp. 3511-3514.

Database Crossfire Bellstein, Belstein Institut, Zur Foerderdung Der Chemischen Wissenchaften, Frankfurt Am Main, XP002431156, J. Chem. Soc. 2000 pp. 6382-6394.

Data Crossfire Bellstein Belstein Institut Zur Foerderdung Der Chemischen Wissenchaften, Frankfurt Am Main, XP002431157, J. Org. Chem. vol. 20, 2001 pp. 6654-6661.

Database Crossfire Bellstein, Belstein Institut Zur Foerderdung Der Chemischen Wissenchaften, Frankfurt Am Main, XP002431158, Chem. Lett, 1997. vol. 9, pp. 953-954.

Sunel et al, Synthesis of Antitumoral Substances, XP002431159, Analele Stiinifice Ale Unversitatii Al, I. Cuza Din Iasi, Chimie, 7(1), 111-116 Coden, Asuctz; ISSN: 1221-5341, 1999.

Morgan, et al, Convergent Functional Groups, 13. High-Affinity Complexation of Adenosine Derivatives witrhin Induces Binding Pockets, XP002431160, Journal of the American Chemical Society, 115(9), 3548-3557 Coden: Jacsat; Issn: 0002-7863, 1993.

Australian Office actuib dated Sep. 19, 2010.

European Search Report dated Jan. 16, 2012.

Brazilian Office Action dated Nov. 12, 2014 issued in the corresponding Brazilian patent application No. BR122014010917-2.

Remy, David C. et al. "Trifluoromethylthiocopper. A Reagent for the Introduction of the Trifluoromethylthio Group into Aromatic Nuclei," J. Org. Chem., vol. 41, No. 9, 1976, pp. 1644-1646.; Brazilian Office Action.

Chinese Office Action dated Jan. 6, 2015 issued in the corresponding Chinese patent application No. 201210199369.0.

L. M. Yagupolskii et al., "A New Method of Perfluoroalkylation," Synthesis, 1978, pp. 835-837.; Chinese Office Action.

Bulow, Carl et al. "Action of potassium cyanide on oxalic ester chloride 2,4-dichlorophenylhydrazone (conversion of aceto- into cyanoacetic ester derivatives)," Berichte der Deutschen Chemischen Gesellschaft, 1916, 49, pp. 2179-203.; Chinese Office Action.

CA accession No. 2137-26165, 2002.

4-(Trifluoromethyl) aniline, CAS No. 455-14-1 at: http://www.sigmaaldrich.com/catalog/ProductDetail.do?N4=07071%7CFLUKA&N5=SEARCH_CONCAT_PNO%7CBRAND_KEY&F=SPEC; Publication date—unknown (admitted prior art)—Applicant presumes the information was published before Aug. 29, 2003.

2-Nitro-4-(trifluoromethyl) aniline, CAS No. 400-98-6 at: http://www.chemicalbook.com/ProductMSDSDetailCB7735576_EN.htm; Publication date—unknown (admitted prior art)—Applicant presumes the information was published before Aug. 29, 2003.

2,6-dichloro-4-(trifluoromethyl) aniline, CAS No. 24279-39-8 at: http://www.alibata.com/product-gs/207419723/2_6_dichloro_4_trifluoromethyl_anline.html; Publication date—unknown (admitted prior art)—Applicant presumes the information was published before Aug. 29, 2003.

4-(Perfluorohexyl) aniline, CAS No. 139613-90-4 at: http://www.chemicalbook.com/ChemicalProductProperty_EN_C B7172720.htm; Publication date—unknown (admitted prior art)—Applicant presumes the information was published before Aug. 29, 2003.

4-(Trifluoromethylsulfonyl) aniline, CAS No. 473-27-8 at: http://www.sigmaaldrich.com/catalog/ProductDetail.do?N4=481920%7CALDRICH&N5=SEARCH_CONCAT_PNO%7CBRAND_KEY&F=SPEC; Publication date—unknown (admitted prior art)—Applicant presumes the information was published before Aug. 29, 2003.

2-nitro-N-propyl-4-(trifluoromethylsulfonyl) aniline, at: http://scitoys.com/scichem/jqp045/3626491.html; Publication date—unknown (admitted prior art)—Applicant presumes the information was published before Aug. 29, 2003.

Database Crossfire Beilstein, Belstein institut Zur Foerderdung Der Chemischen Wissenchaften, Frankfurt Am Main, XP002431161, 1965.

XP-002667153, Perfluoroalkanesulfonate Esters. The Reaction of 2,2,2-Trifluoroethyl Trifluoromethanesulfonate with p-Dimethylaminophenylmagnesium Bromide, 1966.

Chinese Office Action dated Sep. 10, 2013 filed in corresponding Chinese application No. 201210431478.0.

* cited by examiner

INSECTICIDE FOR AGRICULTURAL OR HORTICULTURAL USE AND METHOD OF USE THEREOF

This application is a DIV of 10/570,013 Feb. 28, 2006 now U.S. Pat. No. 8,158,814 which is a 371 of PCT/JP2004/012416, filed Aug. 23, 2004.

TECHNICAL FIELD

The present invention relates to compounds represented by formula (1), insecticides containing the compounds as active ingredients, a method for producing the insecticides, and a method for using the insecticides.

BACKGROUND ART

PCT Japanese Translation Patent Publication No. 11-511442 discloses salicylic compounds similar to compounds of the present invention. However, compounds represented by formula (1) of the present invention do not have a salicylic skeleton, and the compounds disclosed in the above publication are clearly outside the scope of claims of the present invention.

Publication No. WO2003-22806 discloses compounds as production intermediates similar to the compounds of the present invention, but it does not disclose an activity to insects. Also, the compounds disclosed in the publication are clearly outside the scope of claims of the present invention.

J. Org. Chem. 142 (1966) discloses compounds as production intermediates similar to the compounds of the present invention, but it does not disclose an activity to insects. Also, the compounds disclosed in the publication are clearly outside the scope of claims of the present invention.

J. Am. Chem. Soc. 6382 (2000) discloses compounds as production intermediates similar to the compounds of the present invention, but it does not disclose an activity to insects. Also, the compounds disclosed in the publication are clearly outside the scope of claims of the present invention.

DISCLOSURE OF INVENTION

An object of the present invention is to provide insecticides having high effectiveness.

As a result of intensive research for achieving the object, the inventors found that the compounds of the present invention are novel compounds not disclosed in any document and have an excellent insecticidal effect, and the compounds can be used as new insecticides. It is also found that intermediates in production of the compounds of the present invention are not disclosed in any document and are useful production intermediates. The present invention has been achieved based on these findings.

The present invention provides compounds represented by the following formulae:

[1] Compounds represented by formula (1)

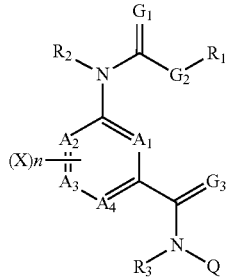

(1)

wherein $A_1$, $A_2$, $A_3$, and $A_4$ independently represent a carbon atom, a nitrogen atom, or an oxidized nitrogen atom; $R_1$ represents a C1-C6 alkyl group which may be substituted, a phenyl group which may be substituted, or a heterocyclic group which may be substituted; $R_2$ and $R_3$ independently represent a hydrogen atom, a C1-C4 alkyl group which may be substituted, or a C1-C4 alkylcarbonyl group which may be substituted; $G_1$, $G_2$, and $G_3$ independently represent an oxygen atom or a sulfur atom; Xs may be the same or different and each represent a hydrogen atom, a halogen atom, a C1-C4 alkyl group which may be substituted, or an amino group which may be substituted; n represents an integer of 0 to 4; Q represents a phenyl group which may be substituted, a naphthyl group which may be substituted, a tetrahydronaphthyl group which may be substituted, or a heterocyclic group which may be substituted.

[2] Compounds represented by formula (1) wherein $A_1$, $A_2$, $A_3$, and $A_4$ independently represent a carbon atom, a nitrogen atom, or an oxidized nitrogen atom; $R_1$ represents the following:

a C1-C6 alkyl group,
a C1-C6 haloalkyl group,
a C2-C6 alkenyl group,
a C2-C6 haloalkenyl group,
a C2-C6 alkynyl group,
a C2-C6 haloalkynyl group,
a C3-C6 cycloalkyl group,
a C3-C6 halocycloalkyl group,
a phenyl group,
a substituted phenyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group,
a naphthyl group,
a substituted naphthyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group,
a heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group),
a substituted heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group) having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group,

-$E_1$-$Z_1$—$R_4$ (wherein $E_1$ represents a C1-C4 alkylene group, a C2-C4 alkynylene group, a C3-C4 alkynylene group, a C1-C4 haloalkylene group, a C2-C4 haloalkenylene group, or a C3-C4 haloalkynylene group; $R_4$ represents a hydrogen atom, a C1-C6 alkyl group, a C2-C6 alkenyl group, a C2-C6 alkynyl group, a C1-C6 haloalkyl group, a C2-C6 haloalkenyl group, a C2-C6 haloalkynyl group, a C3-C8 cycloalkyl group, a C3-C8 halocycloalkyl group, a phenyl group, a substituted phenyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group, a naphthyl group, a substituted naphthyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group, a heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group), or a substituted heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group) having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group), and $Z_1$ represents —O—, —S—, —SO—, —$SO_2$—, —C(=O)—, —C(=O)O—, —OC(=O)—, —N($R_5$)—, —C(=O)N($R_5$)—, or —N($R_5$)C(=O)— ($R_5$ represents a hydrogen atom, a C1-C4 alkyl group, a C1-C4 alkylcarbonyl group, a C1-C4 haloalkylcarbonyl group, or a C1-C4 alkoxycarbonyl group)), or -$E_2$-$R_6$ (wherein $E_2$ represents a C1-C4 alkylene group, a C2-C4 alkenylene group, a C3-C4 alkynylene group, a C1-C4 haloalkylene group, a C2-C4 haloalkenylene group, or a C3-C4 haloalkynylene group, and $R_6$ represents a C3-C8 cycloalkyl group, a C3-C8 halocycloalkyl group, a cyano group, a nitro group, a hydroxyl group, a phenyl group, a substituted phenyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group, a naphthyl group, a substituted naphthyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group, a heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group), or a substituted heterocyclic group (which represents a pyridyl group, a pyridine-N-oxide group, a pyrimidinyl group, a pyridazyl group, a furyl group, a tetrahydrofuryl group, a thienyl group, a tetrahydrothienyl group, a tetrahydropyranyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group) having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, a pentafluorosulfanyl group, a C1-C4 alkylcarbonyl group, a C1-C4 haloalkylcarbonyl group, a C1-C4 alkylcarbonyloxy group, and a C1-C4 alkoxycarbonyl group);

$R_2$ and $R_3$ independently represent a hydrogen atom, a C1-C4 alkyl group, a C1-C4 alkylcarbonyl group, or a C1-C4 haloalkylcarbonyl group; $G_1$, $G_2$, and $G_3$ independently represent an oxygen atom or a sulfur atom; Xs may be the same or different and each represent a hydrogen atom, a halogen atom, a C1-C4 alkyl group, a C1-C4 haloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, a cyano group, a nitro group, an amino group, or an amino group which may be substituted by a C1-C4 alkyl group;

n represents an integer of 0 to 4;

Q represents a phenyl group, a substituted phenyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 haloalkyl group which may be substituted by at least one hydroxyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 haloalkylsulfonyloxy group, a C1-C4 alkylcarbonyl group, a C1-C4 haloalkylcarbonyl group, a cyano group, a nitro group, a hydroxyl group, a pentafluorosulfanyl group, a phenyl group, a substituted phenyl group (which may have the same or different substituents selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 haloalkylsulfonyloxy, a cyano group, a nitro group, a hydroxyl group, and a pentafluorosulfanyl group), a thienyl group, and a substituted thienyl group (which may have the same or different substituents selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 haloalkylsulfonyloxy, a cyano group, a nitro group, a hydroxyl group, and a pentafluorosulfanyl group), a naphthyl group, a substituted naphthyl group having one or more substituents which may be the same or different and which are selected from a halogen atom, a C1-C6 alkyl group, a C1-C6 haloalkyl group, a C3-C8 cycloalkyl group, a C3-C8 halocycloalkyl group, a C1-C6 alkoxy group, a C1-C6 haloalkoxy group, a C1-C6 haloalkyl group which may be substituted by at least one hydroxyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, and a pentafluorosulfanyl group, a heterocyclic group (which represents a pyridyl group, a pyridine-N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group), a substituted heterocyclic group (which represents a pyridyl group, a pyridine-N-oxide group, a pyrimidinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrole group, an imidazolyl group, a triazolyl group, a pyrazolyl group, or a tetrazolyl group) having one or more substituents which may be the same or different and which are selected from a halogen atom, a C1-C6 alkyl group, a C1-C6 haloalkyl group, a C1-C6 alkoxy group, a C1-C6 haloalkoxy group, a C1-C6 haloalkyl group which may be substituted by at least one hydroxyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, and a pentafluorosulfanyl group, a tetrahydronaphthyl group, or a substituted tetrahydronaphthyl group having one or more substituents which may be the same or different and which are selected from a halogen atom, a C1-C6 alkyl group, a C1-C6 haloalkyl group, a C1-C6 alkoxy group, a C1-C6 haloalkoxy group, a C1-C6 haloalkyl group which may be substituted by at least one hydroxyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a cyano group, a nitro group, a hydroxyl group, and a pentafluorosulfanyl group (excluding a case (1) in which Q represents 3,4-dichlorophenyl when R1 represents a methyl group, a case (2) in which Q represents an unsubstituted phenyl group when R1 represents an ethyl group, and a case (3) in which Q represents an unsubstituted pyridyl group when R1 represents an unsubstituted phenyl group).

[3] Compounds represented by formula (2)

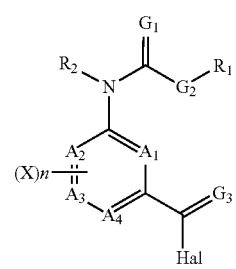

(2)

wherein $A_1$, $A_2$, $A_3$, $A_4$, $R_1$, $R_2$, $R_3$, $G_1$, $G_2$, $G_3$, X, and n each represent the same as in formula [1], and Hal represents a halogen atom.

[4] Compounds represented by formula (3)

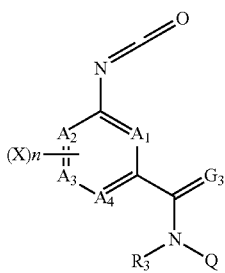
(3)

wherein $A_1, A_2, A_3, A_4, R_3, G_3, X, n$ and $Q$ each represent the same as in formula [1].

[5] Compounds represented by formula (4)

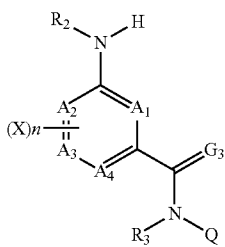
(4)

wherein $A_1, A_2, A_3, A_4, R_2, R_3, G_3, X$, and $n$ each represent the same as in formula [1], and Q represents a group represented by formula (1-2) or (1-3):

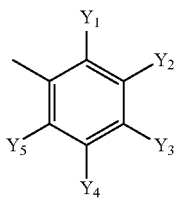
(1-2)

(wherein $Y_1, Y_2, Y_4$, and $Y_5$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, and $Y_3$ represents a C1-C6 haloalkyl group, a C1-C6 haloalkoxy group, a C1-C6 haloalkyl group which may be substituted by at least one hydroxyl group, a C1-C6 haloalkylthio group, a C1-C6 haloalkylsulfinyl group, a C1-C6 haloalkylsulfonyl group, or a pentafluorosulfanyl group, but excluding a case where both $Y_1$ and $Y_5$ represent a hydrogen atom)

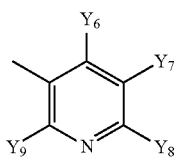
(1-3)

(wherein $Y_6, Y_7$, and $Y_9$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, and $Y_8$ represents a C1-C6 haloalkyl group, a C1-C6 haloalkoxy group, a C1-C6 haloalkyl group which may be substituted by at least one hydroxyl group, a C1-C6 haloalkylthio group, a C1-C6 haloalkylsulfinyl group, a C1-C6 haloalkylsulfonyl group, or a pentafluorosulfanyl group, but excluding a case where both $Y_6$ and $Y_9$ represent a hydrogen atom).

(wherein $Y_6, Y_7$, and $Y_9$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 alkylsulfonyl group, a pentafluorosulfanyl group, a cyano group, or a nitro group, and $Y_8$ represents a C1-C6 haloalkyl group, a C1-C6 haloalkoxy group, a C1-C6 haloalkyl group which may be substituted by at least one hydroxyl group, a C1-C6 haloalkylthio group, a C1-C6 haloalkylsulfinyl group, a C1-C6 haloalkylsulfonyl group, or a pentafluorosulfanyl group, but only one of $Y_6$ and $Y_9$ represents a hydrogen atom).

[6] A method for producing the above-described compounds in [1] comprising reacting the compounds represented in [3] by formula (2) with compounds represented by formula (5):

(5)

wherein $R_3$ and Q each represent the same as in [1].

[7] A method for producing the above-described compounds in [1] comprising reacting the compounds represented in [4] by formula (3) with compounds represented by formula (6):

$H-G_2-R_1$ (6)

wherein $R_1$ and $G_2$ each represent the same as in [1].

[8] A method for producing the above-described compounds in [1] comprising reacting the compounds represented in [5] by formula (4) with compounds represented by formula (7):

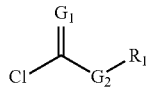
(7)

wherein $R_1, G_1$, and $G_2$ each represent the same as in [1].

[9] Aniline derivatives represented by formula (8):

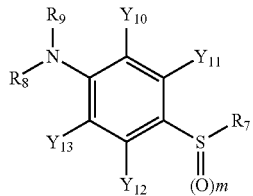
(8)

wherein $R_7$ represents a C1-C6 haloalkyl group, $Y_{10}, Y_{11}, Y_{12}$, and $Y_{13}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, and $R_8$ and $R_9$ independently represent a hydrogen atom, a C1-C4 alkyl group, a m-nitrobenzoyl group, or a substituted m-nitrobenzoyl group, and m represents 0, 1, or 2.

[10] Aniline derivatives represented by formula (9):

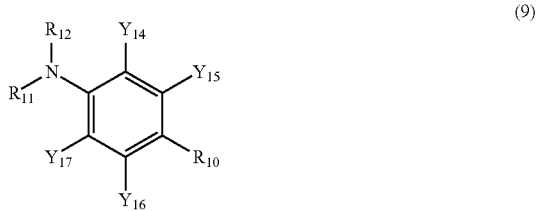

(9)

wherein $R_{10}$ represents a C1-C6 haloalkyl group which may be substituted by at least one hydroxyl group, $Y_{14}, Y_{15}, Y_{16}$, and $Y_{17}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, and $R_{11}$ and $R_{12}$ independently represent a hydrogen atom, a C1-C4 alkyl group, a m-nitrobenzoyl group, or a substituted m-nitrobenzoyl group.

[11] An insecticide comprising any one of the compounds in [1] or [2] as an active ingredient.

[12] A method for using a chemical comprising treating a useful crop or soil with an effective amount of any one of the compounds [1] or [2], for protecting the useful crop from harmful organisms.

[13] A method for preventing pests comprising using the compound [1] or [2] and at least one insecticide and/or fungicide in combination.

The compounds of the present invention exhibit an excellent preventive effect as insecticides in low dosages, and also exhibit an excellent preventive effect when being used in combination with another insecticide, an acaricide, a nematocide, a fungicide, a herbicide, a plant growth regulator, or a biological pesticide.

BEST MODE FOR CARRYING OUT THE INVENTION

In the definitions of formula (1) of the present invention, the term "halogen atom" means a fluorine atom, a chlorine, atom, a bromine atom, or an iodine atom. The characters "n-", "i-", "s-", and "t-" mean "normal", "iso", "secondary", and "tertiary"; respectively. With respect to the expression "Ca-Cb (a and b each represent an integer of 1 or more)", for example, "C1-C6" means that the number of carbon atoms is 1 to 6, "C3-C8" means that the number of carbon atoms is 3 to 8, and "C1-C4" means that the number of carbon atoms is 1 to 4.

In the definitions of the formulae such as formula (1) of the present invention, the used terms have the following meanings:

The term "an alkyl group which may be substituted" means a straight, branched or cyclic alkyl group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "an alkylcarbonyl group which may be substituted" means a straight, branched or cyclic alkylcarbonyl group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "a phenyl group which may be substituted" means a phenyl group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "a naphthyl group which may be substituted" means a naphthyl group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "a tetrahydronaphthyl group which may be substituted" means a tetrahydronaphthyl group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "a heterocyclic group which may be substituted" means a heterocyclic group which may be substituted by the same or different groups selected from a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy, a C1-C6 haloalkylcarbonyloxy group, an amino group, a C1-C6 alkylamino group, a di-C1-C6 alkylamino group, a phenyl group which may be substituted, a phenylcarbonyl group which may be substituted, a phenylamino group which may be substituted, and a heterocyclic group which may be substituted.

The term "a C1-C6 alkyl group" means a straight or branched alkyl group having 1 to 6 carbon atoms, such as methyl, ethyl, n-propyl, i-propyl, n-butyl, s-butyl, t-butyl, n-pentyl, 2-pentyl, neopentyl, 4-methyl-2-pentyl, n-hexyl, or 3-methyl-n-pentyl. The term "a C1-C6 haloalkyl group" means a straight or branched alkyl group having 1 to 6 carbon atoms and substituted by one or more halogen atoms which may be the same or different, such as trifluoromethyl, pentafluoroethyl, heptafluoro-n-propyl, heptafluoro-i-propyl, 2,2-difluoroethyl, 2,2-dichloroethyl, 1,3-difluoro-2-propyl, 1,3-dichloro-2-propyl, 1-chloro-3-fluoro-2-propyl, 1,1,1-trifluoro-2-propyl, 2,2,2-trifluoroethyl, 2,2,2-trichloroethyl, 2,2,2-tribromoethyl, 3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3,3,4,4,4-pentafluoro-2-butyl, nonafluoro-n-butyl, nonafluoro-2-butyl, 2-fluoroethyl, 2-chloroethyl, 2-bromoethyl, 2-iodoethyl, 3-fluoro-n-propyl, 3-chloro-n-propyl, or 3-bromo-n-propyl.

The term "a C2-C6 alkenyl group" means an alkenyl group having 2 to 6 carbon atoms and a double bond in its carbon chain, such as vinyl, allyl, 2-butenyl, or 3-butenyl. The term "a C2-C6 haloalkenyl group" means a straight or branched alkenyl group having 2 to 6 carbon atoms and a double bond in its carbon chain and substituted by one or more halogen atoms which may be the same or different, such as 3,3-difluoro-2-propenyl, 3,3-dichloro-2-propenyl, 3,3-dibromo-2-propenyl, 2,3-dibromo-2-propenyl, 4,4-difluoro-3-butenyl, or 3,4,4-tribromo-3-butenyl.

The term "a C2-C6 alkynyl group" means an alkynyl group having 2 to 6 carbon atoms and a triple bond in its carbon chain, such as propargyl, 1-butyne-3-yl, or 1-butyne-3-methyl-3-yl. The term "a C2-C6 haloalkenyl group" means a straight or branched alkyenyl group having 2 to 6 carbon atoms and a triple bond in its carbon chain and substituted by one or more halogen atoms which may be the same or different.

The term "a C3-C8 cycloalkyl group" means a cycloalkyl group having 3 to 8 carbon atoms and a cyclic structure, such as cyclopropyl, cyclobutyl, cyclopentyl, 2-methylcyclopentyl, 3-methylcyclopentyl, cyclohexyl, 2-methylcyclohexyl, 3-methylcyclohexyl, or 4-methylcyclohexyl. The term "a C3-C8 halocycloalkyl group" means a cycloalkyl group having 3 to 8 carbon atoms and a cyclic structure and substituted by one or more halogen atoms which may be the same or different, such as 2,2,3,3-tetrafluorocyclobutyl, 2-chlorocyclohexyl, or 4-chlorocyclohexyl.

The term "a C1-C6 alkoxy group" means a straight or branched alkoxy group having 1 to 6 carbon atoms, such as methoxy, ethoxy, n-propyloxy, isopropyloxy, n-butoxy, s-butoxy, i-butoxy, or t-butoxy. The term "a C1-C6 haloalkoxy group" means a straight or branched haloalkoxy group having 1 to 6 carbon atoms and substituted by one or more halogen atoms which may be the same or different, such as trifluoromethoxy, pentafluoroethoxy, heptafluoro-n-propyloxy, heptafluoro-i-propyloxy, 1,1,1,3,3,3-hexafluoro-2-propyloxy, 2,2,2-trifluoroethoxy, 2-chloroethoxy, or 3-fluoro-n-propyloxy.

The term "a C1-C6 alkylthio group" means a straight or branched alkylthio group having 1 to 6 carbon atoms, such as methylthio, ethylthio, n-propylthio, i-propylthio, n-butylthio, s-butylthio, or t-butylthio. The term "a C1-C6 haloalkylthio group" means a straight or branched alkylthio group having 1 to 6 carbon atoms and substituted by one or more halogen atoms which may be the same or different, such as trifluoromethylthio, pentafluoroethylthio, 2,2,2-trifluoroethylthio, heptafluoro-n-propylthio, heptafluoro-i-propylthio, nonafluoro-n-butylthio, or nonafluoro-2-butylthio.

The term "a C1-C6 alkylsulfinyl group" means a straight or branched alkylsulfinyl group having 1 to 6 carbon atoms, such as methylsulfinyl, ethylsulfinyl, n-propylsulfinyl, i-propylsulfinyl, n-butylsulfinyl, s-butylsulfinyl, or t-butylsulfinyl. The term "a C1-C6 haloalkylsulfinyl group" means a straight or branched alkylsulfinyl group having 1 to 6 carbon atoms and substituted by one or more halogen atoms which may be the same or different, such as trifluoromethylsulfinyl, pentafluoroethylsulfinyl, 2,2,2-trifluoroethylsulfinyl, heptafluoro-n-propylsulfinyl, heptafluoro-i-propylsulfinyl, nonafluoro-n-butylsulfinyl, or nonafluoro-2-butylsulfinyl.

The term "a C1-C6 alkylsulfonyl group" means a straight or branched alkylsulfonyl group having 1 to 6 carbon atoms, such as methylsulfonyl, ethylsulfonyl, n-propylsulfonyl, i-propylsulfonyl, n-butylsulfonyl, s-butylsulfonyl, or t-butylsulfonyl. The term "a C1-C6 haloalkylsulfonyl group" means a straight or branched alkylsulfonyl group having 1 to 6 carbon atoms and substituted by one or more halogen atoms which may be the same or different, such as trifluoromethylsulfonyl, pentafluoroethylsulfonyl, 2,2,2-trifluoroethylsulfonyl, heptafluoro-n-propylsulfonyl, heptafluoro-i-propylsulfonyl, nonafluoro-n-butylsulfonyl, or nonafluoro-2-butylsulfonyl.

The term "a C1-C4 alkylcarbonyl group" means a straight, branched, or cyclic alkylcarbonyl group having 1 to 4 carbon atoms, such as acetyl, propionyl, isopropylcarbonyl, or cyclopropylcarbonyl. The term "a C1-C4 haloalkylcarbonyl group" means a straight or branched alkylcarbonyl group having 1 to 4 carbon atoms and substituted by one or more halogen atoms which may be the same or different, such as trifluoroacetyl, pentafluoropropionyl, trichloroacetyl, chloroacetyl, bromoacetyl, or 3-chloropropionyl.

The term "a C1-C4 alkoxycarbonyl group" means a straight or branched alkoxycarbonyl group having 1 to 4 carbon atoms, such as methoxycarbonyl, ethoxycarbonyl, or isopropyloxycarbonyl.

The term "a C1-C4 alkylcarbonyloxy group" means a straight or branched alkylcarbonyloxy group having 1 to 4 carbon atoms, such as acetoxy or propionyloxy. The term "a C1-C4 alkylsulfonyloxy group" means a straight or branched alkylsulfonyloxy group having 1 to 4 carbon atoms, such as methylsulfonyloxy. The term "a C1-C4 haloalkylsulfonyloxy group" means a straight or branched alkylsulfonyloxy group having 1 to 4 carbon atoms and substituted by one or more halogen atoms which may be the same or different, such as trifluoromethylsulfonyloxy or pentafluoroethylsulfonyloxy.

The term "a C1-C4 alkylene group" means a straight or branched alkylene group having 1 to 4 carbon atoms, such as methylene, ethylene, propylene, dimethylmethylene, or isobutylene. The term "a C2-C4 alkenylene group" means a straight or branched alkenylene group having 2 to 4 carbon atoms and a double bond in its carbon chain. The term "a C3-C4 alkynylene group" means a straight or branched alkynylene having 3 to 4 carbon atoms and a triple bond in its carbon chain. The term "a C1-C4 haloalkylene group" means a straight or branched alkylene group having 1 to 4 carbon atoms and substituted by one or more halogen atoms which may be the same or different, such as chloromethylene, chloroethylene, dichloromethylene, or difluoromethylene.

The term "a C2-C4 haloalkenylene group" means a straight or branched alkynylene having 2 to 4 carbon atoms and a double bond in its carbon chain, and substituted by one or more halogen atoms which may be the same or different. The term "a C3-C4 haloalkynylene group" means a straight or branched alkynylene group having 3 to 4 carbon atoms and a triple bond in its carbon chain, and substituted by one or more halogen atoms which may be the same or different.

The term "a C1-C6 haloalkyl group which may be substituted by one or more hydroxyl groups" means a straight or branched alkyl group having 1 to 6 carbon atoms and one or more hydroxyl groups in its carbon chain, and substituted by one or more halogen atoms which may be the same or different, such as 1,2,2,2-tetrafluoro-1-hydroxyethyl, 1,1,1,3,3,3-hexafluoro-2-hydroxy-2-propyl, 1,1,1,3,3,4,4,4-octafluoro-2-hydroxy-2-butyl, 1,2,2,3,3,4,4,4-octafluoro-1-hydroxy-n-butyl, or 1,3-dichloro-1,1,3,3-tetrafluoro-2-hydroxy-2-propyl.

The term "a substituted m-nitrobenzoyl group" means a m-nitrobenzoyl group having one or more substituents, such as 2-fluoro-3-nitrobenzoyl, 4-fluoro-3-nitrobenzoyl, 2-fluoro-5-nitrobenzoyl, or 4-chloro-3-nitrobenzoyl.

The compounds represented by formula (1) of the present invention may contain at least one asymmetric carbon atom or asymmetric center and thus have at least two types of optical isomers. The present invention includes the optical isomers and mixtures thereof at any proportions. The compounds represented by formula (1) of the present invention may contain at least two types of geometric isomers derived from carbon-carbon double bonds in the structural formulae. The present invention also includes the geometric isomers and mixtures thereof at any proportions.

Preferred examples of the substituents or atoms in the compounds represented by the formulae such as formula (1) of the present invention include the following:

Preferably, $R_1$ is C1-C6 alkyl, C1-C6 haloalkyl, C2-C6 alkenyl, C2-C6 haloalkenyl, a C2-C6 alkynyl, C2-C6 haloalkynyl, C3-C8 cycloalkyl, C3-C8 halocycloalkyl, -$E_1$-$Z_1$—$R_4$ (wherein $E_1$ represents C1-C4 alkylene, C2-C4 alkenylene, C3-C4 alkynylene, C1-C4 haloalkylene, C2-C4 haloalkenylene, or C3-C4 haloalkynylene, $R_4$ represents a hydrogen atom, C1-C6 alkyl, C2-C6 alkenyl, C2-C6 alkynyl, C1-C6 haloalkyl, C2-C6 haloalkenyl, or C2-C6 haloalkynyl, and $Z_1$ represents —O—, —S—, —SO—, or —SO$_2$—), or -$E_2$-$R_6$ (wherein $E_2$ represents C1-C4 alkyl, C2-C4 alkenyl, C3-C4 alkynyl, C1-C4 haloalkyl, C2-C4 haloalkenyl, or C3-C4 haloalkynyl, and $R_6$ represents C3-C8 cycloalkyl, C3-C8 halocycloalkyl, cyano, nitro, hydroxyl, phenyl, substituted phenyl having one or more substituents which may be the same or different and which are selected from halogen, C1-C6 alkyl, C1-C6 haloalkyl, C1-C6 alkoxy, C1-C6 haloalkoxy, C1-C6 alkylthio, C1-C6 haloalkylthio, C1-C6 alkylsulfinyl, C1-C6 haloalkylsulfinyl, C1-C6 alkylsulfonyl, C1-C6 haloalkylsulfonyl, cyano, nitro, hydroxyl, C1-C4 alkylcarbonyl, C1-C4 haloalkylcarbonyl, C1-C4 alkylcarbonyloxy, and C1-C4 alkoxycarbonyl, pyridyl, or substituted pyridyl having one or more substituents selected from halogen, C1-C6 haloalkyl, and C1-C6 haloalkoxy). More preferably, $R_1$ is C1-C6 alkyl, C1-C6 haloalkyl, C3-C8 cycloalkyl, C3-C8 halocycloalkyl, -$E_1$-$Z_1$—$R_4$ (wherein $E_1$ represents C1-C4 alkylene or C1-C4 haloalkylene, $R_4$ represents C1-C6 alkyl or C1-C6 haloalkyl, and $Z_1$ represents —O—, —S—, —SO—, or —SO$_2$—), or -$E_2$-$R_6$ (wherein $E_2$ represents C1-C4 alkyl, $R_6$ represents C3-C8 cycloalkyl, cyano, substituted phenyl having one or more substituents which may be the same or different and which are selected from halogen, C1-C6 haloalkyl, C1-C6 haloalkoxy, C1-C6 haloalkylthio, C1-C6 haloalkylsulfinyl, C1-C6 haloalkylsulfonyl, cyano, and nitro, pyridyl, substituted pyridyl having one or more substituents selected from halogen, C1-C6 haloalkyl, and C1-C6 haloalkoxy, thienyl, or tetrahydrofuryl).

Preferably, $R_2$ and $R_3$ are independently hydrogen or C1-C4 alkyl, and more preferably hydrogen, methyl, or ethyl.

Preferably, $G_1$, $G_2$, and $G_3$ are independently oxygen or sulfur, and more preferably oxygen.

Preferably, X is hydrogen, halogen or trifluoromethyl, and more preferably hydrogen or fluorine.

Preferably, n is 0 or 1.

Preferably, Q is phenyl, substituted phenyl having one or more substituents selected from halogen, C1-C6 alkyl, C1-C6 haloalkyl, C1-C6 alkoxy, C1-C6 haloalkoxy, C1-C6 haloalkyl which may be substituted by one or more hydroxyl groups, C1-C6 alkylthio, C1-C6 haloalkylthio, C1-C6 alkylsulfinyl, C1-C6 haloalkylsulfinyl, C1-C6 alkylsulfonyl, pentafluorosulfanyl, cyano, and nitro, pyridyl, or substituted pyridyl having one or more substituents selected from halogen, C1-C6 alkyl, C1-C6 haloalkyl, C1-C6 alkoxy, C1-C6 haloalkoxy, C1-C6 haloalkyl which may be substituted by one or more hydroxyl groups, C1-C6 alkylthio, C1-C6 haloalkylthio, C1-C6 alkylsulfinyl, C1-C6 haloalkylsulfinyl, C1-C6 alkylsulfonyl, C1-C6 haloalkylsulfonyl, pentafluorosulfanyl, cyano, and nitro. More preferably, Q is substituted phenyl or substituted pyridyl represented by formula (1-2) or (1-3). In the formula, preferably, $Y_1$ and $Y_5$ are independently hydrogen, C1-C4 alkyl, halogen, or methylthio, and excluding a case where both $Y_1$ and $Y_5$ represent a hydrogen atom.

Preferably, $Y_2$ and $Y_4$ are each hydrogen.

Preferably, $Y_3$ is C1-C6 haloalkyl, C1-C6 haloalkoxy, C1-C6 haloalkyl which may be substituted by one or more hydroxyl groups, C1-C6 haloalkylthio, C1-C6 haloalkylsulfinyl, C1-C6 haloalkylsulfonyl, or pentafluorosulfanyl. More preferably, $Y_3$ is C1-C6 haloalkyl, C1-C6 haloalkyl which may be substituted by one or more hydroxyl group, C1-C6 haloalkylthio, C1-C6 haloalkylsulfinyl, or C1-C6 haloalkylsulfonyl.

Preferably, $Y_6$ and $Y_9$ are independently hydrogen, C1-C4 alkyl, halogen, or methylthio, and excluding a case where both $Y_6$ and $Y_9$ represent a hydrogen atom.

Preferably, $Y_7$ is hydrogen.

Preferably, $Y_8$ is C1-C6 haloalkyl, C1-C6 haloalkoxy, C1-C6 haloalkyl which may be substituted by one or more hydroxyl groups, C1-C6 haloalkylthio, C1-C6 haloalkylsulfinyl, C1-C6 haloalkylsulfonyl, or pentafluorosulfanyl. More preferably, $Y_8$ is C1-C6 haloalkyl or C1-C6 haloalkoxy.

Preferably, Hal is chlorine.

Preferably, $R_7$ is C1-C6 haloalkyl, and more preferably $R_7$ is C1-C6 alkyl substituted by fluorine, such as pentafluoroethyl, heptafluoro-n-propyl, heptafluoroisopropyl, nonafluoro-n-butyl, or nonafluoro-2-butyl.

Preferably, $Y_{10}$ and $Y_{13}$ are independently hydrogen, C1-C4 alkyl, halogen, or methylthio, and excluding a case where both $Y_{10}$ and $Y_{13}$ represent a hydrogen atom. More preferably, $Y_{10}$ and $Y_{13}$ are each chlorine, bromine, or methyl.

Preferably, $Y_{11}$ and $Y_{12}$ are each hydrogen.

Preferably, $R_8$ and $R_9$ are each hydrogen, C1-C4 alkyl, m-nitrobenzoyl, or 2-fluoro-3-nitrobenzoyl, and excluding a case where both $R_8$ and $R_9$ represent C1-C4 alkyl, m-nitrobenzoyl, or 2-fluoro-3-nitrobenzoyl.

Preferably, m is 0, 1, or 2.

Preferably, $R_{10}$ is 1,2,2,2-tetrafluoro-1-hydroxyethyl, 1,1,1,3,3,3-hexafluoro-2-hydroxy-2-propyl, 1,1,1,3,3,4,4,4-octafluoro-2-hydroxy-2-butyl, 1,2,2,3,3,4,4,4-octafluoro-1-hydroxy-n-butyl, or 1,3-dichloro-1,1,3,3-tetrafluoro-2-hydroxy-2-propyl, and more preferably, $R_{10}$ is 1,1,1,3,3,3-hexafluoro-2-hydroxy-2-propyl.

Preferably, $Y_{14}$ and $Y_{17}$ are independently hydrogen, C1-C4 alkyl, halogen, or methylthio, and excluding a case where both $Y_{14}$ and $Y_{17}$ represent a hydrogen atom. More preferably, none of $Y_{14}$ and $Y_{17}$ represents a hydrogen atom.

Preferably, $Y_{15}$ and $Y_{16}$ are each hydrogen.

Preferably, $R_{11}$ and $R_{12}$ are each hydrogen, C1-C4 alkyl, m-nitrobenzoyl, or 2-fluoro-3-nitrobenzoyl, and excluding a case where both $R_{11}$ and $R_{12}$ represent C1-C4 alkyl, m-nitrobenzoyl, or 2-fluoro-3-nitrobenzoyl.

Representative processes for producing the compounds of the present invention will be described below. Although the compounds of the present invention can be produced according to the methods, the production processes are not limited to the processes described below.

An embodiment of the representative processes for producing the compounds of the present invention is Production Method 1 (in the formula, $R_1$, $R_3$, $G_1$, $G_2$, (X)n, and Q represent the same as described above).

Production Method 1

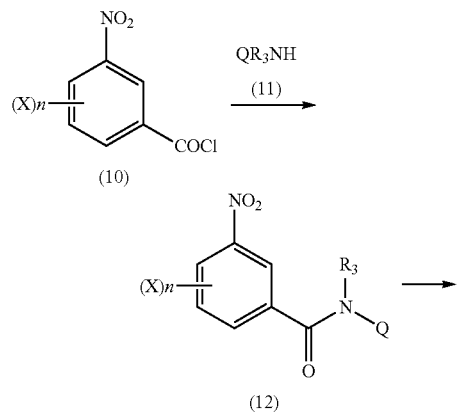

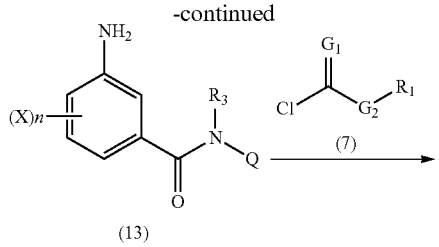

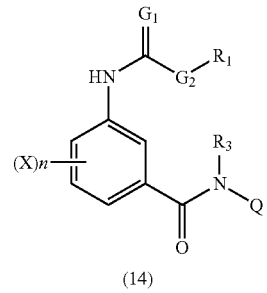

1-(i) Formula (10)→Formula (12)

A m-nitrobenzoyl chloride derivative represented by formula (10) is reacted with an aromatic amine derivative represented by formula (11) in an appropriate solvent to produce a benzamide derivative represented by formula (12). In this step, an appropriate base can also be used. As the solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. Examples of the base include organic bases such as triethylamine, tri-n-butylamine, pyridine, and 4-dimethylaminopyridine; alkali metal hydroxides such as sodium hydroxide and potassium hydroxide; carbonates such as sodium hydrogen carbonate and potassium carbonate; phosphates such as dipotassium hydrogen phosphate and trisodium phosphate; alkali metal hydrides such as sodium hydride; and alkali metal alcoholates such as sodium methoxide and sodium ethoxide. The base may be used in an appropriate amount in the range of molar equivalents of 0.01 to 5 times the amount of the compound represented by formula (10). The reaction temperature may be appropriately determined in the range of −20° C. to the reflux temperature of the solvent used, and the reaction time may be appropriately determined in the range of several minutes to 96 hours. The m-nitrobenzoyl chloride derivative represented by formula (10) can be easily produced from a m-nitrobenzoic acid derivative by a conventional method using a halogenating agent. Examples of the halogenating agent include thionyl chloride, thionyl bromide, phosphorus oxychloride, oxalyl chloride, and phosphorus trichloride. In a process for producing the compound represented by formula (12) using the m-nitrobenzoic acid derivative and the compound represented by formula (11) without using a halogenating agent, 1-hydroxybenzotriazole functioning as an additive, and N,N'-dicyclohexyl carbodiimide functioning as a condensing agent can be used according to the technique disclosed in, for example, Chem. Ber. p. 788 (1970). Other examples of the condensing agent include 1-ethyl-3-(3-dimethylaminopropyl)carbodiimide and 1,1'-carbonyl-bis-1H-imidazole. Alternatively, the compound represented by formula (12) can be produced by a mixed acid anhydride technique using a chloroformic acid ester according to the technique disclosed in J. Am. Chem. Soc. p. 5012 (1967). Examples of the chloroformic acid ester include isobutyl chloroformate and isopropyl chloroformate. Instead of the chloroformic acid ester, diethylacetyl chloride or trimethylacetyl chloride can be used. In the technique using the condensing agent and the mixed acid anhydride technique, the solvent, the reaction temperature, and the reaction time are not limited to those disclosed in the above documents, and an inert solvent which does not inhibit the progress of reaction may be appropriately used. Also, the reaction temperature and the reaction time may be appropriately selected according to the progress of reaction.

1-(ii) Formula (12)→Formula (13)

The benzamide derivative having a nitro group represented by formula (12) can be converted to a benzamide derivative having an amino group represented by formula (13) by reduction reaction. Examples of a technique for the reduction reaction include a technique using hydrogenation and a technique using tin(II) chloride (anhydride). In the former technique, reaction can be performed in a hydrogen atmosphere in the presence of a catalyst in a proper solvent under normal pressure or high pressure. Examples of the catalyst include palladium catalysts such as palladium-carbon, nickel catalysts such as Raney nickel, cobalt catalysts, ruthenium catalysts, rhodium catalysts, and platinum catalysts. Examples of the solvent include water, alcohols such as methanol and ethanol; aromatic hydrocarbons such as benzene and toluene; chained or cyclic ethers such as ethers, dioxane, and tetrahydrofuran; and esters such as ethyl acetate. The reaction temperature may be appropriately determined in the range of $-20°$ C. to the reflux temperature of the solvent used, and the reaction time may be appropriately determined in the range of several minutes to 96 hours. As a result, the compound represented by formula (13) can be produced. In the latter technique, the conditions are not limited, and the compound represented by formula (13) can be produced under the conditions described in, for example, Organic Syntheses, Coll. Vol. III, p. 453.

1-(iii) Formula (13)→Formula (14)

The benzamide derivative having a amino group represented by formula (13) is reacted with a compound represented by formula (7) (for example, a chloroformic ester, a chlorothioformic ester, or a chlorodiformic thioester) in a proper solvent to produce a compound represented by formula (14) of the present invention. In this step, an appropriate base can also be used. As the solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. Examples of the base include organic bases such as triethylamine, tri-n-butylamine, pyridine, and 4-dimethylaminopyridine; alkali metal hydroxides such as sodium hydroxide and potassium hydroxide; carbonates such as sodium hydrogen carbonate and potassium carbonate; phosphates such as dipotassium hydrogen phosphate and trisodium phosphate; alkali metal hydrides such as sodium hydride; and alkali metal alcoholates such as sodium methoxide and sodium ethoxide. The base may be used in an appropriate amount in the range of molar equivalents of 0.01 to 5 times the amount of the compound represented by formula (13). The reaction temperature may be appropriately determined in the range of $-20°$ C. to the reflux temperature of the solvent used, and the reaction time may be appropriately determined in the range of several minutes to 96 hours.

A compound represented by formula (16) of the present invention can be produced by Production Method 2 (in the formula, $R_1$, $R_3$, $G_2$, $(X)n$, and $Q$ represent the same as described above) using a 3-isocyanatobenzoyl chloride represented by formula (15) as a starting material, an alcohol represented by formula (6), a thiol, and an aromatic amine represented by formula (11) according to the technique disclosed in J. Org. Chem., p. 142 (1966).

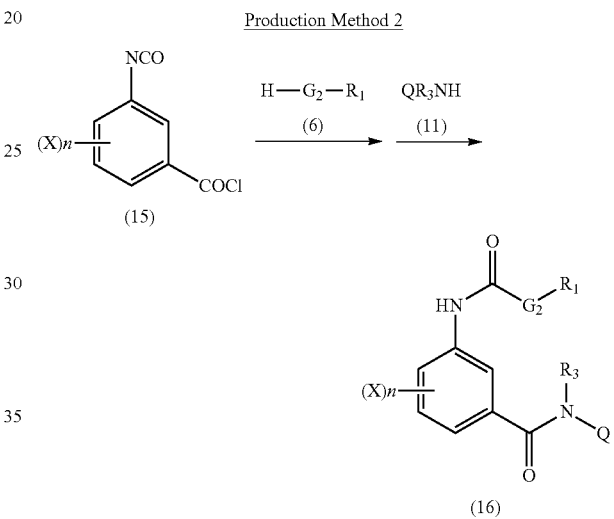

In this step, a solvent can be used. As the solvent, any solvent other than the solvents described in the above document can be used as long as it does not significantly inhibit the progress of reaction. Examples of the solvent include aromatic hydrocarbons such as benzene, toluene, and xylene; halogenated hydrocarbons such as dichloromethane, chloroform, and carbon tetrachloride; chained or cyclic ethers such as dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. Also, a base may be added for accelerating the reaction. Examples of the base other than those disclosed in the above document include organic bases such as triethylamine, pyridine, and 4-dimethylaminopyridine; and inorganic bases such as potassium carbonate. The base may be used in an appropriate amount in the range of molar equivalents of 0.01 to 5 times the amount of the compound represented by formula (15). The reaction temperature may be appropriately determined in the range of $-20°$ C. to the reflux temperature of the solvent used, and the reaction time may be appropriately determined in the range of several minutes to 96 hours.

A thioamide compound can be produced from a compound represented by formula (17) using a Lawson reagent according Production Method 3 (in the formula, $R_1$, $R_2$, $R_3$, $G_1$, $G_2$, (X)n, and Q represent the same as described above).

Production Method 3

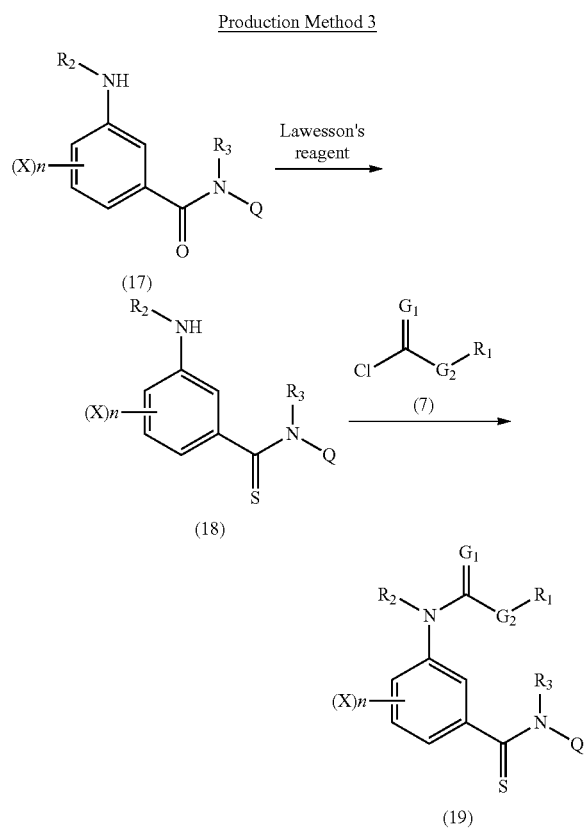

3-(i) Formula (17)→Formula (18)

The reaction can be performed under the conditions described in Synthesis, p. 463 (1993) and Synthesis, p. 829 (1984), but the conditions such as a solvent are not limited to those described in these documents.

3-(ii) Formula (18)→Formula (19)

A compound represented by formula (19) of the present invention can be produced using a compound represented by formula (7) (for example, a chloroformic ester or a chlorothioformic ester) under the conditions properly selected from the reaction conditions described above in the step 1-(iii) of Production Method 1.

A chloropyridinecarboxylic acid can be used as a starting material. For example, a compound represented by formula (23) can be produced from a chloropyridinecarboxylic acid represented by formula (20) according to Production Method 4 (in the formula, $R_1$, $R_2$, $R_3$, Q, $G_1$, and $G_2$ represent the same as described above).

Production Method 4

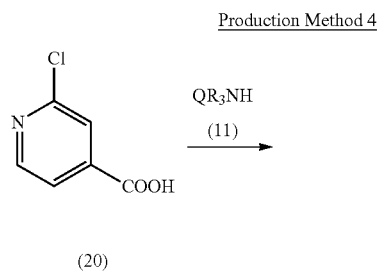

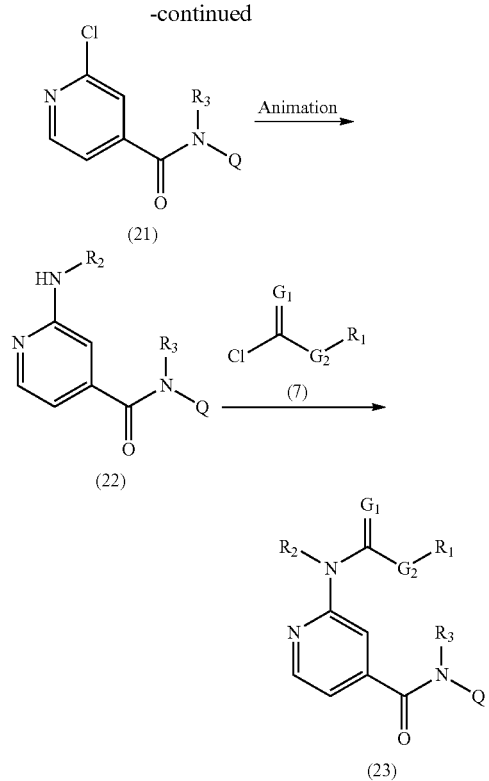

4-(i) Formula (20)→Formula (21)

A compound represented by formula (20) is halogenated in the presence or absence of an inert solvent and then reacted with an aromatic amine represented by formula (11) to produce a compound represented by formula (21). As the solvent usable in the halogenation step, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two ore more kinds. Examples of a halogenating agent include thionyl chloride, thionyl bromide, phosphorus oxychloride, oxalyl chloride, and phosphorus trichloride. The amount of the halogenating agent used may be appropriately determined in the range of molar equivalents of 1 to 10 times the amount of the compound represented by formula (20). Also, N,N-dimethylformamide may be added as an auxiliary for accelerating the reaction. The reaction temperature may be appropriately determined in the range of −20° C. to the reflux temperature of the solvent used, and the reaction time may be appropriately determined in the range of several minutes to 96 hours. As the solvent usable in the amidation step, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2- dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two ore more kinds. Also, a base may be added for accelerating the progress of reaction. Examples of the base include organic bases such as triethylamine, pyridine, 4-dimethylaminopyridine; and inorganic bases such as potassium carbonate. The amount of the base used may be appropriately determined in the range of molar equivalents of 0.01 to 5 times the amount of the compound represented by formula (11). The reaction temperature may be appropriately determined in the range of −20° C. to the reflux temperature of the solvent used, and the reaction time may be appropriately determined in the range of several minutes to 96 hours.

A process for producing a compound represented by formula (21) from a compound represented by formula (20) and a compound represented by formula (11) without using a halogenating agent is presented by a process according to the technique disclosed in, for example, Chem. Ber., p. 788 (1970) where 1-hydroxybenzotriazole as an additive and N,N'-dicyclohexyl carbodiimide as a condensing agent are used, respectively. Other examples of the condensing agent include 1-ethyl-3-(3-dimethylaminopropyl)carbodiimide, and 1,1'-carbonyl-bis-1H-imidazole. The compound represented by formula (21) can also be produced by a mixed acid anhydride technique using a chloroformic ester according to the technique disclosed in J. Am. Chem. Soc., p. 5012 (1967). Examples of a chloroformic ester include isobutyl chloroformate and isopropyl chloroformate. A compound other than a chloroformic ester, for example, diethylacetyl chloride or trimethylacetyl chloride, can also be used. In the technique using the condensing agent and the mixed acid anhydride technique, the solvent, the reaction temperatures, and the reaction times are not limited to those disclosed in the above documents, and an inert solvent which does not significantly inhibit the progress of reaction may be appropriately used. Also, the reaction temperature and the reaction time may be appropriately selected according to the progress of reaction.

4-(ii) Formula (21)→Formula (22)

A compound represented by formula (22) can be produced by amination with ammonia according to the conditions described in, for example, J. Org. Chem., p. 280 (1958). The conditions such as the reaction solvent are not limited to those disclosed in the above document, and an inert solvent which does not significantly inhibit the progress of reaction may be appropriately used. Also, the reaction temperature and the reaction time may be appropriately selected according to the progress of reaction. As an aminating agent, methylamine or ethylamine can be used instead of ammonia.

4-(iii) Formula (22)→Formula (23)

A compound represented by formula (23) of the present invention can be produced by using a compound represented by formula (7) (for example, a chloroformic ester or a chlorothioformic ester) under the conditions appropriately selected from the reaction conditions described above in the step 1-(iii) of Production Method 1.

Even when another nitrogen-containing aromatic carboxylic acid such as 4-chloropyridine-2-carboxylic acid or 6-chloropyridine-2-carboxylic acid is selected as a starting material, the compound of the present invention can be produced according to Production Method 4. In the use of the former starting material, a compound represented by formula (1) wherein $A_1$ is a nitrogen atom, and $A_2$, $A_3$, and $A_4$ are each a carbon atom can be produced. In the use of the latter starting material, a compound represented by formula (1) wherein $A_1$, $A_2$, and $A_3$ are each a carbon atom, and $A_4$ is a nitrogen atom can be produced.

The compound represented by formula (23) is reacted with an appropriate oxidizing agent to produce a corresponding pyridine-N-oxide derivative according to the conditions disclosed in, for example, J. Org. Chem., p. 8576 (1999). Examples of the oxidizing agent include organic peroxy acids such as m-chloroperoxybenzoic acid; sodium metaperiodate; hydrogen peroxide; ozone; selenium dioxide, chromic acid; dinitrogen tetraoxide; acyl nitrate; iodine; bromine; N-bromosuccinimide; iodosylbenzene; and t-butyl hypochlorite. The solvent used in this step is not limited to those disclosed in the above document, and any solvent which does not significantly inhibit the progress of reaction may be used. The solvents can be used alone or in a mixture of one or more kinds. In particular, a polar solvent is preferred. The reaction temperature may be appropriately determined in the range of −20° C. to the reflux temperature of the solvent used, and the reaction time may be appropriately determined in the range of several minutes to 96 hours.

A compound represented by formula (27) of the present invention can be produced from a easily available m-aminobenzoic ester derivative presented by formula (24) according to Production Method 5 (in the formula, $R_1$, $R_2$, $R_3$, $G_1$, $G_2$, (X)n, and Q represent the same as described above, and R represents a lower alkyl group).

Production Method 5

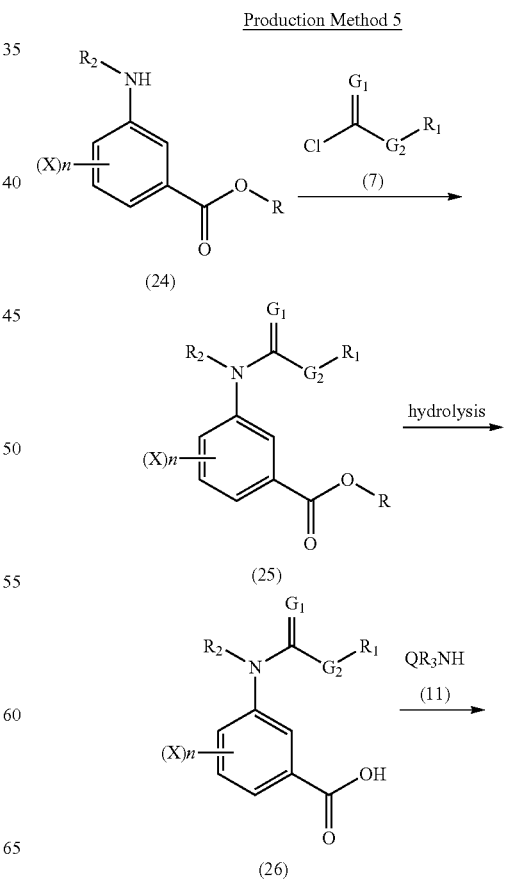

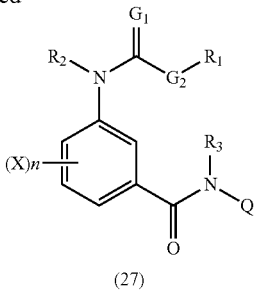

(27)

5-(i) Formula (24)→Formula (25)

A compound represented by formula (25) can be produced by using a compound represented by formula (7) (for example, a chloroformic ester or a chlorothioformic ester) under the conditions appropriately selected from the reaction conditions described above in the step 1-(iii) of Production Method 1.

5-(ii) Formula (25)→Formula (26)

A compound represented formula (26) can be produced by hydrolysis with an alkali metal hydroxide such as sodium hydroxide or potassium hydroxide, an alkali earth metal hydroxide such as calcium hydroxide, or an inorganic acid such as hydrochloric acid or sulfuric acid according to a conventional technique.

5-(iii) Formula (26)→Formula (27)

A compound represented by formula (27) of the present invention can be produced by condensation reaction under appropriate conditions according to the technique described above in the step 4-(i) of Production Method 4. Among the techniques described in the step 4-(i), in the technique using a halogenating agent, the compound represented by formula (27) can be produced through a compound represented by formula (2):

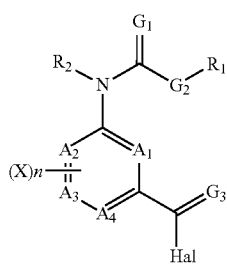

(2)

(wherein $A_1$, $A_2$, $A_3$, $A_4$, $G_1$, $G_2$, $G_3$, (X)n, and Hal each represent the same as described above). The halogenation step and the amidation step can be performed under reaction conditions according to the technique described above in the step 4-(i).

The compound represented by formula (27) of the present invention can be produced from a m-aminobenzoic acid ester represented by formula (28) according to Production Method 6 below (in the formula, $R_1$, $R_2$, $R_3$, $G_1$, $G_2$, (X)n, and Q each represent the same as described above, R represents a lower alkyl group, and L represents a functional group having leaving ability, such as halogen, methanesulfonyloxy, or trifluoromethanesulfonyloxy).

Production Method 6

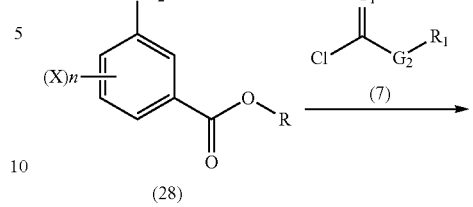

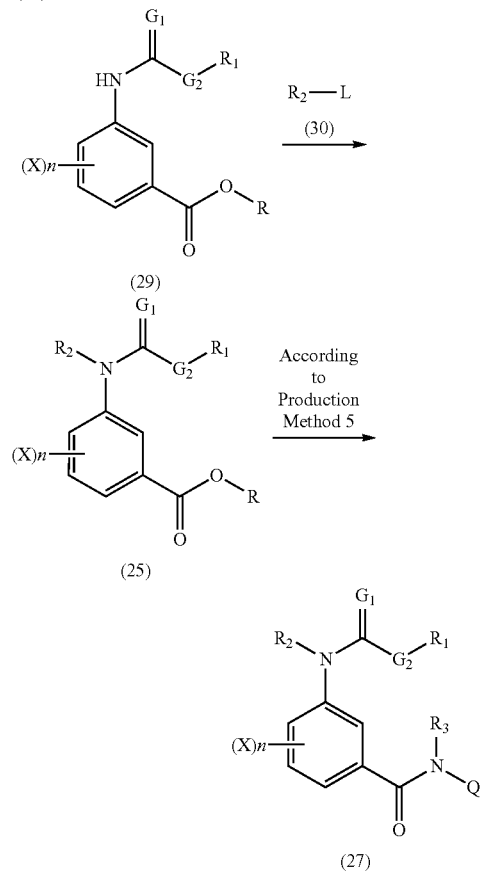

6-(i) Formula (28)→Formula (29)

A compound represented formula (29) can be produced by the technique described above in the step 1-(iii) of Production Method 1 using a compound represented by formula (7) (for example, a chloroformic ester or a chlorothioformic ester) under appropriate conditions.

6-(ii) Formula (29)→Formula (25)

In this step, examples of a compound represented by formula (30) include alkyl halides such as methyl iodide and ethyl iodide; toluenesulfonic esters; methanesulfonic esters; and alkylating agents such as dimethyl sulfate. As a solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. Also, a base may be added for accelerating the progress of reaction. Examples of the base include organic bases such as triethylamine, pyridine, and 4-dimethylaminopyridine; inorganic bases such as potassium carbonate, sodium hydroxide, and potassium hydroxide; and alkali metal hydrides such as sodium hydride. The amount of the base used may be appropriately determined in the range of molar equivalents of 0.01 to 5 times the amount of the compound represented by formula (29). The reaction temperature may be appropriately determined in the range of −20° C. to the reflux temperature of the solvent used, and the reaction time may be appropriately determined in the range of several minutes to 96 hours.

6-(iii) Formula (25)→Formula (27)

A compound represented by formula (27) of the present invention can be produced by the techniques described above in the steps 5-(ii) and 5-(iii) of Production Method 5 under appropriate conditions.

A compound represented by formula (31) of the present invention can be produced according to Production Method 7 (in the formula, $A_1, A_2, A_3, A_4, R_1, R_3, G_2, G_3$, and $(X)n$ each represent the same as described above).

Production Method 7

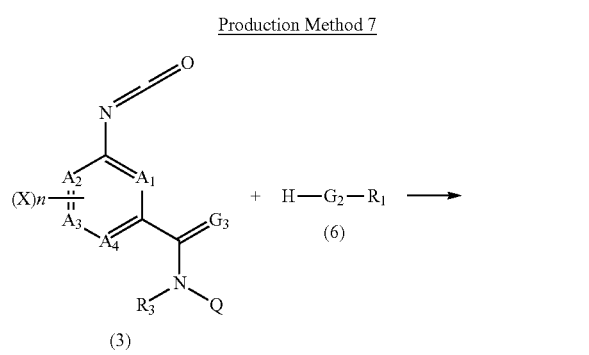

In this step, an appropriate solvent may be used. As the solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. Also, an appropriate base may be used. Examples of the base include organic bases such as triethylamine, tri-n-butylamine, pyridine, 4-dimethylaminopyridine; alkali metal hydroxides such as sodium hydroxide and potassium hydroxide; carbonates such as sodium hydrogen carbonate and potassium carbonate; alkali metal hydrides such as sodium hydride; and alkali metal alcoholates such as sodium methoxide and sodium ethoxide. The amount of the base used may be appropriately determined in the range of molar equivalents of 0.01 to 5 times the amount of the compound represented by formula (6). The reaction temperature may be appropriately determined in the range of −20° C. to the reflux temperature of the solvent used, and the reaction time may be appropriately determined in the range of several minutes to 96 hours.

An isocyanate compound represented by formula (3) can be produced by Production Method 8 (in the formula, $A_1, A_2, A_3, A_4, G_3, R_3, (X)n$, and Q each represent the same as described above) using a m-aminobenzamide derivative or a m-aminopyridinecarboxamide derivative represented by formula (32) as a starting material.

Production Method 8

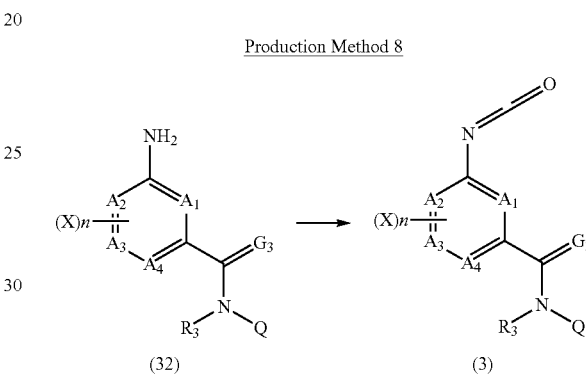

In this step, reaction can be performed by using phosgene according to the technique described in Organic Syntheses, Coll., Vol. II, p. 453. An isocyanate compound represented by formula (3) can also be produced by using a phosgene dimmer, triphosgene, or oxalyl chloride instead of phosgene. In this step, an appropriate solvent may be used. As the solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. The reaction temperature may be appropriately determined in the range of −20° C. to the reflux temperature of the solvent used, and the reaction time may be appropriately determined in the range of several minutes to 96 hours.

An isocyanate compound represented by formula (3) can also be produced by Production Method 9 (in the formula, $A_1, A_2, A_3, A_4, G_3, R_3, (X)n$, and Q each represent the same as described above) utilizing Curtius rearrangement reaction with an isophthaloyl chloride derivative represented by formula (33) used as a starting material according to the technique described in Macromolecules, p. 1046 (1998).

Production Method 9

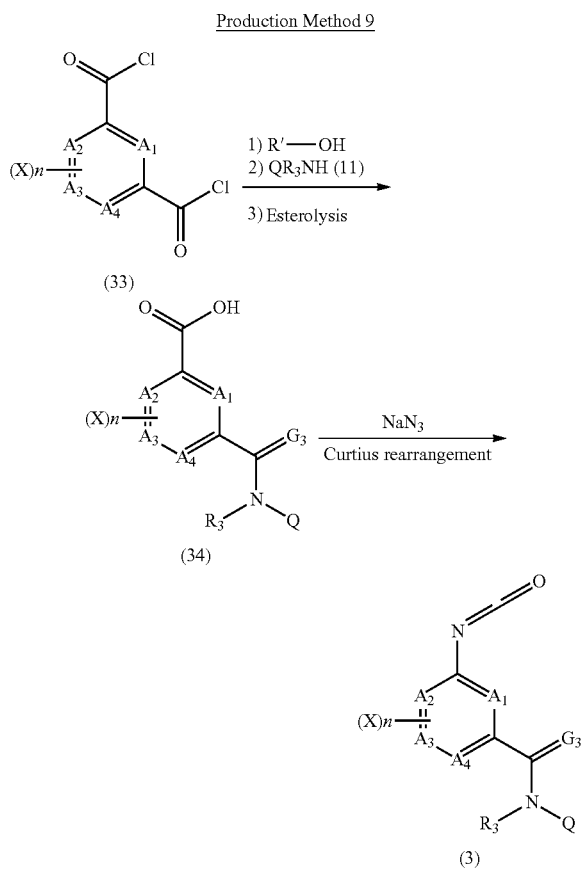

Production Method 10

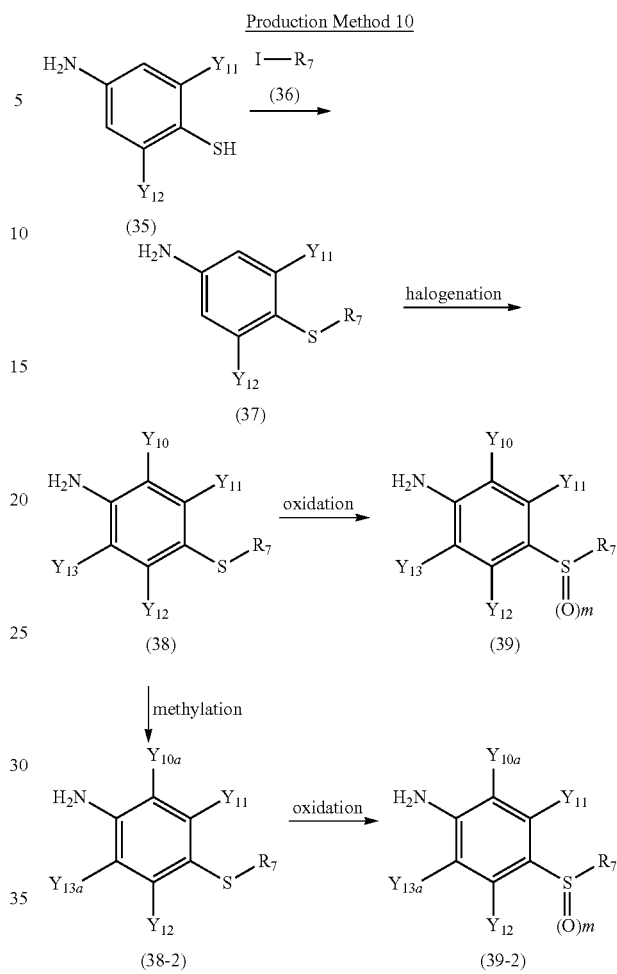

In this step, an appropriate solvent may be used. As the solvent, any solvent which does not significantly inhibit the progress of reaction can be used. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone. These solvents can be used alone or in a mixture of two or more kinds. The reaction temperature may be appropriately determined in the range of −20° C. to the reflux temperature of the solvent used, and the reaction time may be appropriately determined in the range of several minutes to 96 hours. In producing a compound represented formula (34), ethanol, propanol, or benzyl alcohol can be used as an alcohol. In esterolysis, hydrolysis or catalytic hydrogen reduction can be performed by a conventional technique.

An aniline derivative represented by formula (39) can be produced by using an aminothiophenol derivative as a starting material according Production Method 10 (in the formula, $R_7$, $Y_{11}$, $Y_{12}$, and m each represent the same as described above, $Y_{10}$ and $Y_{13}$ each represent a hydrogen atom or a halogen atom except a case in which both groups are hydrogen atoms as far as this Method is concerned, $Y_{10a}$ and $Y_{13a}$ each represent a hydrogen atom, a halogen atom, or a methyl group as far as this Method is concerned, and one of $Y_{10a}$ and $Y_{13a}$ necessarily represents a methyl group).

10-(i) Formula (35)→Formula (37)

A compound represented by formula (38) can be produced by reaction of aminothiophenol represented by formula (35) with a haloalkyl iodide represented by formula (36) according to the method described in J. Fluorine Chem., p. 207 (1994).

Examples of a haloalkyl iodide represented by formula (36) include trifluoromethyl iodide, pentafluoroethyl iodide, heptafluoro-n-propyl iodide, heptafluoroisopropyl iodide, nonafluoro-n-butyl iodide, and nonafluoro-2-butyl iodide. The amount of the haloalkyl iodide used may be appropriately determined in the range of molar equivalents of 1 to 10 times the amount of the compound represented formula (35). The solvent used in this step is not limited to those described in the above document, and any solvent which does not significantly inhibit the progress of reaction can be used as the solvent. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone and hexamethylphosphoric triamide. These solvents can be used alone or in a mixture of two ore more kinds. In particular, a polar solvent is preferred. The reaction temperature may be appropriately determined in the range of −20° C. to the reflux temperature of the solvent used, and the reaction time may be appropriately determined in the range of several minutes to 96 hours.

10-(ii) Formula (37)→Formula (38)

A compound represented by formula (38) can be produced by using an appropriate halogenating agent according to the technique described in, for example, Synth. Commun., p. 1261 (1989). Examples of the halogenating agent include chlorine, bromine, iodine, N-chlorosuccinimide, N-bromosuccinimide, and N-iodosuccinimide. The amount of the halogenating agent used may be appropriately determined in the range of molar equivalents of 1 to 10 times the amount of the compound represented formula (37). The number of equivalents of the halogenating agent used can be appropriately determined so that only $Y_{10}$ or $Y_{13}$ is a halogen atom. In this step, an appropriate solvent may be used. The solvent used is not limited to those described in the above document, and any solvent which does not significantly inhibit the progress of reaction can be used as the solvent. Examples of the solvent include aromatic hydrocarbons such as benzene, toluene, and xylene; halogenated hydrocarbons such as dichloromethane, chloroform, and carbon tetrachloride; chained or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; amides such as dimethylformamide and dimethylacetamide; nitriles such as acetonitrile; and inert solvents such as 1,3-dimethyl-2-imidazolidinone and hexamethylphosphoric triamide. These solvents can be used alone or in a mixture of two or more kinds. In particular, a polar solvent is preferred. The reaction temperature may be appropriately determined in the range of −20° C. to the reflux temperature of the solvent used, and the reaction time may be appropriately determined in the range of several minutes to 96 hours.

10-(iii) Formula (38)→Formula (39)

A compound represented by formula (39) can be produced by using an appropriate oxidizing agent according to the technique described in, for example, Tetrahedron Lett., p. 4955 (1994). Examples of the oxidizing agent include organic peroxy acids such as m-chloroperoxybenzoic acid; sodium metaperiodate; hydrogen peroxide; ozone; selenium dioxide, chromic acid; dinitrogen tetraoxide; acyl nitrate; iodine; bromine; N-bromosuccinimide; iodosylbenzene; and t-butyl hypochlorite. The solvent used in this step is not limited to those disclosed in the above document, and any solvent which does not significantly inhibit the progress of reaction may be used. The solvents can be used alone or in a mixture of one or more kinds. In particular, a polar solvent is preferred. The reaction temperature may be appropriately determined in the range of −20° C. to the reflux temperature of the solvent used, and the reaction time may be appropriately determined in the range of several minutes to 96 hours.

10-(iv) Formula (38)→Formula (38-2)

A compound represented by formula (38-2) (wherein $R_7$, $Y_{11}$, $Y_{12}$, and m each represent the same as described above, $Y_{10a}$ and $Y_{13a}$ each represent a hydrogen atom, a halogen atom, or a methyl group as far as this step is concerned, and one of $Y_{10a}$ and $Y_{13a}$ necessarily represents a methyl group) can be produced from the compound represented by formula (38) using an appropriate methylating agent. This step can be performed according to the technique described in, for example, Tetrahedron. Lett., p. 6237 (2000).

10-(v) Formula (38-2)→Formula (39-2)

A compound represented by formula (39-2) (wherein $R_7$, $Y_{11}$, $Y_{12}$, and m each represent the same as described above, $Y_{10a}$ and $Y_{13a}$ both represent a methyl group or one of $Y_{10a}$ and $Y_{13a}$ represents a methyl group and the other represents a halogen atom as far as this step is concerned) can be produced according to the technique descried above in the step 10-(iii) of Production Method 10.

The compounds represented by formula (1), (3), (4), and (8) can be produced from aniline derivatives represented by formula (38), (39), (38-2) and (39-2) according to any one Method appropriately selected from Production Methods 1 to 9.

The compound represented by formula (39) can also be produced from an aminothiophenol represented by formula (40) according to Production Method 11 (in the formula, $R_7$, $Y_{10}$, $Y_{11}$, $Y_{12}$, $Y_{13}$, and m each represent the same as described above).

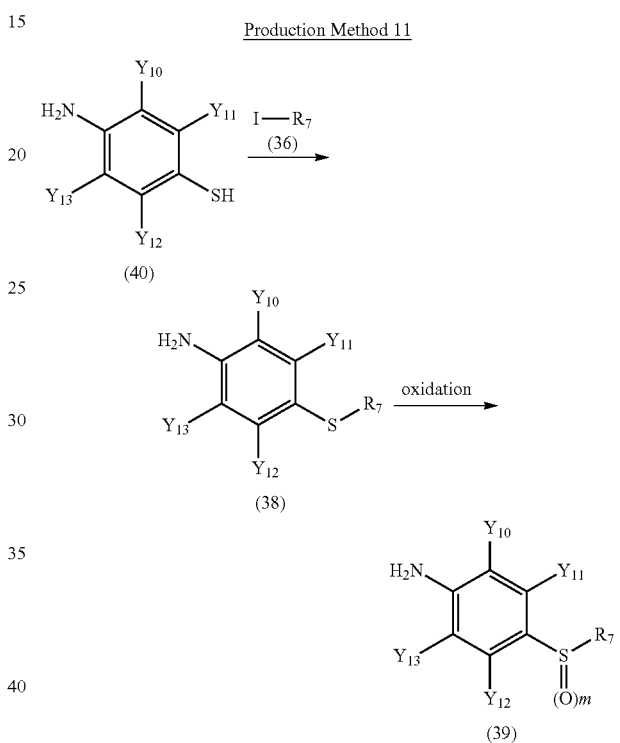

Reaction with a haloalkyl iodide and subsequent oxidation can be performed according to Production Method 10. The compounds represented by formula (1), (3), (4), and (8) can be produced from aniline derivatives represented by formula (41) and (42) according to any one Method appropriately selected from Production Methods 1 to 9.

A compound represented by formula (9) can also be produced from an aniline derivative represented by formula (41) and used as a starting material according to Production Method 12 (in the formula, $R_{10}$, $R_{11}$, $R_{12}$, $Y_{14}$, $Y_{15}$, $Y_{16}$, and $Y_{17}$ each represent the same as described above).

-continued

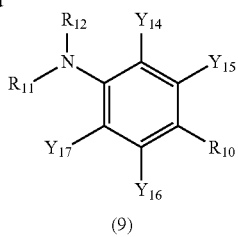

(9)

A compound represented by formula (9) can be produced by using an appropriate perfluorinated aldehyde or perfluorinated ketone according to the technique described in, for example, J. Am. Chem. Soc., p. 2410 (1965) and J. Org. Chem., p. 1001 (1965). Examples of the perfluorinated aldehyde or perfluorinated ketone include hexafluoroacetone and perfluoro-2-butanone. In this step, an appropriate solvent can be used. The solvent used in this step is not limited to those disclosed in the above documents, and any solvent which does not significantly inhibit the progress of reaction may be used. The solvents can be used alone or in a mixture of one or more kinds. The reaction temperature may be appropriately determined in the range of −20° C. to 200° C., and the reaction time may be appropriately determined in the range of several minutes to 96 hours.

The compounds represented by formula (1), (3), and (4) can be produced from an aniline derivative represented by formula (9) according to any one properly selected from Production Methods 1 to 9.

In all the production Methods, the compounds may be isolated from the reaction systems after reactions according to a normal technique. However, the compounds can be optionally purified by an operation such as recrystallization, column chromatography., distillation, or the like. Alternatively, the compounds may be used in next reaction steps without being isolated from the reaction systems.

Although typical examples of the compounds represented by formula (1) and used as active ingredients of insecticides of the present invention are shown in Tables 1 to 5, the present invention is not limited to these examples.

Although typical examples of the compounds represented by formula (4) are shown in Tables 6 to 8, the present invention is not limited to these examples.

In the tables, "n-" denotes normal, "Me" denotes a methyl group, "Et" denotes an ethyl group; "n-Pr" denotes a normal propyl group, "i-Pr, denotes an isopropyl group, "n-Bu" denotes a normal butyl group, "i-Bu" denotes an isobutyl group, "s-Bu" denotes a secondary butyl group, "t-Bu" denotes a tertiary butyl group, "H" denotes a hydrogen atom, "O" denotes an oxygen atom, "S" denotes a sulfur atom, "C" denotes a carbon atom, "N" denotes a nitrogen atom, "F" denotes a fluorine atom, "Cl" denotes a chlorine atom, "Br" denotes a bromine atom, "I" denotes an iodine atom, "$CF_3$" denotes a trifluoromethyl group, "MeO" denotes a methoxy group, "$NH_2$" denotes an amino group, "MeNH" denotes a methylamino group, and "$Me_2N$" denotes a dimethylamino group.

TABLE 1

(1-A)

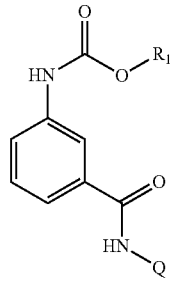

| Compound No. | $R_1$ | Q |
| --- | --- | --- |
| 1 | Me | 2-methyl-4-heptafluoroisopropylphenyl |
| 2 | Et | 2-methyl-4-heptafluoroisopropylphenyl |
| 3 | i-Pr | 2-methyl-4-heptafluoroisopropylphenyl |
| 4 | n-Bu | 2-methyl-4-heptafluoroisopropylphenyl |
| 5 | i-Bu | 2-methyl-4-heptafluoroisopropylphenyl |
| 6 | s-Bu | 2-methyl-4-heptafluoroisopropylphenyl |
| 7 | t-Bu | 2-methyl-4-heptafluoroisopropylphenyl |
| 8 | neopentyl | 2-methyl-4-heptafluoroisopropylphenyl |
| 9 | 3,3-dimethyl-n-butyl | 2-methyl-4-heptafluoroisopropylphenyl |
| 10 | 2-ethyl-n-hexyl | 2-methyl-4-heptafluoroisopropylphenyl |
| 11 | vinyl | 2-methyl-4-heptafluoroisopropylphenyl |
| 12 | allyl | 2-methyl-4-heptafluoroisopropylphenyl |
| 13 | 2-isopropyl-5-methylcyclohexyl | 2-methyl-4-heptafluoroisopropylphenyl |
| 14 | benzyl | 2-methyl-4-heptafluoroisopropylphenyl |
| 15 | 3-cyanobenzyl | 2-methyl-4-heptafluoroisopropylphenyl |
| 16 | 4-cyanobenzyl | 2-methyl-4-heptafluoroisopropylphenyl |
| 17 | 2-methoxyethyl | 2-methyl-4-heptafluoroisopropylphenyl |
| 18 | chloromethyl | 2-methyl-4-heptafluoroisopropylphenyl |
| 19 | 2-chloroethyl | 2-methyl-4-heptafluoroisopropylphenyl |
| 20 | 2,2,2-trichloroethyl | 2-methyl-4-heptafluoroisopropylphenyl |
| 21 | 1,2,2,2-tetrachloroethyl | 2-methyl-4-heptafluoroisopropylphenyl |
| 22 | 1,1-dimethyl-2,2,2-trichloroethyl | 2-methyl-4-heptafluoroisopropylphenyl |
| 23 | 3-trifluoromethylphenyl | 2-methyl-4-heptafluoroisopropylphenyl |
| 24 | 4-methylphenyl | 2-methyl-4-heptafluoroisopropylphenyl |
| 25 | 4-chlorophenyl | 2-methyl-4-heptafluoroisopropylphenyl |

TABLE 1-continued

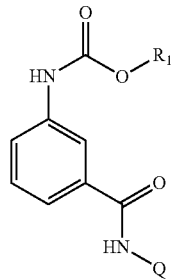

(1-A)

| Compound No. | R₁ | Q |
| --- | --- | --- |
| 26 | cyclobutyl | 2-methyl-4-heptafluoroisopropylphenyl |
| 27 | cyclopentyl | 2-methyl-4-heptafluoroisopropylphenyl |
| 28 | 2-cyanoethyl | 2-methyl-4-heptafluoroisopropylphenyl |
| 29 | 2-(ethylthio)ethyl | 2-methyl-4-heptafluoroisopropylphenyl |
| 30 | 2-(ethylsulfinyl)ethyl | 2-methyl-4-heptafluoroisopropylphenyl |
| 31 | 2-(ethylsulfonyl)ethyl | 2-methyl-4-heptafluoroisopropylphenyl |
| 32 | 2-fluoroethyl | 2-methyl-4-heptafluoroisopropylphenyl |
| 33 | 2,2-difluoroethyl | 2-methyl-4-heptafluoroisopropylphenyl |
| 34 | 2,2,2-trifluoroethyl | 2-methyl-4-heptafluoroisopropylphenyl |
| 35 | 1,3-difluoro-2-propyl | 2-methyl-4-heptafluoroisopropylphenyl |
| 36 | 1-chloro-3-fluoro-2-propyl | 2-methyl-4-heptafluoroisopropylphenyl |
| 37 | 1-methyl-2,2,2-trifluoro-2-propyl | 2-methyl-4-heptafluoroisopropylphenyl |
| 38 | 3,3,3-trifluoro-n-propyl | 2-methyl-4-heptafluoroisopropylphenyl |
| 39 | 3,3,4,4,4-pentafluoro-2-butyl | 2-methyl-4-heptafluoroisopropylphenyl |
| 40 | 4,4,4-trifluoro-n-butyl | 2-methyl-4-heptafluoroisopropylphenyl |
| 41 | 2,2,3,3-tetrafluorocyclobutyl | 2-methyl-4-heptafluoroisopropylphenyl |
| 42 | 2,2-dichloroethyl | 2-methyl-4-heptafluoroisopropylphenyl |
| 43 | 1,3-dichloro-2-propyl | 2-methyl-4-heptafluoroisopropylphenyl |
| 44 | 3-chloro-n-propyl | 2-methyl-4-heptafluoroisopropylphenyl |
| 45 | 3,3,3-trichloro-n-propyl | 2-methyl-4-heptafluoroisopropylphenyl |
| 46 | 2-bromoethyl | 2-methyl-4-heptafluoroisopropylphenyl |
| 47 | 2,2,2-tribromoethyl | 2-methyl-4-heptafluoroisopropylphenyl |
| 48 | 2-iodoethyl | 2-methyl-4-heptafluoroisopropylphenyl |
| 49 | tetrahydrofuran-3-yl | 2-methyl-4-heptafluoroisopropylphenyl |
| 50 | (furan-2-yl)methyl | 2-methyl-4-heptafluoroisopropylphenyl |
| 51 | (furan-3-yl)methyl | 2-methyl-4-heptafluoroisopropylphenyl |
| 52 | (tetrahydrofuran-2-yl)methyl | 2-methyl-4-heptafluoroisopropylphenyl |
| 53 | (tetrahydrofuran-3-yl)methyl | 2-methyl-4-heptafluoroisopropylphenyl |
| 54 | (thiophen-2-yl)methyl | 2-methyl-4-heptafluoroisopropylphenyl |
| 55 | (thiophen-3-yl)methyl | 2-methyl-4-heptafluoroisopropylphenyl |
| 56 | (pyridin-2-yl)methyl | 2-methyl-4-heptafluoroisopropylphenyl |
| 57 | (pyridin-3-yl)methyl | 2-methyl-4-heptafluoroisopropylphenyl |
| 58 | (6-chloropyridin-3-yl)methyl | 2-methyl-4-heptafluoroisopropylphenyl |
| 59 | Me | 2,6-dimethyl-4-heptafluoroisopropylphenyl |
| 60 | Et | 2,6-dimethyl-4-heptafluoroisopropylphenyl |
| 61 | n-Pr | 2,6-dimethyl-4-heptafluoroisopropylphenyl |
| 62 | i-Pr | 2,6-dimethyl-4-heptafluoroisopropylphenyl |
| 63 | n-Bu | 2,6-dimethyl-4-heptafluoroisopropylphenyl |
| 64 | i-Bu | 2,6-dimethyl-4-heptafluoroisopropylphenyl |
| 65 | s-Bu | 2,6-dimethyl-4-heptafluoroisopropylphenyl |
| 66 | t-Bu | 2,6-dimethyl-4-heptafluoroisopropylphenyl |
| 67 | neopentyl | 2,6-dimethyl-4-heptafluoroisopropylphenyl |
| 68 | 1,2-dimethyl-n-propyl | 2,6-dimethyl-4-heptafluoroisopropylphenyl |
| 69 | 1-methyl-n-butyl | 2,6-dimethyl-4-heptafluoroisopropylphenyl |
| 70 | 1,3-dimethyl-n-butyl | 2,6-dimethyl-4-heptafluoroisopropylphenyl |
| 71 | 3,3-dimethyl-n-butyl | 2,6-dimethyl-4-heptafluoroisopropylphenyl |
| 72 | cyclopentylmethyl | 2,6-dimethyl-4-heptafluoroisopropylphenyl |
| 73 | 1-phenylethyl | 2,6-dimethyl-4-heptafluoroisopropylphenyl |
| 74 | 2-phenylethyl | 2,6-dimethyl-4-heptafluoroisopropylphenyl |
| 75 | vinyl | 2,6-dimethyl-4-heptafluoroisopropylphenyl |
| 76 | allyl | 2,6-dimethyl-4-heptafluoroisopropylphenyl |
| 77 | propargyl | 2,6-dimethyl-4-heptafluoroisopropylphenyl |
| 78 | cyclobutyl | 2,6-dimethyl-4-heptafluoroisopropylphenyl |
| 79 | cyclopentyl | 2,6-dimethyl-4-heptafluoroisopropylphenyl |
| 80 | cyclohexyl | 2,6-dimethyl-4-heptafluoroisopropylphenyl |
| 81 | benzyl | 2,6-dimethyl-4-heptafluoroisopropylphenyl |
| 82 | 4-methylbenzyl | 2,6-dimethyl-4-heptafluoroisopropylphenyl |
| 83 | 4-trifluoromethylbenzyl | 2,6-dimethyl-4-heptafluoroisopropylphenyl |
| 84 | 3-cyanobenzyl | 2,6-dimethyl-4-heptafluoroisopropylphenyl |
| 85 | 4-cyanobenzyl | 2,6-dimethyl-4-heptafluoroisopropylphenyl |
| 86 | 2-fluorobenzyl | 2,6-dimethyl-4-heptafluoroisopropylphenyl |
| 87 | 3-fluorobenzyl | 2,6-dimethyl-4-heptafluoroisopropylphenyl |
| 88 | 4-fluorobenzyl | 2,6-dimethyl-4-heptafluoroisopropylphenyl |

TABLE 1-continued

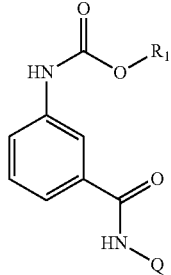

(1-A)

| Compound No. | R₁ | Q |
|---|---|---|
| 89 | 2-chlorobenzyl | 2,6-dimethyl-4-heptafluoroisopropylphenyl |
| 90 | 3-chlorobenzyl | 2,6-dimethyl-4-heptafluoroisopropylphenyl |
| 91 | 4-chlorobenzyl | 2,6-dimethyl-4-heptafluoroisopropylphenyl |
| 92 | 4-nitrobenzyl | 2,6-dimethyl-4-heptafluoroisopropylphenyl |
| 93 | 4-methoxycarbonylbenzyl | 2,6-dimethyl-4-heptafluoroisopropylphenyl |
| 94 | 2-hydroxyethyl | 2,6-dimethyl-4-heptafluoroisopropylphenyl |
| 95 | 2-methoxyethyl | 2,6-dimethyl-4-heptafluoroisopropylphenyl |
| 96 | 2-ethoxyethyl | 2,6-dimethyl-4-heptafluoroisopropylphenyl |
| 97 | 2-isopropyloxyethyl | 2,6-dimethyl-4-heptafluoroisopropylphenyl |
| 98 | 2-benzyloxyethyl | 2,6-dimethyl-4-heptafluoroisopropylphenyl |
| 99 | 3-ethoxy-n-propyl | 2,6-dimethyl-4-heptafluoroisopropylphenyl |
| 100 | ethoxycarbonylmethyl | 2,6-dimethyl-4-heptafluoroisopropylphenyl |
| 101 | 1-(methoxycarbonyl)ethyl | 2,6-dimethyl-4-heptafluoroisopropylphenyl |
| 102 | 1-(ethoxycarbonyl)ethyl | 2,6-dimethyl-4-heptafluoroisopropylphenyl |
| 103 | 3-oxo-n-butyl | 2,6-dimethyl-4-heptafluoroisopropylphenyl |
| 104 | 2-acetoxyethyl | 2,6-dimethyl-4-heptafluoroisopropylphenyl |
| 105 | cyanomethyl | 2,6-dimethyl-4-heptafluoroisopropylphenyl |
| 106 | 2-cyanoethyl | 2,6-dimethyl-4-heptafluoroisopropylphenyl |
| 107 | 3-cyano-n-propyl | 2,6-dimethyl-4-heptafluoroisopropylphenyl |
| 108 | 2-(methylthio)ethyl | 2,6-dimethyl-4-heptafluoroisopropylphenyl |
| 109 | 2-(ethylthio)ethyl | 2,6-dimethyl-4-heptafluoroisopropylphenyl |
| 110 | 2-(isopropylthio)ethyl | 2,6-dimethyl-4-heptafluoroisopropylphenyl |
| 111 | 1-methyl-2-(methylthio)ethyl | 2,6-dimethyl-4-heptafluoroisopropylphenyl |
| 112 | 2-(ethylsulfinyl)ethyl | 2,6-dimethyl-4-heptafluoroisopropylphenyl |
| 113 | 2-(ethylsulfonyl)ethyl | 2,6-dimethyl-4-heptafluoroisopropylphenyl |
| 114 | 3-(methylthio)-n-propyl | 2,6-dimethyl-4-heptafluoroisopropylphenyl |
| 115 | 3-(ethylthio)-n-propyl | 2,6-dimethyl-4-heptafluoroisopropylphenyl |
| 116 | 2-fluoroethyl | 2,6-dimethyl-4-heptafluoroisopropylphenyl |
| 117 | 2,2-difluoroethyl | 2,6-dimethyl-4-heptafluoroisopropylphenyl |
| 118 | 2,2,2-trifluoroethyl | 2,6-dimethyl-4-heptafluoroisopropylphenyl |
| 119 | 1,3-difluoro-2-propyl | 2,6-dimethyl-4-heptafluoroisopropylphenyl |
| 120 | 1-chloro-3-fluoro-2-propyl | 2,6-dimethyl-4-heptafluoroisopropylphenyl |
| 121 | 1-methyl-2,2,2-trifluoroethyl | 2,6-dimethyl-4-heptafluoroisopropylphenyl |
| 122 | 1,1,1,3,3,3-hexafluoro-2-propyl | 2,6-dimethyl-4-heptafluoroisopropylphenyl |
| 123 | 3,3,3-trifluoro-n-propyl | 2,6-dimethyl-4-heptafluoroisopropylphenyl |
| 124 | 2,2,3,3,3-pentafluoro-n-propyl | 2,6-dimethyl-4-heptafluoroisopropylphenyl |
| 125 | 3,3,4,4,4-pentafluoro-2-butyl | 2,6-dimethyl-4-heptafluoroisopropylphenyl |
| 126 | 4,4,4-tifluoro-n-butyl | 2,6-dimethyl-4-heptafluoroisopropylphenyl |
| 127 | 2,2,3,3-tetrafluorocyclobutyl | 2,6-dimethyl-4-heptafluoroisopropylphenyl |
| 128 | chloromethyl | 2,6-dimethyl-4-heptafluoroisopropylphenyl |
| 129 | trichloromethyl | 2,6-dimethyl-4-heptafluoroisopropylphenyl |
| 130 | 2-chloroethyl | 2,6-dimethyl-4-heptafluoroisopropylphenyl |
| 131 | 2,2-dichloroethyl | 2,6-dimethyl-4-heptafluoroisopropylphenyl |
| 132 | 2,2,2-trichloroethyl | 2,6-dimethyl-4-heptafluoroisopropylphenyl |
| 133 | 1,2,2,2-tetrachloroethyl | 2,6-dimethyl-4-heptafluoroisopropylphenyl |
| 134 | 1,3-dichloro-2-propyl | 2,6-dimethyl-4-heptafluoroisopropylphenyl |
| 135 | 1,1-dimethyl-2,2,2-trichloroethyl | 2,6-dimethyl-4-heptafluoroisopropylphenyl |
| 136 | 3-chloro-n-propyl | 2,6-dimethyl-4-heptafluoroisopropylphenyl |
| 137 | 2-bromoethyl | 2,6-dimethyl-4-heptafluoroisopropylphenyl |
| 138 | 2,2,2-tribromoethyl | 2,6-dimethyl-4-heptafluoroisopropylphenyl |
| 139 | 3-bromo-n-propyl | 2,6-dimethyl-4-heptafluoroisopropylphenyl |
| 140 | 2-iodoethyl | 2,6-dimethyl-4-heptafluoroisopropylphenyl |
| 141 | 2-(acetylamino)ethyl | 2,6-dimethyl-4-heptafluoroisopropylphenyl |
| 142 | 2-(dimethylamino)ethyl | 2,6-dimethyl-4-heptafluoroisopropylphenyl |
| 143 | 2-(ethylamino)ethyl | 2,6-dimethyl-4-heptafluoroisopropylphenyl |
| 144 | methylaminocarbonylethyl | 2,6-dimethyl-4-heptafluoroisopropylphenyl |
| 145 | phenyl | 2,6-dimethyl-4-heptafluoroisopropylphenyl |
| 146 | 4-methylphenyl | 2,6-dimethyl-4-heptafluoroisopropylphenyl |
| 147 | 3-trifluoromethylphenyl | 2,6-dimethyl-4-heptafluoroisopropylphenyl |
| 148 | 4-chlorophenyl | 2,6-dimethyl-4-heptafluoroisopropylphenyl |
| 149 | naphthyl | 2,6-dimethyl-4-heptafluoroisopropylphenyl |
| 150 | Pyridine-2-yl | 2,6-dimethyl-4-heptafluoroisopropylphenyl |
| 151 | pyridine-3-yl | 2,6-dimethyl-4-heptafluoroisopropylphenyl |

TABLE 1-continued

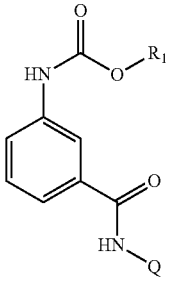

(1-A)

| Compound No. | R₁ | Q |
|---|---|---|
| 152 | pyridine-4-yl | 2,6-dimethyl-4-heptafluoroisopropylphenyl |
| 153 | tetrahydrofuran-2-yl | 2,6-dimethyl-4-heptafluoroisopropylphenyl |
| 154 | tetrahydrofuran-3-yl | 2,6-dimethyl-4-heptafluoroisopropylphenyl |
| 155 | (furan-2-yl)methyl | 2,6-dimethyl-4-heptafluoroisopropylphenyl |
| 156 | (furan-3-yl)methyl | 2,6-dimethyl-4-heptafluoroisopropylphenyl |
| 157 | (tetrahydrofuran-2-yl)methyl | 2,6-dimethyl-4-heptafluoroisopropylphenyl |
| 158 | (tetrahydrofuran-3-yl)methyl | 2,6-dimethyl-4-heptafluoroisopropylphenyl |
| 159 | (thiophen-2-yl)methyl | 2,6-dimethyl-4-heptafluoroisopropylphenyl |
| 160 | (thiophen-3-yl)methyl | 2,6-dimethyl-4-heptafluoroisopropylphenyl |
| 161 | (pyridin-2-yl)methyl | 2,6-dimethyl-4-heptafluoroisopropylphenyl |
| 162 | (pyridin-3-yl)methyl | 2,6-dimethyl-4-heptafluoroisopropylphenyl |
| 163 | (6-chloropyridin-3-yl)methyl | 2,6-dimethyl-4-heptafluoroisopropylphenyl |
| 164 | Me | 2-methyl-6-isopropyl-4-heptafluoro isopropylphenyl |
| 165 | Et | 2-methyl-6-isopropyl-4-heptafluoro isopropylphenyl |
| 166 | i-Pr | 4-heptafluoroisopropylphenyl |
| 167 | i-Pr | 3-methyl-4-heptafluoroisopropylphenyl |
| 168 | i-Pr | 2-ethyl-4-heptafluoroisopropylphenyl |
| 169 | i-Pr | 2-propyl-4-heptafluoroisopropylphenyl |
| 170 | i-Pr | 3-methoxy-4-heptafluoroisopropylphenyl |
| 171 | i-Pr | 3-chloro-4-heptafluoroisopropylphenyl |
| 172 | i-Pr | 2,3-dimethyl-4-heptafluoroisopropylphenyl |
| 173 | i-Pr | 2,5-dimethyl-4-heptafluoroisopropylphenyl |
| 174 | i-Pr | 2,6-diethyl-4-heptafluoroisopropylphenyl |
| 175 | i-Pr | 2-ethyl-6-methyl-4-heptafluoroisopropylphenyl |
| 176 | i-Pr | 2-methyl-6-isopropyl-4-heptafluoroisopropyl phenyl |
| 177 | i-Pr | 2-methoxy-6-methyl-4-heptafluoroisopropylphenyl |
| 178 | i-Pr | 2-methyl-6-phenyl4-heptafluoroisopropylphenyl |
| 179 | i-Pr | 2-chloro-5-methyl-4-heptafluoroisopropylphenyl |
| 180 | i-Pr | 2-chloro-6-ethyl-4-heptafluoroisopropylphenyl |
| 181 | i-Pr | 2-chloro-6-n-propyl-4-heptafluoroisopropyl phenyl |
| 182 | i-Pr | 2-chloro-5-methoxy-4-heptafluoroisopropylphenyl |
| 183 | i-Pr | 2,3-dimethyl-6-chloro-4-heptafluoroisopropyl phenyl |
| 184 | i-Pr | 2-chloro-3,6-dimethyl-4-heptafluoroisopropyl phenyl |
| 185 | i-Pr | 2-methyl-3-chloromethyl-6-chloro-4-heptafluoro isopropylphenyl |
| 186 | i-Pr | 2-methyl-3-iodo-6-chloro-4-heptafluoro isopropylphenyl |
| 187 | 2,2,2-trichloroethyl | 4-heptafluoroisopropylphenyl |
| 188 | 2,2,2-trichloroethyl | 3-methyl-4-heptafluoroisopropylphenyl |
| 189 | 2,2,2-trichloroethyl | 2-ethyl-4-heptafluoroisopropylphenyl |
| 190 | 2,2,2-trichloroethyl | 2-propyl-4-heptafluoroisopropylphenyl |
| 191 | 2,2,2-trichloroethyl | 3-methoxy-4-heptafluoroisopropylphenyl |
| 192 | 2,2,2-trichloroethyl | 2-chloro-4-heptafluoroisopropylphenyl |
| 193 | 2,2,2-trichloroethyl | 3-chloro-4-heptafluoroisopropylphenyl |
| 194 | 2,2,2-trichloroethyl | 2,3-dimethyl-4-heptafluoroisopropylphenyl |
| 195 | 2,2,2-trichloroethyl | 2,5-dimethyl-4-heptafluoroisopropylphenyl |
| 196 | 2,2,2-trichloroethyl | 2,6-diethyl-4-heptafluoroisopropylphenyl |
| 197 | 2,2,2-trichloroethyl | 2-ethyl-6-methyl-4-heptafluoroisopropylphenyl |
| 198 | 2,2,2-trichloroethyl | 2-methyl-6-isopropyl-4-heptafluoro isopropylphenyl |
| 199 | 2,2,2-trichloroethyl | 2-methoxy-6-methyl-4-heptafluoroisopropylphenyl |
| 200 | 2,2,2-trichloroethyl | 2-methyl-6-phenyl-4-heptafluoroisopropylphenyl |
| 201 | 2,2,2-trichloroethyl | 2-hydroxy-6-methyl-4-heptafluoroisopropyl phenyl |
| 202 | 2,2,2-trichloroethyl | 2-chloro-5-methyl-4-heptafluoroisopropylphenyl |
| 203 | 2,2,2-trichloroethyl | 2-methyl-3-amino-4-heptafluoroisopropylphenyl |

TABLE 1-continued (1-A)

| Compound No. | R₁ | Q |
| --- | --- | --- |
| 204 | 2,2,2-trichloroethyl | 2-methyl-3-t-butoxycarbonylamino-4-heptafluoro isopropylphenyl |
| 205 | 2,2,2-trichloroethyl | 2-chloro-6-ethyl-4-heptafluoroisopropylphenyl |
| 206 | 2,2,2-trichloroethyl | 2-bromo-6-ethyl-4-heptafluoroisopropylphenyl |
| 207 | 2,2,2-trichloroethyl | 2-ethyl-6-iodo-4-heptafluoroisopropylphenyl |
| 208 | 2,2,2-trichloroethyl | 2-chloro-6-n-propyl-4-heptafluoro isopropylphenyl |
| 209 | 2,2,2-trichloroethyl | 2-bromo-6-n-propyl-4-heptafluoro isopropylphenyl |
| 210 | 2,2,2-trichloroethyl | 2-bromo-6-n-butyl-4-heptafluoro isopropylphenyl |
| 211 | 2,2,2-trichloroethyl | 2-chloro-5-methoxy-4-heptafluoro isopropylphenyl |
| 212 | 2,2,2-trichloroethyl | 2-bromo-6-methylthio-4-heptafluoro isopropylphenyl |
| 213 | 2,2,2-trichloroethyl | 2,6-dichloro-4-heptafluoroisopropylphenyl |
| 214 | 2,2,2-trichloroethyl | 2,3-dimethyl-6-chloro-4-heptafluoro isopropylphenyl |
| 215 | 2,2,2-trichloroethyl | 2-chloro-3,6-dimethyl-4-heptafluoro isopropylphenyl |
| 216 | 2,2,2-trichloroethyl | 2-methyl-3-chloromethyl-6-chloro-4-heptafluoro isopropylphenyl |
| 217 | 2,2,2-trichloroethyl | 2-methyl-3,6-dichloro-4-heptafluoro isopropylphenyl |
| 218 | 2,2,2-trichloroethyl | 2-methyl-3-bromo-6-chloro-4-heptafluoro isopropylphenyl |
| 219 | 2,2,2-trichloroethyl | 2-methyl-3-iodo-6-chloro-4-heptafluoro isopropylphenyl |
| 220 | 2,2,2-trichloroethyl | 2-methyl-3-amino-6-chloro-4-heptafluoro isopropylphenyl |
| 221 | 3,3,3-trifluoro-n-propyl | 2-bromo-6-n-butyl-4-heptafluoro isopropylphenyl |
| 222 | i-Pr | 2-chloro-6-methyl-4-trifluoromethylphenyl |
| 223 | i-Pr | 2,6-dichloro-4-trifluoromethylphenyl |
| 224 | i-Pr | 2-bromo-4,6-bis(trifluoromethyl)phenyl |
| 225 | i-Pr | 2,6-dimethyl-4-heptafluoro-n-propylphenyl |
| 226 | i-Pr | 2,6-dimethyl-4-nonafluoro-n-butylphenyl |
| 227 | 2,2,2-trichloroethyl | 4-trifluoromethylphenyl |
| 228 | 2,2,2-trichloroethyl | 2-chloro-6-methyl-4-trifluoromethylphenyl |
| 229 | 2,2,2-trichloroethyl | 2-bromo-6-chloro-4-trifluoromethylphenyl |
| 230 | 2,2,2-trichloroethyl | 2,6-dichloro-4-trifluoromethylphenyl |
| 231 | 2,2,2-trichloroethyl | 2-chloro4,6-bistrifluoromethylphenyl |
| 232 | 2,2,2-trichloroethyl | 2-bromo-4,6-bistrifluoromethylphenyl |
| 233 | 2,2,2-trichloroethyl | 2,6-dimethyl-4-heptafluoro-n-propylphenyl |
| 234 | 2,2,2-trichloroethyl | 2,6-dimethyl-4-nonafluoro-n-butylphenyl |
| 235 | 2,2,2-trichloroethyl | 2,3,5,6-tetrafluoro-4-trifluoromethylphenyl |
| 236 | 2,2,2-trichloroethyl | 2,6-dibromo-4-pentafluoroethylphenyl |
| 237 | 3,3,3-trifluoro-n-propyl | 2,6-dibromo-4-pentafluoroethylphenyl |
| 238 | 3,3,3-trifluoro-n-propyl | 2-bromo6-chloro-4-trifluoromethylphenyl |
| 239 | Et | 2,4-bis(trifluoromethyl)phenyl |
| 240 | i-Pr | 2,4-bis(trifluoromethyl)phenyl |
| 241 | vinyl | 2,4-bis(trifluoromethyl)phenyl |
| 242 | cyclopentyl | 2,4-bis(trifluoromethyl)phenyl |
| 243 | 2-chloroethyl | 2,4-bis(trifluoromethyl)phenyl |
| 244 | 2-cyanoethyl | 2,4-bis(trifluoromethyl)phenyl |
| 245 | 2,2-difluoroethyl | 2,4-bis(trifluoromethyl)phenyl |
| 246 | 2,2-dichloroethyl | 2,4-bis(trifluoromethyl)phenyl |
| 247 | 2,2,2-trichloroethyl | 2,4-bis(trifluoromethyl)phenyl |
| 248 | 2,2,2-tribromoethyl | 2,4-bis(trifluoromethyl)phenyl |
| 249 | 3,3,3-trifluoro-n-propyl | 2,4-bis(trifluoromethyl)phenyl |
| 250 | 2,2,3,3,3-pentafluoro-n-propyl | 2,4-bis(trifluoromethyl)phenyl |
| 251 | 4-cyanobenzyl | 2,4-bis(trifluoromethyl)phenyl |
| 252 | (6-chloropyridin-3-yl)methyl | 2,4-bis(trifluoromethyl)phenyl |

TABLE 1-continued

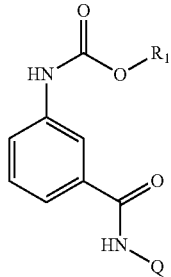

(1-A)

| Compound No. | $R_1$ | Q |
| --- | --- | --- |
| 253 | i-Pr | 2,6-dimethyl-4-(nonafluoro-2-butyl)phenyl |
| 254 | 2,2-difluoroethyl | 2,6-dimethyl-4-(nonafluoro-2-butyl)phenyl |
| 255 | 1,3-difluoro-2-propyl | 2,6-dimethyl-4-(nonafluoro-2-butyl)phenyl |
| 256 | 2,2,2-trifluoroethyl | 2,6-dimethyl-4-(nonafluoro-2-butyl)phenyl |
| 257 | 2,2,2-trichloroethyl | 2,6-dimethyl-4-(noanfluoro-2-butyl)phenyl |
| 258 | 1-methyl-2,2,2-trifluoroethyl | 2,6-dimethyl-4-(nonafluoro-2-butyl)phenyl |
| 259 | 3,3,3-trifluoro-n-propyl | 2,6-dimethyl-4-(nonafluoro-2-butyl)phenyl |
| 260 | Et | 2,6-dimethyl-4-(nonafluoro-2-butyl)phenyl |
| 261 | vinyl | 2,6-dimethyl-4-(nonafluoro-2-butyl)phenyl |
| 262 | propargyl | 2,6-dimethyl-4-(nonafluoro-2-butyl)phenyl |
| 263 | cyclobutyl | 2,6-dimethyl-4-(nonafluoro-2-butyl)phenyl |
| 264 | cyclopentyl | 2,6-dimethyl-4-(nonafluoro-2-butyl)phenyl |
| 265 | benzyl | 2,6-dimethyl-4-(nonafluoro-2-butyl)phenyl |
| 266 | 3-cyanobenzyl | 2,6-dimethyl-4-(nonafluoro-2-butyl)phenyl |
| 267 | 4-cyanobenzyl | 2,6-dimethyl-4-(nonafluoro-2-butyl)phenyl |
| 268 | 3-chlorobenzyl | 2,6-dimethyl-4-(nonafluoro-2-butyl)phenyl |
| 269 | 2-methoxyethyl | 2,6-dimethyl-4-(nonafluoro-2-butyl)phenyl |
| 270 | 2-cyanoethyl | 2,6-dimethyl-4-(nonafluoro-2-butyl)phenyl |
| 271 | 2-(methylthio)ethyl | 2,6-dimethyl-4-(nonafluoro-2-butyl)phenyl |
| 272 | 2-(ethylthio)ethyl | 2,6-dimethyl-4-(nonafluoro-2-butyl)phenyl |
| 273 | 1-methyl-2-(methylthio)ethyl | 2,6-dimethyl-4-(nonafluoro-2-butyl)phenyl |
| 274 | 2-(ethylsulfinyl)ethyl | 2,6-dimethyl-4-(nonafluoro-2-butyl)phenyl |
| 275 | 2-(ethylsulfonyl)ethyl | 2,6-dimethyl-4-(nonafluoro-2-butyl)phenyl |
| 276 | 2-fluoroethyl | 2,6-dimethyl-4-(nonafluoro-2-butyl)phenyl |
| 277 | 1-chloro-3-fluoro-2-propyl | 2,6-dimethyl-4-(nonafluoro-2-butyl)phenyl |
| 278 | 2,2,3,3,3-pentafluoro-n-propyl | 2,6-dimethyl-4-(nonafluoro-2-butyl)phenyl |
| 279 | 3,3,4,4,4-pentafluoro-2-butyl | 2,6-dimethyl-4-(nonafluoro-2-butyl)phenyl |
| 280 | 4,4,4-trifluoro-n-butyl | 2,6-dimethyl-4-(nonafluoro-2-butyl)phenyl |
| 281 | 2,2,3,3-tetrafluorocyclobutyl | 2,6-dimethyl-4-(nonafluoro-2-butyl)phenyl |
| 282 | 2-chloroethyl | 2,6-dimethyl-4-(nonafluoro-2-butyl)phenyl |
| 283 | 2,2-dichloroethyl | 2,6-dimethyl-4-(nonafluoro-2-butyl)phenyl |
| 284 | 1,3-dichloro-2-propyl | 2,6-dimethyl-4-(nonafluoro-2-butyl)phenyl |
| 285 | 3-chloro-n-propyl | 2,6-dimethyl-4-(nonafluoro-2-butyl)phenyl |
| 286 | 2-bromoethyl | 2,6-dimethyl-4-(nonafluoro-2-butyl)phenyl |
| 287 | 2,2,2-tribromoethyl | 2,6-dimethyl-4-(nonafluoro-2-butyl)phenyl |
| 288 | 3-bromo-n-propyl | 2,6-dimethyl-4-(nonafluoro-2-butyl)phenyl |
| 289 | 2-iodoethyl | 2,6-dimethyl-4-(nonafluoro-2-butyl)phenyl |
| 290 | tetrahydrofuran-3-yl | 2,6-dimethyl-4-(nonafluoro-2-butyl)phenyl |
| 291 | (furan-2-yl)methyl | 2,6-dimethyl-4-(nonafluoro-2-butyl)phenyl |
| 292 | (furan-3-yl)methyl | 2,6-dimethyl-4-(nonafluoro-2-butyl)phenyl |
| 293 | (tetrahydrofuran-2-yl)methyl | 2,6-dimethyl-4-(nonafluoro-2-butyl)phenyl |
| 294 | (tetrahydrofuran-3-yl)methyl | 2,6-dimethyl-4-(nonafluoro-2-butyl)phenyl |
| 295 | (thiophen-2-yl)methyl | 2,6-dimethyl-4-(nonafluoro-2-butyl)phenyl |
| 296 | (thiophen-3-yl)methyl | 2,6-dimethyl-4-(nonafluoro-2-butyl)phenyl |
| 297 | (pyridin-2-yl)methyl | 2,6-dimethyl-4-(nonafluoro-2-butyl)phenyl |
| 298 | (pyridin-3-yl)methyl | 2,6-dimethyl-4-(nonafluoro-2-butyl)phenyl |
| 299 | (6-chloropyridin-3-yl)methyl | 2,6-dimethyl-4-(nonafluoro-2-butyl)phenyl |
| 300 | 2,2,2-trichloroethyl | 2,6-dichloro-4-(trifluoromethylthio)phenyl |
| 301 | 2,2,2-trichloroethyl | 2,6-dichloro-4-(trifluoromethylsulfonyl)phenyl |
| 302 | Et | 2,6-dimethyl-4-pentafluoroethylphenyl |
| 303 | i-Pr | 2,6-dimethyl-4-pentafluoroethylphenyl |
| 304 | propargyl | 2,6-dimethyl-4-pentafluoroethylphenyl |
| 305 | cyclobutyl | 2,6-dimethyl-4-pentafluoroethylphenyl |
| 306 | cyclopentyl | 2,6-dimethyl-4-pentafluoroethylphenyl |
| 307 | benzyl | 2,6-dimethyl-4-pentafluoroethylphenyl |
| 308 | 3-cyanobenzyl | 2,6-dimethyl-4-pentafluoroethylphenyl |
| 309 | 4-cyanobenzyl | 2,6-dimethyl-4-pentafluoroethylphenyl |
| 310 | 3-chlorobenzyl | 2,6-dimethyl-4-pentafluoroethylphenyl |
| 311 | 2-methoxyethyl | 2,6-dimethyl-4-pentafluoroethylphenyl |
| 312 | 2-cyanoethyl | 2,6-dimethyl-4-pentafluoroethylphenyl |
| 313 | 2-(methylthio)ethyl | 2,6-dimethyl-4-pentafluoroethylphenyl |
| 314 | 2-(ethylthio)ethyl | 2,6-dimethyl-4-pentafluoroethylphenyl |
| 315 | 1-methyl2-(methylthio)ethyl | 2,6-dimethyl-4-pentafluoroethylphenyl |

TABLE 1-continued (1-A)

| Compound No. | R₁ | Q |
|---|---|---|
| 316 | 2-(ethylsulfinyl)ethyl | 2,6-dimethyl-4-pentafluoroethylphenyl |
| 317 | 2-(ethylsulfonyl)ethyl | 2,6-dimethyl-4-pentafluoroethylphenyl |
| 318 | 2-fluoroethyl | 2,6-dimethyl-4-pentafluoroethylphenyl |
| 319 | 2,2-difluoroethyl | 2,6-dimethyl-4-pentafluoroethylphenyl |
| 320 | 2,2,2-trifluoroethyl | 2,6-dimethyl-4-pentafluoroethylphenyl |
| 321 | 1,3-difluoro-2-propyl | 2,6-dimethyl-4-pentafluoroethylphenyl |
| 322 | 1-chloro-3-fluoro-2-propyl | 2,6-dimethyl-4-pentafluoroethylphenyl |
| 323 | 1-methyl-2,2,2-trifluoroethyl | 2,6-dimethyl-4-pentafluoroethylphenyl |
| 324 | 3,3,3-trifluoro-n-propyl | 2,6-dimethyl-4-pentafluoroethylphenyl |
| 325 | 2,2,3,3,3-pentafluoro-n-propyl | 2,6-dimethyl-4-pentafluoroethylphenyl |
| 326 | 3,3,4,4,4-pentafluoro-2-butyl | 2,6-dimethyl-4-pentafluoroethylphenyl |
| 327 | 4,4,4-trifluoro-n-butyl | 2,6-dimethyl-4-pentafluoroethylphenyl |
| 328 | 2,2,3,3-tetrafluorocyclobutyl | 2,6-dimethyl-4-pentafluoroethylphenyl |
| 329 | 2-chloroethyl | 2,6-dimethyl-4-pentafluoroethylphenyl |
| 330 | 2,2-dichloroethyl | 2,6-dimethyl-4-pentafluoroethylphenyl |
| 331 | 2,2,2-trichloroethyl | 2,6-dimethyl-4-pentafluoroethylphenyl |
| 332 | 1,3-dichloro-2-propyl | 2,6-dimethyl-4-pentafluoroethylphenyl |
| 333 | 3-chloro-n-propyl | 2,6-dimethyl-4-pentafluoroethylphenyl |
| 334 | 2-bromoethyl | 2,6-dimethyl-4-pentafluoroethylphenyl |
| 335 | 2,2,2-tribromoethyl | 2,6-dimethyl-4-pentafluoroethylphenyl |
| 336 | 3-bromo-n-propyl | 2,6-dimethyl-4-pentafluoroethylphenyl |
| 337 | 2-iodoethyl | 2,6-dimethyl-4-pentafluoroethylphenyl |
| 338 | tetrahydrofuran-3-yl | 2,6-dimethyl-4-pentafluoroethylphenyl |
| 339 | (furan-2-yl)methyl | 2,6-dimethyl-4-pentafluoroethylphenyl |
| 340 | (furan-3-yl)methyl | 2,6-dimethyl-4-pentafluoroethylphenyl |
| 341 | (tetrahydrofuran-2-yl)methyl | 2,6-dimethyl-4-pentafluoroethylphenyl |
| 342 | (tetrahydrofuran-3-yl)methyl | 2,6-dimethyl-4-pentafluoroethylphenyl |
| 343 | (thiophen-2-yl)methyl | 2,6-dimethyl-4-pentafluoroethylphenyl |
| 344 | (thiophen-3-yl)methyl | 2,6-dimethyl-4-pentafluoroethylphenyl |
| 345 | (pyridin-2-yl)methyl | 2,6-dimethyl-4-pentafluoroethylphenyl |
| 346 | (pyridin-3-yl)methyl | 2,6-dimethyl-4-pentafluoroethylphenyl |
| 347 | (6-chloropyridin-3-yl)methyl | 2,6-dimethyl-4-pentafluoroethylphenyl |
| 348 | Me | 2,6-dimethyl-4-(2-bromo-1,1,2,3,3,3-hexafluoro-isopropyl)phenyl |
| 349 | Et | 2,6-dimethyl-4-(2-bromo-1,1,2,3,3,3-hexafluoro-isopropyl)phenyl |
| 350 | i-Pr | 2,6-dimethyl-4-(2-bromo-1,1,2,3,3,3-hexafluoro-isopropyl)phenyl |
| 351 | propargyl | 2,6-dimethyl-4-(2-bromo-1,1,2,3,3,3-hexafluoro-isopropyl)phenyl |
| 352 | cyclobutyl | 2,6-dimethyl-4-(2-bromo-1,1,2,3,3,3-hexafluoro-isopropyl)phenyl |
| 353 | cyclopentyl | 2,6-dimethyl-4-(2-bromo-1,1,2,3,3,3-hexafluoro-isopropyl)phenyl |
| 354 | 3-cyanobenzyl | 2,6-dimethyl-4-(2-bromo-1,1,2,3,3,3-hexafluoro-isopropyl)phenyl |
| 355 | 4-cyanobenzyl | 2,6-dimethyl-4-(2-bromo-1,1,2,3,3,3-hexafluoro-isopropyl)phenyl |
| 356 | 3-chlorobenzyl | 2,6-dimethyl-4-(2-bromo-1,1,2,3,3,3-hexafluoro-isopropyl)phenyl |
| 357 | 2-methoxyethyl | 2,6-dimethyl-4-(2-bromo-1,1,2,3,3,3-hexafluoro-isopropyl)phenyl |
| 358 | 2-cyanoethyl | 2,6-dimethyl-4-(2-bromo-1,1,2,3,3,3-hexafluoro-isopropyl)phenyl |
| 359 | 2-(methylthio)ethyl | 2,6-dimethyl-4-(2-bromo-1,1,2,3,3,3-hexafluoro-isopropyl)phenyl |
| 360 | 2-(ethylthio)ethyl | 2,6-dimethyl-4-(2-bromo-1,1,2,3,3,3-hexafluoro-isopropyl)phenyl |
| 361 | 1-methyl-2-(methylthio)ethyl | 2,6-dimethyl-4-(2-bromo-1,1,2,3,3,3-hexafluoro-isopropyl)phenyl |
| 362 | 2-(ethylsulfinyl)ethyl | 2,6-dimethyl-4-(2-bromo-1,1,2,3,3,3-hexafluoro-isopropyl)phenyl |

TABLE 1-continued (1-A)

[Chemical structure: benzene ring with HN-C(=O)-O-R₁ group and C(=O)-NH-Q group in meta positions]

| Compound No. | R₁ | Q |
|---|---|---|
| 363 | 2-(ethylsulfonyl)ethyl | 2,6-dimethyl-4-(2-bromo-1,1,2,3,3,3-hexafluoroisopropyl)phenyl |
| 364 | 2-fluoroethyl | 2,6-dimethyl-4-(2-bromo-1,1,2,3,3,3-hexafluoroisopropyl)phenyl |
| 365 | 2,2-difluoroethyl | 2,6-dimethyl-4-(2-bromo-1,1,2,3,3,3-hexafluoroisopropyl)phenyl |
| 366 | 2,2,2-trifluoroethyl | 2,6-dimethyl-4-(2-bromo-1,1,2,3,3,3-hexafluoroisopropyl)phenyl |
| 367 | 1,3-difluoro-2-propyl | 2,6-dimethyl-4-(2-bromo-1,1,2,3,3,3-hexafluoroisopropyl)phenyl |
| 368 | 1-chloro-3-fluoro-2-propyl | 2,6-dimethyl-4-(2-bromo-1,1,2,3,3,3-hexafluoroisopropyl)phenyl |
| 369 | 1-methyl-2,2,2-trifluoroethyl | 2,6-dimethyl-4-(2-bromo-1,1,2,3,3,3-hexafluoroisopropyl)phenyl |
| 370 | 3,3,3-trifluoro-n-propyl | 2,6-dimethyl-4-(2-bromo-1,1,2,3,3,3-hexafluoroisopropyl)phenyl |
| 371 | 2,2,3,3,3-pentafluoro-n-propyl | 2,6-dimethyl-4-(2-bromo-1,1,2,3,3,3-hexafluoroisopropyl)phenyl |
| 372 | 3,3,4,4-pentafluoro-2-butyl | 2,6-dimethyl-4-(2-bromo-1,1,2,3,3,3-hexafluoroisopropyl)phenyl |
| 373 | 4,4,4-trifluoro-n-butyl | 2,6-dimethyl-4-(2-bromo-1,1,2,3,3,3-hexafluoroisopropyl)phenyl |
| 374 | 2,2,3,3-tetrafluorocyclobutyl | 2,6-dimethyl-4-(2-bromo-1,1,2,3,3,3-hexafluoroisopropyl)phenyl |
| 375 | 2-chloroethyl | 2,6-dimethyl-4-(2-bromo-1,1,2,3,3,3-hexafluoroisopropyl)phenyl |
| 376 | 2,2-dichloroethyl | 2,6-dimethyl-4-(2-bromo-1,1,2,3,3,3-hexafluoroisopropyl)phenyl |
| 377 | 2,2,2-trichloroethyl | 2,6-dimethyl-4-(2-bromo-1,1,2,3,3,3-hexafluoroisopropyl)phenyl |
| 378 | 1,3-dichloro-2-propyl | 2,6-dimethyl-4-(2-bromo-1,1,2,3,3,3-hexafluoroisopropyl)phenyl |
| 379 | 3-chloro-n-propyl | 2,6-dimethyl-4-(2-bromo-1,1,2,3,3,3-hexafluoroisopropyl)phenyl |
| 380 | 2-bromoethyl | 2,6-dimethyl-4-(2-bromo-1,1,2,3,3,3-hexafluoroisopropyl)phenyl |
| 381 | 2,2,2-tribromoethyl | 2,6-dimethyl-4-(2-bromo-1,1,2,3,3,3-hexafluoroisopropyl)phenyl |
| 382 | 3-bromo-n-propyl | 2,6-dimethyl-4-(2-bromo-1,1,2,3,3,3-hexafluoroisopropyl)phenyl |
| 383 | 2-iodoethyl | 2,6-dimethyl-4-(2-bromo-1,1,2,3,3,3-hexafluoroisopropyl)phenyl |
| 384 | tetrahydrofuran-3-yl | 2,6-dimethyl-4-(2-bromo-1,1,2,3,3,3-hexafluoroisopropyl)phenyl |
| 385 | (furan-2-yl)methyl | 2,6-dimethyl-4-(2-bromo-1,1,2,3,3,3-hexafluoroisopropyl)phenyl |
| 386 | (furan-3-yl)methyl | 2,6-dimethyl-4-(2-bromo-1,1,2,3,3,3-hexafluoroisopropyl)phenyl |
| 387 | (tetrahydrofuran-2-yl)methyl | 2,6-dimethyl-4-(2-bromo-1,1,2,3,3,3-hexafluoroisopropyl)phenyl |
| 388 | (tetrahydrofuran-3-yl)methyl | 2,6-dimethyl-4-(2-bromo-1,1,2,3,3,3-hexafluoroisopropyl)phenyl |
| 389 | (thiophen-2-yl)methyl | 2,6-dimethyl-4-(2-bromo-1,1,2,3,3,3-hexafluoroisopropyl)phenyl |
| 390 | (thiophen-3-yl)methyl | 2,6-dimethyl-4-(2-bromo-1,1,2,3,3,3-hexafluoroisopropyl)phenyl |
| 391 | (pyridin-2-yl)methyl | 2,6-dimethyl-4-(2-bromo-1,1,2,3,3,3-hexafluoroisopropyl)phenyl |
| 392 | (pyridin-3-yl)methyl | 2,6-dimethyl-4-(2-bromo-1,1,2,3,3,3-hexafluoroisopropyl)phenyl |
| 393 | (6-chloropyridin-3-yl)methyl | 2,6-dimethyl-4-(2-bromo-1,1,2,3,3,3-hexafluoroisopropyl)phenyl |
| 394 | Et | 2,6-dichloro-4-(heptafluoro-n-propylthio)phenyl |

TABLE 1-continued

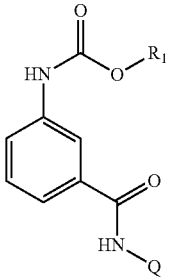

(1-A)

| Compound No. | $R_1$ | Q |
|---|---|---|
| 395 | i-Pr | 2,6-dichloro-4-(heptafluoro-n-propylthio)phenyl |
| 396 | vinyl | 2,6-dichloro-4-(heptafluoro-n-propylthio)phenyl |
| 397 | propargyl | 2,6-dichloro-4-(heptafluoro-n-propylthio)phenyl |
| 398 | cyclobutyl | 2,6-dichloro-4-(heptafluoro-n-propylthio)phenyl |
| 399 | cyclopentyl | 2,6-dichloro-4-(heptafluoro-n-propylthio)phenyl |
| 400 | benzyl | 2,6-dichloro-4-(heptafluoro-n-propylthio)phenyl |
| 401 | 3-cyanobenzyl | 2,6-dichloro-4-(heptafluoro-n-propylthio)phenyl |
| 402 | 4-cyanobenzyl | 2,6-dichloro-4-(heptafluoro-n-propylthio)phenyl |
| 403 | 3-chlorobenzyl | 2,6-dichloro-4-(heptafluoro-n-propylthio)phenyl |
| 404 | 2-methoxyethyl | 2,6-dichloro-4-(heptafluoro-n-propylthio)phenyl |
| 405 | 2-cyanoethyl | 2,6-dichloro-4-(heptafluoro-n-propylthio)phenyl |
| 406 | 2-(methylthio)ethyl | 2,6-dichloro-4-(heptafluoro-n-propylthio)phenyl |
| 407 | 2-(ethylthio)ethyl | 2,6-dichloro-4-(heptafluoro-n-propylthio)phenyl |
| 408 | 1-methyl-2-(methylthio)ethyl | 2,6-dlchloro-4-(heptafluoro-n-propylthio)phenyl |
| 409 | 2-(ethylsulfinyl)ethyl | 2,6-dichloro-4-(heptafluoro-n-propylthio)phenyl |
| 410 | 2-(ethylsulfonyl)ethyl | 2,6-dichloro-4-(heptafluoro-n-propylthio)phenyl |
| 411 | 2-fluoroethyl | 2,6-dichloro-4-(heptafluoro-n-propylthio)phenyl |
| 412 | 2,2-difluoroethyl | 2,6-dichloro-4-(heptafluoro-n-propylthio)phenyl |
| 413 | 2,2,2-trifluoroethyl | 2,6-dichloro-4-(heptafluoro-n-propylthio)phenyl |
| 414 | 1,3-difluoro-2-propyl | 2,6-dichloro4-(heptafluoro-n-propylthio)phenyl |
| 415 | 1-chloro-3-fluoro-2-propyl | 2,6-dichloro-4-(heptafluoro-n-propylthio)phenyl |
| 416 | 1-methyl-2,2,2-trifluoroethyl | 2,6-dichloro-4-(heptafluoro-n-propylthio)phenyl |
| 417 | 3,3,3-trifluoro-n-propyl | 2,6-dichloro-4-(heptafluoro-n-propylthio)phenyl |
| 418 | 2,2,3,3,3-pentafluoro-n-propyl | 2,6-dichloro-4-(heptafluoro-n-propylthio)phenyl |
| 419 | 3,3,4,4,4-pentafluoro-2-butyl | 2,6-dichloro-4-(heptafluoro-n-propylthio)phenyl |
| 420 | 4,4,4-trifluoro-n-butyl | 2,6-dichloro-4-(heptafluoro-n-propylthio)phenyl |
| 421 | 2,2,3,3-tetrafluorocyclobutyl | 2,6-dichloro-4-(heptafluoro-n-propylthio)phenyl |
| 422 | 2-chloroethyl | 2,6-dichloro-4-(heptafluoro-n-propylthio)phenyl |
| 423 | 2,2-dichloroethyl | 2,6-dichloro-4-(heptafluoro-n-propylthio)phenyl |
| 424 | 2,2,2-trichloroethyl | 2,6-dichloro-4-(heptafluoro-n-propylthio)phenyl |
| 425 | 1,3-dichloro-2-propyl | 2,6-dichloro-4-(heptafluoro-n-propylthio)phenyl |
| 426 | 3-chloro-n-propyl | 2,6-dichloro-4-(heptafluoro-n-propylthio)phenyl |
| 427 | 2-bromoethyl | 2,6-dichloro-4-(heptafluoro-n-propylthio)phenyl |
| 428 | 2,2,2-tribromoethyl | 2,6-dichloro-4-(heptafluoro-n-propylthio)phenyl |
| 429 | 3-bromo-n-propyl | 2,6-dichloro-4-(heptafluoro-n-propylthio)phenyl |
| 430 | 2-iodoethyl | 2,6-dichloro-4-(heptafluoro-n-propylthio)phenyl |
| 431 | tetrahydrofuran-3-yl | 2,6-dichloro-4-(heptafluoro-n-propylthio)phenyl |
| 432 | (furan-2-yl)methyl | 2,6-dichloro-4-(heptafluoro-n-propylthio)phenyl |
| 433 | (furan-3-yl)methyl | 2,6-dichloro-4-(heptafluoro-n-propylthio)phenyl |
| 434 | (tetrahydrofuran-2-yl)methyl | 2,6-dichloro-4-(heptafluoro-n-propylthio)phenyl |
| 435 | (tetrahydrofuran-3-yl)methyl | 2,6-dichloro-4-(heptafluoro-n-propylthio)phenyl |
| 436 | (thiophen-2-yl)methyl | 2,6-dichloro-4-(heptafluoro-n-propylthio)phenyl |
| 437 | (thiophen-3-yl)methyl | 2,6-dichloro-4-(heptafluoro-n-propylthio)phenyl |
| 438 | (pyridin-2-yl)methyl | 2,6-dichloro-4-(heptafluoro-n-propylthio)phenyl |
| 439 | (pyridin-3-yl)methyl | 2,6-dichloro-4-(heptafluoro-n-propylthio)phenyl |
| 440 | (6-chloropyridin-3-yl)methyl | 2,6-dichloro-4-(heptafluoro-n-propylthio)phenyl |
| 441 | Et | 2,6-dibromo-4-(trifluoromethylthio)phenyl |
| 442 | i-Pr | 2,6-dibromo-4-(trifluoromethylthio)phenyl |
| 443 | vinyl | 2,6-dibromo-4-(trifluoromethylthio)phenyl |
| 444 | propargyl | 2,6-dibromo-4-(trifluoromethylthio)phenyl |
| 445 | cyclobutyl | 2,6-dibromo-4-(trifluoromethylthio)phenyl |
| 446 | cyclopentyl | 2,6-dibromo-4-(trifluoromethylthio)phenyl |
| 447 | benzyl | 2,6-dibromo-4-(trifluoromethylthio)phenyl |
| 448 | 3-cyanobenzyl | 2,6-dibromo-4-(trifluoromethylthio)phenyl |
| 449 | 4-cyanobenzyl | 2,6-dibromo-4-(trifluoromethylthio)phenyl |
| 450 | 3-chlorobenzyl | 2,6-dibromo-4-(trifluoromethylthio)phenyl |
| 451 | 2-methoxyethyl | 2,6-dibromo-4-(trifluoromethylthio)phenyl |
| 452 | 2-cyanoethyl | 2,6-dibromo-4-(trifluoromethylthio)phenyl |
| 453 | 2-(methylthio)ethyl | 2,6-dibromo-4-(trifluoromethylthio)phenyl |
| 454 | 2-(ethylthio)ethyl | 2,6-dibromo-4-(trifluoromethylthio)phenyl |
| 455 | 1-methyl-2-(methylthio)ethyl | 2,6-dibromo-4-(trifluoromethylthio)phenyl |
| 456 | 2-(ethylsulfinyl)ethyl | 2,6-dibromo-4-(trifluoromethylthio)phenyl |
| 457 | 2-(ethylsulfonyl)ethyl | 2,6-dibromo-4-(trifluoromethylthio)phenyl |

TABLE 1-continued (1-A)

| Compound No. | R₁ | Q |
|---|---|---|
| 458 | 2-fluoroethyl | 2,6-dibromo-4-(trifluoromethylthio)phenyl |
| 459 | 2,2-difluoroethyl | 2,6-dibromo-4-(trifluoromethylthio)phenyl |
| 460 | 2,2,2-trifluoroethyl | 2,6-dibromo-4-(trifluoromethylthio)phenyl |
| 461 | 1,3-difluoro-2-propyl | 2,6-dibromo-4-(trifluoromethylthio)phenyl |
| 462 | 1-chloro-3-fluoro-2-propyl | 2,6-dibromo-4-(trifluoromethylthio)phenyl |
| 463 | 1-methyl-2,2,2-trifluoroethyl | 2,6-dibromo-4-(trifluoromethylthio)phenyl |
| 464 | 3,3,3-trifluoro-n-propyl | 2,6-dibromo-4-(trifluoromethylthio)phenyl |
| 465 | 2,2,3,3,3-pentafluoro-n-propyl | 2,6-dibromo-4-(trifluoromethylthio)phenyl |
| 466 | 3,3,4,4,4-pentafluoro-2-butyl | 2,6-dibromo-4-(trifluoromethylthio)phenyl |
| 467 | 4,4,4-trifluoro-n-butyl | 2,6-dibromo-4-(trifluoromethylthio)phenyl |
| 468 | 2,2,3,3-tetrafluorocyclobutyl | 2,6-dibromo-4-(trifluoromethylthio)phenyl |
| 469 | 2-chloroethyl | 2,6-dibromo-4-(trifluoromethylthio)phenyl |
| 470 | 2,2-dichloroethyl | 2,6-dibromo-4-(trifluoromethylthio)phenyl |
| 471 | 2,2,2-trichloroethyl | 2,6-dibromo-4-(trifluoromethylthio)phenyl |
| 472 | 1,3-dichloro-2-propyl | 2,6-dibromo-4-(trifluoromethylthio)phenyl |
| 473 | 3-chloro-n-propyl | 2,6-dibromo-4-(trifluoromethylthio)phenyl |
| 474 | 2-bromoethyl | 2,6-dibromo-4-(trifluoromethylthio)phenyl |
| 475 | 2,2,2-tribromoethyl | 2,6-dibromo-4-(trifluoromethylthio)phenyl |
| 476 | 3-bromo-n-propyl | 2,6-dibromo-4-(trifluoromethylthio)phenyl |
| 477 | 2-iodoethyl | 2,6-dibromo-4-(trifluoromethylthio)phenyl |
| 478 | tetrahydrofuran-3-yl | 2,6-dibromo-4-(trifluoromethylthio)phenyl |
| 479 | (furan-2-yl)methyl | 2,6-dibromo-4-(trifluoromethylthio)phenyl |
| 480 | (furan-3-yl)methyl | 2,6-dibromo-4-(trifluoromethylthio)phenyl |
| 481 | (tetrahydrofuran-2-yl)methyl | 2,6-dibromo-4-(trifluoromethylthio)phenyl |
| 482 | (tetrahydrofuran-3-yl)methyl | 2,6-dibromo-4-(trifluoromethylthio)phenyl |
| 483 | (thiophen-2-yl)methyl | 2,6-dibromo-4-(trifluoromethylthio)phenyl |
| 484 | (thiophen-3-yl)methyl | 2,6-dibromo-4-(trifluoromethylthio)phenyl |
| 485 | (pyridin-2-yl)methyl | 2,6-dibromo-4-(trifluoromethylthio)phenyl |
| 486 | (pyridin-3-yl)methyl | 2,6-dibromo-4-(trifluoromethylthio)phenyl |
| 487 | (6-chloropyridin-3-yl)methyl | 2,6-dibromo-4-(trifluoromethylthio)phenyl |
| 488 | Et | 2,6-dibromo-4-(trifluoromethylsulfonyl)phenyl |
| 489 | i-Pr | 2,6-dibromo-4-(trifluoromethylsulfonyl)phenyl |
| 490 | vinyl | 2,6-dibromo-4-(trifluoromethylsulfonyl)phenyl |
| 491 | propargyl | 2,6-dibromo-4-(trifluoromethylsulfonyl)phenyl |
| 492 | cyclobutyl | 2,6-dibromo-4-(trifluoromethylsulfonyl)phenyl |
| 493 | cyclopentyl | 2,6-dibromo-4-(trifluoromethylsulfonyl)phenyl |
| 494 | benzyl | 2,6-dibromo-4-(trifluoromethylsulfonyl)phenyl |
| 495 | 3-cyanobenzyl | 2,6-dibromo-4-(trifluoromethylsulfonyl)phenyl |
| 496 | 4-cyanobenzyl | 2,6-dibromo-4-(trifluoromethylsulfonyl)phenyl |
| 497 | 3-chlorobenzyl | 2,6-dibromo-4-(trifluoromethylsulfonyl)phenyl |
| 498 | 2-methoxyethyl | 2,6-dibromo-4-(trifluoromethylsulfonyl)phenyl |
| 499 | 2-cyanoethyl | 2,6-dibromo-4-(trifluoromethylsulfonyl)phenyl |
| 500 | 2-(methylthio)ethyl | 2,6-dibromo-4-(trifluoromethylsulfonyl)phenyl |
| 501 | 2-(ethylthio)ethyl | 2,6-dibromo-4-(trifluoromethylsulfonyl)phenyl |
| 502 | 1-methyl-2-(methylthio)ethyl | 2,6-dibromo-4-(trifluoromethylsulfonyl)phenyl |
| 503 | 2-(ethylsulfinyl)ethyl | 2,6-dibromo-4-(trifluoromethylsulfonyl)phenyl |
| 504 | 2-(ethylsulfonyl)ethyl | 2,6-dibromo-4-(trifluoromethylsulfonyl)phenyl |
| 505 | 2-fluoroethyl | 2,6-dibromo-4-(trifluoromethylsulfonyl)phenyl |
| 506 | 2,2-difluoroethyl | 2,6-dibromo-4-(trifluoromethylsulfonyl)phenyl |
| 507 | 2,2,2-trifluoroethyl | 2,6-dibromo-4-(trifluoromethylsulfonyl)phenyl |
| 508 | 1,3-difluoro-2-propyl | 2,6-dibromo-4-(trifluoromethylsulfonyl)phenyl |
| 509 | 1-chloro-3-fluoro-2-propyl | 2,6-dibromo-4-(trifluoromethylsulfonyl)phenyl |
| 510 | 1-methyl-2,2,2-trifluoroethyl | 2,6-dibromo-4-(trifluoromethylsulfonyl)phenyl |
| 511 | 3,3,3-trifluoro-n-propyl | 2,6-dibromo-4-(trifluoromethylsulfonyl)phenyl |
| 512 | 2,2,3,3,3-pentafluoro-n-propyl | 2,6-dibromo-4-(trifluoromethylsulfonyl)phenyl |
| 513 | 3,3,4,4,4-pentafluoro-2-butyl | 2,6-dibromo-4-(trifluoromethylsulfonyl)phenyl |
| 514 | 4,4,4-trifluoro-n-butyl | 2,6-dibromo-4-(trifluoromethylsulfonyl)phenyl |
| 515 | 2,2,3,3-tetrafluorocyclobutyl | 2,6-dibromo-4-(trifluoromethylsulfonyl)phenyl |
| 516 | 2-chloroethyl | 2,6-dibromo-4-(trifluoromethylsulfonyl)phenyl |
| 517 | 2,2-dichloroethyl | 2,6-dibromo-4-(trifluoromethylsulfonyl)phenyl |
| 518 | 2,2,2-trichloroethyl | 2,6-dibromo-4-(trifluoromethylsulfonyl)phenyl |
| 519 | 1,3-dichloro-2-propyl | 2,6-dibromo-4-(trifluoromethylsulfonyl)phenyl |
| 520 | 3-chloro-n-propyl | 2,6-dibromo-4-(trifluoromethylsulfonyl)phenyl |

TABLE 1-continued (1-A)

| Compound No. | R₁ | Q |
|---|---|---|
| 521 | 2-bromoethyl | 2,6-dibromo-4-(trifluoromethylsulfonyl)phenyl |
| 522 | 2,2,2-tribromoethyl | 2,6-dibromo-4-(trifluoromethylsulfonyl)phenyl |
| 523 | 3-bromo-n-propyl | 2,6-dibromo-4-(trifluoromethylsulfonyl)phenyl |
| 524 | 2-iodoethyl | 2,6-dibromo-4-(trifluoromethylsulfonyl)phenyl |
| 525 | tetrahydrofuran-3-yl | 2,6-dibromo-4-(trifluoromethylsulfonyl)phenyl |
| 526 | (furan-2-yl)methyl | 2,6-dibromo-4-(trifluoromethylsulfonyl)phenyl |
| 527 | (furan-3-yl)methyl | 2,6-dibromo-4-(trifluoromethylsulfonyl)phenyl |
| 528 | (tetrahydrofuran-2-yl)methyl | 2,6-dibromo-4-(trifluoromethylsulfonyl)phenyl |
| 529 | (tetrahydrofuran-3-yl)methyl | 2,6-dibromo-4-(trifluoromethylsulfonyl)phenyl |
| 530 | (thiophen-2-yl)methyl | 2,6-dibromo-4-(trifluoromethylsulfonyl)phenyl |
| 531 | (thiophen-3-yl)methyl | 2,6-dibromo-4-(trifluoromethylsulfonyl)phenyl |
| 532 | (pyridin-2-yl)methyl | 2,6-dibromo-4-(trifluoromethylsulfonyl)phenyl |
| 533 | (pyridin-3-yl)methyl | 2,6-dibromo-4-(trifluoromethylsulfonyl)phenyl |
| 534 | (6-chloropyridin-3-yl)methyl | 2,6-dibromo-4-(trifluoromethylsulfonyl)phenyl |
| 535 | Et | 2,6-dibromo-4-(pentafluoroethylthio)phenyl |
| 536 | i-Pr | 2,6-dibromo-4-(pentafluoroethylthio)phenyl |
| 537 | vinyl | 2,6-dibromo-4-(pentafluoroethylthio)phenyl |
| 538 | propargyl | 2,6-dibromo-4-(pentafluoroethylthio)phenyl |
| 539 | cyclobutyl | 2,6-dibromo-4-(pentafluoroethylthio)phenyl |
| 540 | cyclopentyl | 2,6-dibromo-4-(pentafluoroethylthio)phenyl |
| 541 | benzyl | 2,6-dibromo-4-(pentafluoroethylthio)phenyl |
| 542 | 3-cyanobenzyl | 2,6-dibromo-4-(pentafluoroethylthio)phenyl |
| 543 | 4-cyanobenzyl | 2,6-dibromo-4-(pentafluoroethylthio)phenyl |
| 544 | 3-chlorobenzyl | 2,6-dibromo-4-(pentafluoroethylthio)phenyl |
| 545 | 2-methoxyethyl | 2,6-dibromo-4-(pentafluoroethylthio)phenyl |
| 546 | 2-cyanoethyl | 2,6-dibromo-4-(pentafluoroethylthio)phenyl |
| 547 | 2-(methylthio)ethyl | 2,6-dibromo-4-(pentafluoroethylthio)phenyl |
| 548 | 2-(ethylthio)ethyl | 2,6-dibromo-4-(pentafluoroethylthio)phenyl |
| 549 | 1-methyl-2-(methylthio)ethyl | 2,6-dibromo-4-(pentafluoroethylthio)phenyl |
| 550 | 2-(ethylsulfinyl)ethyl | 2,6-dibromo-4-(pentafluoroethylthio)phenyl |
| 551 | 2-(ethylsulfonyl)ethyl | 2,6-dibromo-4-(pentafluoroethylthio)phenyl |
| 552 | 2-fluoroethyl | 2,6-dibromo-4-(pentafluoroethylthio)phenyl |
| 553 | 2,2-difluoroethyl | 2,6-dibromo-4-(pentafluoroethylthio)phenyl |
| 554 | 2,2,2-trifluoroethyl | 2,6-dibromo-4-(pentafluoroethylthio)phenyl |
| 555 | 1,3-difluoro-2-propyl | 2,6-dibromo-4-(pentafluoroethylthio)phenyl |
| 556 | 1-chloro-3-fluoro-2-propyl | 2,6-dibromo-4-(pentafluoroethylthio)phenyl |
| 557 | 1-methyl-2,2,2-trifluoroethyl | 2,6-dibromo-4-(pentafluoroethylthio)phenyl |
| 558 | 3,3,3-trifluoro-n-propyl | 2,6-dibromo-4-(pentafluoroethylthio)phenyl |
| 559 | 2,2,3,3,3-pentafluoro-n-propyl | 2,6-dibromo-4-(pentafluoroethylthio)phenyl |
| 560 | 3,3,4,4,4-pentafluoro-2-butyl | 2,6-dibromo-4-(pentafluoroethylthio)phenyl |
| 561 | 4,4,4-trifluoro-n-butyl | 2,6-dibromo-4-(pentafluoroethylthio)phenyl |
| 562 | 2,2,3,3-tetrafluorocyclobutyl | 2,6-dibromo-4-(pentafluoroethylthio)phenyl |
| 563 | 2-chloroethyl | 2,6-dibromo-4-(pentafluoroethylthio)phenyl |
| 564 | 2,2-dichloroethyl | 2,6-dibromo-4-(pentafluoroethylthio)phenyl |
| 565 | 2,2,2-trichloroethyl | 2,6-dibromo-4-(pentafluoroethylthio)phenyl |
| 566 | 1,3-dichloro-2-propyl | 2,6-dibromo-4-(pentafluoroethylthio)phenyl |
| 567 | 3-chloro-n-propyl | 2,6-dibromo-4-(pentafluoroethylthio)phenyl |
| 568 | 2-bromoethyl | 2,6-dibromo-4-(pentafluoroethylthio)phenyl |
| 569 | 2,2,2-tribromoethyl | 2,6-dibromo-4-(pentafluoroethylthio)phenyl |
| 570 | 3-bromo-n-propyl | 2,6-dibromo-4-(pentafluoroethylthio)phenyl |
| 571 | 2-iodoethyl | 2,6-dibromo-4-(pentafluoroethylthio)phenyl |
| 572 | tetrahydrofuran-3-yl | 2,6-dibromo-4-(pentafluoroethylthio)phenyl |
| 573 | (furan-2-yl)methyl | 2,6-dibromo-4-(pentafluoroethylthio)phenyl |
| 574 | (furan-3-yl)methyl | 2,6-dibromo-4-(pentafluoroethylthio)phenyl |
| 575 | (tetrahydrofuran-2-yl)methyl | 2,6-dibromo-4-(pentafluoroethylthio)phenyl |
| 576 | (tetrahydrofuran-3-yl)methyl | 2,6-dibromo-4-(pentafluoroethylthio)phenyl |
| 577 | (thiophen-2-yl)methyl | 2,6-dibromo-4-(pentafluoroethylthio)phenyl |
| 578 | (thiophen-3-yl)methyl | 2,6-dibromo-4-(pentafluoroethylthio)phenyl |
| 579 | (pyridin-2-yl)methyl | 2,6-dibromo-4-(pentafluoroethylthio)phenyl |
| 580 | (pyridin-3-yl)methyl | 2,6-dibromo-4-(pentafluoroethylthio)phenyl |
| 581 | (6-chloropyridin-3-yl)methyl | 2,6-dibromo-4-(pentafluoroethylthio)phenyl |
| 582 | Et | 2,6-dibromo-4-(heptafluoro-n-propylthio)phenyl |
| 583 | i-Pr | 2,6-dibromo-4-(heptafluoro-n-propylthio)phenyl |

TABLE 1-continued (1-A)

$$\text{structure with HN-C(=O)-O-R}_1 \text{ on benzene ring, and C(=O)-NH-Q at meta position}$$

| Compound No. | R₁ | Q |
| --- | --- | --- |
| 584 | vinyl | 2,6-dibromo-4-(heptafluoro-n-propylthio)phenyl |
| 585 | propargyl | 2,6-dibromo-4-(heptafluoro-n-propylthio)phenyl |
| 586 | cyclobutyl | 2,6-dibromo-4-(heptafluoro-n-propylthio)phenyl |
| 587 | cyclopentyl | 2,6-dibromo-4-(heptafluoro-n-propylthio)phenyl |
| 588 | benzyl | 2,6-dibromo-4-(heptafluoro-n-propylthio)phenyl |
| 589 | 3-cyanobenzyl | 2,6-dibromo-4-(heptafluoro-n-propylthio)phenyl |
| 590 | 4-cyanobenzyl | 2,6-dibromo-4-(heptafluoro-n-propylthio)phenyl |
| 591 | 3-chlorobenzyl | 2,6-dibromo-4-(heptafluoro-n-propylthio)phenyl |
| 592 | 2-methoxyethyl | 2,6-dibromo-4-(heptafluoro-n-propylthio)phenyl |
| 593 | 2-cyanoethyl | 2,6-dibromo-4-(heptafluoro-n-propylthio)phenyl |
| 594 | 2-(methylthio)ethyl | 2,6-dibromo-4-(heptafluoro-n-propylthio)phenyl |
| 595 | 2-(ethylthio)ethyl | 2,6-dibromo-4-(heptafluoro-n-propylthio)phenyl |
| 596 | 1-methyl-2-(methylthio)ethyl | 2,6-dibromo-4-(heptafluoro-n-propylthio)phenyl |
| 597 | 2-(ethylsulfinyl)ethyl | 2,6-dibromo-4-(heptafluoro-n-propylthio)phenyl |
| 598 | 2-(ethylsulfonyl)ethyl | 2,6-dibromo-4-(heptafluoro-n-propylthio)phenyl |
| 599 | 2-fluoroethyl | 2,6-dibromo-4-(heptafluoro-n-propylthio)phenyl |
| 600 | 2,2-difluoroethyl | 2,6-dibromo-4-(heptafluoro-n-propylthio)phenyl |
| 601 | 2,2,2-trifluoroethyl | 2,6-dibromo-4-(heptafluoro-n-propylthio)phenyl |
| 602 | 1,3-difluoro-2-propyl | 2,6-dibromo-4-(heptafluoro-n-propylthio)phenyl |
| 603 | 1-chloro-3-fluoro-2-propyl | 2,6-dibromo-4-(heptafluoro-n-propylthio)phenyl |
| 604 | 1-methyl-2,2,2-trifluoroethyl | 2,6-dibromo-4-(heptafluoro-n-propylthio)phenyl |
| 605 | 3,3,3-trifluoro-n-propyl | 2,6-dibromo-4-(heptafluoro-n-propylthio)phenyl |
| 606 | 2,2,3,3,3-pentafluoro-n-propyl | 2,6-dibromo-4-(heptafluoro-n-propylthio)phenyl |
| 607 | 3,3,4,4,4-pentafluoro-2-butyl | 2,6-dibromo-4-(heptafluoro-n-propylthio)phenyl |
| 608 | 4,4,4-trifluoro-n-butyl | 2,6-dibromo-4-(heptafluoro-n-propylthio)phenyl |
| 609 | 2,2,3,3-tetrafluorocyclobutyl | 2,6-dibromo-4-(heptafluoro-n-propylthio)phenyl |
| 610 | 2-chloroethyl | 2,6-dibromo-4-(heptafluoro-n-propylthio)phenyl |
| 611 | 2,2-dichloroethyl | 2,6-dibromo-4-(heptafluoro-n-propylthio)phenyl |
| 612 | 2,2,2-trichloroethyl | 2,6-dibromo-4-(heptafluoro-n-propylthio)phenyl |
| 613 | 1,3-dichloro-2-propyl | 2,6-dibromo-4-(heptafluoro-n-propylthio)phenyl |
| 614 | 3-chloro-n-propyl | 2,6-dibromo-4-(heptafluoro-n-propylthio)phenyl |
| 615 | 2-bromoethyl | 2,6-dibromo-4-(heptafluoro-n-propylthio)phenyl |
| 616 | 2,2,2-tribromoethyl | 2,6-dibromo-4-(heptafluoro-n-propylthio)phenyl |
| 617 | 3-bromo-n-propyl | 2,6-dibromo-4-(heptafluoro-n-propylthio)phenyl |
| 618 | 2-iodoethyl | 2,6-dibromo-4-(heptafluoro-n-propylthio)phenyl |
| 619 | tetrahydrofuran-3-yl | 2,6-dibromo-4-(heptafluoro-n-propylthio)phenyl |
| 620 | (furan-2-yl)methyl | 2,6-dibromo-4-(heptafluoro-n-propylthio)phenyl |
| 621 | (furan-3-yl)methyl | 2,6-dibromo-4-(heptafluoro-n-propylthio)phenyl |
| 622 | (tetrahydrofuran-2-yl)methyl | 2,6-dibromo-4-(heptafluoro-n-propylthio)phenyl |
| 623 | (tetrahydrofuran-3-yl)methyl | 2,6-dibromo-4-(heptafluoro-n-propylthio)phenyl |
| 624 | (thiophen-2-yl)methyl | 2,6-dibromo-4-(heptafluoro-n-propylthio)phenyl |
| 625 | (thiophen-3-yl)methyl | 2,6-dibromo-4-(heptafluoro-n-propylthio)phenyl |
| 626 | (pyridin-2-yl)methyl | 2,6-dibromo-4-(heptafluoro-n-propylthio)phenyl |
| 627 | (pyridin-3-yl)methyl | 2,6-dibromo-4-(heptafluoro-n-propylthio)phenyl |
| 628 | (6-chloropyridin-3-yl)methyl | 2,6-dibromo-4-(heptafluoro-n-propylthio)phenyl |
| 629 | Et | 2,6-dibromo-4-(heptafluoroisopropylthio)phenyl |
| 630 | i-Pr | 2,6-dibromo-4-(heptafluoroisopropylthio)phenyl |
| 631 | vinyl | 2,6-dibromo-4-(heptafluoroisopropylthio)phenyl |
| 632 | propargyl | 2,6-dibromo-4-(heptafluoroisopropylthio)phenyl |
| 633 | cyclobutyl | 2,6-dibromo-4-(heptafluoroisopropylthio)phenyl |
| 634 | cyclopentyl | 2,6-dibromo-4-(heptafluoroisopropylthio)phenyl |
| 635 | benzyl | 2,6-dibromo-4-(heptafluoroisopropylthio)phenyl |
| 636 | 3-cyanobenzyl | 2,6-dibromo-4-(heptafluoroisopropylthio)phenyl |
| 637 | 4-cyanobenzyl | 2,6-dibromo-4-(heptafluoroisopropylthio)phenyl |
| 638 | 3-chlorobenzyl | 2,6-dibromo-4-(heptafluoroisopropylthio)phenyl |
| 639 | 2-methoxyethyl | 2,6-dibromo-4-(heptafluoroisopropylthio)phenyl |
| 640 | 2-cyanoethyl | 2,6-dibromo-4-(heptafluoroisopropylthio)phenyl |
| 641 | 2-(methylthio)ethyl | 2,6-dibromo-4-(heptafluoroisopropylthio)phenyl |
| 642 | 2-(ethylthio)ethyl | 2,6-dibromo-4-(heptafluoroisopropylthio)phenyl |
| 643 | 1-methyl-2-(methylthio)ethyl | 2,6-dibromo-4-(heptafluoroisopropylthio)phenyl |
| 644 | 2-(ethylsulfinyl)ethyl | 2,6-dibromo-4-(heptafluoroisopropylthio)phenyl |
| 645 | 2-(ethylsulfonyl)ethyl | 2,6-dibromo-4-(heptafluoroisopropylthio)phenyl |
| 646 | 2-fluoroethyl | 2,6-dibromo-4-(heptafluoroisopropylthio)phenyl |

TABLE 1-continued (1-A)

| Compound No. | R₁ | Q |
|---|---|---|
| 647 | 2,2-difluoroethyl | 2,6-dibromo-4-(heptafluoroisopropylthio)phenyl |
| 648 | 2,2,2-trifluoroethyl | 2,6-dibromo-4-(heptafluoroisopropylthio)phenyl |
| 649 | 1,3-difluoro-2-propyl | 2,6-dibromo-4-(heptafluoroisopropylthio)phenyl |
| 650 | 1-chloro-3-fluoro-2-propyl | 2,6-dibromo-4-(heptafluoroisopropylthio)phenyl |
| 651 | 1-methyl-2,2,2-trifluoroethyl | 2,6-dibromo-4-(heptafluoroisopropylthio)phenyl |
| 652 | 3,3,3-trifluoro-n-propyl | 2,6-dibromo-4-(heptafluoroisopropylthio)phenyl |
| 653 | 2,2,3,3,3-pentafluoro-n-propyl | 2,6-dibromo-4-(heptafluoroisopropylthio)phenyl |
| 654 | 3,3,4,4,4-pentafluoro-2-butyl | 2,6-dibromo-4-(heptafluoroisopropylthio)phenyl |
| 655 | 4,4,4-trifluoro-n-butyl | 2,6-dibromo-4-(heptafluoroisopropylthio)phenyl |
| 656 | 2,2,3,3-tetrafluorocyclobutyl | 2,6-dibromo-4-(heptafluoroisopropylthio)phenyl |
| 657 | 2-chloroethyl | 2,6-dibromo-4-(heptafluoroisopropylthio)phenyl |
| 658 | 2,2-dichloroethyl | 2,6-dibromo-4-(heptafluoroisopropylthio)phenyl |
| 659 | 2,2,2-trichloroethyl | 2,6-dibromo-4-(heptafluoroisopropylthio)phenyl |
| 660 | 1,3-dichloro-2-propyl | 2,6-dibromo-4-(heptafluoroisopropylthio)phenyl |
| 661 | 3-chloro-n-propyl | 2,6-dibromo-4-(heptafluoroisopropylthio)phenyl |
| 662 | 2-bromoethyl | 2,6-dibromo-4-(heptafluoroisopropylthio)phenyl |
| 663 | 2,2,2-tribromoethyl | 2,6-dibromo-4-(heptafluoroisopropylthio)phenyl |
| 664 | 3-bromo-n-propyl | 2,6-dibromo-4-(heptafluoroisopropylthio)phenyl |
| 665 | 2-iodoethyl | 2,6-dibromo-4-(heptafluoroisopropylthio)phenyl |
| 666 | tetrahydrofuran-3-yl | 2,6-dibromo-4-(heptafluoroisopropylthio)phenyl |
| 667 | (furan-2-yl)methyl | 2,6-dibromo-4-(heptafluoroisopropylthio)phenyl |
| 668 | (furan-3-yl)methyl | 2,6-dibromo-4-(heptafluoroisopropylthio)phenyl |
| 669 | (tetrahydrofuran-2-yl)methyl | 2,6-dibromo-4-(heptafluoroisopropylthio)phenyl |
| 670 | (tetrahydrofuran-3-yl)methyl | 2,6-dibromo-4-(heptafluoroisopropylthio)phenyl |
| 671 | (thiophen-2-yl)methyl | 2,6-dibromo-4-(heptafluoroisopropylthio)phenyl |
| 672 | (thiophen-3-yl)methyl | 2,6-dibromo-4-(heptafluoroisopropylthio)phenyl |
| 673 | (pyridin-2-yl)methyl | 2,6-dibromo-4-(heptafluoroisopropylthio)phenyl |
| 674 | (pyridin-3-yl)methyl | 2,6-dibromo-4-(heptafluoroisopropylthio)phenyl |
| 675 | (6-chloropyridin-3-yl)methyl | 2,6-dibromo-4-(heptafluoroisopropylthio)phenyl |
| 676 | Et | 2,6-dibromo-4-(heptafluoro-n-propyl sulfinyl)phenyl |
| 677 | i-Pr | 2,6-dibromo-4-(heptafluoro-n-propyl sulfinyl)phenyl |
| 678 | vinyl | 2,6-dibromo-4-(heptafluoro-n-propyl sulfinyl)phenyl |
| 679 | propargyl | 2,6-dibromo-4-(heptafluoro-n-propyl sulfinyl)phenyl |
| 600 | cyclobutyl | 2,6-dibromo-4-(heptafluoro-n-propyl sulfinyl)phenyl |
| 681 | cyclopentyl | 2,6-dibromo-4-(heptafluoro-n-propyl sulfinyl)phenyl |
| 662 | benzyl | 2,6-dibromo-4-(heptafluoro-n-propyl sulfinyl)phenyl |
| 683 | 3-cyanobenzyl | 2,6-dibromo-4-(heptafluoro-n-propyl sulfinyl)phenyl |
| 684 | 4-cyanobenzyl | 2,6-dibromo-4-(heptafluoro-n-propyl sulfinyl)phenyl |
| 685 | 3-chlorobenzyl | 2,6-dibromo-4-(heptafluoro-n-propyl sulfinyl)phenyl |
| 686 | 2-methoxyethyl | 2,6-dibromo-4-(heptafluoro-n-propyl sulfinyl)phenyl |
| 687 | 2-cyanoethyl | 2,6-dibromo-4-(heptafluoro-n-propyl sulfinyl)phenyl |
| 688 | 2-(methylthio)ethyl | 2,6-dibromo-4-(heptafluoro-n-propyl sulfinyl)phenyl |
| 689 | 2-(ethylthio)ethyl | 2,6-dibromo-4-(heptafluoro-n-propyl sulfinyl)phenyl |
| 690 | 1-methyl-2-(methylthio)ethyl | 2,6-dibromo-4-(heptafluoro-n-propyl sulfinyl)phenyl |
| 691 | 2-(ethylsulfinyl)ethyl | 2,6-dibromo-4-(heptafluoro-n-propyl sulfinyl)phenyl |
| 692 | 2-(ethylsulfonyl)ethyl | 2,6-dibromo-4-(heptafluoro-n-propyl sulfinyl)phenyl |

TABLE 1-continued

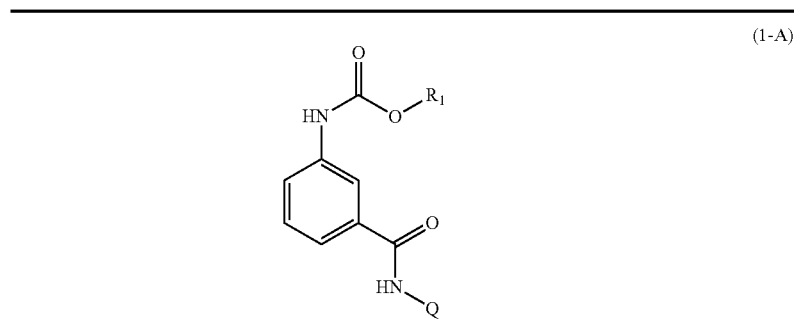

(1-A)

| Compound No. | R₁ | Q |
|---|---|---|
| 693 | 2-fluoroethyl | 2,6-dibromo-4-(heptafluoro-n-propyl sulfinyl)phenyl |
| 694 | 2,2-difluoroethyl | 2,6-dibromo-4-(heptafluoro-n-propyl sulfinyl)phenyl |
| 695 | 2,2,2-trifluoroethyl | 2,6-dibromo-4-(heptafluoro-n-propyl sulfinyl)phenyl |
| 696 | 1,3-difluoro-2-propyl | 2,6-dibromo-4-(heptafluoro-n-propyl sulfinyl)phenyl |
| 697 | 1-chloro-3-fluoro-2-propyl | 2,6-dibromo-4-(heptafluoro-n-propyl sulfinyl)phenyl |
| 698 | 1-methyl-2,2,2-trifluoroethyl | 2,6-dibromo-4-(heptafluoro-n-propyl sulfinyl)phenyl |
| 699 | 3,3,3-trifluoro-n-propyl | 2,6-dibromo-4-(heptafluoro-n-propyl sulfinyl)phenyl |
| 700 | 2,2,3,3,3-pentafluoro-n-propyl | 2,6-dibromo-4-(heptafluoro-n-propyl sulfinyl)phenyl |
| 701 | 3,3,4,4,4-pentafluoro-2-butyl | 2,6-dibromo-4-(heptafluoro-n-propyl sulfinyl)phenyl |
| 702 | 4,4,4-trifluoro-n-butyl | 2,6-dibromo-4-(heptafluoro-n-propyl sulfinyl)phenyl |
| 703 | 2,2,3,3-tetrafluorocyclobutyl | 2,6-dibromo-4-(heptafluoro-n-propyl sulfinyl)phenyl |
| 704 | 2-chloroethyl | 2,6-dibromo-4-(heptafluoro-n-propyl sulfinyl)phenyl |
| 705 | 2,2-dichloroethyl | 2,6-dibromo-4-(heptafluoro-n-propyl sulfinyl)phenyl |
| 706 | 2,2,2-trichloroethyl | 2,6-dibromo-4-(heptafluoro-n-propyl sulfinyl)phenyl |
| 707 | 1,3-dichloro-2-propyl | 2,6-dibromo-4-(heptafluoro-n-propyl sulfinyl)phenyl |
| 708 | 3-chloro-n-propyl | 2,6-dibromo-4-(heptafluoro-n-propyl sulfinyl)phenyl |
| 709 | 2-bromoethyl | 2,6-dibromo-4-(heptafluoro-n-propyl sulfinyl)phenyl |
| 710 | 2,2,2-tribromoethyl | 2,6-dibromo-4-(heptafluoro-n-propyl sulfinyl)phenyl |
| 711 | 3-bromo-n-propyl | 2,6-dibromo-4-(heptafluoro-n-propyl sulfinyl)phenyl |
| 712 | 2-iodoethyl | 2,6-dibromo-4-(heptafluoro-n-propyl sulfinyl)phenyl |
| 713 | tetrahydrofuran-3-yl | 2,6-dibromo-4-(heptafluoro-n-propyl sulfinyl)phenyl |
| 714 | (furan-2-yl)methyl | 2,6-dibromo-4-(heptafluoro-n-propyl sulfinyl)phenyl |
| 715 | (furan-3-yl)methyl | 2,6-dibromo-4-(heptafluoro-n-propyl sulfinyl)phenyl |
| 716 | (tetrahydrofuran-2-yl)methyl | 2,6-dibromo-4-(heptafluoro-n-propyl sulfinyl)phenyl |
| 717 | (tetrahydrofuran-3-yl)methyl | 2,6-dibromo-4-(heptafluoro-n-propyl sulfinyl)phenyl |
| 718 | (thiophen-2-yl)methyl | 2,6-dibromo-4-(heptafluoro-n-propyl sulfinyl)phenyl |
| 719 | (thiophen-3-yl)methyl | 2,6-dibromo-4-(heptafluoro-n-propyl sulfinyl)phenyl |
| 720 | (pyridin-2-yl)methyl | 2,6-dibromo-4-(heptafluoro-n-propyl sulfinyl)phenyl |
| 721 | (pyridin-3-yl)methyl | 2,6-dibromo-4-(heptafluoro-n-propyl sulfinyl)phenyl |
| 722 | (6-chloropyridin-3-yl)methyl | 2,6-dibramo-4-(heptafluoro-n-propyl sulfinyl)phenyl |
| 723 | Et | 2,6-dibromo-4-(heptafluoro-n-propyl sulfonyl)phenyl |

TABLE 1-continued

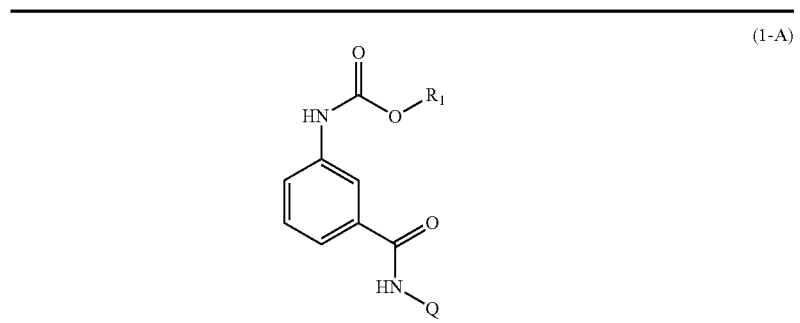

(1-A)

| Compound No. | R₁ | Q |
| --- | --- | --- |
| 724 | i-Pr | 2,6-dibromo-4-(heptafluoro-n-propylsulfonyl)phenyl |
| 725 | vinyl | 2,6-dibromo-4-(heptafluoro-n-propylsulfonyl)phenyl |
| 726 | propargyl | 2,6-dibromo-4-(heptafluoro-n-propylsulfonyl)phenyl |
| 727 | cyclobutyl | 2,6-dibromo-4-(heptafluoro-n-propylsulfonyl)phenyl |
| 728 | cyclopentyl | 2,6-dibromo-4-(heptafluoro-n-propylsulfonyl)phenyl |
| 729 | benzyl | 2,6-dibromo-4-(heptafluoro-n-propylsulfonyl)phenyl |
| 730 | 3-cyanobenzyl | 2,6-dibromo-4-(heptafluoro-n-propylsulfonyl)phenyl |
| 731 | 4-cyanobenzyl | 2,6-dibromo-4-(heptafluoro-n-propylsulfonyl)phenyl |
| 732 | 3-chlorobenzyl | 2,6-dibromo-4-(heptafluoro-n-propylsulfonyl)phenyl |
| 733 | 2-methoxyethyl | 2,6-dibromo-4-(heptafluoro-n-propylsulfonyl)phenyl |
| 734 | 2-cyanoethyl | 2,6-dibromo-4-(heptafluoro-n-propylsulfonyl)phenyl |
| 735 | 2-(methylthio)ethyl | 2,6-dibromo-4-(heptafluoro-n-propylsulfonyl)phenyl |
| 736 | 2-(ethylthio)ethyl | 2,6-dibromo-4-(heptafluoro-n-propylsulfonyl)phenyl |
| 737 | 1-methyl-2-(methylthio)ethyl | 2,6-dibromo-4-(heptafluoro-n-propylsulfonyl)phenyl |
| 738 | 2-(ethylsulfinyl)ethyl | 2,6-dibromo-4-(heptafluoro-n-propylsulfonyl)phenyl |
| 739 | 2-(ethylsulfonyl)ethyl | 2,6-dibromo-4-(heptafluoro-n-propylsulfonyl)phenyl |
| 740 | 2-fluoroethyl | 2,6-dibromo-4-(heptafluoro-n-propylsulfonyl)phenyl |
| 741 | 2,2-difluoroethyl | 2,6-dibromo-4-(heptafluoro-n-propylsulfonyl)phenyl |
| 742 | 2,2,2-trifluoroethyl | 2,6-dibromo-4-(heptafluoro-n-propylsulfonyl)phenyl |
| 743 | 1,3-difluoro-2-propyl | 2,6-dibromo-4-(heptafluoro-n-propylsulfonyl)phenyl |
| 744 | 1-chloro-3-fluoro-2-propyl | 2,6-dibromo-4-(heptafluoro-n-propylsulfonyl)phenyl |
| 745 | 1-methyl-2,2,2-trifluoroethyl | 2,6-dibromo-4-(heptafluoro-n-propylsulfonyl)phenyl |
| 746 | 3,3,3-trifluoro-n-propyl | 2,6-dibromo-4-(heptafluoro-n-propylsulfonyl)phenyl |
| 747 | 2,2,3,3,3-pentafluoro-n-propyl | 2,6-dibromo-4-(heptafluoro-n-propylsulfonyl)phenyl |
| 748 | 3,3,4,4,4-pentafluoro-2-butyl | 2,6-dibromo-4-(heptafluoro-n-propylsulfonyl)phenyl |
| 749 | 4,4,4-trifluoro-n-butyl | 2,6-dibromo-4-(heptafluoro-n-propylsulfonyl)phenyl |
| 750 | 2,2,3,3-tetrafluorocyclobutyl | 2,6-dibromo-4-(heptafluoro-n-propylsulfonyl)phenyl |
| 751 | 2-chloroethyl | 2,6-dibromo-4-(heptafluoro-n-propylsulfonyl)phenyl |
| 752 | 2,2-dichloroethyl | 2,6-dibromo-4-(heptafluoro-n-propylsulfonyl)phenyl |
| 753 | 2,2,2-trichloroethyl | 2,6-dibromo-4-(heptafluoro-n-propylsulfonyl)phenyl |
| 754 | 1,3-dichloro-2-propyl | 2,6-dibromo-4-(heptafluoro-n-propylsulfonyl)phenyl |

TABLE 1-continued (1-A)

| Compound No. | R₁ | Q |
|---|---|---|
| 755 | 3-chloro-n-propyl | 2,6-dibromo-4-(heptafluoro-n-propyl sulfonyl)phenyl |
| 756 | 2-bromoethyl | 2,6-dibromo-4-(heptafluoro-n-propyl sulfonyl)phenyl |
| 757 | 2,2,2-tribromoethyl | 2,6-dibromo-4-(heptafluoro-n-propyl sulfonyl)phenyl |
| 758 | 3-bromo-n-propyl | 2,6-dibromo-4-(heptafluoro-n-propyl sulfonyl)phenyl |
| 759 | 2-iodoethyl | 2,6-dibromo-4-(heptafluoro-n-propyl sulfonyl)phenyl |
| 760 | tetrahydrofuran-3-yl | 2,6-dibromo-4-(heptafluoro-n-propyl sulfonyl)phenyl |
| 761 | (furan-2-yl)methyl | 2,6-dibromo-4-(heptafluoro-n-propyl sulfonyl)phenyl |
| 762 | (furan-3-yl)methyl | 2,6-dibromo-4-(heptafluoro-n-propyl sulfonyl)phenyl |
| 763 | (tetrahydrofuran-2-yl)methyl | 2,6-dibromo-4-(heptafluoro-n-propyl sulfonyl)phenyl |
| 764 | (tetrahydrofuran-3-yl)methyl | 2,6-dibromo-4-(heptafluoro-n-propyl sulfonyl)phenyl |
| 765 | (thiophen-2-yl)methyl | 2,6-dibromo-4-(heptafluoro-n-propyl sulfonyl)phenyl |
| 766 | (thiophen-3-yl)methyl | 2,6-dibromo-4-(heptafluoro-n-propyl sulfonyl)phenyl |
| 767 | (pyridin-2-yl)methyl | 2,6-dibromo-4-(heptafluoro-n-propyl sulfonyl)phenyl |
| 768 | (pyridin-3-yl)methyl | 2,6-dibromo-4-(heptafluoro-n-propyl sulfonyl)phenyl |
| 769 | (6-chloropyridin-3-yl)methyl | 2,6-dibromo-4-(heptafluoro-n-propyl sulfonyl)phenyl |
| 770 | 2,2,2-trichloroethyl | 2-methyl-4-(heptafluoro-n-propylthio)phenyl |
| 771 | Et | 2,6-dimethyl-4-(heptafluoro-n-propylthio)phenyl |
| 772 | i-Pr | 2,6-dimethyl-4-(heptafluoro-n-propylthio)phenyl |
| 773 | propargyl | 2,6-dimethyl-4-(heptafluoro-n-propylthio)phenyl |
| 774 | cyclobutyl | 2,6-dimethyl-4-(heptafluoro-n-propylthio)phenyl |
| 775 | cyclopentyl | 2,6-dimethyl-4-(heptafluoro-n-propylthio)phenyl |
| 776 | benzyl | 2,6-dimethyl-4-(heptafluoro-n-propylthio)phenyl |
| 777 | 3-cyanobenzyl | 2,6-dimethyl-4-(heptafluoro-n-propylthio)phenyl |
| 778 | 4-cyanobenzyl | 2,6-dimethyl-4-(heptafluoro-n-propylthio)phenyl |
| 779 | 3-chlorobenzyl | 2,6-dimethyl-4-(heptafluoro-n-propylthio)phenyl |
| 780 | 2-methoxyethyl | 2,6-dimethyl-4-(heptafluoro-n-propylthio)phenyl |
| 781 | 2-cyanoethyl | 2,6-dimethyl-4-(heptafluoro-n-propylthio)phenyl |
| 782 | 2-(methylthio)ethyl | 2,6-dimethyl-4-(heptafluoro-n-propylthio)phenyl |
| 783 | 2-(ethylthio)ethyl | 2,6-dimethyl-4-(heptafluoro-n-propylthio)phenyl |
| 784 | 1-methyl-2-(methylthio)ethyl | 2,6-dimethyl-4-(heptafluoro-n-propylthio)phenyl |
| 785 | 2-(ethylsulfinyl)ethyl | 2,6-dimethyl-4-(heptafluoro-n-propylthio)phenyl |
| 786 | 2-(ethylsulfonyl)ethyl | 2,6-dimethyl-4-(heptafluoro-n-propylthio)phenyl |
| 787 | 2-fluoroethyl | 2,6-dimethyl-4-(heptafluoro-n-propylthio)phenyl |
| 788 | 2,2-difluoroethyl | 2,6-dimethyl-4-(heptafluoro-n-propylthio)phenyl |
| 789 | 2,2,2-trifluoroethyl | 2,6-dimethyl-4-(heptafluoro-n-propylthio)phenyl |
| 790 | 1,3-difluoro-2-propyl | 2,6-dimethyl-4-(heptafluoro-n-propylthio)phenyl |
| 791 | 1-chloro-3-fluoro-2-propyl | 2,6-dimethyl-4-(heptafluoro-n-propylthio)phenyl |
| 792 | 1-methyl-2,2,2-trifluoroethyl | 2,6-dimethyl-4-(heptafluoro-n-propylthio)phenyl |
| 793 | 3,3,3-trifluoro-n-propyl | 2,6-dimethyl-4-(heptafluoro-n-propylthio)phenyl |
| 794 | 2,2,3,3,3-pentafluoro-n-propyl | 2,6-dimethyl-4-(heptafluoro-n-propylthio)phenyl |
| 795 | 3,3,4,4-pentafluoro-2-butyl | 2,6-dimethyl-4-(heptafluoro-n-propylthio)phenyl |
| 796 | 4,4,4-trifluoro-n-butyl | 2,6-dimethyl-4-(heptafluoro-n-propylthio)phenyl |
| 797 | 2,2,3,3-tetrafluorocyclobutyl | 2,6-dimethyl-4-(heptafluoro-n-propylthio)phenyl |
| 798 | 2-chloroethyl | 2,6-dimethyl-4-(heptafluoro-n-propylthio)phenyl |
| 799 | 2,2-dichloroethyl | 2,6-dimethyl-4-(heptafluoro-n-propylthio)phenyl |
| 800 | 2,2,2-trichloroethyl | 2,6-dimethyl-4-(heptafluoro-n-propylthio)phenyl |
| 801 | 1,3-dichloro-2-propyl | 2,6-dimethyl-4-(heptafluoro-n-propylthio)phenyl |
| 802 | 3-chloro-n-propyl | 2,6-dimethyl-4-(heptafluoro-n-propylthio)phenyl |

TABLE 1-continued (1-A)

| Compound No. | R₁ | Q |
|---|---|---|
| 803 | 2-bromoethyl | 2,6-dimethyl-4-(heptafluoro-n-propylthio)phenyl |
| 804 | 2,2,2-tribromoethyl | 2,6-dimethyl-4-(heptafluoro-n-propylthio)phenyl |
| 805 | 3-bromo-n-propyl | 2,6-dimethyl-4-(heptafluoro-n-propylthio)phenyl |
| 806 | 2-iodoethyl | 2,6-dimethyl-4-(heptafluoro-n-propylthio)phenyl |
| 807 | tetrahydrofuran-3-yl | 2,6-dimethyl-4-(heptafluoro-n-propylthio)phenyl |
| 808 | (furan-2-yl)methyl | 2,6-dimethyl-4-(heptafluoro-n-propylthio)phenyl |
| 809 | (furan-3-yl)methyl | 2,6-dimethyl-4-(heptafluoro-n-propylthio)phenyl |
| 810 | (tetrahydrofuran-2-yl)methyl | 2,6-dimethyl-4-(heptafluoro-n-propylthio)phenyl |
| 811 | (tetrahydrofuran-3-yl)methyl | 2,6-dimethyl-4-(heptafluoro-n-propylthio)phenyl |
| 812 | (thiophen-2-yl)methyl | 2,6-dimethyl-4-(heptafluoro-n-propylthio)phenyl |
| 813 | (thiophen-3-yl)methyl | 2,6-dimethyl-4-(heptafluoro-n-propylthio)phenyl |
| 814 | (pyridin-2-yl)methyl | 2,6-dimethyl-4-(heptafluoro-n-propylthio)phenyl |
| 815 | (pyridin-3-yl)methyl | 2,6-dimethyl-4-(heptafluoro-n-propylthio)phenyl |
| 816 | (6-chloropyridin-3-yl)methyl | 2,6-dimethyl-4-(heptafluoro-n-propylthio)phenyl |
| 817 | 3,3,3-trifluoro-n-propyl | 2-(n-butyl)-6-chloro-4-heptafluoroisopropylphenyl |
| 818 | 3,3,3-trifluoro-n-propyl | 2-(n-butyl)-4-heptafluoroisopropyl-6-iodophenyl |
| 819 | 3,3,3-trifluoro-n-propyl | 2-bromo-6-(2-butyl)-4-heptafluoroisopropylphenyl |
| 820 | i-Pr | 2-methyl-4-trifluoromethoxyphenyl |
| 821 | i-Pr | 2-trifluoromethyl-4-isopropylphenyl |
| 822 | i-Pr | 3,5-bistrifluoromethylphenyl |
| 823 | i-Pr | 2,3,4-trifluorophenyl |
| 824 | i-Pr | 2-heptafluoroisopropyl-3,5-dimethylphenyl |
| 825 | i-Pr | 2,4-dichloro-6-methylphenyl |
| 826 | i-Pr | 2-chloro-4,6-dimethylphenyl |
| 827 | i-Pr | 2,6-dimethyl-4-chlorophenyl |
| 828 | i-Pr | 2,6-dimethyl-4-bromophenyl |
| 829 | i-Pr | 2,6-dimethyl-4-iodophenyl |
| 830 | i-Pr | 2,6-dimethyl-4-(phenyl)phenyl |
| 831 | i-Pr | 2,6-dimethyl-4-(2-methylphenyl)phenyl |
| 832 | i-Pr | 2,6-dimethyl-4-(3-methylphenyl)phenyl |
| 833 | i-Pr | 2,6-dimethyl-4-(4-methylphenyl)phenyl |
| 834 | i-Pr | 2,6-dimethyl-4-(2-methoxyphenyl)phenyl |
| 835 | i-Pr | 2,6-dimethyl-4-(3-methoxyphenyl)phenyl |
| 836 | i-Pr | 2,6-dimethyl-4-(4-methoxyphenyl)phenyl |
| 837 | i-Pr | 2,6-dimethyl-4-(4-ethoxyphenyl)phenyl |
| 838 | i-Pr | 2,6-dimethyl-4-(4-methylthiophenyl)phenyl |
| 839 | i-Pr | 2,6-dimethyl-4-(2-fluorophenyl)phenyl |
| 840 | i-Pr | 2,6-dimethyl-4-(3-fluorophenyl)phenyl |
| 841 | i-Pr | 2,6-dimethyl-4-(4-fluorophenyl)phenyl |
| 842 | i-Pr | 2-bromo-4-isopropyl-6-methylphenyl |
| 843 | i-Pr | 2-chloro-4-cyano-6-methylphenyl |
| 844 | i-Pr | 2-chloro-4-trifluoromethoxy-6-methylphenyl |
| 845 | i-Pr | 2-chloro-4-isopropyl-6-trifluoromethylphenyl |
| 846 | i-Pr | pentafluorophenyl |
| 847 | 2,2,2-trichloroethyl | 4-cyclohexylphenyl |
| 848 | 2,2,2-trichloroethyl | 2-trifluoromethylphenyl |
| 849 | 2,2,2-trichloroethyl | 4-(trifluoromethylthio)phenyl |
| 850 | 2,2,2-trichloroethyl | 4-(trifluoromethylsulfonyl)phenyl |
| 851 | 2,2,2-trichloroethyl | 4-(heptafluoro-n-propylthio)phenyl |
| 852 | 2,2,2-trichloroethyl | 4-(heptafluoro-n-propylsulfinyl)phenyl |
| 853 | 2,2,2-trichloroethyl | 4-(heptafluoroisopropylthio)phenyl |
| 854 | 2,2,2-trichloroethyl | 2-(n-butyl)-6-chloro-4-heptafluoroisopropylphenyl |
| 855 | 2,2,2-trichloroethyl | 2-(n-butyl)-4-heptafluoroisopropyl-6-iodophenyl |
| 856 | 2,2,2-trichloroethyl | 2-bromo-6-(2-butyl)-4-heptafluoroisopropylphenyl |
| 857 | 2,2,2-trichloroethyl | 2-(2-butyl)-4-heptafluoroisopropylphenyl |
| 858 | 2,2,2-trichloroethyl | 2-methyl-4-trifluoromethoxyphenyl |
| 859 | 2,2,2-trichloroethyl | 2-methyl-4-(2,2,2-trifluoroethoxy)phenyl |
| 860 | 2,2,2-trichloroethyl | 2-methyl-4-(trifluoromethylsulfonyloxy)phenyl |
| 861 | 2,2,2-trichloroethyl | 2-methyl-4-chlorophenyl |
| 862 | 2,2,2-trichloroethyl | 2-trifluoromethyl-4-isopropylphenyl |
| 863 | 2,2,2-trichloroethyl | 2,5-bistrifluoromethylphenyl |
| 864 | 2,2,2-trichloroethyl | 3,5-bistrifluoromethylphenyl |
| 865 | 2,2,2-trichloroethyl | 2-trifluoromethyl-4-chlorophenyl |

TABLE 1-continued

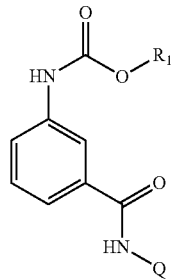

(1-A)

| Compound No. | R₁ | Q |
|---|---|---|
| 866 | 2,2,2-trichloroethyl | 2-chloro-6-trifluoromethylphenyl |
| 867 | 2,2,2-trichloroethyl | 2-trifluoromethyl-4-iodophenyl |
| 868 | 2,2,2-trichloroethyl | 2-trifluoromethoxy-4-bromophenyl |
| 869 | 2,2,2-trichloroethyl | 2,3,4-trifluorophenyl |
| 870 | 2,2,2-trichloroethyl | 2-heptafluoroisopropyl-3,5-dimethylphenyl |
| 871 | 2,2,2-trichloroethyl | 2,5-dimethyl-4-trifluoromethane sulfonyloxyphenyl |
| 872 | 2,2,2-trichloroethyl | 2,6-dimethyl-4-(bis(trifluoromethyl) hydroxymethyl)phenyl |
| 873 | 2,2,2-trichloroethyl | 2,6-dimethyl-4-(bis(chlorodifluoromethyl) hydroxymethyl)phenyl |
| 874 | 2,2,2-trichloroethyl | 2,6-dimethyl-4-cyanothiophenyl |
| 875 | 2,2,2-trichloroethyl | 2,6-dimethyl-4-chlorophenyl |
| 876 | 2,2,2-trichloroethyl | 2-chloro-4,6-dimethylphenyl |
| 877 | 2,2,2-trichloroethyl | 2,6-dimethyl-4-bromophenyl |
| 878 | 2,2,2-trichloroethyl | 2,6-dimethyl-4-iodophenyl |
| 879 | 2,2,2-trichloroethyl | 2,6-dimethyl-4-(phenyl)phenyl |
| 880 | 2,2,2-trichloroethyl | 2,6-dimethyl-4-(2-methylphenyl)phenyl |
| 881 | 2,2,2-trichloroethyl | 2,6-dimethyl-4-(3-methylphenyl)phenyl |
| 882 | 2,2,2-trichloroethyl | 2,6-dimethyl-4-(4-methylphenyl)phenyl |
| 883 | 2,2,2-trichloroethyl | 2,6-dimethyl-4-(2-methoxyphenyl)phenyl |
| 884 | 2,2,2-trichloroethyl | 2,6-dimethyl-4-(3-methoxyphenyl)phenyl |
| 885 | 2,2,2-trichloroethyl | 2,6-dimethyl-4-(4-methoxyphenyl)phenyl |
| 886 | 2,2,2-trichloroethyl | 2,6-dimethyl-4-(4-ethoxyphenyl)phenyl |
| 887 | 2,2,2-trichloroethyl | 2,6-dimethyl-4-(4-methylthiophenyl)phenyl |
| 888 | 2,2,2-trichloroethyl | 2,6-dimethyl-4-(2-fluorophenyl)phenyl |
| 889 | 2,2,2-trichloroethyl | 2,6-dimethyl-4-(3-fluorophenyl)phenyl |
| 890 | 2,2,2-trichloroethyl | 2,6-dimethyl-4-(4-fluorophenyl)phenyl |
| 891 | 2,2,2-trichloroethyl | 2,6-dimethyl-4-(3,4-difluorophenyl)phenyl |
| 892 | 2,2,2-trichloroethyl | 2,6-dimethyl-4-(3-methyl-4-fluorophenyl)phenyl |
| 893 | 2,2,2-trichloroethyl | 2,6-dimethyl-4-(furan-3-yl)phenyl |
| 894 | 2,2,2-trichloroethyl | 2,6-dimethyl-4-(thiophene-2-yl)phenyl |
| 895 | 2,2,2-trichloroethyl | 2,6-dimethyl-4-(thiophene-3-yl)phenyl |
| 896 | 2,2,2-trichloroethyl | 2,4-dichloro-6-methylphenyl |
| 897 | 2,2,2-trichloroethyl | 2,4-dichloro-6-trifluoromethylphenyl |
| 898 | 2,2,2-trichloroethyl | 2,6-dichloro-4-(heptafluoroisopropylthio)phenyl |
| 899 | 2,2,2-trichloroethyl | 2,6-dichloro-4-(heptafluoroisopropyl sulfonyl)phenyl |
| 900 | 2,2,2-trichloroethyl | 2,6-dichloro-4-pentafluorosulfanylphenyl |
| 901 | 2,2,2-trichloroethyl | 2,6-dibromo-4-cyclohexylphenyl |
| 902 | 2,2,2-trichloroethyl | 2,4-dibromo-6-trifluoromethylphenyl |
| 903 | 2,2,2-trichloroethyl | 2,6-dibromo-4-(nonafluoro-n-butylthio)phenyl |
| 904 | 2,2,2-trichloroethyl | 2-chloro-4-hydroxy-6-methylphenyl |
| 905 | 2,2,2-trichloroethyl | 2-chloro-4-trifluoromethoxy-6-methylphenyl |
| 906 | 2,2,2-trichloroethyl | 2-chloro-4-((2,2,2-trichloroethoxy)carbonyloxy)-6-methylphenyl |
| 907 | 2,2,2-trichloroethyl | 2-chloro-4-cyano-6-methylphenyl |
| 908 | 2,2,2-trichloroethyl | 2-chloro-4-iodo-6-methylphenyl |
| 909 | 2,2,2-trichloroethyl | 2-bromo-4-isopropyl-6-methylphenyl |
| 910 | 2,2,2-trichloroethyl | 2-bromo-4-hydroxy-6-methylphenyl |
| 911 | 2,2,2-trichloroethyl | 2-chloro-4-isopropyl-6-trifluoromethylphenyl |
| 912 | 2,2,2-trichloroethyl | 2-bromo-4-((2,2,2-trichloroethoxy)carbonyloxy)-6-methylphenyl |
| 913 | 2,2,2-trichloroethyl | 2-chloro-4-bromo-6-trifluoromethylphenyl |
| 914 | 2,2,2-trichloroethyl | 2-bromo-4-isopropyl-6-trifluoromethylphenyl |
| 915 | 2,2,2-trichloroethyl | 2-bromo-4-chloro-6-trifluoromethylphenyl |
| 916 | 2,2,2-trichloroethyl | pentafluorophenyl |
| 917 | 2-chloroethyl | 2,6-dimethyl-4-iodophenyl |
| 918 | 3,3,3-trifluoro-n-propyl | 2,6-dimethyl-4-(1,1,1,3,3,3-hexafluoro2-hydroxy-2-propyl)phenyl |
| 919 | 3,3,3-trifluoro-n-propyl | 2,6-dichloro-4-pentafluorosulfanylphenyl |
| 920 | i-Pr | 2-methyl-4-heptafluoroisopropyl-1-naphthyl |

TABLE 1-continued (1-A)

| Compound No. | R₁ | Q |
|---|---|---|
| 921 | i-Pr | 4-heptafluoroisopropyl-5,6,7,8-tetrahydro-1-naphthyl |
| 922 | i-Pr | 2-chloro-4-heptafluoroisopropyl-5,6,7,8-tetrahydro-1-naphthyl |
| 923 | i-Pr | 1-methyl-3-trifluoromethylpyrazol-5-yl |
| 924 | i-Pr | 1-methyl-3-trifluoromethyl-4-chloropyrazol-5-yl |
| 925 | i-Pr | 1-methyl-3-trifluoromethyl-4-bromopyrazol-5-yl |
| 926 | i-Pr | 1-methyl-3-trifluoromethyl-4-methoxy carbonylpyrazol-5-yl |
| 927 | i-Pr | 2-chloro-4-methylpyridin-5-yl |
| 928 | i-Pr | 2-bromo4-methyl-6-chloropyridin-3-yl |
| 929 | i-Pr | 2-(1,1,1,3,3,3-hexafluoroisopropyloxy)pyridin-5-yl |
| 930 | i-Pr | 2-(1,1,1,3,3,3-hexafluoroisopropyloxy)-4-methylpyridin-5-yl |
| 931 | i-Pr | 2-bromo-6-(1,1,1,3,3,3-hexafluoroisopropyloxy)pyridin-3-yl |
| 932 | i-Pr | 2,4-dimethyl-6-(1,1,1,3,3,3-hexafluoroisopropyloxy)pyridin-3-yl |
| 933 | 2,2,2-trichloroethyl | 2-methyl-4-heptafluoroisopropyl-1-naphthyl |
| 934 | 2,2,2-trichloroethyl | 4-heptafluoroisopropyl-5,6,7,8-tetrahydro-1-naphthyl |
| 935 | 2,2,2-trichloroethyl | 2-chloro-4-heptafluoroisopropyl 5,6,7,8-tetrahydro-1-naphthyl |
| 936 | 2,2,2-trichloroethyl | 1-methyl-3-trifluoromethylpyrazol-5-yl |
| 937 | 2,2,2-trichloroethyl | 1-methyl-3-trifluoromethyl-4-chloropyrazol-5-yl |
| 938 | 2,2,2-trichloroethyl | 1-methyl-3-trifluoromethyl-4-bromopyrazol-5-yl |
| 939 | 2,2,2-trichloroethyl | 1-methyl-3-trifluoromethyl-4-methoxy carbonylpyrazol-5-yl |
| 940 | 2,2,2-trichloroethyl | 1-(3-chloropyridine-2-yl)-3-bromopyrazol-5-yl |
| 941 | 2,2,2-trichloroethyl | 1-(3-chloropyridin-2-yl)-3-bromo-4-chloropyrazol-5-yl |
| 942 | 2,2,2-trichloroethyl | 2-heptafluoroisopropyl-4-methylpyridin-5-yl |
| 943 | 2,2,2-trichloroethyl | 2-(1,1,1,3,3,3-hexafluoroisopropyloxy)pyridin-5-yl |
| 944 | 2,2,2-trichloroethyl | 2-(1,1,1,3,3,3-hexafluoroisopropyloxy)-4-methylpyridin-5-yl |
| 945 | 2,2,2-trichloroethyl | 2-chloro-4-methylpyridin-5-yl |
| 946 | 2,2,2-trichloroethyl | 3-chloro-5-trifluoromethylpyridin-2-yl |
| 947 | 2,2,2-trichloroethyl | 2-bromo-4-methyl-6-chloropyridin-3-yl |
| 948 | 2,2,2-trichloroethyl | 2-bromo-6-(1,1,1,3,3,3-hexafluoroisopropyloxy)pyridin-3-yl |
| 949 | 2,2,2-trichloroethyl | 2,6-dichloro-4-(trifluoromethylsulfinyl)phenyl |
| 950 | 2,2,2-trichloroethyl | 2,6-dibromo-4-(trifluoromethylsulfinyl)phenyl |
| 951 | 2,2,2-trichloroethyl | 2,6-dichloro-4-(pentafluoroethylsulfinyl)phenyl |
| 952 | 2,2,2-trichloroethyl | 2,6-dibromo-4-(pentafluoroethylsulfinyl)phenyl |
| 953 | 2,2,2-trichloroethyl | 2,6-dichloro-4-(pentafluoroethylsulfonyl)phenyl |
| 954 | 2,2,2-trichloroethyl | 2,6-dibromo-4-(pentafluoroethylsulfonyl)phenyl |
| 955 | 2,2,2-trichloroethyl | 2,6-dichloro-4-(heptafluoro-n-propyl sulfinyl)phenyl |
| 956 | 2,2,2-trichloroethyl | 2,6-dibromo-4-(heptafluoro-n-propyl sulfinyl)phenyl |
| 957 | 2,2,2-trichloroethyl | 2-chloro-6-methyl-4-(nonafluoro-2-butyl)phenyl |
| 958 | 2,2,2-trichloroethyl | 2-bromo-6-methyl-4-(nonafluoro-2-butyl)phenyl |
| 959 | 2,2,2-trichloroethyl | 2-iodo-6-methyl-4-(nonafluoro-2-butyl)phenyl |
| 960 | 2,2,2-trichloroethyl | 2,6-dichloro-4-(nonafluoro-2-butyl)phenyl |
| 961 | 2,2,2-trichloroethyl | 2,6-dibromo-4-(nonafluoro-2-butyl)phenyl |
| 962 | 2,2,2-trichloroethyl | 2,6-dimethyl-4-pentafluoroethylphenyl |
| 963 | 2,2,2-trichloroethyl | 2,6-dichloro-4-pentafluoroethylphenyl |
| 964 | 2,2,2-trichloroethyl | 2,6-dimethyl-4-(pentafluoroethylthio)phenyl |
| 965 | 2,2,2-trichloroethyl | 2,6-dimethyl-4-(pentafluoroethylsulfinyl)phenyl |

TABLE 1-continued (1-A)

| Compound No. | R₁ | Q |
|---|---|---|
| 966 | 2,2,2-trichloroethyl | 2,6-dimethyl-4-(pentafluoroethylsulfonyl)phenyl |
| 967 | 2,2,2-trichloroethyl | 2,6-dichloro-4-(pentafluoroethylthio)phenyl |
| 968 | i-Pr | 2-chloro-4-methyl-6-(1,1,1,3,3,3-hexafluoroisopropyloxy)pyridin-3-yl |
| 969 | cyclobutyl | 2-chloro-4-methyl-6-(1,1,1,3,3,3-hexafluoroisopropyloxy)pyridin-3-yl |
| 970 | cyclopentyl | 2-chloro-4-methyl-6-(1,1,1,3,3,3-hexafluoroisopropyloxy)pyridin-3-yl |
| 971 | 4-cyanobenzyl | 2-chloro4-methyl-6-(1,1,1,3,3,3-hexafluoro-isopropyloxy)pyridin-3-yl |
| 972 | 2-methoxyethyl | 2-chloro-4-methyl-6-(1,1,1,3,3,3-hexafluoroisopropyloxy)pyridin-3-yl |
| 973 | 2-cyanoethyl | 2-chloro-4-methyl-6-(1,1,1,3,3,3-hexafluoroisopropyloxy)pyridin-3-yl |
| 974 | 2-(methylthio)ethyl | 2-chloro-4-methyl-6-(1,1,1,3,3,3-hexafluoroisopropyloxy)pyridin-3-yl |
| 975 | 2-(ethylthio)ethyl | 2-chloro-4-methyl-6-(1,1,1,3,3,3-hexafluoroisopropyloxy)pyridin-3-yl |
| 976 | 1-methyl-2-(methylthio)ethyl | 2-chloro-4-methyl-6-(1,1,1,3,3,3-hexafluoroisopropyloxy)pyridin-3-yl |
| 977 | 2-(ethylsulfinyl)ethyl | 2-chloro-4-methyl-6-(1,1,1,3,3,3-hexafluoroisopropyloxy)pyridin-3-yl |
| 978 | 2-(ethylsulfonyl)ethyl | 2-chloro-4-methyl-6-(1,1,1,3,3,3-hexafluoroisopropyloxy)pyridin-3-yl |
| 979 | 2-fluoroethyl | 2-chloro-4-methyl-6-(1,1,1,3,3,3-hexafluoroisopropyloxy)pyridin-3-yl |
| 980 | 2,2-difluoroethyl | 2-chloro-4-methyl-6-(1,1,1,3,3,3-hexafluoroisopropyloxy)pyridin-3-yl |
| 981 | 2,2,2-trifluoroethyl | 2-chloro-4-methyl-6-(1,1,1,3,3,3-hexafluoroisopropyloxy)pyridin-3-yl |
| 982 | 1,3-difluoro-2-propyl | 2-chloro-4-methyl-6-(1,1,1,3,3,3-hexafluoroisopropyloxy)pyridin-3-yl |
| 983 | 1-chloro-3-fluoro-2-propyl | 2-chloro-4-methyl-6-(1,1,1,3,3,3-hexafluoroisopropyloxy)pyridin-3-yl |
| 984 | 1-methyl-2,2,2-trifluoroethyl | 2-chloro-4-methyl-6-(1,1,1,3,3,3-hexafluoroisopropyloxy)pyridin-3-yl |
| 985 | 3,3,3-trifluoro-n-propyl | 2-chloro-4-methyl-6-(1,1,1,3,3,3-hexafluoroisopropyloxy)pyridin-3-yl |
| 986 | 2,2,3,3,3-pentafluoro-n-propyl | 2-chloro-4-methyl-6-(1,1,1,3,3,3-hexafluoroisopropyloxy)pyridin-3-yl |
| 987 | 3,3,4,4,4-pentafluoro-2-butyl | 2-chloro-4-methyl-6-(1,1,1,3,3,3-hexafluoroisopropyloxy)pyridin-3-yl |
| 988 | 4,4,4-trifluoro-n-butyl | 2-chloro-4-methyl-6-(1,1,1,3,3,3-hexafluoroisopropyloxy)pyridin-3-yl |
| 989 | 2,2,3,3-tetrafluorocyclobutyl | 2-chloro-4-methyl-6-(1,1,1,3,3,3-hexafluoroisopropyloxy)pyridin-3-yl |
| 990 | 2-chloroethyl | 2-chloro-4-methyl-6-(1,1,1,3,3,3-hexafluoroisopropyloxy)pyridin-3-yl |
| 991 | 2,2-dichloroethyl | 2-chloro-4-methyl-6-(1,1,1,3,3,3-hexafluoroisopropyloxy)pyridin-3-yl |
| 992 | 2,2,2-trichloroethyl | 2-chloro-4-methyl-6-(1,1,1,3,3,3-hexafluoroisopropyloxy)pyridin-3-yl |
| 993 | 1,3-dichloro-2-propyl | 2-chloro-4-methyl-6-(1,1,1,3,3,3-hexafluoroisopropyloxy)pyridin-3-yl |
| 994 | 3-chloro-n-propyl | 2-chloro-4-methyl-6-(1,1,1,3,3,3-hexafluoroisopropyloxy)pyridin-3-yl |
| 995 | 2-bromoethyl | 2-chloro-4-methyl-6-(1,1,1,3,3,3-hexafluoroisopropyloxy)pyridin-3-yl |
| 996 | 2,2,2-tribromoethyl | 2-chloro-4-methyl-6-(1,1,1,3,3,3-hexafluoroisopropyloxy)pyridin-3-yl |

TABLE 1-continued

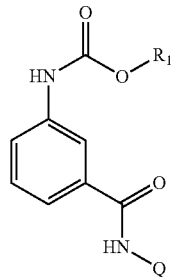

(1-A)

| Compound No. | R₁ | Q |
|---|---|---|
| 997 | 3-bromo-n-propyl | 2-chloro-4-methyl-6-(1,1,1,3,3,3-hexafluoro isopropyloxy)pyridin-3-yl |
| 998 | 2-iodoethyl | 2-chloro-4-methyl-6-(1,1,1,3,3,3-hexafluoro isopropyloxy)pyridin-3-yl |
| 999 | tetrahydrofuran-3-yl | 2-chloro-4-methyl-6-(1,1,1,3,3,3-hexafluoro isopropyloxy)pyridin-3-yl |
| 1000 | (furan-2-yl)methyl | 2-chloro-4-methyl-6-(1,1,1,3,3,3-hexafluoro isopropyloxy)pyridin-3-yl |
| 1001 | (furan-3-yl)methyl | 2-chloro-4-methyl-6-(1,1,1,3,3,3-hexafluoro isopropyloxy)pyridin-3-yl |
| 1002 | (tetrahydrofuran-2-yl)methyl | 2-chloro-4-methyl-6-(1,1,1,3,3,3-hexafluoro isopropyloxy)pyridin-3-yl |
| 1003 | (tetrahydrofuran-3-yl)methyl | 2-chloro-4-methyl-6-(1,1,1,3,3,3-hexafluoro isopropyloxy)pyridin-3-yl |
| 1004 | (thiophen-2-yl)methyl | 2-chloro-4-methyl-6-(1,1,1,3,3,3-hexafluoro isopropyloxy)pyridin-3-yl |
| 1005 | (thiophen-3-yl)methyl | 2-chloro-4-methyl-6-(1,1,1,3,3,3-hexafluoro isopropyloxy)pyridin-3-yl |
| 1006 | (pyridin-2-yl)methyl | 2-chloro-4-methyl-6-(1,1,1,3,3,3-hexafluoro isopropyloxy)pyridin-3-yl |
| 1007 | (pyridin-3-yl)methyl | 2-chloro-4-methyl-6-(1,1,1,3,3,3-hexafluoro isopropyloxy)pyridin-3-yl |
| 1008 | (6-chloropyridin-3-yl)methyl | 2-chloro-4-methyl-6-(1,1,1,3,3,3-hexafluoro isopropyloxy)pyridin-3-yl |
| 1009 | Et | 2-bromo-4-methyl-6-(1,1,1,3,3,3-hexafluoro isopropyloxy)pyridin-3-yl |
| 1010 | i-Pr | 2-bromo-4-methyl-6-(1,1,1,3,3,3-hexafluoro isopropyloxy)pyridin-3-yl |
| 1011 | vinyl | 2-bromo-4-methyl-6-(1,1,1,3,3,3-hexafluoro isopropyloxy)pyridin-3-yl |
| 1012 | propargyl | 2-bromo-4-methyl-6-(1,1,1,3,3,3-hexafluoro isopropyloxy)pyridin-3-yl |
| 1013 | cyclobutyl | 2-bromo-4-methyl-6-(1,1,1,3,3,3-hexafluoro isopropyloxy)pyridin-3-yl |
| 1014 | cyclopentyl | 2-bromo-4-methyl-6-(1,1,1,3,3,3-hexafluoro isopropyloxy)pyridin-3-yl |
| 1015 | benzyl | 2-bromo-4-methyl-6-(1,1,1,3,3,3-hexafluoro isopropyloxy)pyridin-3-yl |
| 1016 | 3-cyanobenzyl | 2-bromo-4-methyl-6-(1,1,1,3,3,3-hexafluoro isopropyloxy)pyridin-3-yl |
| 1017 | 4-cyanobenzyl | 2-bromo-4-methyl-6-(1,1,1,3,3,3-hexafluoro isopropyloxy)pyridin-3-yl |
| 1018 | 3-chlorobenzyl | 2-bromo-4-methyl-6-(1,1,1,3,3,3-hexafluoro isopropyloxy)pyridin-3-yl |
| 1019 | 2-methoxyethyl | 2-bromo-4-methyl-6-(1,1,1,3,3,3-hexafluoro isopropyloxy)pyridin-3-yl |
| 1020 | 2-cyanoethyl | 2-bromo-4-methyl-6-(1,1,1,3,3,3-hexafluoro isopropyloxy)pyridin-3-yl |
| 1021 | 2-(methylthio)ethyl | 2-bromo-4-methyl-6-(1,1,1,3,3,3-hexafluoro isopropyloxy)pyridin-3-yl |
| 1022 | 2-(ethylthio)ethyl | 2-bromo-4-methyl-6-(1,1,1,3,3,3-hexafluoro isopropyloxy)pyridin-3-yl |
| 1023 | 1-methyl-2-(methylthio)ethyl | 2-bromo-4-methyl-6-(1,1,1,3,3,3-hexafluoro isopropyloxy)pyridin-3-yl |
| 1024 | 2-(ethylsulfinyl)ethyl | 2-bromo-4-methyl-6-(1,1,1,3,3,3-hexafluoro isopropyloxy)pyridin-3-yl |
| 1025 | 2-(ethylsulfonyl)ethyl | 2-bromo-4-methyl-6-(1,1,1,3,3,3-hexafluoro isopropyloxy)pyridin-3-yl |
| 1026 | 2-fluoroethyl | 2-bromo-4-methyl-6-(1,1,1,3,3,3-hexafluoro isopropyloxy)pyridin-3-yl |
| 1027 | 2,2-difluoroethyl | 2-bromo-4-methyl-6-(1,1,1,3,3,3-hexafluoro isopropyloxy)pyridin-3-yl |

TABLE 1-continued (1-A)

| Compound No. | R₁ | Q |
|---|---|---|
| 1028 | 2,2,2-trifluoroethyl | 2-bromo-4-methyl-6-(1,1,1,3,3,3-hexafluoro isopropyloxy)pyridin-3-yl |
| 1029 | 1,3-difluoro-2-propyl | 2-bromo-4-methyl-6-(1,1,1,3,3,3-hexafluoro isopropyloxy)pyridin-3-yl |
| 1030 | 1-chloro-3-fluoro-2-propyl | 2-bromo-4-methyl-6-(1,1,1,3,3,3-hexafluoro isopropyloxy)pyridin-3-yl |
| 1031 | 1-methyl-2,2,2-trifluoroethyl | 2-bromo-4-methyl-6-(1,1,1,3,3,3-hexafluoro isopropyloxy)pyridin-3-yl |
| 1032 | 3,3,3-trifluoro-n-propyl | 2-bromo-4-methyl-6-(1,1,1,3,3,3-hexafluoro isopropyloxy)pyridin-3-yl |
| 1033 | 2,2,3,3,3-pentafluoro-n-propyl | 2-bromo-4-methyl-6-(1,1,1,3,3,3-hexafluoro isopropyloxy)pyridin-3-yl |
| 1034 | 3,3,4,4-pentafluoro-2-butyl | 2-bromo-4-methyl-6-(1,1,1,3,3,3-hexafluoro isopropyloxy)pyridin-3-yl |
| 1035 | 4,4,4-trifluoro-n-butyl | 2-bromo-4-methyl-6-(1,1,1,3,3,3-hexafluoro isopropyloxy)pyridin-3-yl |
| 1036 | 2,2,3,3-tetrafluorocyclobutyl | 2-bromo-4-methyl-6-(1,1,1,3,3,3-hexafluoro isopropyloxy)pyridin-3-yl |
| 1037 | 2-chloroethyl | 2-bromo-4-methyl-6-(1,1,1,3,3,3-hexafluoro isopropyloxy)pyridin-3-yl |
| 1038 | 2,2-dichloroethyl | 2-bromo-4-methyl-6-(1,1,1,3,3,3-hexafluoro isopropyloxy)pyridin-3-yl |
| 1039 | 2,2,2-trichloroethyl | 2-bromo-4-methyl-6-(1,1,1,3,3,3-hexafluoro isopropyloxy)pyridin-3-yl |
| 1040 | 1,3-dichloro-2-propyl | 2-bromo-4-methyl-6-(1,1,1,3,3,3-hexafluoro isopropyloxy)pyridin-3-yl |
| 1041 | 3-chloro-n-propyl | 2-bromo-4-methyl-6-(1,1,1,3,3,3-hexafluoro isopropyloxy)pyridin-3-yl |
| 1042 | 2-bromoethyl | 2-bromo-4-methyl-6-(1,1,1,3,3,3-hexafluoro isopropyloxy)pyridin-3-yl |
| 1043 | 2,2,2-tribromoethyl | 2-bromo-4-methyl-6-(1,1,1,3,3,3-hexafluoro isopropyloxy)pyridin-3-yl |
| 1044 | 3-bromo-n-propyl | 2-bromo-4-methyl-6-(1,1,1,3,3,3-hexafluoro isopropyloxy)pyridin-3-yl |
| 1045 | 2-iodoethyl | 2-bromo-4-methyl-6-(1,1,1,3,3,3-hexafluoro isopropyloxy)pyridin-3-yl |
| 1046 | tetrahydrofuran-3-yl | 2-bromo-4-methyl-6-(1,1,1,3,3,3-hexafluoro isopropyloxy)pyridin-3-yl |
| 1047 | (furan-2-yl)methyl | 2-bromo-4-methyl-6-(1,1,1,3,3,3-hexafluoro isopropyloxy)pyridin-3-yl |
| 1048 | (furan-3-yl)methyl | 2-bromo-4-methyl-6-(1,1,1,3,3,3-hexafluoro isopropyloxy)pyridin-3-yl |
| 1049 | (tetrahydrofuran-2-yl)methyl | 2-bromo-4-methyl-6-(1,1,1,3,3,3-hexafluoro isopropyloxy)pyridin-3-yl |
| 1050 | (tetrahydrofuran-3-yl)methyl | 2-bromo-4-methyl-6-(1,1,1,3,3,3-hexafluoro isopropyloxy)pyridin-3-yl |
| 1051 | (thiophen-2-yl)methyl | 2-bromo-4-methyl-6-(1,1,1,3,3,3-hexafluoro isopropyloxy)pyridin-3-yl |
| 1052 | (thiophen-3-yl)methyl | 2-bromo-4-methyl-6-(1,1,1,3,3,3-hexafluoro isopropyloxy)pyridin-3-yl |
| 1053 | (pyridin-2-yl)methyl | 2-bromo-4-methyl-6-(1,1,1,3,3,3-hexafluoro isopropyloxy)pyridin-3-yl |
| 1054 | (pyridin-3-yl)methyl | 2-bromo-4-methyl-6-(1,1,1,3,3,3-hexafluoro isopropyloxy)pyridin-3-yl |
| 1055 | (6-chloropyridin-3-yl)methyl | 2-bromo-4-methyl-6-(1,1,1,3,3,3-hexafluoro isopropyloxy)pyridin-3-yl |
| 1056 | Et | 2-iodo-4-methyl-6-(1,1,1,3,3,3-hexafluoro isopropyloxy)pyridin-3-yl |
| 1057 | i-Pr | 2-iodo-4-methyl-6-(1,1,1,3,3,3-hexafluoro isopropyloxy)pyridin-3-yl |
| 1058 | vinyl | 2-iodo-4-methyl-6-(1,1,1,3,3,3-hexafluoro isopropyloxy)pyridin-3-yl |

TABLE 1-continued

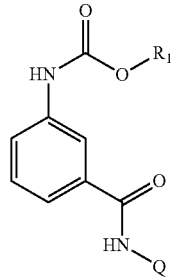

(1-A)

| Compound No. | R$_1$ | Q |
|---|---|---|
| 1059 | propargyl | 2-iodo-4-methyl-6-(1,1,1,3,3,3-hexafluoro isopropyloxy)pyridin-3-yl |
| 1060 | cyclobutyl | 2-iodo-4-methyl-6-(1,1,1,3,3,3-hexafluoro isopropyloxy)pyridin-3-yl |
| 1061 | cyclopentyl | 2-iodo-4-methyl-6-(1,1,1,3,3,3-hexafluoro isopropyloxy)pyridin-3-yl |
| 1062 | benzyl | 2-iodo-4-methyl-6-(1,1,1,3,3,3-hexafluoro isopropyloxy)pyridin-3-yl |
| 1063 | 3-cyanobenzyl | 2-iodo-4-methyl-6-(1,1,1,3,3,3-hexafluoro isopropyloxy)pyridin-3-yl |
| 1064 | 4-cyanobenzyl | 2-iodo-4-methyl-6-(1,1,1,3,3,3-hexafluoro isopropyloxy)pyridin-3-yl |
| 1065 | 3-chlorobenzyl | 2-iodo-4-methyl-6-(1,1,1,3,3,3-hexafluoro isopropyloxy)pyridin-3-yl |
| 1066 | 2-methoxyethyl | 2-iodo-4-methyl-6-(1,1,1,3,3,3-hexafluoro isopropyloxy)pyridin-3-yl |
| 1067 | 2-cyanoethyl | 2-iodo-4-methyl-6-(1,1,1,3,3,3-hexafluoro isopropyloxy)pyridin-3-yl |
| 1068 | 2-(methylthio)ethyl | 2-iodo-4-methyl-6-(1,1,1,3,3,3-hexafluoro isopropyloxy)pyridin-3-yl |
| 1069 | 2-(ethylthio)ethyl | 2-iodo-4-methyl-6-(1,1,1,3,3,3-hexafluoro isopropyloxy)pyridin-3-yl |
| 1070 | 1-methyl-2-(methylthio)ethyl | 2-iodo-4-methyl-6-(1,1,1,3,3,3-hexafluoro isopropyloxy)pyridin-3-yl |
| 1071 | 2-(ethylsulfinyl)ethyl | 2-iodo-4-methyl-6-(1,1,1,3,3,3-hexafluoro isopropyloxy)pyridin-3-yl |
| 1072 | 2-(ethylsulfonyl)ethyl | 2-iodo-4-methyl-6-(1,1,1,3,3,3-hexafluoro isopropyloxy)pyridin-3-yl |
| 1073 | 2-fluoroethyl | 2-iodo-4-methyl-6-(1,1,1,3,3,3-hexafluoro isopropyloxy)pyridin-3-yl |
| 1074 | 2,2-difluoroethyl | 2-iodo-4-methyl-6-(1,1,1,3,3,3-hexafluoro isopropyloxy)pyridin-3-yl |
| 1075 | 2,2,2-trifluoroethyl | 2-iodo-4-methyl-6-(1,1,1,3,3,3-hexafluoro isopropyloxy)pyridin-3-yl |
| 1076 | 1,3-difluoro-2-propyl | 2-iodo-4-methyl-6-(1,1,1,3,3,3-hexafluoro isopropyloxy)pyridin-3-yl |
| 1077 | 1-chloro-3-fluoro-2-propyl | 2-iodo-4-methyl-6-(1,1,1,3,3,3-hexafluoro isopropyloxy)pyridin-3-yl |
| 1078 | 1-methyl-2,2,2-trifluoroethyl | 2-iodo-4-methyl-6-(1,1,1,3,3,3-hexafluoro isopropyloxy)pyridin-3-yl |
| 1079 | 3,3,3-trifluoro-n-propyl | 2-iodo-4-methyl-6-(1,1,1,3,3,3-hexafluoro isopropyloxy)pyridin-3-yl |
| 1080 | 2,2,3,3,3-pentafluoro-n-propyl | 2-iodo-4-methyl-6-(1,1,1,3,3,3-hexafluoro isopropyloxy)pyridin-3-yl |
| 1081 | 3,3,4,4,4-pentafluoro-2-butyl | 2-iodo-4-methyl-6-(1,1,1,3,3,3-hexafluoro isopropyloxy)pyridin-3-yl |
| 1082 | 4,4,4-trifluoro-n-butyl | 2-iodo-4-methyl-6-(1,1,1,3,3,3-hexafluoro isopropyloxy)pyridin-3-yl |
| 1083 | 2,2,3,3-tetrafluorocyclobutyl | 2-iodo-4-methyl-6-(1,1,1,3,3,3-hexafluoro isopropyloxy)pyridin-3-yl |
| 1084 | 2-chloroethyl | 2-iodo-4-methyl-6-(1,1,1,3,3,3-hexafluoro isopropyloxy)pyridin-3-yl |
| 1085 | 2,2-dichloroethyl | 2-iodo-4-methyl-6-(1,1,1,3,3,3-hexafluoro isopropyloxy)pyridin-3-yl |
| 1086 | 2,2,2-trichloroethyl | 2-iodo-4-methyl-6-(1,1,1,3,3,3-hexafluoro isopropyloxy)pyridin-3-yl |
| 1087 | 1,3-dichloro-2-propyl | 2-iodo-4-methyl-6-(1,1,1,3,3,3-hexafluoro isopropyloxy)pyridin-3-yl |
| 1088 | 3-chloro-n-propyl | 2-iodo-4-methyl-6-(1,1,1,3,3,3-hexafluoro isopropyloxy)pyridin-3-yl |
| 1089 | 2-bromoethyl | 2-iodo-4-methyl-6-(1,1,1,3,3,3-hexafluoro isopropyloxy)pyridin-3-yl |

TABLE 1-continued

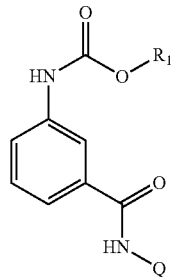

(1-A)

| Compound No. | $R_1$ | Q |
|---|---|---|
| 1090 | 2,2,2-tribromoethyl | 2-iodo-4-methyl-6-(1,1,1,3,3,3-hexafluoro isopropyloxy)pyridin-3-yl |
| 1091 | 3-bromo-n-propyl | 2-iodo-4-methyl-6-(1,1,1,3,3,3-hexafluoro isopropyloxy)pyridin-3-yl |
| 1092 | 2-iodoethyl | 2-iodo-4-methyl-6-(1,1,1,3,3,3-hexafluoro isopropyloxy)pyridin-3-yl |
| 1093 | tetrahydrofuran-3-yl | 2-iodo-4-methyl-6-(1,1,1,3,3,3-hexafluoro isopropyloxy)pyridin-3-yl |
| 1094 | (furan-2-yl)methyl | 2-iodo-4-methyl-6-(1,1,1,3,3,3-hexafluoro isopropyloxy)pyridin-3-yl |
| 1095 | (furan-3-yl)methyl | 2-iodo-4-methyl-6-(1,1,1,3,3,3-hexafluoro isopropyloxy)pyridin-3-yl |
| 1096 | (tetrahydrofuran-2-yl)methyl | 2-iodo-4-methyl-6-(1,1,1,3,3,3-hexafluoro isopropyloxy)pyridin-3-yl |
| 1097 | (tetrahydrofuran-3-yl)methyl | 2-iodo-4-methyl-6-(1,1,1,3,3,3-hexafluoro isopropyloxy)pyridin-3-yl |
| 1098 | (thiophen-2-yl)methyl | 2-iodo-4-methyl-6-(1,1,1,3,3,3-hexafluoro isopropyloxy)pyridin-3-yl |
| 1099 | (thiophen-3-yl)methyl | 2-iodo-4-methyl-6-(1,1,1,3,3,3-hexafluoro isopropyloxy)pyridin-3-yl |
| 1100 | (pyridin-2-yl)methyl | 2-iodo-4-methyl-6-(1,1,1,3,3,3-hexafluoro isopropyloxy)pyridin-3-yl |
| 1101 | (pyridin-3-yl)methyl | 2-iodo-4-methyl-6-(1,1,1,3,3,3-hexafluoro isopropyloxy)pyridin-3-yl |
| 1102 | (6-chloropyridin-3-yl)methyl | 2-iodo-4-methyl-6-(1,1,1,3,3,3-hexafluoro isopropyloxy)pyridin-3-yl |
| 1103 | Et | 2,4-dimethyl-6-(1,1,1,3,3,3-hexafluoro isopropyloxy)pyridin-3-yl |
| 1104 | i-Pr | 2,4-dimethyl-6-(1,1,1,3,3,3-hexafluoro isopropyloxy)pyridin-3-yl |
| 1105 | vinyl | 2,4-dimethyl-6-(1,1,1,3,3,3-hexafluoro isopropyloxy)pyridin-3-yl |
| 1106 | propargyl | 2,4-dimethyl-6-(1,1,1,3,3,3-hexafluoro isopropyloxy)pyridin-3-yl |
| 1107 | cyclobutyl | 2,4-dimethyl-6-(1,1,1,3,3,3-hexafluoro isopropyloxy)pyridin-3-yl |
| 1108 | cyclopentyl | 2,4-dimethyl-6-(1,1,1,3,3,3-hexafluoro isopropyloxy)pyridin-3-yl |
| 1109 | benzyl | 2,4-dimethyl-6-(1,1,1,3,3,3-hexafluoro isopropyloxy)pyridin-3-yl |
| 1110 | 3-cyanobenzyl | 2,4-dimethyl-6-(1,1,1,3,3,3-hexafluoro isopropyloxy)pyridin-3-yl |
| 1111 | 4-cyanobenzyl | 2,4-dimethyl-6-(1,1,1,3,3,3-hexafluoro isopropyloxy)pyridin-3-yl |
| 1112 | 3-chlorobenzyl | 2,4-dimethyl-6-(1,1,1,3,3,3-hexafluoro isopropyloxy)pyridin-3-yl |
| 1113 | 2-methoxyethyl | 2,4-dimethyl-6-(1,1,1,3,3,3-hexafluoro isopropyloxy)pyridin-3-yl |
| 1114 | 2-cyanoethyl | 2,4-dimethyl-6-(1,1,1,3,3,3-hexafluoro isopropyloxy)pyridin-3-yl |
| 1115 | 2-(methylthio)ethyl | 2,4-dimethyl-6-(1,1,1,3,3,3-hexafluoro isopropyloxy)pyridin-3-yl |
| 1116 | 2-(ethylthio)ethyl | 2,4-dimethyl-6-(1,1,1,3,3,3-hexafluoro isopropyloxy)pyridin-3-yl |
| 1117 | 1-methyl-2-(methylthio)ethyl | 2,4-dimethyl-6-(1,1,1,3,3,3-hexafluoro isopropyloxy)pyridin-3-yl |
| 1118 | 2-(ethylsulfinyl)ethyl | 2,4-dimethyl-6-(1,1,1,3,3,3-hexafluoro isopropyloxy)pyridin-3-yl |
| 1119 | 2-(ethylsulfonyl)ethyl | 2,4-dimethyl-6-(1,1,1,3,3,3-hexafluoro isopropyloxy)pyridin-3-yl |
| 1120 | 2-fluoroethyl | 2,4-dimethyl-6-(1,1,1,3,3,3-hexafluoro isopropyloxy)pyridin-3-yl |

TABLE 1-continued (1-A)

| Compound No. | R₁ | Q |
|---|---|---|
| 1121 | 2,2-difluoroethyl | 2,4-dimethyl-6-(1,1,1,3,3,3-hexafluoro isopropyloxy)pyridin-3-yl |
| 1122 | 2,2,2-trifluoroethyl | 2,4-dimethyl-6-(1,1,1,3,3,3-hexafluoro isopropyloxy)pyridin-3-yl |
| 1123 | 1,3-difluoro-2-propyl | 2,4-dimethyl-6-(1,1,1,3,3,3-hexafluoro isopropyloxy)pyridin-3-yl |
| 1124 | 1-chloro-3-fluoro-2-propyl | 2,4-dimethyl-6-(1,1,1,3,3,3-hexafluoro isopropyloxy)pyridin-3-yl |
| 1125 | 1-methyl-2,2,2-trifluoroethyl | 2,4-dimethyl-6-(1,1,1,3,3,3-hexafluoro isopropyloxy)pyridin-3-yl |
| 1126 | 3,3,3-trifluoro-n-propyl | 2,4-dimethyl-6-(1,1,1,3,3,3-hexafluoro isopropyloxy)pyridin-3-yl |
| 1127 | 2,2,3,3,3-pentafluoro-n-propyl | 2,4-dimethyl-6-(1,1,1,3,3,3-hexafluoro isopropyloxy)pyridin-3-yl |
| 1128 | 3,3,4,4,4-pentafluoro-2-butyl | 2,4-dimethyl-6-(1,1,1,3,3,3-hexafluoro isopropyloxy)pyridin-3-yl |
| 1129 | 4,4,4-trifluoro-n-butyl | 2,4-dimethyl-6-(1,1,1,3,3,3-hexafluoro isopropyloxy)pyridin-3-yl |
| 1130 | 2,2,3,3-tetrafluorocyclobutyl | 2,4-dimethyl-6-(1,1,1,3,3,3-hexafluoro isopropyloxy)pyridin-3-yl |
| 1131 | 2-chloroethyl | 2,4-dimethyl-6-(1,1,1,3,3,3-hexafluoro isopropyloxy)pyridin-3-yl |
| 1132 | 2,2-dichloroethyl | 2,4-dimethyl-6-(1,1,1,3,3,3-hexafluoro isopropyloxy)pyridin-3-yl |
| 1133 | 2,2,2-trichloroethyl | 2,4-dimethyl-6-(1,1,1,3,3,3-hexafluoro isopropyloxy)pyridin-3-yl |
| 1134 | 1,3-dichloro-2-propyl | 2,4-dimethyl-6-(1,1,1,3,3,3-hexafluoro isopropyloxy)pyridin-3-yl |
| 1135 | 3-chloron-propyl | 2,4-dimethyl-6-(1,1,1,3,3,3-hexafluoro isopropyloxy)pyridin-3-yl |
| 1136 | 2-bromoethyl | 2,4-dimethyl-6-(1,1,1,3,3,3-hexafluoro isopropyloxy)pyridin-3-yl |
| 1137 | 2,2,2-tribromoethyl | 2,4-dimethyl-6-(1,1,1,3,3,3-hexafluoro isopropyloxy)pyridin-3-yl |
| 1138 | 3-bromo-n-propyl | 2,4-dimethyl-6-(1,1,1,3,3,3-hexafluoro isopropyloxy)pyridin-3-yl |
| 1139 | 2-iodoethyl | 2,4-dimethyl-6-(1,1,1,3,3,3-hexafluoro isopropyloxy)pyridin-3-yl |
| 1140 | tetrahydrofuran-3-yl | 2,4-dimethyl-6-(1,1,1,3,3,3-hexafluoro isopropyloxy)pyridin-3-yl |
| 1141 | (furan-2-yl)methyl | 2,4-dimethyl-6-(1,1,1,3,3,3-hexafluoro isopropyloxy)pyridin-3-yl |
| 1142 | (furan-3-yl)methyl | 2,4-dimethyl-6-(1,1,1,3,3,3-hexafluoro isopropyloxy)pyridin-3-yl |
| 1143 | (tetrahydrofuran-2-yl)methyl | 2,4-dimethyl-6-(1,1,1,3,3,3-hexafluoro isopropyloxy)pyridin-3-yl |
| 1144 | (tetrahydrofuran-3-yl)methyl | 2,4-dimethyl-6-(1,1,1,3,3,3-hexafluoro isopropyloxy)pyridin-3-yl |
| 1145 | (thiophen-2-yl)methyl | 2,4-dimethyl-6-(1,1,1,3,3,3-hexafluoro isopropyloxy)pyridin-3-yl |
| 1146 | (thiophen-3-yl)methyl | 2,4-dimethyl-6-(1,1,1,3,3,3-hexafluoro isopropyloxy)pyridin-3-yl |
| 1147 | (pyridin-2-yl)methyl | 2,4-dimethyl-6-(1,1,1,3,3,3-hexafluoro isopropyloxy)pyridin-3-yl |
| 1148 | (pyridin-3-yl)methyl | 2,4-dimethyl-6-(1,1,1,3,3,3-hexafluoro isopropyloxy)pyridin-3-yl |
| 1149 | (6-chloropyridin-3-yl)methyl | 2,4-dimethyl-6-(1,1,1,3,3,3-hexafluoro isopropyloxy)pyridin-3-yl |
| 1150 | Et | 2-bromo-4-methyl-6-(heptafluoro isopropyl)pyridin-3-yl |
| 1151 | i-Pr | 2-bromo-4-methyl-6-(heptafluoro isopropyl)pyridin-3-yl |

TABLE 1-continued (1-A)

| Compound No. | R₁ | Q |
|---|---|---|
| 1152 | vinyl | 2-bromo-4-methyl-6-(heptafluoro isopropyl)pyridin-3-yl |
| 1153 | propargyl | 2-bromo-4-methyl-6-(heptafluoro isopropyl)pyridin-3-yl |
| 1154 | cyclobutyl | 2-bromo-4-methyl-6-(heptafluoro isopropyl)pyridin-3-yl |
| 1155 | cyclopentyl | 2-bromo-4-methyl-6-(heptafluoro isopropyl)pyridin-3-yl |
| 1156 | benzyl | 2-bromo-4-methyl-6-(heptafluoro isopropyl)pyridin-3-yl |
| 1157 | 3-cyanobenzyl | 2-bromo-4-methyl-6-(heptafluoro isopropyl)pyridin-3-yl |
| 1158 | 4-cyanobenzyl | 2-bromo-4-methyl-6-(heptafluoro isopropyl)pyridin-3-yl |
| 1159 | 3-chlorobenzyl | 2-bromo-4-methyl-6-(heptafluoro isopropyl)pyridin-3-yl |
| 1160 | 2-methoxyethyl | 2-bromo-4-methyl-6-(heptafluoro isopropyl)pyridin-3-yl |
| 1161 | 2-cyanoethyl | 2-bromo-4-methyl6-(heptafluoro isopropyl)pyridin-3-yl |
| 1162 | 2-(methylthio)ethyl | 2-bromo-4-methyl-6-(heptafluoro isopropyl)pyridin-3-yl |
| 1163 | 2-(ethylthio)ethyl | 2-bromo-4-methyl-6-(heptafluoro isopropyl)pyridin-3-yl |
| 1164 | 1-methyl-2-(methylthio)ethyl | 2-bromo-4-methyl-6-(heptafluoro isopropyl)pyridin-3-yl |
| 1165 | 2-(ethylsulfinyl)ethyl | 2-bromo-4-methyl-6-(heptafluoro isopropyl)pyridin-3-yl |
| 1166 | 2-(ethylsulfonyl)ethyl | 2-bromo-4-methyl-6-(heptafluoro isopropyl)pyridin-3-yl |
| 1167 | 2-fluoroethyl | 2-bromo-4-methyl-6-(heptafluoro isopropyl)pyridin-3-yl |
| 1168 | 2,2-difluoroethyl | 2-bromo-4-methyl-6-(heptafluoro isopropyl)pyridin-3-yl |
| 1169 | 2,2,2-trifluoroethyl | 2-bromo-4-methyl-6-(heptafluoro isopropyl)pyridin-3-yl |
| 1170 | 1,3-difluoro-2-propyl | 2-bromo-4-methyl-6-(heptafluoro isopropyl)pyridin-3-yl |
| 1171 | 1-chloro-3-fluoro-2-propyl | 2-bromo-4-methyl-6-(heptafluoro isopropyl)pyridin-3-yl |
| 1172 | 1-methyl-2,2,2-trifluoroethyl | 2-bromo-4-methyl-6-(heptafluoro isopropyl)pyridin-3-yl |
| 1173 | 3,3,3-trifluoro-n-propyl | 2-bromo-4-methyl-6-(heptafluoro isopropyl)pyridin-3-yl |
| 1174 | 2,2,3,3,3-pentafluoro-n-propyl | 2-bromo-4-methyl-6-(heptafluoro isopropyl)pyridin-3-yl |
| 1175 | 3,3,4,4,4-pentafluoro-2-butyl | 2-bromo-4-methyl-6-(heptafluoro isopropyl)pyridin-3-yl |
| 1176 | 4,4,4-trifluoro-n-butyl | 2-bromo-4-methyl-6-(heptafluoro isopropyl)pyridin-3-yl |
| 1177 | 2,2,3,3-tetrafluorocyclobutyl | 2-bromo-4-methyl-6-(heptafluoro isopropyl)pyridin-3-yl |
| 1178 | 2-chloroethyl | 2-bromo-4-methyl-6-(heptafluoro isopropyl)pyridin-3-yl |
| 1179 | 2,2-dichloroethyl | 2-bromo-4-methyl-6-(heptafluoro isopropyl)pyridin-3-yl |
| 1180 | 2,2,2-trichloroethyl | 2-bromo-4-methyl-6-(heptafluoro isopropyl)pyridin-3-yl |
| 1181 | 1,3-dichloro-2-propyl | 2-bromo-4-methyl-6-(heptafluoro isopropyl)pyridin-3-yl |
| 1182 | 3-chloro-n-propyl | 2-bromo-4-methyl-6-(heptafluoro isopropyl)pyridin-3-yl |

TABLE 1-continued (1-A)

| Compound No. | R₁ | Q |
|---|---|---|
| 1183 | 2-bromoethyl | 2-bromo-4-methyl-6-(heptafluoro isopropyl)pyridin-3-yl |
| 1184 | 2,2,2-tribromoethyl | 2-bromo-4-methyl-6-(heptafluoro isopropyl)pyridin-3-yl |
| 1185 | 3-bromo-n-propyl | 2-bromo-4-methyl-6-(heptafluoro isopropyl)pyridin-3-yl |
| 1186 | 2-iodoethyl | 2-bromo-4-methyl-6-(heptafluoro isopropyl)pyridin-3-yl |
| 1187 | tetrahydrofuran-3-yl | 2-bromo-4-methyl-6-(heptafluoro isopropyl)pyridin-3-yl |
| 1188 | (furan-2-yl)methyl | 2-bromo-4-methyl-6-(heptafluoro isopropyl)pyridin-3-yl |
| 1189 | (furan-3-yl)methyl | 2-bromo-4-methyl-6-(heptafluoro isopropyl)pyridin-3-yl |
| 1190 | (tetrahydrofuran-2-yl)methyl | 2-bromo-4-methyl-6-(heptafluoro isopropyl)pyridin-3-yl |
| 1191 | (tetrahydrofuran-3-yl)methyl | 2-bromo-4-methyl-6-(heptafluoro isopropyl)pyridin-3-yl |
| 1192 | (thiophen-2-yl)methyl | 2-bromo-4-methyl-6-(heptafluoro isopropyl)pyridin-3-yl |
| 1193 | (thiophen-3-yl)methyl | 2-bromo-4-methyl-6-(heptafluoro isopropyl)pyridin-3-yl |
| 1194 | (pyridin-2-yl)methyl | 2-bromo-4-methyl-6-(heptafluoro isopropyl)pyridin-3-yl |
| 1195 | (pyridin-3-yl)methyl | 2-bromo-4-methyl-6-(heptafluoro isopropyl)pyridin-3-yl |
| 1196 | (6-chloropyridin-3-yl)methyl | 2-bromo-4-methyl-6-(heptafluoro isopropyl)pyridin-3-yl |
| 1197 | Et | 2-chloro-6-methyl-4-heptafluoroisopropylphenyl |
| 1198 | i-Pr | 2-chloro-6-methyl-4-heptafluoroisopropylphenyl |
| 1199 | vinyl | 2-chloro-6-methyl-4-heptafluoroisopropylphenyl |
| 1200 | propargyl | 2-chloro-6-methyl-4-heptafluoroisopropylphenyl |
| 1201 | cyclobutyl | 2-chloro-6-methyl-4-heptafluoroisopropylphenyl |
| 1202 | cyclopentyl | 2-chloro-6-methyl-4-heptafluoroisopropylphenyl |
| 1203 | benzyl | 2-chloro-6-methyl-4-heptafluoroisopropylphenyl |
| 1204 | 3-cyanobenzyl | 2-chloro-6-methyl-4-heptafluoroisopropylphenyl |
| 1205 | 4-cyanobenzyl | 2-chloro-6-methyl-4-heptafluoroisopropylphenyl |
| 1206 | 3-chlorobenzyl | 2-chloro-6-methyl-4-heptafluoroisopropylphenyl |
| 1207 | 2-methoxyethyl | 2-chloro-6-methyl-4-heptafluoroisopropylphenyl |
| 1208 | 2-cyanoethyl | 2-chloro-6-methyl-4-heptafluoroisopropylphenyl |
| 1209 | 2-(methylthio)ethyl | 2-chloro-6-methyl-4-heptafluoroisopropylphenyl |
| 1210 | 2-(ethylthio)ethyl | 2-chloro-6-methyl-4-heptafluoroisopropylphenyl |
| 1211 | 1-methyl-2-(methylthio)ethyl | 2-chloro-6-methyl-4-heptafluoroisopropylphenyl |
| 1212 | 2-(ethylsulfinyl)ethyl | 2-chloro-6-methyl-4-heptafluoroisopropylphenyl |
| 1213 | 2-(ethylsulfonyl)ethyl | 2-chloro-6-methyl-4-heptafluoroisopropylphenyl |
| 1214 | 2-fluoroethyl | 2-chloro-6-methyl-4-heptafluoroisopropylphenyl |
| 1215 | 2,2-difluoroethyl | 2-chloro-6-methyl-4-heptafluoroisopropylphenyl |
| 1216 | 2,2,2-trifluoroethyl | 2-chloro-6-methyl-4-heptafluoroisopropylphenyl |
| 1217 | 1,3-difluoro-2-propyl | 2-chloro-6-methyl-4-heptafluoroisopropylphenyl |
| 1218 | 1-chloro3-fluoro-2-propyl | 2-chloro-6-methyl-4-heptafluoroisopropylphenyl |
| 1219 | 1-methyl-2,2,2-trifluoroethyl | 2-chloro-6-methyl-4-heptafluoroisopropylphenyl |
| 1220 | 3,3,3-trifluoro-n-propyl | 2-chloro-6-methyl-4-heptafluoroisopropylphenyl |
| 1221 | 2,2,3,3,3-pentafluoro-n-propyl | 2-chloro-6-methyl-4-heptafluoroisopropylphenyl |
| 1222 | 3,3,4,4,4-pentafluoro-2-butyl | 2-chloro-6-methyl-4-heptafluoroisopropylphenyl |
| 1223 | 4,4,4-trifluoro-n-butyl | 2-chloro-6-methyl-4-heptafluoroisopropylphenyl |
| 1224 | 2,2,3,3-tetrafluorocyclobutyl | 2-chloro-6-methyl-4-heptafluoroisopropylphenyl |
| 1225 | 2-chloroethyl | 2-chloro-6-methyl-4-heptafluoroisopropylphenyl |
| 1226 | 2,2-dichloroethyl | 2-chloro-6-methyl-4-heptafluoroisopropylphenyl |
| 1227 | 2,2,2-trichloroethyl | 2-chloro-6-methyl-4-heptafluoroisopropylphenyl |
| 1228 | 1,3-dichloro-2-propyl | 2-chloro-6-methyl-4-heptafluoroisopropylphenyl |
| 1229 | 3-chloro-n-propyl | 2-chloro-6-methyl-4-heptafluoroisopropylphenyl |
| 1230 | 2-bromoethyl | 2-chloro-6-methyl-4-heptafluoroisopropylphenyl |
| 1231 | 2,2,2-tribromoethyl | 2-chloro-6-methyl-4-heptafluoroisopropylphenyl |

TABLE 1-continued (1-A)

| Compound No. | R₁ | Q |
|---|---|---|
| 1232 | 3-bromo-n-propyl | 2-chloro-6-methyl-4-heptafluoroisopropylphenyl |
| 1233 | 2-iodoethyl | 2-chloro-6-methyl-4-heptafluoroisopropylphenyl |
| 1234 | tetrahydrofuran-3-yl | 2-chloro-6-methyl-4-heptafluoroisopropylphenyl |
| 1235 | (furan-2-yl)methyl | 2-chloro-6-methyl-4-heptafluoroisopropylphenyl |
| 1236 | (furan-3-yl)methyl | 2-chloro-6-methyl-4-heptafluoroisopropylphenyl |
| 1237 | (tetrahydrofuran-2-yl)methyl | 2-chloro-6-methyl-4-heptafluoroisopropylphenyl |
| 1238 | (tetrahydrofuran-3-yl)methyl | 2-chloro-6-methyl-4-heptafluoroisopropylphenyl |
| 1239 | (thiophen-2-yl)methyl | 2-chloro-6-methyl-4-heptafluoroisopropylphenyl |
| 1240 | (thiophen-3-yl)methyl | 2-chloro-6-methyl-4-heptafluoroisopropylphenyl |
| 1241 | (pyridin-2-yl)methyl | 2-chloro-6-methyl-4-heptafluoroisopropylphenyl |
| 1242 | (pyridin-3-yl)methyl | 2-chloro-6-methyl-4-heptafluoroisopropylphenyl |
| 1243 | (6-chloropyridin-3-yl)methyl | 2-chloro-6-methyl-4-heptafluoroisopropylphenyl |
| 1244 | Et | 2-bromo-6-methyl-4-heptafluoroisopropylphenyl |
| 1245 | i-Pr | 2-bromo-6-methyl-4-heptafluoroisopropylphenyl |
| 1246 | vinyl | 2-bromo-6-methyl-4-heptafluoroisopropylphenyl |
| 1247 | propargyl | 2-bromo-6-methyl-4-heptafluoroisopropylphenyl |
| 1248 | cyclobutyl | 2-bromo-6-methyl-4-heptafluoroisopropylphenyl |
| 1249 | cyclopentyl | 2-bromo-6-methyl-4-heptafluoroisopropylphenyl |
| 1250 | benzyl | 2-bromo-6-methyl-4-heptafluoroisopropylphenyl |
| 1251 | 3-cyanobenzyl | 2-bromo-6-methyl-4-heptafluoroisopropylphenyl |
| 1252 | 4-cyanobenzyl | 2-bromo-6-methyl-4-heptafluoroisopropylphenyl |
| 1253 | 3-chlorobenzyl | 2-bromo-6-methyl-4-heptafluoroisopropylphenyl |
| 1254 | 2-methoxyethyl | 2-bromo-6-methyl-4-heptafluoroisopropylphenyl |
| 1255 | 2-cyanoethyl | 2-bromo-6-methyl-4-heptafluoroisopropylphenyl |
| 1256 | 2-(methylthio)ethyl | 2-bromo-6-methyl-4-heptafluoroisopropylphenyl |
| 1257 | 2-(ethylthio)ethyl | 2-bromo-6-methyl-4-heptafluoroisopropylphenyl |
| 1258 | 1-methyl-2-(methylthio)ethyl | 2-bromo-6-methyl-4-heptafluoroisopropylphenyl |
| 1259 | 2-(ethylsulfinyl)ethyl | 2-bromo-6-methyl-4-heptafluoroisopropylphenyl |
| 1260 | 2-(ethylsulfonyl)ethyl | 2-bromo-6-methyl-4-heptafluoroisopropylphenyl |
| 1261 | 2-fluoroethyl | 2-bromo-6-methyl-4-heptafluoroisopropylphenyl |
| 1262 | 2,2-difluoroethyl | 2-bromo-6-methyl-4-heptafluoroisopropylphenyl |
| 1263 | 2,2,2-trifluoroethyl | 2-bromo-6-methyl-4-heptafluoroisopropylphenyl |
| 1264 | 1,3-difluoro-2-propyl | 2-bromo-6-methyl-4-heptafluoroisopropylphenyl |
| 1265 | 1-chloro-3-fluoro-2-propyl | 2-bromo-6-methyl-4-heptafluoroisopropylphenyl |
| 1266 | 1-methyl-2,2,2-trifluoroethyl | 2-bromo-6-methyl-4-heptafluoroisopropylphenyl |
| 1267 | 3,3,3-trifluoro-n-propyl | 2-bromo-6-methyl-4-heptafluoroisopropylphenyl |
| 1268 | 2,2,3,3,3-pentafluoro-n-propyl | 2-bromo-6-methyl-4-heptafluoroisopropylphenyl |
| 1269 | 3,3,4,4,4-pentafluoro-2-butyl | 2-bromo-6-methyl-4-heptafluoroisopropylphenyl |
| 1270 | 4,4,4-trifluoro-n-butyl | 2-bromo-6-methyl-4-heptafluoroisopropylphenyl |
| 1271 | 2,2,3,3-tetrafluorocyclobutyl | 2-bromo-6-methyl-4-heptafluoroisopropylphenyl |
| 1272 | 2-chloroethyl | 2-bromo-6-methyl-4-heptafluoroisopropylphenyl |
| 1273 | 2,2-dichloroethyl | 2-bromo-6-methyl-4-heptafluoroisopropylphenyl |
| 1274 | 2,2,2-trichloroethyl | 2-bromo-6-methyl-4-heptafluoroisopropylphenyl |
| 1275 | 1,3-dichloro-2-propyl | 2-bromo-6-methyl-4-heptafluoroisopropylphenyl |
| 1276 | 3-chloro-n-propyl | 2-bromo-6-methyl-4-heptafluoroisopropylphenyl |
| 1277 | 2-bromoethyl | 2-bromo-6-methyl-4-heptafluoroisopropylphenyl |
| 1278 | 2,2,2-tribromoethyl | 2-bromo-6-methyl-4-heptafluoroisopropylphenyl |
| 1279 | 3-bromo-n-propyl | 2-bromo-6-methyl-4-heptafluoroisopropylphenyl |
| 1280 | 2-iodoethyl | 2-bromo-6-methyl-4-heptafluoroisopropylphenyl |
| 1281 | tetrahydrofuran-3-yl | 2-bromo-6-methyl-4-heptafluoroisopropylphenyl |
| 1282 | (furan-2-yl)methyl | 2-bromo-6-methyl-4-heptafluoroisopropylphenyl |
| 1283 | (furan-3-yl)methyl | 2-bromo-6-methyl-4-heptafluoroisopropylphenyl |
| 1284 | (tetrahydrofuran-2-yl)methyl | 2-bromo-6-methyl-4-heptafluoroisopropylphenyl |
| 1285 | (tetrahydrofuran-3-yl)methyl | 2-bromo-6-methyl-4-heptafluoroisopropylphenyl |
| 1286 | (thiophen-2-yl)methyl | 2-bromo-6-methyl-4-heptafluoroisopropylphenyl |
| 1287 | (thiophen-3-yl)methyl | 2-bromo-6-methyl-4-heptafluoroisopropylphenyl |
| 1288 | (pyridin-2-yl)methyl | 2-bromo-6-methyl-4-heptafluoroisopropylphenyl |
| 1289 | (pyridin-3-yl)methyl | 2-bromo-6-methyl-4-heptafluoroisopropylphenyl |
| 1290 | (6-chloropyridin-3-yl)methyl | 2-bromo-6-methyl-4-heptafluoroisopropylphenyl |
| 1291 | Et | 2-iodo-6-methyl-4-heptafluoroisopropylphenyl |
| 1292 | i-Pr | 2-iodo-6-methyl-4-heptafluoroisopropylphenyl |
| 1293 | vinyl | 2-iodo-6-methyl-4-heptafluoroisopropylphenyl |
| 1294 | propargyl | 2-iodo-6-methyl-4-heptafluoroisopropylphenyl |

TABLE 1-continued

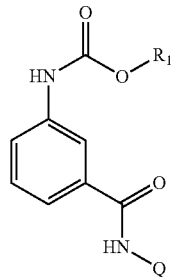

(1-A)

| Compound No. | R₁ | Q |
| --- | --- | --- |
| 1295 | cyclobutyl | 2-iodo-6-methyl-4-heptafluoroisopropylphenyl |
| 1296 | cyclopentyl | 2-iodo-6-methyl-4-heptafluoroisopropylphenyl |
| 1297 | benzyl | 2-iodo-6-methyl-4-heptafluoroisopropylphenyl |
| 1298 | 3-cyanobenzyl | 2-iodo-6-methyl-4-heptafluoroisopropylphenyl |
| 1299 | 4-cyanobenzyl | 2-iodo-6-methyl-4-heptafluoroisopropylphenyl |
| 1300 | 3-chlorobenzyl | 2-iodo-6-methyl-4-heptafluoroisopropylphenyl |
| 1301 | 2-methoxyethyl | 2-iodo-6-methyl-4-heptafluoroisopropylphenyl |
| 1302 | 2-cyanoethyl | 2-iodo-6-methyl-4-heptafluoroisopropylphenyl |
| 1303 | 2-(methylthio)ethyl | 2-iodo-6-methyl-4-heptafluoroisopropylphenyl |
| 1304 | 2-(ethylthio)ethyl | 2-iodo-6-methyl-4-heptafluoroisopropylphenyl |
| 1305 | 1-methyl-2-(methylthio)ethyl | 2-iodo-6-methyl-4-heptafluoroisopropylphenyl |
| 1306 | 2-(ethylsulfinyl)ethyl | 2-iodo-6-methyl-4-heptafluoroisopropylphenyl |
| 1307 | 2-(ethylsulfonyl)ethyl | 2-iodo-6-methyl-4-heptafluoroisopropylphenyl |
| 1308 | 2-fluoroethyl | 2-iodo-6-methyl-4-heptafluoroisopropylphenyl |
| 1309 | 2,2-difluoroethyl | 2-iodo-6-methyl-4-heptafluoroisopropylphenyl |
| 1310 | 2,2,2-trifluoroethyl | 2-iodo-6-methyl-4-heptafluoroisopropylphenyl |
| 1311 | 1,3-difluoro-2-propyl | 2-iodo-6-methyl-4-heptafluoroisopropylphenyl |
| 1312 | 1-chloro-3-fluoro-2-propyl | 2-iodo-6-methyl-4-heptafluoroisopropylphenyl |
| 1313 | 1-methyl-2,2,2-trifluoroethyl | 2-iodo-6-methyl-4-heptafluoroisopropylphenyl |
| 1314 | 3,3,3-trifluoro-n-propyl | 2-iodo-6-methyl-4-heptafluoroisopropylphenyl |
| 1315 | 2,2,3,3,3-pentafluoro-n-propyl | 2-iodo-6-methyl-4-heptafluoroisopropylphenyl |
| 1316 | 3,3,4,4,4-pentafluoro-2-butyl | 2-iodo-6-methyl-4-heptafluoroisopropylphenyl |
| 1317 | 4,4,4-trifluoro-n-butyl | 2-iodo-6-methyl-4-heptafluoroisopropylphenyl |
| 1318 | 2,2,3,3-tetrafluorocyclobutyl | 2-iodo-6-methyl-4-heptafluoroisopropylphenyl |
| 1319 | 2-chloroethyl | 2-iodo-6-methyl-4-heptafluoroisopropylphenyl |
| 1320 | 2,2-dichloroethyl | 2-iodo-6-methyl-4-heptafluoroisopropylphenyl |
| 1321 | 2,2,2-trichloroethyl | 2-iodo-6-methyl-4-heptafluoroisopropylphenyl |
| 1322 | 1,3-dichloro-2-propyl | 2-iodo-6-methyl-4-heptafluoroisopropylphenyl |
| 1323 | 3-chloro-n-propyl | 2-iodo-6-methyl-4-heptafluoroisopropylphenyl |
| 1324 | 2-bromoethyl | 2-iodo-6-methyl-4-heptafluoroisopropylphenyl |
| 1325 | 2,2,2-tribromoethyl | 2-iodo-6-methyl-4-heptafluoroisopropylphenyl |
| 1326 | 3-bromo-n-propyl | 2-iodo-6-methyl-4-heptafluoroisopropylphenyl |
| 1327 | 2-iodoethyl | 2-iodo-6-methyl-4-heptafluoroisopropylphenyl |
| 1328 | tetrahydrofuran-3-yl | 2-iodo-6-methyl-4-heptafluoroisopropylphenyl |
| 1329 | (furan-2-yl)methyl | 2-iodo-6-methyl-4-heptafluoroisopropylphenyl |
| 1330 | (furan-3-yl)methyl | 2-iodo-6-methyl-4-heptafluoroisopropylphenyl |
| 1331 | (tetrahydrofuran-2-yl)methyl | 2-iodo-6-methyl-4-heptafluoroisopropylphenyl |
| 1332 | (tetrahydrofuran-3-yl)methyl | 2-iodo-6-methyl-4-heptafluoroisopropylphenyl |
| 1333 | (thiophen-2-yl)methyl | 2-iodo-6-methyl-4-heptafluoroisopropylphenyl |
| 1334 | (thiophen-3-yl)methyl | 2-iodo-6-methyl-4-heptafluoroisopropylphenyl |
| 1335 | (pyridin-2-yl)methyl | 2-iodo-6-methyl-4-heptafluoroisopropylphenyl |
| 1336 | (pyridin-3-yl)methyl | 2-iodo-6-methyl-4-heptafluoroisopropylphenyl |
| 1337 | (6-chloropyridin-3-yl)methyl | 2-iodo-6-methyl-4-heptafluoroisopropylphenyl |
| 1338 | Et | 2-iodo-6-n-propyl-4-heptafluoro isopropylphenyl |
| 1339 | i-Pr | 2-iodo-6-n-propyl-4-heptafluoro isopropylphenyl |
| 1340 | vinyl | 2-iodo-6-n-propyl-4-heptafluoro isopropylphenyl |
| 1341 | propargyl | 2-iodo-6-n-propyl-4-heptafluoro isopropylphenyl |
| 1342 | cyclobutyl | 2-iodo-6-n-propyl-4-heptafluoro isopropylphenyl |
| 1343 | cyclopentyl | 2-iodo-6-n-propyl-4-heptafluoro isopropylphenyl |
| 1344 | benzyl | 2-iodo-6-n-propyl-4-heptafluoro isopropylphenyl |
| 1345 | 3-cyanobenzyl | 2-iodo-6-n-propyl-4-heptafluoro isopropylphenyl |
| 1346 | 4-cyanobenzyl | 2-iodo-6-n-propyl-4-heptafluoro isopropylphenyl |
| 1347 | 3-chlorobenzyl | 2-iodo-6-n-propyl-4-heptafluoro isopropylphenyl |

TABLE 1-continued (1-A)

| Compound No. | R₁ | Q |
|---|---|---|
| 1348 | 2-methoxyethyl | 2-iodo-6-n-propyl-4-heptafluoroisopropylphenyl |
| 1349 | 2-cyanoethyl | 2-iodo-6-n-propyl-4-heptafluoroisopropylphenyl |
| 1350 | 2-(methylthio)ethyl | 2-iodo-6-n-propyl-4-heptafluoroisopropylphenyl |
| 1351 | 2-(ethylthio)ethyl | 2-iodo-6-n-propyl-4-heptafluoroisopropylphenyl |
| 1352 | 1-methyl-2-(methylthio)ethyl | 2-iodo-6-n-propyl-4-heptafluoroisopropylphenyl |
| 1353 | 2-(ethylsulfinyl)ethyl | 2-iodo-6-n-propyl-4-heptafluoroisopropylphenyl |
| 1354 | 2-(ethylsulfonyl)ethyl | 2-iodo-6-n-propyl-4-heptafluoroisopropylphenyl |
| 1355 | 2-fluoroethyl | 2-iodo-6-n-propyl-4-heptafluoroisopropylphenyl |
| 1356 | 2,2-difluoroethyl | 2-iodo-6-n-propyl-4-heptafluoroisopropylphenyl |
| 1357 | 2,2,2-trifluoroethyl | 2-iodo-6-n-propyl-4-heptafluoroisopropylphenyl |
| 1358 | 1,3-difluoro-2-propyl | 2-iodo-6-n-propyl-4-heptafluoroisopropylphenyl |
| 1359 | 1-chloro3-fluoro-2-propyl | 2-iodo-6-n-propyl-4-heptafluoroisopropylphenyl |
| 1360 | 1-methyl-2,2,2-trifluoroethyl | 2-iodo-6-n-propyl-4-heptafluoroisopropylphenyl |
| 1361 | 3,3,3-trifluoro-n-propyl | 2-iodo-6-n-propyl-4-heptafluoroisopropylphenyl |
| 1362 | 2,2,3,3,3-pentafluoro-n-propyl | 2-iodo-6-n-propyl-4-heptafluoroisopropylphenyl |
| 1363 | 3,3,4,4,4-pentafluoro-2-butyl | 2-iodo-6-n-propyl-4-heptafluoroisopropylphenyl |
| 1364 | 4,4,4-trifluoro-n-butyl | 2-iodo-6-n-propyl-4-heptafluoroisopropylphenyl |
| 1365 | 2,2,3,3-tetrafluorocyclobutyl | 2-iodo-6-n-propyl-4-heptafluoroisopropylphenyl |
| 1366 | 2-chloroethyl | 2-iodo-6-n-propyl-4-heptafluoroisopropylphenyl |
| 1367 | 2,2-dichloroethyl | 2-iodo-6-n-propyl-4-heptafluoroisopropylphenyl |
| 1368 | 2,2,2-trichloroethyl | 2-iodo-6-n-propyl-4-heptafluoroisopropylphenyl |
| 1369 | 1,3-dichloro-2-propyl | 2-iodo-6-n-propyl-4-heptafluoroisopropylphenyl |
| 1370 | 3-chloro-n-propyl | 2-iodo-6-n-propyl-4-heptafluoroisopropylphenyl |
| 1371 | 2-bromoethyl | 2-iodo-6-n-propyl-4-heptafluoroisopropylphenyl |
| 1372 | 2,2,2-tribromoethyl | 2-iodo-6-n-propyl-4-heptafluoroisopropylphenyl |
| 1373 | 3-bromo-n-propyl | 2-iodo-6-n-propyl-4-heptafluoroisopropylphenyl |
| 1374 | 2-iodoethyl | 2-iodo-6-n-propyl-4-heptafluoroisopropylphenyl |
| 1375 | tetrahydrofuran-3-yl | 2-iodo-6-n-propyl-4-heptafluoroisopropylphenyl |
| 1376 | (furan-2-yl)methyl | 2-iodo-6-n-propyl-4-heptafluoroisopropylphenyl |
| 1377 | (furan-3-yl)methyl | 2-iodo-6-n-propyl-4-heptafluoroisopropylphenyl |
| 1378 | (tetrahydrofuran-2-yl)methyl | 2-iodo-6-n-propyl-4-heptafluoroisopropylphenyl |

TABLE 1-continued (1-A)

| Compound No. | R₁ | Q |
|---|---|---|
| 1379 | (tetrahydrofuran-3-yl)methyl | 2-iodo-6-n-propyl-4-heptafluoro isopropylphenyl |
| 1380 | (thiophen-2-yl)methyl | 2-iodo-6-n-propyl-4-heptafluoro isopropylphenyl |
| 1381 | (thiophen-3-yl)methyl | 2-iodo-6-n-propyl-4-heptafluoro isopropylphenyl |
| 1382 | (pyridin-2-yl)methyl | 2-iodo-6-n-propyl-4-heptafluoro isopropylphenyl |
| 1383 | (pyridin-3-yl)methyl | 2-iodo-6-n-propyl-4-heptafluoro isopropylphenyl |
| 1384 | (6-chloropyridin-3-yl)methyl | 2-iodo-6-n-propyl-4-heptafluoro isopropylphenyl |

TABLE 2

(1-B)

| Compound No. | $X_1$ | $X_2$ | $X_3$ | $X_4$ | R₁ | Q |
|---|---|---|---|---|---|---|
| 1385 | Me | H | H | H | 2,2,2-trichloroethyl | 2-methyl-4-heptafluoroisopropyl phenyl |
| 1386 | Me | H | H | H | i-Pr | 2,6-dimethy-4-heptafluoroisopropyl phenyl |
| 1387 | Me | H | H | H | 2,2,2-trichloroethyl | 2,6-dimethyl-4-heptafluoroisopropyl phenyl |
| 1388 | F | H | H | H | Et | 2,6-dimethyl-4-heptafluoroisopropyl phenyl |
| 1389 | F | H | H | H | i-Pr | 2,6-dimethyl-4-heptafluoroisopropyl phenyl |
| 1390 | F | H | H | H | vinyl | 2,6-dimethyl-4-heptafluoroisopropyl phenyl |
| 1391 | F | H | H | H | propargyl | 2,6-dimethyl-4-heptafluoroisopropyl phenyl |
| 1392 | F | H | H | H | cyclobutyl | 2,6-dimethyl-4-heptafluoroisopropyl phenyl |
| 1393 | F | H | H | H | cyclopentyl | 2,6-dimethyl-4-heptafluoroisopropyl phenyl |
| 1394 | F | H | H | H | benzyl | 2,6-dimethyl-4-heptafluoroisopropyl phenyl |
| 1395 | F | H | H | H | 3-cyanobenzyl | 2,6-dimethyl-4-heptafluoroisopropyl phenyl |
| 1396 | F | H | H | H | 4-cyanobenzyl | 2,6-dimethyl-4-heptafluoroisopropyl phenyl |
| 1397 | F | H | H | H | 3-chlorobenzyl | 2,6-dimethyl-4-heptafluoroisopropyl phenyl |
| 1398 | F | H | H | H | 2-methoxyethyl | 2,6-dimethyl-4-heptafluoroisopropyl phenyl |

TABLE 2-continued (1-B)

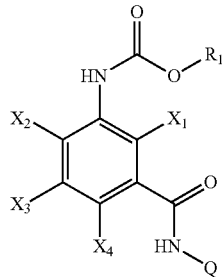

| Compound No. | X₁ | X₂ | X₃ | X₄ | R₁ | Q |
|---|---|---|---|---|---|---|
| 1399 | F | H | H | H | 2-cyanoethyl | 2,6-dimethyl-4-heptafluoroisopropyl phenyl |
| 1400 | F | H | H | H | 2-(methylthio)ethyl | 2,6-dimethyl-4-heptafluoroisopropyl phenyl |
| 1401 | F | H | H | H | 2-(ethylthi)ethyl | 2,6-dimethyl-4-heptafluoroisopropylphenyl |
| 1402 | F | H | H | H | 1-methyl-2-(methylthio)-ethyl | 2,6-dimethyl-4-heptafluoroisopropylphenyl |
| 1403 | F | H | H | H | 2-(ethylsulfinyl)ethyl | 2,6-dimethyl-4-heptafluoroisopropylphenyl |
| 1404 | F | H | H | H | 2-(ethylsulfonyl)ethyl | 2,6-dimethyl-4-heptafluoroisopropylphenyl |
| 1405 | F | H | H | H | 2-fluoroethyl | 2,6-dimethyl-4-heptafluoroisopropylphenyl |
| 1406 | F | H | H | H | 2,2-difluoroethyl | 2,6-dimethyl-4-heptafluoroisopropylphenyl |
| 1407 | F | H | H | H | 2,2,2-trifluoroethyl | 2,6-dimethyl-4-heptafluoroisopropylphenyl |
| 1408 | F | H | H | H | 1,3-difluoro-2-propyl | 2,6-dimethyl-4-heptafluoroisopropylphenyl |
| 1409 | F | H | H | H | 1-chloro-3-fluoro-2-propyl | 2,6-dimethyl-4-heptafluoroisopropylphenyl |
| 1410 | F | H | H | H | 1-methyl-2,2,2-trifluoro ethyl | 2,6-dimethyl-4-heptafluoroisopropylphenyl |
| 1411 | F | H | H | H | 3,3,3-trifluoro-n-propyl | 2,6-dimethyl-4-heptafluoroisopropylphenyl |
| 1412 | F | H | H | H | 2,2,3,3,3-pentafluoro-n-propyl | 2,6-dimethyl-4-heptafluoroisopropylphenyl |
| 1413 | F | H | H | H | 3,3,4,4,4-pentafluoro-2-butyl | 2,6-dimethyl-4-heptafluoroisopropylphenyl |
| 1414 | F | H | H | H | 4,4,4-trifluoro-n-butyl | 2,6-dimethyl-4-heptafluoroisopropylphenyl |
| 1415 | F | H | H | H | 2,2,3,3-tetrafluoro cyclobutyl | 2,6-dimethyl-4-heptafluoroisopropylphenyl |
| 1416 | F | H | H | H | 2-chloroethyl | 2,6-dimethyl-4-heptafluoroisopropylphenyl |
| 1417 | F | H | H | H | 2,2-dichloroethyl | 2,6-dimethyl-4-heptafluoroisopropylphenyl |
| 1418 | F | H | H | H | 2,2,2-trichloroethyl | 2,6-dimethyl-4-heptafluoroisopropylphenyl |
| 1419 | F | H | H | H | 1,3-dichloro-2-propyl | 2,6-dimethyl-4-heptafluoroisopropylphenyl |
| 1420 | F | H | H | H | 3-chloro-n-propyl | 2,6-dimethyl-4-heptafluoroisopropylphenyl |
| 1421 | F | H | H | H | 2-bromoethyl | 2,6-dimethyl-4-heptafluoroisopropylphenyl |
| 1422 | F | H | H | H | 2,2,2-tribromoethyl | 2,6-dimethyl-4-heptafluoroisopropylphenyl |
| 1423 | F | H | H | H | 3-bromo-n-propyl | 2,6-dimethyl-4-heptafluoroisopropylphenyl |
| 1424 | F | H | H | H | 2-idoethyl | 2,6-dimethyl-4-heptafluoroisopropylphenyl |
| 1425 | F | H | H | H | tetrahydrofuran-3-yl | 2,6-dimethyl-4-heptafluoroisopropylphenyl |
| 1426 | F | H | H | H | (furan-2-yl)methyl | 2,6-dimethyl-4-heptafluoroisopropylphenyl |
| 1427 | F | H | H | H | (furan-3-yl)methyl | 2,6-dimethyl-4-heptafluoroisopropylphenyl |
| 1428 | F | H | H | H | (tetrahydrofuran-2-yl)methyl | 2,6-dimethyl-4-heptafluoroisopropylphenyl |
| 1429 | F | H | H | H | (tetrahydrofuran-3-yl)methyl | 2,6-dimethyl-4-heptafluoroisopropylphenyl |
| 1430 | F | H | H | H | (thiophen-2-yl)methyl | 2,6-dimethyl-4-heptafluoroisopropylphenyl |
| 1431 | F | H | H | H | (thiophen-3-yl)methyl | 2,6-dimethyl-4-heptafluoroisopropylphenyl |
| 1432 | F | H | H | H | (pyridin-2-yl)methyl | 2,6-dimethyl-4-heptafluoroisopropylphenyl |
| 1433 | F | H | H | H | (pyridin-3-yl)methyl | 2,6-dimethyl-4-heptafluoroisopropylphenyl |
| 1434 | F | H | H | H | (6-chloropyridin-3-yl)methyl | 2,6-dimethyl-4-heptafluoroisopropylphenyl |
| 1435 | F | H | H | H | Et | 2,6-dimethyl-4-(nonafluoro-2-butyl)phenyl |
| 1436 | F | H | H | H | i-Pr | 2,6-dimethyl-4-(nonafluoro-2-butyl)phenyl |
| 1437 | F | H | H | H | vinyl | 2,6-dimethyl-4-(nonafluoro-2-butyl)phenyl |
| 1438 | F | H | H | H | propargyl | 2,6-dimethyl-4-(nonafluoro-2-butyl)phenyl |
| 1439 | F | H | H | H | cyclobutyl | 2,6-dimethyl-4-(nonafluoro-2-butyl)phenyl |
| 1440 | F | H | H | H | cyclopentyl | 2,6-dimethyl-4-(nonafluoro-2-butyl)phenyl |
| 1441 | F | H | H | H | benzyl | 2,6-dimethyl-4-(nonafluoro2-butyl) phenyl |
| 1442 | F | H | H | H | 3-cyanobenzyl | 2,6-dimethyl-4-(nonafluoro2-butyl) phenyl |
| 1443 | F | H | H | H | 4-cyanobenzyl | 2,6-dimethyl-4-(nonafluoro2-butyl) phenyl |
| 1444 | F | H | H | H | 3-chlorobenzyl | 2,6-dimethyl-4-(nonafluoro2-butyl) phenyl |

TABLE 2-continued (1-B)

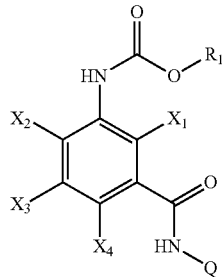

| Compound No. | $X_1$ | $X_2$ | $X_3$ | $X_4$ | $R_1$ | Q |
|---|---|---|---|---|---|---|
| 1445 | F | H | H | H | 2-methoxyethyl | 2,6-dimethyl-4-(nonafluoro2-butyl)phenyl |
| 1446 | F | H | H | H | 2-cyanoethyl | 2,6-dimethyl-4-(nonafluoro2-butyl)phenyl |
| 1447 | F | H | H | H | 2-(methylthio)ethyl | 2,6-dimethyl-4-(nonafluoro2-butyl)phenyl |
| 1448 | F | H | H | H | 2-(ethylthio)ethyl | 2,6-dimethyl-4-(nonafluoro2-butyl)phenyl |
| 1449 | F | H | H | H | 1-methyl-2-(methylthio)ethyl | 2,6-dimethyl-4-(nonafluoro2-butyl)phenyl |
| 1450 | F | H | H | H | 2-(ethylsulfinyl)ethyl | 2,6-dimethyl-4-(nonafluoro2-butyl)phenyl |
| 1451 | F | H | H | H | 2-(ethylsulfonyl)ethyl | 2,6-dimethyl-4-(nonafluoro2-butyl)phenyl |
| 1452 | F | H | H | H | 2-fluoroethyl | 2,6-dimethyl-4-(nonafluoro2-butyl)phenyl |
| 1453 | F | H | H | H | 2,2-difluoroethyl | 2,6-dimethyl-4-(nonafluoro2-butyl)phenyl |
| 1454 | F | H | H | H | 2,2,2-trifluoroethyl | 2,6-dimethyl-4-(nonafluoro2-butyl)phenyl |
| 1455 | F | H | H | H | 1,3-difluoro-2-propyl | 2,6-dimethyl-4-(nonafluoro2-butyl)phenyl |
| 1456 | F | H | H | H | 1-chloro-3-fluoro-2-propyl | 2,6-dimethyl-4-(nonafluoro2-butyl)phenyl |
| 1457 | F | H | H | H | 1-methyl-2,2,2-trifluoroethyl | 2,6-dimethyl-4-(nonafluoro2-butyl)phenyl |
| 1458 | F | H | H | H | 3,3,3-trifluoro-n-propyl | 2,6-dimethyl-4-(nonafluoro2-butyl)phenyl |
| 1459 | F | H | H | H | 2,2,3,3,3-pentafluoro-n-propyl | 2,6-dimethyl-4-(nonafluoro2-butyl)phenyl |
| 1460 | F | H | H | H | 3,3,4,4,4-pentafluoro-2-butyl | 2,6-dimethyl-4-(nonafluoro2-butyl)phenyl |
| 1385 | Me | H | H | H | 2,2,2-trichloroethyl | 2-methyl-4-heptafluoroisopropylphenyl |
| 1386 | Me | H | H | H | i-Pr | 2,6-dimethyl-4-heptafluoroisopropylphenyl |
| 1387 | Me | H | H | H | 2,2,2-trichloroethyl | 2,6-dimethyl-4-heptafluoroisopropylphenyl |
| 1388 | F | H | H | H | Et | 2,6-dimethyl-4-heptafluoroisopropylphenyl |
| 1389 | F | H | H | H | i-Pr | 2,6-dimethyl-4-heptafluoroisopropylphenyl |
| 1390 | F | H | H | H | vinyl | 2,6-dimethyl-4-heptafluoroisopropylphenyl |
| 1391 | F | H | H | H | propargyl | 2,6-dimethyl-4-heptafluoroisopropylphenyl |
| 1392 | F | H | H | H | cyclobutyl | 2,6-dimethyl-4-heptafluoroisopropylphenyl |
| 1393 | F | H | H | H | cyclopentyl | 2,6-dimethyl-4-heptafluoroisopropylphenyl |
| 1394 | F | H | H | H | benzyl | 2,6-dimethyl-4-heptafluoroisopropylphenyl |
| 1395 | F | H | H | H | 3-cyanobenzyl | 2,6-dimethyl-4-heptafluoroisopropylphenyl |
| 1396 | F | H | H | H | 4-cyanobenzyl | 2,6-dimethyl-4-heptafluoroisopropylphenyl |
| 1397 | F | H | H | H | 3-chlorobenzyl | 2,6-dimethyl-4-heptafluoroisopropylphenyl |
| 1398 | F | H | H | H | 2-methoxyethyl | 2,6-dimethyl-4-heptafluoroisopropylphenyl |
| 1399 | F | H | H | H | 2-cyanoethyl | 2,6-dimethyl-4-heptafluoroisopropylphenyl |
| 1400 | F | H | H | H | 2-(methylthio)ethyl | 2,6-dimethyl-4-heptafluoroisopropylphenyl |
| 1401 | F | H | H | H | 2-(ethylthio)ethyl | 2,6-dimethyl-4-heptafluoroisopropylphenyl |
| 1402 | F | H | H | H | 1-methyl-2-(methylthio)ethyl | 2,6-dimethyl-4-heptafluoroisopropylphenyl |
| 1403 | F | H | H | H | 2-(ethylsulfinyl)ethyl | 2,6-dimethyl-4-heptafluoroisopropylphenyl |
| 1404 | F | H | H | H | 2-(ethylsulfonyl)ethyl | 2,6-dimethyl-4-heptafluoroisopropylphenyl |
| 1481 | F | H | H | H | (6-chloropyridin-3-yl)methyl | 2,6-dimethyl-4-(nonafluoro-2-butyl)phenyl |
| 1482 | F | H | H | H | Et | 2,6-dichloro-4-(heptafluoro-n-propylthio)phenyl |
| 1483 | F | H | H | H | i-Pr | 2,6-dichloro-4-(heptafluoro-n-propylthio)phenyl |
| 1484 | F | H | H | H | vinyl | 2,6-dichloro-4-(heptafluoro-n-propylthio)phenyl |
| 1485 | F | H | H | H | cyclobutyl | 2,6-dichloro-4-(heptafluoro-n-propylthio)phenyl |
| 1486 | F | H | H | H | cyclopentyl | 2,6-dichloro-4-(heptafluoro-n-propylthio)phenyl |
| 1487 | F | H | H | H | 3-cyanobenzyl | 2,6-dichloro-4-(heptafluoro-n-propylthio)phenyl |

TABLE 2-continued (1-B)

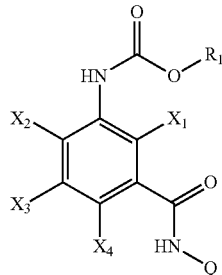

| Compound No. | X₁ | X₂ | X₃ | X₄ | R₁ | Q |
|---|---|---|---|---|---|---|
| 1488 | F | H | H | H | 4-cyanobenzyl | 2,6-dichloro-4-(heptafluoro-n-propylthio)phenyl |
| 1489 | F | H | H | H | 2-cyanoethyl | 2,6-dichloro-4-(heptafluoro-n-propylthio)phenyl |
| 1490 | F | H | H | H | 2-(methylthio)ethyl | 2,6-dichloro-4-(heptafluoro-n-propylthio)phenyl |
| 1491 | F | H | H | H | 2-(ethylthio)ethyl | 2,6-dichloro-4-(heptafluoro-n-propylthio)phenyl |
| 1492 | F | H | H | H | 1-methyl-2-(methylthio)ethyl | 2,6-dichloro-4-(heptafluoro-n-propylthio)phenyl |
| 1493 | F | H | H | H | 2-(ethylsulfinyl)ethyl | 2,6-dichloro-4-(heptafluoro-n-propylthio)phenyl |
| 1494 | F | H | H | H | 2-fluoroethyl | 2,6-dichloro-4-(heptafluoro-n-propylthio)phenyl |
| 1495 | F | H | H | H | 2,2-difluoroethyl | 2,6-dichloro-4-(heptafluoro-n-propylthio)phenyl |
| 1496 | F | H | H | H | 2,2,2-trifluoroethyl | 2,6-dichloro-4-(heptafluoro-n-propylthio)phenyl |
| 1497 | F | H | H | H | 1,3-difluoro-2-propyl | 2,6-dichloro-4-(heptafluoro-n-propylthio)phenyl |
| 1498 | F | H | H | H | 1-chloro-3-fluoro-2-propyl | 2,6-dichloro-4-(heptafluoro-n-propylthio)phenyl |
| 1499 | F | H | H | H | 1-methyl-2,2,2-trifluoroethyl | 2,6-dichloro-4-(heptafluoro-n-propylthio)phenyl |
| 1500 | F | H | H | H | 3,3,3-trifluoro-n-propyl | 2,6-dichloro-4-(heptafluoro-n-propylthio)phenyl |
| 1501 | F | H | H | H | 2,2,3,3,3-pentafluoro-n-propyl | 2,6-dichloro-4-(heptafluoro-n-propylthio)phenyl |
| 1502 | F | H | H | H | 4,4,4-trifluoro-n-butyl | 2,6-dichloro-4-(heptafluoro-n-propylthio)phenyl |
| 1503 | F | H | H | H | 2,2,3,3-tetrafluorocyclobutyl | 2,6-dichloro-4-(heptafluoro-n-propylthio)phenyl |
| 1504 | F | H | H | H | 2-chloroethyl | 2,6-dichloro-4-(heptafluoro-n-propylthio)phenyl |
| 1505 | F | H | H | H | 2,2-dichloroethyl | 2,6-dichloro-4-(heptafluoro-n-propylthio)phenyl |
| 1506 | F | H | H | H | 2,2,2-trichloroethyl | 2,6-dichloro-4-(heptafluoro-n-propylthio)phenyl |
| 1507 | F | H | H | H | 1,3-dichloro-2-propyl | 2,6-dichloro-4-(heptafluoro-n-propylthio)phenyl |
| 1508 | F | H | H | H | 3-chloro-n-propyl | 2,6-dichloro-4-(heptafluoro-n-propylthio)phenyl |
| 1509 | F | H | H | H | 2-bromoethyl | 2,6-dichloro-4-(heptafluoro-n-propylthio)phenyl |
| 1510 | F | H | H | H | 3-bromo-n-propyl | 2,6-dichloro-4-(heptafluoro-n-propylthio)phenyl |
| 1511 | F | H | H | H | 2-iodoethyl | 2,6-dichloro-4-(heptafluoro-n-propylthio)phenyl |
| 1512 | F | H | H | H | (6-chloropyridin-3-yl)methyl | 2,6-dichloro-4-(heptafluoro-n-propylthio)phenyl |
| 1513 | F | H | H | H | Et | 2,6-dibromo-4-(trifluoromethylsulfonyl)phenyl |
| 1514 | F | H | H | H | i-Pr | 2,6-dibromo-4-(trifluoromethylsulfonyl)phenyl |
| 1515 | F | H | H | H | vinyl | 2,6-dibromo-4-(trifluoromethylsulfonyl)phenyl |
| 1516 | F | H | H | H | cyclobutyl | 2,6-dibromo-4-(trifluoromethylsulfonyl)phenyl |
| 1517 | F | H | H | H | cyclopentyl | 2,6-dibromo-4-(trifluoromethylsulfonyl)phenyl |
| 1518 | F | H | H | H | 3-cyanobenzyl | 2,6-dibromo-4-(trifluoromethylsulfonyl)phenyl |
| 1519 | F | H | H | H | 4-cyanobenzyl | 2,6-dibromo-4-(trifluoromethylsulfonyl)phenyl |
| 1520 | F | H | H | H | 2-cyanoethyl | 2,6-dibromo-4-(trifluoromethylsulfonyl)phenyl |
| 1521 | F | H | H | H | 2-(methylthio)ethyl | 2,6-dibromo-4-(trifluoromethylsulfonyl)phenyl |
| 1522 | F | H | H | H | 2-(ethylthio)ethyl | 2,6-dibromo-4-(trifluoromethylsulfonyl)phenyl |
| 1523 | F | H | H | H | 1-methyl-2-(methylthio)ethyl | 2,6-dibromo-4-(trifluoromethylsulfonyl)phenyl |
| 1524 | F | H | H | H | 2-(ethylsulfinyl)ethyl | 2,6-dibromo-4-(trifluoromethylsulfonyl)phenyl |
| 1525 | F | H | H | H | 2-fluoroethyl | 2,6-dibromo-4-(trifluoromethylsulfonyl)phenyl |
| 1526 | F | H | H | H | 2,2-difluoroethyl | 2,6-dibromo-4-(trifluoromethylsulfonyl)phenyl |
| 1527 | F | H | H | H | 2,2,2-trifluoroethyl | 2,6-dibromo-4-(trifluoromethylsulfonyl)phenyl |
| 1528 | F | H | H | H | 1,3-difluoro-2-propyl | 2,6-dibromo-4-(trifluoromethylsulfonyl)phenyl |
| 1529 | F | H | H | H | 1-chloro-3-fluoro-2-propyl | 2,6-dibromo-4-(trifluoromethylsulfonyl)phenyl |
| 1530 | F | H | H | H | 1-methyl-2,2,2-trifluoroethyl | 2,6-dibromo-4-(trifluoromethylsulfonyl)phenyl |
| 1531 | F | H | H | H | 3,3,3-trifluoro-n-propyl | 2,6-dibromo-4-(trifluoromethylsulfonyl)phenyl |
| 1532 | F | H | H | H | 2,2,3,3,3-pentafluoro-n-propyl | 2,6-dibromo-4-(trifluoromethylsulfonyl)phenyl |
| 1533 | F | H | H | H | 4,4,4-trifluoro-n-butyl | 2,6-dibromo-4-(trifluoromethylsulfonyl)phenyl |
| 1534 | F | H | H | H | 2,2,3,3-tetrafluorocyclobutyl | 2,6-dibromo-4-(trifluoromethylsulfonyl)phenyl |
| 1535 | F | H | H | H | 2-chloroethyl | 2,6-dibromo-4-(trifluoromethylsulfonyl)phenyl |
| 1536 | F | H | H | H | 2,2-dichloroethyl | 2,6-dibromo-4-(trifluoromethylsulfonyl)phenyl |
| 1537 | F | H | H | H | 2,2,2-trichloroethyl | 2,6-dibromo-4-(trifluoromethylsulfonyl)phenyl |
| 1538 | F | H | H | H | 1,3-dichloro-2-propyl | 2,6-dibromo-4-(trifluoromethylsulfonyl)phenyl |

TABLE 2-continued

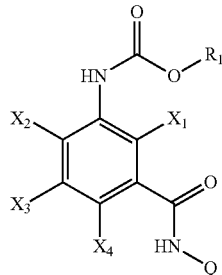

(1-B)

| Compound No. | $X_1$ | $X_2$ | $X_3$ | $X_4$ | $R_1$ | Q |
|---|---|---|---|---|---|---|
| 1539 | F | H | H | H | 3-chloro-n-propyl | 2,6-dibromo-4-(trifluoromethylsulfonyl)phenyl |
| 1540 | F | H | H | H | 2-bromoethyl | 2,6-dibromo-4-(trifluoromethylsulfonyl)phenyl |
| 1541 | F | H | H | H | 3-bromo-n-propyl | 2,6-dibromo-4-(trifluoromethylsulfonyl)phenyl |
| 1542 | F | H | H | H | 2-iodoethyl | 2,6-dibromo-4-(trifluoromethylsulfonyl)phenyl |
| 1543 | F | H | H | H | (6-chloropyridin-3-yl)methyl | 2,6-dibromo-4-(trifluoromethylsulfonyl)phenyl |
| 1544 | F | H | H | H | Et | 2,6-dibromo-4-(pentafluoroethylthio)phenyl |
| 1545 | F | H | H | H | i-Pr | 2,6-dibromo-4-(pentafluoroethylthio)phenyl |
| 1546 | F | H | H | H | vinyl | 2,6-dibromo-4-(pentafluoroethylthio)phenyl |
| 1547 | F | H | H | H | cyclobutyl | 2,6-dibromo-4-(pentafluoroethylthio)phenyl |
| 1548 | F | H | H | H | cyclopentyl | 2,6-dibromo-4-(pentafluoroethylthio)phenyl |
| 1549 | F | H | H | H | 3-cyanobenzyl | 2,6-dibromo-4-(pentafluoroethylthio)phenyl |
| 1550 | F | H | H | H | 4-cyanobenzyl | 2,6-dibromo-4-(pentafluoroethylthio)phenyl |
| 1551 | F | H | H | H | 2-cyanoethyl | 2,6-dibromo-4-(pentafluoroethylthio)phenyl |
| 1552 | F | H | H | H | 2-(methylthio)ethyl | 2,6-dibromo-4-(pentafluoroethylthio)phenyl |
| 1553 | F | H | H | H | 2-(ethylthio)ethyl | 2,6-dibromo-4-(pentafluoroethylthio)phenyl |
| 1554 | F | H | H | H | 1-methyl 2-(methylthio)ethyl | 2,6-dibromo-4-(pentafluoroethylthio)phenyl |
| 1555 | F | H | H | H | 2-(ethylsulfinyl)ethyl | 2,6-dibromo-4-(pentafluoroethylthio)phenyl |
| 1556 | F | H | H | H | 2-fluoroethyl | 2,6-dibromo-4-(pentafluoroethylthio)phenyl |
| 1557 | F | H | H | H | 2,2-difluoroethyl | 2,6-dibromo-4-(pentafluoroethylthio)phenyl |
| 1558 | F | H | H | H | 2,2,2-trifluoroethyl | 2,6-dibromo-4-(pentafluoroethylthio)phenyl |
| 1559 | F | H | H | H | 1,3-difluoro2-propyl | 2,6-dibromo-4-(pentafluoroethylthio)phenyl |
| 1560 | F | H | H | H | 1-chloro-3-fluoro-2-propyl | 2,6-dibromo-4-(pentafluoroethylthio)phenyl |
| 1561 | F | H | H | H | 1-methyl-2,2,2-trifluoro ethyl | 2,6-dibromo-4-(pentafluoroethylthio)phenyl |
| 1562 | F | H | H | H | 3,3,3-trifluoro-n-propyl | 2,6-dibromo-4-(pentafluoroethylthio)phenyl |
| 1563 | F | H | H | H | 2,2,3,3,3-pentafluoro-n-propyl | 2,6-dibromo-4-(pentafluoroethylthio)phenyl |
| 1564 | F | H | H | H | 4,4,4-trifluoro-n-butyl | 2,6-dibromo-4-(pentafluoroethylthio)phenyl |
| 1565 | F | H | H | H | 2,2,3,3-tetrafluoro cyclobutyl | 2,6-dibromo-4-(pentafluoroethylthio)phenyl |
| 1566 | F | H | H | H | 2-chloroethyl | 2,6-dibromo-4-(pentafluoroethylthio)phenyl |
| 1567 | F | H | H | H | 2,2-dichloroethyl | 2,6-dibromo-4-(pentafluoroethylthio)phenyl |
| 1568 | F | H | H | H | 2,2,2-trichloroethyl | 2,6-dibromo-4-(pentafluoroethylthio)phenyl |
| 1569 | F | H | H | H | 1,3-dichloro-2-propyl | 2,6-dibromo-4-(pentafluoroethylthio)phenyl |
| 1570 | F | H | H | H | 3-chloro-n-propyl | 2,6-dibromo-4-(pentafluoroethylthio)phenyl |
| 1571 | F | H | H | H | 2-bromoethyl | 2,6-dibromo-4-(pentafluoroethylthio)phenyl |
| 1572 | F | H | H | H | 3-bromo-n-propyl | 2,6-dibromo-4-(pentafluoroethylthio)phenyl |
| 1573 | F | H | H | H | 2-iodoethyl | 2,6-dibromo-4-(pentafluoroethylthio)phenyl |
| 1574 | F | H | H | H | (6-chloropyridin-3-yl)methyl | 2,6-dibromo-4-(pentafluoroethylthio)phenyl |
| 1575 | F | H | H | H | Et | 2,6-dibromo-4-(heptafluoro-n-propylthio)phenyl |
| 1576 | F | H | H | H | i-Pr | 2,6-dibromo-4-(heptafluoro-n-propylthio)phenyl |
| 1577 | F | H | H | H | vinyl | 2,6-dibromo-4-(heptafluoro-n-propylthio)phenyl |
| 1578 | F | H | H | H | cyclobutyl | 2,6-dibromo-4-(heptafluoro-n-propylthio)phenyl |
| 1579 | F | H | H | H | cyclopentyl | 2,6-dibromo-4-(heptafluoro-n-propylthio)phenyl |
| 1580 | F | H | H | H | 3-cyanobenzyl | 2,6-dibromo-4-(heptafluoro-n-propylthio)phenyl |
| 1581 | F | H | H | H | 4-cyanobenzyl | 2,6-dibromo-4-(heptafluoro-n-propylthio)phenyl |
| 1582 | F | H | H | H | 2-cyanoethyl | 2,6-dibromo-4-(heptafluoro-n-propylthio)phenyl |
| 1583 | F | H | H | H | 2-(methylthio)ethyl | 2,6-dibromo-4-(heptafluoro-n-propylthio)phenyl |
| 1584 | F | H | H | H | 2-(ethylthio)ethyl | 2,6-dibromo-4-(heptafluoro-n-propylthio)phenyl |
| 1585 | F | H | H | H | 1-methyl-2-(methylthio)ethyl | 2,6-dibromo-4-(heptafluoro-n-propylthio)phenyl |
| 1586 | F | H | H | H | 2-(ethylsulfinyl)ethyl | 2,6-dibromo-4-(heptafluoro-n-propylthio)phenyl |
| 1587 | F | H | H | H | 2-fluoroethyl | 2,6-dibromo-4-(heptafluoro-n-propylthio)phenyl |
| 1588 | F | H | H | H | 2,2-difluoroethyl | 2,6-dibromo-4-(heptafluoro-n-propylthio)phenyl |
| 1589 | F | H | H | H | 2,2,2-trifluoroethyl | 2,6-dibromo-4-(heptafluoro-n-propylthio)phenyl |
| 1590 | F | H | H | H | 1,3-difluoro-2-propyl | 2,6-dibromo-4-(heptafluoro-n-propylthio)phenyl |
| 1591 | F | H | H | H | 1-chloro-3-fluoro-2-propyl | 2,6-dibromo-4-(heptafluoro-n-propylthio)phenyl |

TABLE 2-continued

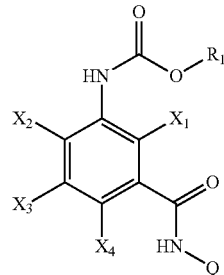

(1-B)

| Compound No. | $X_1$ | $X_2$ | $X_3$ | $X_4$ | $R_1$ | Q |
|---|---|---|---|---|---|---|
| 1592 | F | H | H | H | 1-methyl-2,2,2-trifluoro ethyl | 2,6-dibromo-4-(heptafluoro-n-propylthio)phenyl |
| 1593 | F | H | H | H | 3,3,3-trifluoro-n-propyl | 2,6-dibromo-4-(heptafluoro-n-propylthio)phenyl |
| 1594 | F | H | H | H | 2,2,3,3,3-pentafluoro-n-propyl | 2,6-dibromo-4-(heptafluoro-n-propylthio)phenyl |
| 1595 | F | H | H | H | 4,4,4-trifluoro-n-butyl | 2,6-dibromo-4-(heptafluoro-n-propylthio)phenyl |
| 1596 | F | H | H | H | 2,2,3,3-tetrafluoro cyclobutyl | 2,6-dibromo-4-(heptafluoro-n-propylthio)phenyl |
| 1597 | F | H | H | H | 2-chloroethyl | 2,6-dibromo-4-(heptafluoro-n-propylthio)phenyl |
| 1598 | F | H | H | H | 2,2-dichloroethyl | 2,6-dibromo-4-(heptafluoro-n-propylthio)phenyl |
| 1599 | F | H | H | H | 2,2,2-trichloroethyl | 2,6-dibromo-4-(heptafluoro-n-propylthio)phenyl |
| 1600 | F | H | H | H | 1,3-dichloro-2-propyl | 2,6-dibromo-4-(heptafluoro-n-propylthio)phenyl |
| 1601 | F | H | H | H | 3-chloro-n-propyl | 2,6-dibromo-4-(heptafluoro-n-propylthio)phenyl |
| 1602 | F | H | H | H | 2-bromoethyl | 2,6-dibromo-4-(heptafluoro-n-propylthio)phenyl |
| 1603 | F | H | H | H | 3-bromo-n-propyl | 2,6-dibromo-4-(heptafluoro-n-propylthio)phenyl |
| 1604 | F | H | H | H | 2-iodoethyl | 2,6-dibromo-4-(heptafluoro-n-propylthio)phenyl |
| 1605 | F | H | H | H | (6-chloropyridin-3-yl) methyl | 2,6-dibromo-4-(heptafluoro-n-propylthio)phenyl |
| 1606 | F | H | H | H | Et | 2,6-dibromo-4-(heptafluoroisopropylthio)phenyl |
| 1607 | F | H | H | H | i-Pr | 2,6-dibromo-4-(heptafluoroisopropylthio)phenyl |
| 1608 | F | H | H | H | vinyl | 2,6-dibromo-4-(heptafluoroisopropylthio)phenyl |
| 1609 | F | H | H | H | cyclobutyl | 2,6-dibromo-4-(heptafluoroisopropylthio)phenyl |
| 1610 | F | H | H | H | cyclopentyl | 2,6-dibromo-4-(heptafluoroisopropylthio)phenyl |
| 1611 | F | H | H | H | 3-cyanobenzyl | 2,6-dibromo-4-(heptafluoroisopropylthio)phenyl |
| 1612 | F | H | H | H | 4-cyanobenzyl | 2,6-dibromo-4-(heptafluoroisopropylthio)phenyl |
| 1613 | F | H | H | H | 2-cyanoethyl | 2,6-dibromo-4-(heptafluoroisopropylthio)phenyl |
| 1614 | F | H | H | H | 2-(methylthio)ethyl | 2,6-dibromo-4-(heptafluoroisopropylthio)phenyl |
| 1615 | F | H | H | H | 2-(ethylthio)ethyl | 2,6-dibromo-4-(heptafluoroisopropylthio)phenyl |
| 1616 | F | H | H | H | 1-methyl-2-(methylthio) ethyl | 2,6-dibromo-4-(heptafluoroisopropylthio)phenyl |
| 1617 | F | H | H | H | 2-(ethylsulfinyl)ethyl | 2,6-dibromo-4-(heptafluoroisopropylthio)phenyl |
| 1618 | F | H | H | H | 2-fluoroethyl | 2,6-dibromo-4-(heptafluoroisopropylthio)phenyl |
| 1619 | F | H | H | H | 2,2-difluoroethyl | 2,6-dibromo-4-(heptafluoroisopropylthio)phenyl |
| 1620 | F | H | H | H | 2,2,2-trifluoroethyl | 2,6-dibromo-4-(heptafluoroisopropylthio)phenyl |
| 1621 | F | H | H | H | 1,3-difluoro-2-propyl | 2,6-dibromo-4-(heptafluoroisopropylthio)phenyl |
| 1622 | F | H | H | H | 1-chloro-3-fluoro2-propyl | 2,6-dibromo-4-(heptafluoroisopropylthio)phenyl |
| 1623 | F | H | H | H | 1-methyl-2,2,2-trifluoro ethyl | 2,6-dibromo-4-(heptafluoroisopropylthio)phenyl |
| 1624 | F | H | H | H | 3,3,3-trifluoro-n-propyl | 2,6-dibromo-4-(heptafluoroisopropylthio)phenyl |
| 1625 | F | H | H | H | 2,2,3,3,3-pentafluoro-n-propyl | 2,6-dibromo-4-(heptafluoroisopropylthio)phenyl |
| 1626 | F | H | H | H | 4,4,4-trifluoro-n-butyl | 2,6-dibromo-4-(heptafluoroisopropylthio)phenyl |
| 1627 | F | H | H | H | 2,2,3,3-tetrafluorocyclo butyl | 2,6-dibromo-4-(heptafluoroisopropylthio)phenyl |
| 1628 | F | H | H | H | 2-chloroethyl | 2,6-dibromo-4-(heptafluoroisopropylthio)phenyl |
| 1629 | F | H | H | H | 2,2-dichloroethyl | 2,6-dibromo-4-(heptafluoroisopropylthio)phenyl |
| 1630 | F | H | H | H | 2,2,2-trichloroethyl | 2,6-dibromo-4-(heptafluoroisopropylthio)phenyl |
| 1631 | F | H | H | H | 1,3-dichloro-2-propyl | 2,6-dibromo-4-(heptafluoroisopropylthio)phenyl |
| 1632 | F | H | H | H | 3-chloro-n-propyl | 2,6-dibromo-4-(heptafluoroisopropylthio)phenyl |
| 1633 | F | H | H | H | 2-bromoethyl | 2,6-dibromo-4-(heptafluoroisopropylthio)phenyl |
| 1634 | F | H | H | H | 3-bromo-n-propyl | 2,6-dibromo-4-(heptafluoroisopropylthio)phenyl |
| 1635 | F | H | H | H | 2-iodoethyl | 2,6-dibromo-4-(heptafluoroisopropylthio)phenyl |
| 1636 | F | H | H | H | (6-chloropyridin-3-yl) methyl | 2,6-dibromo-4-(heptafluoroisopropylthio)phenyl |
| 1637 | F | H | H | H | Et | 2,6-dimethyl-4-(heptafluoro-n-propylthio)phenyl |
| 1638 | F | H | H | H | i-Pr | 2,6-dimethyl-4-(heptafluoro-n-propylthio)phenyl |
| 1639 | F | H | H | H | vinyl | 2,6-dimethyl-4-(heptafluoro-n-propylthio)phenyl |
| 1640 | F | H | H | H | cyclobutyl | 2,6-dimethyl-4-(heptafluoro-n-propylthio)phenyl |
| 1641 | F | H | H | H | cyclopentyl | 2,6-dimethyl-4-(heptafluoro-n-propylthio)phenyl |
| 1642 | F | H | H | H | 3-cyanobenzyl | 2,6-dimethyl-4-(heptafluoro-n-propylthio)phenyl |
| 1643 | F | H | H | H | 4-cyanobenzyl | 2,6-dimethyl-4-(heptafluoro-n-propylthio)phenyl |

TABLE 2-continued

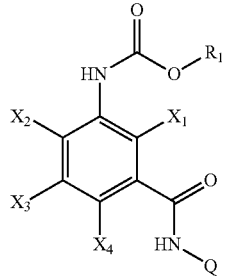
(1-B)

| Compound No. | X₁ | X₂ | X₃ | X₄ | R₁ | Q |
|---|---|---|---|---|---|---|
| 1644 | F | H | H | H | 2-cyanoethyl | 2,6-dimethyl-4-(heptafluoro-n-propylthio)phenyl |
| 1645 | F | H | H | H | 2-(methylthio)ethyl | 2,6-dimethyl-4-(heptafluoro-n-propylthio)phenyl |
| 1646 | F | H | H | H | 2-(ethylthio)ethyl | 2,6-dimethyl-4-(heptafluoro-n-propylthio)phenyl |
| 1647 | F | H | H | H | 1-methyl-2-(methylthio)ethyl | 2,6-dimethyl-4-(heptafluoro-n-propylthio)phenyl |
| 1648 | F | H | H | H | 2-(ethylsulfinyl)ethyl | 2,6-dimethyl-4-(heptafluoro-n-propylthio)phenyl |
| 1649 | F | H | H | H | 2-fluoroethyl | 2,6-dimethyl-4-(heptafluoro-n-propylthio)phenyl |
| 1650 | F | H | H | H | 2,2-difluoroethyl | 2,6-dimethyl-4-(heptafluoro-n-propylthio)phenyl |
| 1651 | F | H | H | H | 2,2,2-trifluoroethyl | 2,6-dimethyl-4-(heptafluoro-n-propylthio)phenyl |
| 1652 | F | H | H | H | 1,3-difluoro-2-propyl | 2,6-dimethyl-4-(heptafluoro-n-propylthio)phenyl |
| 1653 | F | H | H | H | 1-chloro-3-fluoro-2-propyl | 2,6-dimethyl-4-(heptafluoro-n-propylthio)phenyl |
| 1654 | F | H | H | H | 1-methyl-2,2,2-trifluoroethyl | 2,6-dimethyl-4-(heptafluoro-n-propylthio)phenyl |
| 1655 | F | H | H | H | 3,3,3-trifluoro-n-propyl | 2,6-dimethyl-4-(heptafluoro-n-propylthio)phenyl |
| 1656 | F | H | H | H | 2,2,3,3,3-pentafluoro-n-propyl | 2,6-dimethyl-4-(heptafluoro-n-propylthio)phenyl |
| 1657 | F | H | H | H | 4,4,4-trifluoro-n-butyl | 2,6-dimethyl-4-(heptafluoro-n-propylthio)phenyl |
| 1658 | F | H | H | H | 2,2,3,3-tetrafluorocyclobutyl | 2,6-dimethyl-4-(heptafluoro-n-propylthio)phenyl |
| 1659 | F | H | H | H | 2-chloroethyl | 2,6-dimethyl-4-(heptafluoro-n-propylthio)phenyl |
| 1660 | F | H | H | H | 2,2-dichloroethyl | 2,6-dimethyl-4-(heptafluoro-n-propylthio)phenyl |
| 1661 | F | H | H | H | 2,2,2-trichloroethyl | 2,6-dimethyl-4-(heptafluoro-n-propylthio)phenyl |
| 1662 | F | H | H | H | 1,3-dichloro-2-propyl | 2,6-dimethyl-4-(heptafluoro-n-propylthio)phenyl |
| 1663 | F | H | H | H | 3-chloro-n-propyl | 2,6-dimethyl-4-(heptafluoro-n-propylthio)phenyl |
| 1664 | F | H | H | H | 2-bromoethyl | 2,6-dimethyl-4-(heptafluoro-n-propylthio)phenyl |
| 1665 | F | H | H | H | 3-bromo-n-propyl | 2,6-dimethyl-4-(heptafluoro-n-propylthio)phenyl |
| 1666 | F | H | H | H | 2-iodoethyl | 2,6-dimethyl-4-(heptafluoro-n-propylthio)phenyl |
| 1667 | F | H | H | H | (6-chloropyridin-3-yl)methyl | 2,6-dimethyl-4-(heptafluoro-n-propylthio)phenyl |
| 1668 | F | H | H | H | 2,2,2-trichloroethyl | 2,6-dichloro-4-(trifluoromethylsulfinyl)phenyl |
| 1669 | F | H | H | H | 2,2,2-trichloroethyl | 2,6-dibromo-4-(trifluoromethylsulfinyl)phenyl |
| 1670 | F | H | H | H | 2,2,2-trichloroethyl | 2,6-dichloro-4-(pentafluoroethylsulfinyl)phenyl |
| 1671 | F | H | H | H | 2,2,2-trichloroethyl | 2,6-dibromo-4-(pentafluoroethylsulfinyl)phenyl |
| 1672 | F | H | H | H | 2,2,2-trichloroethyl | 2,6-dichloro-4-(pentafluoroethylsulfonyl)phenyl |
| 1673 | F | H | H | H | 2,2,2-trichloroethyl | 2,6-dibromo-4-(pentafluoroethylsulfonyl)phenyl |
| 1674 | F | H | H | H | 2,2,2-trichloroethyl | 2,6-dichloro-4-(heptafluoro-n-propylsulfinyl)phenyl |
| 1675 | F | H | H | H | 2,2,2-trichloroethyl | 2,6-dibromo-4-(heptafluoro-n-propylsulfinyl)phenyl |
| 1676 | F | H | H | H | 2,2,2-trichloroethyl | 2-chloro-6-methyl-4-(nonafluoro-2-butyl)phenyl |
| 1677 | F | H | H | H | 2,2,2-trichloroethyl | 2-bromo-6-methyl-4-(nonafluoro-2-butyl)phenyl |
| 1678 | F | H | H | H | 2,2,2-trichloroethyl | 2-iodo-6-methyl-4-(nonafluoro-2-butyl)phenyl |
| 1679 | F | H | H | H | 2,2,2-trichloroethyl | 2,6-dichloro-4-(nonafluoro-2-butyl)phenyl |
| 1680 | F | H | H | H | 2,2,2-trichloroethyl | 2,6-dibromo-4-(nonafluoro-2-butyl)phenyl |
| 1681 | F | H | H | H | Et | 2-chloro-4-methyl-6-(1,1,1,3,3,3-hexafluoroisopropyloxy)pyridin-3-yl |
| 1682 | F | H | H | H | i-Pr | 2-chloro-4-methyl-6-(1,1,1,3,3,3-hexafluoroisopropyloxy)pyridin-3-yl |
| 1683 | F | H | H | H | vinyl | 2-chloro-4-methyl-6-(1,1,1,3,3,3-hexafluoroisopropyloxy)pyridin-3-yl |
| 1684 | F | H | H | H | cyclobutyl | 2-chloro-4-methyl-6-(1,1,1,3,3,3-hexafluoroisopropyloxy)pyridin-3-yl |
| 1685 | F | H | H | H | cyclopentyl | 2-chloro-4-methyl-6-(1,1,1,3,3,3-hexafluoroisopropyloxy)pyridin-3-yl |
| 1686 | F | H | H | H | 3-cyanobenzyl | 2-chloro-4-methyl-6-(1,1,1,3,3,3-hexafluoroisopropyloxy)pyridin-3-yl |
| 1687 | F | H | H | H | 4-cyanobenzyl | 2-chloro-4-methyl-6-(1,1,1,3,3,3-hexafluoroisopropyloxy)pyridin-3-yl |
| 1688 | F | H | H | H | 2-cyanoethyl | 2-chloro-4-methyl-6-(1,1,1,3,3,3-hexafluoroisopropyloxy)pyridin-3-yl |

TABLE 2-continued (1-B)

| Compound No. | X₁ | X₂ | X₃ | X₄ | R₁ | Q |
|---|---|---|---|---|---|---|
| 1689 | F | H | H | H | 2-(methylthio)ethyl | 2-chloro-4-methyl-6-(1,1,1,3,3,3-hexafluoro isopropyloxy)pyridin-3-yl |
| 1690 | F | H | H | H | 2-(ethylthio)ethyl | 2-chloro-4-methyl-6-(1,1,1,3,3,3-hexafluoro isopropyloxy)pyridin-3-yl |
| 1691 | F | H | H | H | 1-methyl-2-(methylthio)ethyl | 2-chloro-4-methyl-6-(1,1,1,3,3,3-hexafluoro isopropyloxy)pyridin-3-yl |
| 1692 | F | H | H | H | 2-(ethylsulfinyl)ethyl | 2-chloro-4-methyl-6-(1,1,1,3,3,3-hexafluoro isopropyloxy)pyridin-3-yl |
| 1693 | F | H | H | H | 2-fluoroethyl | 2-chloro-4-methyl-6-(1,1,1,3,3,3-hexafluoro isopropyloxy)pyridin-3-yl |
| 1694 | F | H | H | H | 2,2-difluoroethyl | 2-chloro-4-methyl-6-(1,1,1,3,3,3-hexafluoro isopropyloxy)pyridin-3-yl |
| 1695 | F | H | H | H | 2,2,2-trifluoroethyl | 2-chloro-4-methyl-6-(1,1,1,3,3,3-hexafluoro isopropyloxy)pyridin-3-yl |
| 1696 | F | H | H | H | 1,3-difluoro-2-propyl | 2-chloro-4-methyl-6-(1,1,1,3,3,3-hexafluoro isopropyloxy)pyridin-3-yl |
| 1697 | F | H | H | H | 1-chloro-3-fluoro-2-propyl | 2-chloro-4-methyl-6-(1,1,1,3,3,3-hexafluoro isopropyloxy)pyridin-3-yl |
| 1698 | F | H | H | H | 1-methyl-2,2,2-trifluoro ethyl | 2-chloro-4-methyl-6-(1,1,1,3,3,3-hexafluoro isopropyloxy)pyridin-3-yl |
| 1699 | F | H | H | H | 3,3,3-trifluoro-n-propyl | 2-chloro-4-methyl-6-(1,1,1,3,3,3-hexafluoro isopropyloxy)pyridin-3-yl |
| 1700 | F | H | H | H | 2,2,3,3,3-pentafluoro-n-propyl | 2-chloro-4-methyl-6-(1,1,1,3,3,3-hexafluoro isopropyloxy)pyridin-3-yl |
| 1701 | F | H | H | H | 4,4,4-trifluoro-n-butyl | 2-chloro-4-methyl-6-(1,1,1,3,3,3-hexafluoro isopropyloxy)pyridin-3-yl |
| 1702 | F | H | H | H | 2,2,3,3-tetrafluoro cyclobutyl | 2-chloro-4-methyl-6-(1,1,1,3,3,3-hexafluoro isopropyloxy)pyridin-3-yl |
| 1703 | F | H | H | H | 2-chloroethyl | 2-chloro-4-methyl-6-(1,1,1,3,3,3-hexafluoro isopropyloxy)pyridin-3-yl |
| 1704 | F | H | H | H | 2,2-dichloroethyl | 2-chloro-4-methyl-6-(1,1,1,3,3,3-hexafluoro isopropyloxy)pyridin-3-yl |
| 1705 | F | H | H | H | 2,2,2-trichloroethyl | 2-chloro-4-methyl-6-(1,1,1,3,3,3-hexafluoro isopropyloxy)pyridin-3-yl |
| 1706 | F | H | H | H | 1,3-dichloro-2-propyl | 2-chloro-4-methyl-6-(1,1,1,3,3,3-hexafluoro isopropyloxy)pyridin-3-yl |
| 1707 | F | H | H | H | 3-chloro-n-propyl | 2-chloro-4-methyl-6-(1,1,1,3,3,3-hexafluoro isopropyloxy)pyridin-3-yl |
| 1708 | F | H | H | H | 2-bromoethyl | 2-chloro-4-methyl-6-(1,1,1,3,3,3-hexafluoro isopropyloxy)pyridin-3-yl |
| 1709 | F | H | H | H | 3-bromo-n-propyl | 2-chloro-4-methyl-6-(1,1,1,3,3,3-hexafluoro isopropyloxy)pyridin-3-yl |
| 1710 | F | H | H | H | 2-iodoethyl | 2-chloro-4-methyl-6-(1,1,1,3,3,3-hexafluoro isopropyloxy)pyridin-3-yl |
| 1711 | F | H | H | H | (6-chloropyridin-3-yl)methyl | 2-chloro-4-methyl-6-(1,1,1,3,3,3-hexafluoro isopropyloxy)pyridin-3-yl |
| 1712 | F | H | H | H | Et | 2-bromo-4-methyl-6-(1,1,1,3,3,3-hexafluoro isopropyloxy)pyridin-3-yl |
| 1713 | F | H | H | H | i-Pr | 2-bromo-4-methyl-6-(1,1,1,3,3,3-hexafluoro isopropyloxy)pyridin-3-yl |
| 1714 | F | H | H | H | vinyl | 2-bromo-4-methyl-6-(1,1,1,3,3,3-hexafluoro isopropyloxy)pyridin-3-yl |
| 1715 | F | H | H | H | cyclobutyl | 2-bromo-4-methyl-6-(1,1,1,3,3,3-hexafluoro isopropyloxy)pyridin-3-yl |
| 1716 | F | H | H | H | cyclopentyl | 2-bromo-4-methyl-6-(1,1,1,3,3,3-hexafluoro isopropyloxy)pyridin-3-yl |
| 1717 | F | H | H | H | 3-cyanobenzyl | 2-bromo-4-methyl-6-(1,1,1,3,3,3-hexafluoro isopropyloxy)pyridin-3-yl |
| 1718 | F | H | H | H | 4-cyanobenzyl | 2-bromo-4-methyl-6-(1,1,1,3,3,3-hexafluoro isopropyloxy)pyridin-3-yl |

TABLE 2-continued (1-B)

| Compound No. | $X_1$ | $X_2$ | $X_3$ | $X_4$ | $R_1$ | Q |
|---|---|---|---|---|---|---|
| 1719 | F | H | H | H | 2-cyanoethyl | 2-bromo-4-methyl-6-(1,1,1,3,3,3-hexafluoro isopropyloxy)pyridin-3-yl |
| 1720 | F | H | H | H | 2-(methylthio)ethyl | 2-bromo-4-methyl-6-(1,1,1,3,3,3-hexafluoro isopropyloxy)pyridin-3-yl |
| 1721 | F | H | H | H | 2-(ethylthio)ethyl | 2-bromo-4-methyl-6-(1,1,1,3,3,3-hexafluoro isopropyloxy)pyridin-3-yl |
| 1722 | F | H | H | H | 1-methyl-2-(methylthio) ethyl | 2-bromo-4-methyl-6-(1,1,1,3,3,3-hexafluoro isopropyloxy)pyridin-3-yl |
| 1723 | F | H | H | H | 2-(ethylsulfinyl)ethyl | 2-bromo-4-methyl-6-(1,1,1,3,3,3-hexafluoro isopropyloxy)pyridin-3-yl |
| 1724 | F | H | H | H | 2-fluoroethyl | 2-bromo-4-methyl-6-(1,1,1,3,3,3-hexafluoro isopropyloxy)pyridin-3-yl |
| 1725 | F | H | H | H | 2,2-difluoroethyl | 2-bromo-4-methyl-6-(1,1,1,3,3,3-hexafluoro isopropyloxy)pyridin-3-yl |
| 1726 | F | H | H | H | 2,2,2-trifluoroethyl | 2-bromo-4-methyl-6-(1,1,1,3,3,3-hexafluoro isopropyloxy)pyridin-3-yl |
| 1727 | F | H | H | H | 1,3-difluoro-2-propyl | 2-bromo-4-methyl-6-(1,1,1,3,3,3-hexafluoro isopropyloxy)pyridin-3-yl |
| 1728 | F | H | H | H | 1-chloro-3-fluoro-2-propyl | 2-bromo-4-methyl-6-(1,1,1,3,3,3-hexafluoro isopropyloxy)pyridin-3-yl |
| 1729 | F | H | H | H | 1-methyl-2,2,2-trifluoro ethyl | 2-bromo-4-methyl-6-(1,1,1,3,3,3-hexafluoro isopropyloxy)pyridin-3-yl |
| 1730 | F | H | H | H | 3,3,3-trifluoro-n-propyl | 2-bromo-4-methyl-6-(1,1,1,3,3,3-hexafluoro isopropyloxy)pyridin-3-yl |
| 1731 | F | H | H | H | 2,2,3,3,3-pentafluoro-n-propyl | 2-bromo-4-methyl-6-(1,1,1,3,3,3-hexafluoro isopropyloxy)pyridin-3-yl |
| 1732 | F | H | H | H | 4,4,4-trifluoro-n-butyl | 2-bromo-4-methyl-6-(1,1,1,3,3,3-hexafluoro isopropyloxy)pyridin-3-yl |
| 1733 | F | H | H | H | 2,2,3,3-tetrafluoro cyclobutyl | 2-bromo-4-methyl-6-(1,1,1,3,3,3-hexafluoro isopropyloxy)pyridin-3-yl |
| 1734 | F | H | H | H | 2-chloroethyl | 2-bromo-4-methyl-6-(1,1,1,3,3,3-hexafluoro isopropyloxy)pyridin-3-yl |
| 1735 | F | H | H | H | 2,2-dichloroethyl | 2-bromo-4-methyl-6-(1,1,1,3,3,3-hexafluoro isopropyloxy)pyridin-3-yl |
| 1736 | F | H | H | H | 2,2,2-trichloroethyl | 2-bromo-4-methyl-6-(1,1,1,3,3,3-hexafluoro isopropyloxy)pyridin-3-yl |
| 1737 | F | H | H | H | 1,3-dichloro-2-propyl | 2-bromo-4-methyl-6-(1,1,1,3,3,3-hexafluoro isopropyloxy)pyridin-3-yl |
| 1738 | F | H | H | H | 3-chloro-n-propyl | 2-bromo-4-methyl-6-(1,1,1,3,3,3-hexafluoro isopropyloxy)pyridin-3-yl |
| 1739 | F | H | H | H | 2-bromoethyl | 2-bromo-4-methyl-6-(1,1,1,3,3,3-hexafluoro isopropyloxy)pyridin-3-yl |
| 1740 | F | H | H | H | 3-bromo-n-propyl | 2-bromo-4-methyl-6-(1,1,1,3,3,3-hexafluoro isopropyloxy)pyridin-3-yl |
| 1741 | F | H | H | H | 2-iodoethyl | 2-bromo-4-methyl-6-(1,1,1,3,3,3-hexafluoro isopropyloxy)pyridin-3-yl |
| 1742 | F | H | H | H | (6-chloropyridin-3-yl) methyl | 2-bromo-4-methyl-6-(1,1,1,3,3,3-hexafluoro isopropyloxy)pyridin-3-yl |
| 1743 | F | H | H | H | Et | 2-iodo-4-methyl-6-(1,1,1,3,3,3-hexafluoro isopropyloxy)pyridin-3-yl |
| 1744 | F | H | H | H | i-Pr | 2-iodo-4-methyl-6-(1,1,1,3,3,3-hexafluoro isopropyloxy)pyridin-3-yl |
| 1745 | F | H | H | H | vinyl | 2-iodo-4-methyl-6-(1,1,1,3,3,3-hexafluoro isopropyloxy)pyridin-3-yl |
| 1746 | F | H | H | H | cyclobutyl | 2-iodo-4-methyl-6-(1,1,1,3,3,3-hexafluoro isopropyloxy)pyridin-3-yl |
| 1747 | F | H | H | H | cyclopentyl | 2-iodo-4-methyl-6-(1,1,1,3,3,3-hexafluoro isopropyloxy)pyridin-3-yl |
| 1748 | F | H | H | H | 3-cyanobenzyl | 2-iodo-4-methyl-6-(1,1,1,3,3,3-hexafluoro isopropyloxy)pyridin-3-yl |

TABLE 2-continued

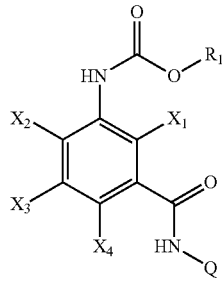

(1-B)

| Compound No. | $X_1$ | $X_2$ | $X_3$ | $X_4$ | $R_1$ | Q |
|---|---|---|---|---|---|---|
| 1749 | F | H | H | H | 4-cyanobenzyl | 2-iodo-4-methyl-6-(1,1,1,3,3,3-hexafluoro isopropyloxy)pyridin-3-yl |
| 1750 | F | H | H | H | 2-cyanoethyl | 2-iodo-4-methyl-6-(1,1,1,3,3,3-hexafluoro isopropyloxy)pyridin-3-yl |
| 1751 | F | H | H | H | 2-(methylthio)ethyl | 2-iodo-4-methyl-6-(1,1,1,3,3,3-hexafluoro isopropyloxy)pyridin-3-yl |
| 1752 | F | H | H | H | 2-(ethylthio)ethyl | 2-iodo-4-methyl-6-(1,1,1,3,3,3-hexafluoro isopropyloxy)pyridin-3-yl |
| 1753 | F | H | H | H | 1-methyl-2-(methylthio)ethyl | 2-iodo-4-methyl-6-(1,1,1,3,3,3-hexafluoro isopropyloxy)pyridin-3-yl |
| 1754 | F | H | H | H | 2-(ethylsulfinyl)ethyl | 2-iodo-4-methyl-6-(1,1,1,3,3,3-hexafluoro isopropyloxy)pyridin-3-yl |
| 1755 | F | H | H | H | 2-fluoroethyl | 2-iodo-4-methyl-6-(1,1,1,3,3,3-hexafluoro isopropyloxy)pyridin-3-yl |
| 1756 | F | H | H | H | 2,2-difluoroethyl | 2-iodo-4-methyl-6-(1,1,1,3,3,3-hexafluoro isopropyloxy)pyridin-3-yl |
| 1757 | F | H | H | H | 2,2,2-trifluoroethyl | 2-iodo-4-methyl-6-(1,1,1,3,3,3-hexafluoro isopropyloxy)pyridin-3-yl |
| 1758 | F | H | H | H | 1,3-difluoro-2-propyl | 2-iodo-4-methyl-6-(1,1,1,3,3,3-hexafluoro isopropyloxy)pyridin-3-yl |
| 1759 | F | H | H | H | 1-chloro-3-fluoro-2-propyl | 2-iodo-4-methyl-6-(1,1,1,3,3,3-hexafluoro isopropyloxy)pyridin-3-yl |
| 1760 | F | H | H | H | 1-methyl-2,2,2-trifluoro ethyl | 2-iodo-4-methyl-6-(1,1,1,3,3,3-hexafluoro isopropyloxy)pyridin-3-yl |
| 1761 | F | H | H | H | 3,3,3-trifluoro-n-propyl | 2-iodo-4-methyl-6-(1,1,1,3,3,3-hexafluoro isopropyloxy)pyridin-3-yl |
| 1762 | F | H | H | H | 2,2,3,3,3-pentafluoro-n-propyl | 2-iodo-4-methyl-6-(1,1,1,3,3,3-hexafluoro isopropyloxy)pyridin-3-yl |
| 1763 | F | H | H | H | 4,4,4-trifluoro-n-butyl | 2-iodo-4-methyl-6-(1,1,1,3,3,3-hexafluoro isopropyloxy)pyridin-3-yl |
| 1764 | F | H | H | H | 2,2,3,3-tetrafluoro cyclobutyl | 2-iodo-4-methyl-6-(1,1,1,3,3,3-hexafluoro isopropyloxy)pyridin-3-yl |
| 1765 | F | H | H | H | 2-chloroethyl | 2-iodo-4-methyl-6-(1,1,1,3,3,3-hexafluoro isopropyloxy)pyridin-3-yl |
| 1766 | F | H | H | H | 2,2-dichloroethyl | 2-iodo-4-methyl-6-(1,1,1,3,3,3-hexafluoro isopropyloxy)pyridin-3-yl |
| 1767 | F | H | H | H | 2,2,2-trichloroethyl | 2-iodo-4-methyl-6-(1,1,1,3,3,3-hexafluoro isopropyloxy)pyridin-3-yl |
| 1768 | F | H | H | H | 1,3-dichloro-2-propyl | 2-iodo-4-methyl-6-(1,1,1,3,3,3-hexafluoro isopropyloxy)pyridin-3-yl |
| 1769 | F | H | H | H | 3-chloro-n-propyl | 2-iodo-4-methyl-6-(1,1,1,3,3,3-hexafluoro isopropyloxy)pyridin-3-yl |
| 1770 | F | H | H | H | 2-bromoethyl | 2-iodo-4-methyl-6-(1,1,1,3,3,3-hexafluoro isopropyloxy)pyridin-3-yl |
| 1771 | F | H | H | H | 3-bromo-n-propyl | 2-iodo-4-methyl-6-(1,1,1,3,3,3-hexafluoro isopropyloxy)pyridin-3-yl |
| 1772 | F | H | H | H | 2-iodoethyl | 2-iodo-4-methyl-6-(1,1,1,3,3,3-hexafluoro isopropyloxy)pyridin-3-yl |
| 1773 | F | H | H | H | (6-chloropyridin-3-yl) methyl | 2-iodo-4-methyl-6-(1,1,1,3,3,3-hexafluoro isopropyloxy)pyridin-3-yl |
| 1774 | F | H | H | H | Et | 2,4-dimethyl-6-(1,1,1,3,3,3-hexafluoro isopropyloxy)pyridin-3-yl |
| 1775 | F | H | H | H | i-Pr | 2,4-dimethyl-6-(1,1,1,3,3,3-hexafluoro isopropyloxy)pyridin-3-yl |
| 1776 | F | H | H | H | vinyl | 2,4-dimethyl-6-(1,1,1,3,3,3-hexafluoro isopropyloxy)pyridin-3-yl |
| 1777 | F | H | H | H | cyclobutyl | 2,4-dimethyl-6-(1,1,1,3,3,3-hexafluoro isopropyloxy)pyridin-3-yl |
| 1778 | F | H | H | H | cyclopentyl | 2,4-dimethyl-6-(1,1,1,3,3,3-hexafluoro isopropyloxy)pyridin-3-yl |

TABLE 2-continued (1-B)

$$\text{structure with substituents } X_1, X_2, X_3, X_4 \text{ on benzene ring, HN-C(O)-O-R_1 and C(O)-NH-Q groups}$$

| Compound No. | $X_1$ | $X_2$ | $X_3$ | $X_4$ | $R_1$ | Q |
|---|---|---|---|---|---|---|
| 1779 | F | H | H | H | 3-cyanobenzyl | 2,4-dimethyl-6-(1,1,1,3,3,3-hexafluoro isopropyloxy)pyridin-3-yl |
| 1780 | F | H | H | H | 4-cyanobenzyl | 2,4-dimethyl-6-(1,1,1,3,3,3-hexafluoro isopropyloxy)pyridin-3-yl |
| 1781 | F | H | H | H | 2-cyanoethyl | 2,4-dimethyl-6-(1,1,1,3,3,3-hexafluoro isopropyloxy)pyridin-3-yl |
| 1782 | F | H | H | H | 2-(methylthio)ethyl | 2,4-dimethyl-6-(1,1,1,3,3,3-hexafluoro isopropyloxy)pyridin-3-yl |
| 1783 | F | H | H | H | 2(ethylthio)ethyl | 2,4-dimethyl-6-(1,1,1,3,3,3-hexafluoro isopropyloxy)pyridin-3-yl |
| 1784 | F | H | H | H | 1-methyl-2-(methylthio)ethyl | 2,4-dimethyl-6-(1,1,1,3,3,3-hexafluoro isopropyloxy)pyridin-3-yl |
| 1785 | F | H | H | H | 2-(ethylsulfinyl)ethyl | 2,4-dimethyl-6-(1,1,1,3,3,3-hexafluoro isopropyloxy)pyridin-3-yl |
| 1786 | F | H | H | H | 2-fluoroethyl | 2,4-dimethyl-6-(1,1,1,3,3,3-hexafluoro isopropyloxy)pyridin-3-yl |
| 1787 | F | H | H | H | 2,2-difluoroethyl | 2,4-dimethyl-6-(1,1,1,3,3,3-hexafluoro isopropyloxy)pyridin-3-yl |
| 1788 | F | H | H | H | 2,2,2-trifluoroethyl | 2,4-dimethyl-6-(1,1,1,3,3,3-hexafluoro isopropyloxy)pyridin-3-yl |
| 1789 | F | H | H | H | 1,3-difluoro-2-propyl | 2,4-dimethyl-6-(1,1,1,3,3,3-hexafluoro isopropyloxy)pyridin-3-yl |
| 1790 | F | H | H | H | 1-chloro-3-fluoro-2-propyl | 2,4-dimethyl-6-(1,1,1,3,3,3-hexafluoro isopropyloxy)pyridin-3-yl |
| 1791 | F | H | H | H | 1-methyl-2,2,2-trifluoro ethyl | 2,4-dimethyl-6-(1,1,1,3,3,3-hexafluoro isopropyloxy)pyridin-3-yl |
| 1792 | F | H | H | H | 3,3,3-trifluoro-n-propyl | 2,4-dimethyl-6-(1,1,1,3,3,3-hexafluoro isopropyloxy)pyridin-3-yl |
| 1793 | F | H | H | H | 2,2,3,3,3-pentafluoro-n-propyl | 2,4-dimethyl-6-(1,1,1,3,3,3-hexafluoro isopropyloxy)pyridin-3-yl |
| 1794 | F | H | H | H | 4,4,4-trifluoro-n-butyl | 2,4-dimethyl-6-(1,1,1,3,3,3-hexafluoro isopropyloxy)pyridin-3-yl |
| 1795 | F | H | H | H | 2,2,3,3-tetrafluoro cyclobutyl | 2,4-dimethyl-6-(1,1,1,3,3,3-hexafluoro isopropyloxy)pyridin-3-yl |
| 1796 | F | H | H | H | 2-chloroethyl | 2,4-dimethyl-6-(1,1,1,3,3,3-hexafluoro isopropyloxy)pyridin-3-yl |
| 1797 | F | H | H | H | 2,2-dichloroethyl | 2,4-dimethyl-6-(1,1,1,3,3,3-hexafluoro isopropyloxy)pyridin-3-yl |
| 1798 | F | H | H | H | 2,2,2-trichloroethyl | 2,4-dimethyl-6-(1,1,1,3,3,3-hexafluoro isopropyloxy)pyridin-3-yl |
| 1799 | F | H | H | H | 1,3-dichloro-2-propyl | 2,4-dimethyl-6-(1,1,1,3,3,3-hexafluoro isopropyloxy)pyridin-3-yl |
| 1800 | F | H | H | H | 3-chloro-n-propyl | 2,4-dimethyl-6-(1,1,1,3,3,3-hexafluoro isopropyloxy)pyridin-3-yl |
| 1801 | F | H | H | H | 2-bromoethyl | 2,4-dimethyl-6-(1,1,1,3,3,3-hexafluoro isopropyloxy)pyridin-3-yl |
| 1802 | F | H | H | H | 3-bromo-n-propyl | 2,4-dimethyl-6-(1,1,1,3,3,3-hexafluoro isopropyloxy)pyridin-3-yl |
| 1803 | F | H | H | H | 2-iodoethyl | 2,4-dimethyl-6-(1,1,1,3,3,3-hexafluoro isopropyloxy)pyridin-3-yl |
| 1804 | F | H | H | H | (6-chloropyridin-3-yl)methyl | 2,4-dimethyl-6-(1,1,1,3,3,3-hexafluoro isopropyloxy)pyridin-3-yl |
| 1805 | F | H | H | H | Et | 2-bromo-4-methyl-6-(heptafluoro isopropyl)pyridin-3-yl |
| 1806 | F | H | H | H | i-Pr | 2-bromo-4-methyl-6-(heptafluoro isopropyl)pyridin-3-yl |
| 1807 | F | H | H | H | vinyl | 2-bromo-4-methyl-6-(heptafluoro isopropyl)pyridin-3-yl |
| 1808 | F | H | H | H | cyclobutyl | 2-bromo-4-methyl-6-(heptafluoro isopropyl)pyridin-3-yl |

TABLE 2-continued (1-B)

Structure: benzene ring with HN-C(=O)-O-R₁ substituent, X₁, X₂, X₃, X₄ substituents, and C(=O)-NH-Q substituent.

| Compound No. | X₁ | X₂ | X₃ | X₄ | R₁ | Q |
|---|---|---|---|---|---|---|
| 1809 | F | H | H | H | cyclopentyl | 2-bromo-4-methyl-6-(heptafluoroisopropyl)pyridin-3-yl |
| 1810 | F | H | H | H | 3-cyanobenzyl | 2-bromo-4-methyl-6-(heptafluoroisopropyl)pyridin-3-yl |
| 1811 | F | H | H | H | 4-cyanobenzyl | 2-bromo-4-methyl-6-(heptafluoroisopropyl)pyridin-3-yl |
| 1812 | F | H | H | H | 2-cyanoethyl | 2-bromo-4-methyl-6-(heptafluoroisopropyl)pyridin-3-yl |
| 1813 | F | H | H | H | 2-(methylthio)ethyl | 2-bromo-4-methyl-6-(heptafluoroisopropyl)pyridin-3-yl |
| 1814 | F | H | H | H | 2-(ethylthio)ethyl | 2-bromo-4-methyl-6-(heptafluoroisopropyl)pyridin-3-yl |
| 1815 | F | H | H | H | 1-methyl-2-(methylthio)ethyl | 2-bromo-4-methyl-6-(heptafluoroisopropyl)pyridin-3-yl |
| 1816 | F | H | H | H | 2-(ethylsulfinyl)ethyl | 2-bromo-4-methyl-6-(heptafluoroisopropyl)pyridin-3-yl |
| 1817 | F | H | H | H | 2-fluoroethyl | 2-bromo-4-methyl-6-(heptafluoroisopropyl)pyridin-3-yl |
| 1818 | F | H | H | H | 2,2-difluoroethyl | 2-bromo-4-methyl-6-(heptafluoroisopropyl)pyridin-3-yl |
| 1819 | F | H | H | H | 2,2,2-trifluoroethyl | 2-bromo-4-methyl-6-(heptafluoroisopropyl)pyridin-3-yl |
| 1820 | F | H | H | H | 1,3-difluoro-2-propyl | 2-bromo-4-methyl-6-(heptafluoroisopropyl)pyridin-3-yl |
| 1821 | F | H | H | H | 1-chloro-3-fluoro-2-propyl | 2-bromo-4-methyl-6-(heptafluoroisopropyl)pyridin-3-yl |
| 1822 | F | H | H | H | 1-methyl-2,2,2-trifluoroethyl | 2-bromo-4-methyl-6-(heptafluoroisopropyl)pyridin-3-yl |
| 1823 | F | H | H | H | 3,3,3-trifluoro-n-propyl | 2-bromo-4-methyl-6-(heptafluoroisopropyl)pyridin-3-yl |
| 1824 | F | H | H | H | 2,2,3,3,3-pentafluoro-n-propyl | 2-bromo-4-methyl-6-(heptafluoroisopropyl)pyridin-3-yl |
| 1825 | F | H | H | H | 4,4,4-trifluoro-n-butyl | 2-bromo-4-methyl-6-(heptafluoroisopropyl)pyridin-3-yl |
| 1826 | F | H | H | H | 2,2,3,3-tetrafluorocyclobutyl | 2-bromo-methyl-6-(heptafluoroisopropyl)pyridin-3-yl |
| 1827 | F | H | H | H | 2-chloroethyl | 2-bromo-4-methyl-6-(heptafluoroisopropyl)pyridin-3-yl |
| 1828 | F | H | H | H | 2,2-dichloroethyl | 2-bromo-4-methyl-6-(heptafluoroisopropyl)pyridin-3-yl |
| 1829 | F | H | H | H | 2,2,2-trichloroethyl | 2-bromo-4-methyl-6-(heptafluoroisopropyl)pyridin-3-yl |
| 1830 | F | H | H | H | 1,3-dichloro-2-propyl | 2-bromo-4-methyl-6-(heptafluoroisopropyl)pyridin-3-yl |
| 1831 | F | H | H | H | 3-chloro-n-propyl | 2-bromo-4-methyl-6-(heptafluoroisopropyl)pyridin-3-yl |
| 1832 | F | H | H | H | 2-bromoethyl | 2-bromo-4-methyl-6-(heptafluoroisopropyl)pyridin-3-yl |
| 1833 | F | H | H | H | 3-bromo-n-propyl | 2-bromo-4-methyl-6-(heptafluoroisopropyl)pyridin-3-yl |
| 1834 | F | H | H | H | 2-iodoethyl | 2-bromo-4-methyl-6-(heptafluoroisopropyl)pyridin-3-yl |
| 1835 | F | H | H | H | (6-chloropyridin-3-yl)methyl | 2-bromo-4-methyl-6-(heptafluoroisopropyl)pyridin-3-yl |
| 1836 | F | H | H | H | Et | 2-chloro-6-methyl-4-heptafluoroisopropylphenyl |
| 1837 | F | H | H | H | i-Pr | 2-chloro-6-methyl-4-heptafluoroisopropylphenyl |
| 1838 | F | H | H | H | vinyl | 2-chloro-6-methyl-4-heptafluoroisopropylphenyl |

TABLE 2-continued

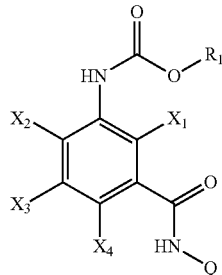

(1-B)

| Compound No. | X₁ | X₂ | X₃ | X₄ | R₁ | Q |
|---|---|---|---|---|---|---|
| 1839 | F | H | H | H | cyclobutyl | 2-chloro-6-methyl-4-heptafluoroisopropylphenyl |
| 1840 | F | H | H | H | cyclopentyl | 2-chloro-6-methyl-4-heptafluoroisopropylphenyl |
| 1841 | F | H | H | H | 3-cyanobenzyl | 2-chloro-6-methyl-4-heptafluoroisopropylphenyl |
| 1842 | F | H | H | H | 4-cyanobenzyl | 2-chloro-6-methyl-4-heptafluoroisopropylphenyl |
| 1843 | F | H | H | H | 2-cyanoethyl | 2-chloro-6-methyl-4-heptafluoroisopropylphenyl |
| 1844 | F | H | H | H | 2-(methylthio)ethyl | 2-chloro-6-methyl-4-heptafluoroisopropylphenyl |
| 1845 | F | H | H | H | 2-(ethylthio)ethyl | 2-chloro-6-methyl-4-heptafluoroisopropylphenyl |
| 1846 | F | H | H | H | 1-methyl-2-(methylthio)ethyl | 2-chloro-6-methyl-4-heptafluoroisopropylphenyl |
| 1847 | F | H | H | H | 2-(ethylsulfinyl)ethyl | 2-chloro-6-methyl-4-heptafluoroisopropylphenyl |
| 1848 | F | H | H | H | 2-fluoroethyl | 2-chloro-6-methyl-4-heptafluoroisopropylphenyl |
| 1849 | F | H | H | H | 2,2-difluoroethyl | 2-chloro-6-methyl-4-heptafluoroisopropylphenyl |
| 1850 | F | H | H | H | 2,2,2 trifluoroethyl | 2-chloro-6-methyl-4-heptafluoroisopropylphenyl |
| 1851 | F | H | H | H | 1,3-difluoro-2-Propyl | 2-chloro-6-methyl-4-heptafluoroisopropylphenyl |
| 1852 | F | H | H | H | 1-chloro-3-fluoro-2-propyl | 2-chloro-6-methyl-4-heptafluoroisopropylphenyl |
| 1853 | F | H | H | H | 1-methyl-2,2,2-trifluoroethyl | 2-chloro-6-methyl-4-heptafluoroisopropylphenyl |
| 1854 | F | H | H | H | 3,3,3-trifluoro-n-propyl | 2-chloro-6-methyl-4-heptafluoroisopropylphenyl |
| 1855 | F | H | H | H | 2,2,3,3,3-pentafluoro-n-propyl | 2-chloro-6-methyl-4-heptafluoroisopropylphenyl |
| 1856 | F | H | H | H | 4,4,4-trifluoro-n-butyl | 2-chloro-6-methyl-4-heptafluoroisopropylphenyl |
| 1857 | F | H | H | H | 2,2,3,3-tetrafluoro cyclobutyl | 2-chloro-6-methyl-4-heptafluoroisopropylphenyl |
| 1858 | F | H | H | H | 2-chloroethyl | 2-chloro-6-methyl-4-heptafluoroisopropylphenyl |
| 1859 | F | H | H | H | 2,2-dichloroethyl | 2-chloro-6-methyl-4-heptafluoroisopropylphenyl |
| 1860 | F | H | H | H | 2,2,2-trichloroethyl | 2-chloro-6-methyl-4-heptafluoroisopropylphenyl |
| 1861 | F | H | H | H | 1,3-dichloro-2-propyl | 2-chloro-6-methyl-4-heptafluoroisopropylphenyl |
| 1862 | F | H | H | H | 3-chloro-n-propyl | 2-chloro-6-methyl-4-heptafluoroisopropylphenyl |
| 1863 | F | H | H | H | 2-bromoethyl | 2-chloro-6-methyl-4-heptafluoroisopropylphenyl |
| 1864 | F | H | H | H | 3-bromo-n-propyl | 2-chloro-6-methyl-4-heptafluoroisopropylphenyl |
| 1865 | F | H | H | H | 2-iodoethyl | 2-chloro-6-methyl-4-heptafluoroisopropylphenyl |
| 1866 | F | H | H | H | (6-chloropyridin-3-yl)methyl | 2-chloro-6-methyl-4-heptafluoroisopropylphenyl |
| 1867 | F | H | H | H | Et | 2-iodo-6-n-propyl-4-heptafluoroisopropylphenyl |
| 1868 | F | H | H | H | i-Pr | 2-iodo-6-n-propyl-4-heptafluoroisopropylphenyl |
| 1869 | F | H | H | H | vinyl | 2-iodo-6-n-propyl-4-heptafluoroisopropylphenyl |
| 1870 | F | H | H | H | cyclobutyl | 2-iodo-6-n-propyl-4-heptafluoroisopropylphenyl |
| 1871 | F | H | H | H | cyclopentyl | 2-iodo-6-n-propyl-4-heptafluoroisopropylphenyl |

TABLE 2-continued (1-B)

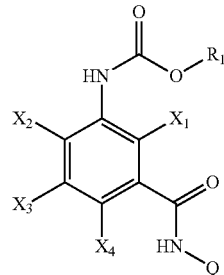

| Compound No. | X₁ | X₂ | X₃ | X₄ | R₁ | Q |
|---|---|---|---|---|---|---|
| 1872 | F | H | H | H | 3-cyanobenzyl | 2-iodo-6-n-propyl-4-heptafluoro isopropylphenyl |
| 1873 | F | H | H | H | 4-cyanobenzyl | 2-iodo-6-n-propyl-4-heptafluoro isopropylphenyl |
| 1874 | F | H | H | H | 2-cyanoethyl | 2-iodo-6-n-propyl-4-heptafluoro isopropylphenyl |
| 1875 | F | H | H | H | 2-(methylthio)ethyl | 2-iodo-6-n-propyl-4-heptafluoro isopropylphenyl |
| 1876 | F | H | H | H | 2-(ethylthio)ethyl | 2-iodo-6-n-propyl-4-heptafluoro isopropylphenyl |
| 1877 | F | H | H | H | 1-methyl-2-(methylthio) ethyl | 2-iodo-6-n-propyl-4-heptafluoro isopropylphenyl |
| 1878 | F | H | H | H | 2-(ethylsulfinyl)ethyl | 2-iodo-6-n-propyl-4-heptafluoro isopropylphenyl |
| 1879 | F | H | H | H | 2-fluoroethyl | 2-iodo-6-n-propyl-4-heptafluoro isopropylphenyl |
| 1880 | F | H | H | H | 2,2-difluoroethyl | 2-iodo-6-n-propyl-4-heptafluoro isopropylphenyl |
| 1881 | F | H | H | H | 2,2,2-trifluoroethyl | 2-iodo-6-n-propyl-4-heptafluoro isopropylphenyl |
| 1882 | F | H | H | H | 1,3-difluoro-2-propyl | 2-iodo-6-n-propyl-4-heptafluoro isopropylphenyl |
| 1883 | F | H | H | H | 1-chloro-3-fluoro-2-propyl | 2-iodo-6-n-propyl-4-heptafluoro isopropylphenyl |
| 1884 | F | H | H | H | 1-methyl-2,2,2-trifluoro ethyl | 2-iodo-6-n-propyl-4-heptafluoro isopropylphenyl |
| 1885 | F | H | H | H | 3,3,3-trfluoro-n-propyl | 2-iodo-6-n-propyl-4-heptafluoro isopropylphenyl |
| 1886 | F | H | H | H | 2,2,3,3,3-pentafluoro-n-propyl | 2-iodo-6-n-propyl-4-heptafluoro isopropylphenyl |
| 1887 | F | H | H | H | 4,4,4-trifluoro-n-butyl | 2-iodo-6-n-propyl-4-heptafluoro isopropylphenyl |
| 1888 | F | H | H | H | 2,2,3,3-tetrafluoro cyclobutyl | 2-iodo-6-n-propyl-4-heptafluoro isopropylphenyl |
| 1889 | F | H | H | H | 2-chloroethyl | 2-iodo-6-n-propyl-4-heptafluoro isopropylphenyl |
| 1890 | F | H | H | H | 2,2-dichloroethyl | 2-iodo-6-n-propyl-4-heptafluoro isopropylphenyl |
| 1891 | F | H | H | H | 2,2,2-trichloroethyl | 2-iodo-6-n-propyl-4-heptafluoro isopropylphenyl |
| 1892 | F | H | H | H | 1,3-dichloro-2-propyl | 2-iodo-6-n-propyl-4-heptafluoro isopropylphenyl |
| 1893 | F | H | H | H | 3-chloro-n-propyl | 2-iodo-6-n-propyl-4-heptafluoro isopropylphenyl |
| 1894 | F | H | H | H | 2-bromoethyl | 2-iodo-6-n-propyl-4-heptafluoro isopropylphenyl |
| 1895 | F | H | H | H | 3-bromo-n-propyl | 2-iodo-6-n-propyl-4-heptafluoro isopropylphenyl |
| 1896 | F | H | H | H | 2-iodoethyl | 2-iodo-6-n-propyl-4-heptafluoro isopropylphenyl |
| 1897 | F | H | H | H | (6-chloropyridin-3-yl)methyl | 2-iodo-6-n-propyl-4-heptafluoro isopropylphenyl |
| 1898 | Cl | H | H | H | i-Pr | 2-methyl-4-heptafluoroisopropylphenyl |
| 1899 | Cl | H | H | H | 2,2,2-trichloroethyl | 2-methyl-4-heptafluoroisopropylphenyl |
| 1900 | Cl | H | H | H | i-Pr | 2,6-dimethyl-4-heptafluoroisopropylphenyl |
| 1901 | Cl | H | H | H | 2,2,2-trichloroethyl | 2,6-dimethyl-4-heptafluoroisopropylphenyl |
| 1902 | Cl | H | H | H | 2,2,2-trichloroethyl | 2,4-bistrifluoromethylphenyl |
| 1903 | Cl | H | H | H | 2,2,2-trichloroethyl | 2-(1,1,1,3,3,3-hexafluoroisopropyloxy)-4-methylpyridin-5-yl |
| 1904 | Br | H | H | H | i-Pr | 2,6-dimethyl-4-heptafluoroisopropylphenyl |
| 1905 | Br | H | H | H | 2,2,2-trichloroethyl | 2,6-dimethyl-4-heptafluoroisopropylphenyl |

TABLE 2-continued

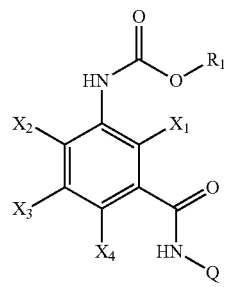

(1-B)

| Compound No. | $X_1$ | $X_2$ | $X_3$ | $X_4$ | $R_1$ | Q |
|---|---|---|---|---|---|---|
| 1906 | F | F | H | H | 2,2,2-trichloroethyl | 2-methyl-4-heptafluoroisopropylphenyl |
| 1907 | F | F | H | H | 2,2,2-trichloroethyl | 2,6-dimethyl-4-heptafluoroisopropylphenyl |
| 1908 | F | F | F | H | i-Pr | 2,6-dimethyl-4-heptafluoroisopropylphenyl |
| 1909 | H | Me | H | H | i-Pr | 2-methyl-4-heptafluoroisopropylphenyl |
| 1910 | H | Me | H | H | 2,2,2-trichloroethyl | 2-methyl-4-heptafluoroisopropylphenyl |
| 1911 | H | Me | H | H | i-Pr | 2,6-dimethyl-4-heptafluoroisopropylphenyl |
| 1912 | H | Me | H | H | 2,2,2-trichloroethyl | 2,6-dimethyl-4-heptafluoroisopropylphenyl |
| 1913 | H | MeO | H | H | i-Pr | 2-methyl-4-heptafluoroisopropylphenyl |
| 1914 | H | MeO | H | H | 2,2,2-trichloroethyl | 2-methyl-4-heptafluoroisopropylphenyl |
| 1915 | H | F | H | H | i-Pr | 2-methyl-4-heptafluoroisopropylphenyl |
| 1916 | H | F | H | H | 2,2,2-trichloroethyl | 2-methyl-4-heptafluoroisopropylphenyl |
| 1917 | H | F | H | H | i-Pr | 2,6-dimethyl-4-heptafluoroisopropylphenyl |
| 1918 | H | F | H | H | 2,2,2-trichloroethyl | 2,6-dimethyl-4-heptafluoroisopropylphenyl |
| 1919 | H | Cl | H | H | i-Pr | 2-methyl-4-heptafluoroisopropylphenyl |
| 1920 | H | Cl | H | H | 2,2,2-trichloroethyl | 2-methyl-4-heptafluoroisopropylphenyl |
| 1921 | H | Cl | H | H | i-Pr | 2,6-dimethyl-4-heptafluoroisopropylphenyl |
| 1922 | H | Cl | H | H | 2,2,2-trichloroethyl | 2,6-dimethyl-4-heptafluoroisopropylphenyl |
| 1923 | H | H | Me | H | 2,2,2-trichloroethyl | 2,6-dimethyl-4-heptafluoroisopropylphenyl |
| 1924 | H | H | $CF_3$ | H | i-Pr | 2-methyl-4-heptafluoroisopropylphenyl |
| 1925 | H | H | $CF_3$ | H | 2,2,2-trichloroethyl | 2-methyl-4-heptafluoroisopropylphenyl |
| 1926 | H | H | $CF_3$ | H | i-Pr | 2,6-dimethyl-4-heptafluoroisopropylphenyl |
| 1927 | H | H | $CF_3$ | H | 2,2,2-trichloroethyl | 2,6-dimethyl-4-heptafluoroisopropylphenyl |
| 1928 | H | H | $NH_2$ | H | i-Pr | 2,6-dimethyl-4-heptafluoroisopropylphenyl |
| 1929 | H | H | $Me_2N$ | H | 2,2,2-trichloroethyl | 2,6-dimethyl-4-heptafluoroisopropylphenyl |
| 1930 | H | H | H | Me | i-Pr | 2-methyl-4-heptafluoroisopropylphenyl |
| 1931 | H | H | H | Me | 2,2,2-trichloroethyl | 2-methyl-4-heptafluoroisopropylphenyl |
| 1932 | H | H | H | Me | i-Pr | 2,6-dimethyl-4-heptafluoroisopropylphenyl |
| 1933 | H | H | H | Me | 2,2,2-trichloroethyl | 2,6-dimethyl-4-heptafluoroisopropylphenyl |
| 1934 | H | H | H | F | i-Pr | 2-methyl-4-heptafluoroisopropylphenyl |
| 1935 | H | H | H | F | 2,2,2-trichloroethyl | 2-methyl-4-heptafluoroisopropylphenyl |
| 1936 | H | H | H | F | i-Pr | 2,6-dimethyl-4-heptafluoroisopropylphenyl |
| 1937 | H | H | H | F | 2,2,2-trichloroethyl | 2,6-dimethyl-4-heptafluoroisopropylphenyl |
| 1938 | H | H | H | Cl | i-Pr | 2-methyl-4-heptafluoroisopropylphenyl |
| 1939 | H | H | H | Cl | 2,2,2-trichloroethyl | 2-methyl-4-heptafluoroisopropylphenyl |
| 1940 | H | H | H | Cl | i-Pr | 2,6-dimethyl-4-heptafluoroisopropylphenyl |
| 1941 | H | H | H | Cl | 2,2,2-trichloroethyl | 2,6-dimethyl-4-heptafluoroisopropylphenyl |
| 1942 | H | H | H | Br | i-Pr | 2-methyl-4-heptafluoroisopropylphenyl |
| 1943 | H | H | H | Br | 2,2,2-trichloroethyl | 2-methyl-4-heptafluoroisopropylphenyl |
| 1944 | H | H | H | I | 2,2,2-trichloroethyl | 2-methyl-4-heptafluoroisopropylphenyl |
| 1945 | H | H | H | I | i-Pr | 2,6-dimethyl-4-heptafluoroisopropylphenyl |
| 1946 | H | H | H | I | t-Bu | 2-methyl-4-heptafluoroisopropylphenyl |
| 1947 | H | H | H | I | 2,2,2-trichloroethyl | 2,6-dimethyl-4-heptafluoroisopropylphenyl |

TABLE 3

(1-C)

[Structure: benzene ring with R2-N(-C(=O)-O-R1) substituent, X1, X2, X3, X4 on ring, and C(=O)-N(R3)-Q group]

| Compound No. | X1 | X2 | X3 | X4 | R1 | R2 | R3 | Q |
|---|---|---|---|---|---|---|---|---|
| 1948 | H | H | H | H | 2,2,2-trichloroethyl | Me | H | 2,6-dibromo-4-(heptafluoro-n-propylthio)phenyl |
| 1949 | H | H | H | H | 2,2,2-trichloroethyl | H | Me | 2-methyl-4-heptafluoroisopropyl-phenyl |
| 1950 | H | H | H | H | i-Pr | H | Me | 2,6-dimethyl-4-heptafluoroisopropyl-phenyl |
| 1951 | H | H | H | H | 2,2,2-trichloroethyl | H | Me | 2,6-dimethyl-4-heptafluoroisopropyl-phenyl |
| 1952 | H | H | H | H | i-Pr | H | Me | 2-methyl-6-chloro-4-heptafluoroisopropyl-phenyl |
| 1953 | H | H | H | H | 2,2,2-trichloroethyl | H | Me | 2-methyl-6-chloro-4-heptafluoroisopropyl-phenyl |
| 1954 | H | H | H | H | i-Pr | H | Me | 2-methyl-6-bromo-4-heptafluoroisopropyl-phenyl |
| 1955 | H | H | H | H | 2,2,2-trichloroethyl | H | Me | 2-methyl-6-bromo-4-heptafluoroisopropyl-phenyl |
| 1956 | H | H | H | H | 2,2,2-trichloroethyl | H | Et | 2,6-dimethyl-4-heptafluoroisopropyl-phenyl |
| 1957 | H | H | H | H | 2,2,2-trichloroethyl | H | i-Pr | 2,6-dimethyl-4-heptafluoroisopropyl-phenyl |
| 1958 | H | H | H | H | 2,2,2-trichloro | Me | H | 2,6-dimethyl-4-heptafluoroisopropyl-phenyl |
| 1959 | F | H | H | H | 2,2,2-trichloroethyl | Me | H | 2,6-dimethyl-4-heptafluoroisopropyl-phenyl |
| 1960 | H | H | MeNH | H | i-Pr | Me | H | 2,6-dimethyl-4-heptafluoroisopropyl-phenyl |

TABLE 4

(1-D)

[Structure: benzene ring with HN-C(=G1)-G2-R1 and C(=G3)-NH-Q substituents in meta position]

| Compound No. | G1 | G2 | G3 | R1 | Q |
|---|---|---|---|---|---|
| 1961 | O | S | O | Me | 2,6-dimethyl-4-heptafluoro-isopropylphenyl |
| 1962 | O | S | O | Et | 2,6-dimethyl-4-heptafluoro-isopropylphenyl |
| 1963 | O | O | S | iPr | 2,6-dimethyl-4-heptafluoro-isopropylphenyl |
| 1964 | O | O | S | 2,2,2-trichloroethyl | 2,6-dimethyl-4-heptafluoro-isopropylphenyl |

TABLE 5

(1-E)

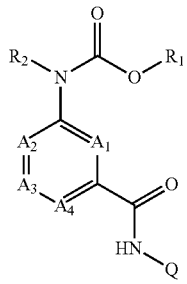

| Compound No. | A₁ | A₂ | A₃ | A₄ | R₁ | R₂ | Q |
|---|---|---|---|---|---|---|---|
| 1965 | N | C | C | C | i-Pr | H | 2-methyl-4-heptafluoroisopropylphenyl |
| 1966 | N | C | C | C | 2,2,2-trichloroethyl | H | 2-methyl-4-heptafluoroisopropylphenyl |
| 1967 | N | C | C | C | i-Pr | H | 2,6-dimethyl-4-heptafluoroisopropylphenyl |
| 1968 | N | C | C | C | 2,2,2-trichloroethyl | H | 2,6-dimethyl-4-heptafluoroisopropylphenyl |
| 1969 | N | C | C | C | 2-chloroethyl | H | 2,6-dimethyl-4-heptafluoroisopropylphenyl |
| 1970 | N | C | C | C | 2-fluoroethyl | H | 2,6-dimethyl-4-heptafluoroisopropylphenyl |
| 1971 | N | C | C | C | Et | H | 2,6-dimethyl-4-heptafluoroisopropylphenyl |
| 1972 | N | C | C | C | vinyl | H | 2,6-dimethyl-4-heptafluoroisopropylphenyl |
| 1973 | N | C | C | C | cyclobutyl | H | 2,6-dimethyl-4-heptafluoroisopropylphenyl |
| 1974 | N | C | C | C | cyclopentyl | H | 2,6-dimethyl-4-heptafluoroisopropylphenyl |
| 1975 | N | C | C | C | 3-cyanobenzyl | H | 2,6-dimethyl-4-heptafluoroisopropylphenyl |
| 1976 | N | C | C | C | 4-cyanobenzyl | H | 2,6-dimethyl-4-heptafluoroisopropylphenyl |
| 1977 | N | C | C | C | 2-cyanoethyl | H | 2,6-dimethyl-4-heptafluoroisopropylphenyl |
| 1978 | N | C | C | C | 2-(methylthio)ethyl | H | 2,6-dimethyl-4-heptafluoroisopropylphenyl |
| 1979 | N | C | C | C | 2-(ethylthio)ethyl | H | 2,6-dimethyl-4-heptafluoroisopropylphenyl |
| 1980 | N | C | C | C | 1-methyl-2-(methylthio)ethyl | H | 2,6-dimethyl-4-heptafluoroisopropylphenyl |
| 1981 | N | C | C | C | 2-(ethylsulfinyl)ethyl | H | 2,6-dimethyl-4-heptafluoroisopropylphenyl |
| 1982 | N | C | C | C | 2-fluoroethyl | H | 2,6-dimethyl-4-heptafluoroisopropylphenyl |
| 1983 | N | C | C | C | 2,2-difluoroethyl | H | 2,6-dimethyl-4-heptafluoroisopropylphenyl |
| 1984 | N | C | C | C | 2,2,2-trifluoroethyl | H | 2,6-dimethyl-4-heptafluoroisopropylphenyl |
| 1985 | N | C | C | C | 1,3-difluoro-2-propyl | H | 2,6-dimethyl-4-heptafluoroisopropylphenyl |
| 1986 | N | C | C | C | 1-chloro-3-fluoro-2-propyl | H | 2,6-dimethyl-4-heptafluoroisopropylphenyl |
| 1987 | N | C | C | C | 1-methyl-2,2,2-trifluoroethyl | H | 2,6-dimethyl-4-heptafluoroisopropylphenyl |
| 1988 | N | C | C | C | 3,3,3-trifluoro-n-propyl | H | 2,6-dimethyl-4-heptafluoroisopropylphenyl |
| 1989 | N | C | C | C | 2,2,3,3,3-pentafluoro-n-propyl | H | 2,6-dimethyl-4-heptafluoroisopropylphenyl |
| 1990 | N | C | C | C | 4,4,4-trifluoro-n-butyl | H | 2,6-dimethyl-4-heptafluoroisopropylphenyl |
| 1991 | N | C | C | C | 2,2,3,3-tetrafluorocyclobutyl | H | 2,6-dimethyl-4-heptafluoroisopropylphenyl |
| 1992 | N | C | C | C | 2,2-dichloroethyl | H | 2,6-dimethyl-4-heptafluoroisopropylphenyl |
| 1993 | N | C | C | C | 1,3-dichloro-2-propyl | H | 2,6-dimethyl-4-heptafluoroisopropylphenyl |
| 1994 | N | C | C | C | 3-chloro-n-propyl | H | 2,6-dimethyl-4-heptafluoroisopropylphenyl |
| 1995 | N | C | C | C | 2-bromoethyl | H | 2,6-dimethyl-4-heptafluoroisopropylphenyl |
| 1996 | N | C | C | C | 3-bromo-n-propyl | H | 2,6-dimethyl-4-heptafluoroisopropylphenyl |

TABLE 5-continued (1-E)

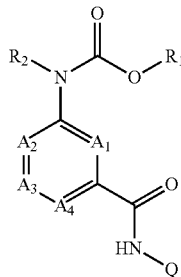

| Compound No. | A₁ | A₂ | A₃ | A₄ | R₁ | R₂ | Q |
|---|---|---|---|---|---|---|---|
| 1997 | N | C | C | C | 2-iodoethyl | H | 2,6-dimethyl-4-heptafluoroisopropyl-phenyl |
| 1998 | N | C | C | C | (6-chloropyridin-3-yl)methyl | H | 2,6-dimethyl-4-heptafluoroisopropyl-phenyl |
| 1999 | N | C | C | C | Et | H | 2,6-dimethyl-4-(nonafluoro-2-butyl)phenyl |
| 2000 | N | C | C | C | i-Pr | H | 2,6-dimethyl-4-(nonafluoro-2-butyl)phenyl |
| 2001 | N | C | C | C | vinyl | H | 2,6-dimethyl-4-(nonafluoro-2-butyl)phenyl |
| 2002 | N | C | C | C | cyclobutyl | H | 2,6-dimethyl-4-(nonafluoro-2-butyl)phenyl |
| 2003 | N | C | C | C | cyclopentyl | H | 2,6-dimethyl-4-(nonafluoro-2-butyl)phenyl |
| 2004 | N | C | C | C | 3-cyanobenzyl | H | 2,6-dimethyl-4-(nonafluoro-2-butyl)phenyl |
| 2005 | N | C | C | C | 4-cyanobenzyl | H | 2,6-dimethyl-4-(nonafluoro-2-butyl)phenyl |
| 2006 | N | C | C | C | 2-cyanoethyl | H | 2,6-dimethyl-4-(nonafluoro-2-butyl)phenyl |
| 2007 | N | C | C | C | 2-(methylthio)ethyl | H | 2,6-dimethyl-4-(nonafluoro-2-butyl)phenyl |
| 2008 | N | C | C | C | 2-(ethylthio)ethyl | H | 2,6-dimethyl-4-(nonafluoro-2-butyl)phenyl |
| 2009 | N | C | C | C | 1-methyl-2-(methylthio)ethyl | H | 2,6-dimethyl-4-(nonafluoro-2-butyl)phenyl |
| 2010 | N | C | C | C | 2-(ethylsulfinyl)ethyl | H | 2,6-dimethyl-4-(nonafluoro-2-butyl)phenyl |
| 2011 | N | C | C | C | 2-fluoroethyl | H | 2,6-dimethyl-4-(nonafluoro-2-butyl)phenyl |
| 2012 | N | C | C | C | 2,2-difluoroethyl | H | 2,6-dimethyl-4-(nonafluoro-2-butyl)phenyl |
| 2013 | N | C | C | C | 2,2,2-trifluoroethyl | H | 2,6-dimethyl-4-(nonafluoro-2-butyl)phenyl |
| 2014 | N | C | C | C | 1,3-difluoro-2-propyl | H | 2,6-dimethyl-4-(nonafluoro-2-butyl)phenyl |
| 2015 | N | C | C | C | 1-chloro-3-fluoro-2-propyl | H | 2,6-dimethyl-4-(nonafluoro-2-butyl)phenyl |
| 2016 | N | C | C | C | 1-methyl-2,2,2-trifluoro-ethyl | H | 2,6-dimethyl-4-(nonafluoro-2-butyl)phenyl |
| 2017 | N | C | C | C | 3,3,3-trifluoro-n-propyl | H | 2,6-dimethyl-4-(nonafluoro-2-butyl)phenyl |
| 2018 | N | C | C | C | 2,2,3,3,3-pentafluoro-n-propyl | H | 2,6-dimethyl-4-(nonafluoro-2-butyl)phenyl |
| 2019 | N | C | C | C | 4,4,4-trifluoro-n-butyl | H | 2,6-dimethyl-4-(nonafluoro-2-butyl)phenyl |
| 2020 | N | C | C | C | 2,2,3,3-tetrafluoro-cyclobutyl | H | 2,6-dimethyl-4-(nonafluoro-2-butyl)phenyl |
| 2021 | N | C | C | C | 2-chloroethyl | H | 2,6-dimethyl-4-(nonafluoro-2-butyl)phenyl |
| 2022 | N | C | C | C | 2,2-dichloroethyl | H | 2,6-dimethyl-4-(nonafluoro-2-butyl)phenyl |
| 2023 | N | C | C | C | 2,2,2-trichloroethyl | H | 2,6-dimethyl-4-(nonafluoro-2-butyl)phenyl |
| 2024 | N | C | C | C | 1,3-dichloro-2-propyl | H | 2,6-dimethyl-4-(nonafluoro-2-butyl)phenyl |
| 2025 | N | C | C | C | 3-chloro-n-propyl | H | 2,6-dimethyl-4-(nonafluoro-2-butyl)phenyl |
| 2026 | N | C | C | C | 2-bromoethyl | H | 2,6-dimethyl-4-(nonafluoro-2-butyl)phenyl |
| 2027 | N | C | C | C | 3-bromo-n-propyl | H | 2,6-dimethyl-4-(nonafluoro-2-butyl)phenyl |

TABLE 5-continued (1-E)

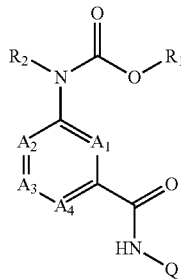

| Compound No. | A₁ | A₂ | A₃ | A₄ | R₁ | R₂ | Q |
|---|---|---|---|---|---|---|---|
| 2028 | N | C | C | C | 2-iodoethyl | H | 2,6-dimethyl-4-(nonafluoro-2-butyl)phenyl |
| 2029 | N | C | C | C | (6-chloropyridin-3-yl)methyl | H | 2,6-dimethyl-4-(nonafluoro-2-butyl)phenyl |
| 2030 | N | C | C | C | Et | H | 2,6-dibromo-4-(heptafluoro-n-propylthio)phenyl |
| 2031 | N | C | C | C | i-Pr | H | 2,6-dibromo-4-(heptafluoro-n-propylthio)phenyl |
| 2032 | N | C | C | C | vinyl | H | 2,6-dibromo-4-(heptafluoro-n-propylthio)phenyl |
| 2033 | N | C | C | C | cyclobutyl | H | 2,6-dibromo-4-(heptafluoro-n-propylthio)phenyl |
| 2034 | N | C | C | C | cyclopentyl | H | 2,6-dibromo4-(heptafluoro-n-propylthio)phenyl |
| 2035 | N | C | C | C | 3-cyanobenzyl | H | 2,6-dibromo-4-(heptafluoro-n-propylthio)phenyl |
| 2036 | N | C | C | C | 4-cyanobenzyl | H | 2,6-dibromo-4-(heptafluoro-n-propylthio)phenyl |
| 2037 | N | C | C | C | 2-cyanoethyl | H | 2,6-dibromo-4-(heptafluoro-n-propylthio)phenyl |
| 2038 | N | C | C | C | 2-(methylthio)ethyl | H | 2,6-dibromo-4-(heptafluoro-n-propylthio)phenyl |
| 2039 | N | C | C | C | 2-(ethylthio)ethyl | H | 2,6-dibromo-4-(heptafluoro-n-propylthio)phenyl |
| 2040 | N | C | C | C | 1-methyl-2-(methylthio)ethyl | H | 2,6-dibromo4-(heptafluoro-n-propylthio)phenyl |
| 2041 | N | C | C | C | 2-(ethylsulfinyl)ethyl | H | 2,6-dibromo-4-(heptafluoro-n-propylthio)phenyl |
| 2042 | N | C | C | C | 2-fluoroethyl | H | 2,6-dibromo-4-(heptafluoro-n-propylthio)phenyl |
| 2043 | N | C | C | C | 2,2-difluoroethyl | H | 2,6-dibromo-4-(heptafluoro-n-propylthio)phenyl |
| 2044 | N | C | C | C | 2,2,2-trifluoroethyl | H | 2,6-dibromo-4-(heptafluoro-n-propylthio)phenyl |
| 2045 | N | C | C | C | 1,3-difluoro-2-propyl | H | 2,6-dibromo-4-(heptafluoro-n-propylthio)phenyl |
| 2046 | N | C | C | C | 1-chloro-3-fluoro-2-propyl | H | 2,6-dibromo-4-(heptafluoro-n-propylthio)phenyl |
| 2047 | N | C | C | C | 1-methyl-2,2,2-trifluoro-ethyl | H | 2,6-dibromo-4-(heptafluoro-n-propylthio)phenyl |
| 2048 | N | C | C | C | 3,3,3-trifluoro-n-propyl | H | 2,6-dibromo-4-(heptafluoro-n-propylthio)phenyl |
| 2049 | N | C | C | C | 2,2,3,3,3-pentafluoro-n-propyl | H | 2,6-dibromo-4-(heptafluoro-n-propylthio)phenyl |
| 2050 | N | C | C | C | 4,4,4-trifluoro-n-butyl | H | 2,6-dibromo-4-(heptafluoro-n-propylthio)phenyl |
| 2051 | N | C | C | C | 2,2,3,3-tetrafluoro-cyclobutyl | H | 2,6-dibromo-4-(heptafluoro-n-propylthio)phenyl |
| 2052 | N | C | C | C | 2-chloroethyl | H | 2,6-dibromo-4-(heptafluoro-n-propylthio)phenyl |
| 2053 | N | C | C | C | 2,2-dichloroethyl | H | 2,6-dibromo-4-(heptafluoro-n-propylthio)phenyl |
| 2054 | N | C | C | C | 2,2,2-trichloroethyl | H | 2,6-dibromo-4-(heptafluoro-n-propylthio)phenyl |
| 2055 | N | C | C | C | 1,3-dichloro-2-propyl | H | 2,6-dibromo-4-(heptafluoro-n-propylthio)phenyl |
| 2056 | N | C | C | C | 3-chloro-n-propyl | H | 2,6-dibromo-4-(heptafluoro-n-propylthio)phenyl |
| 2057 | N | C | C | C | 2-bromoethyl | H | 2,6-dibromo-4-(heptafluoro-n-propylthio)phenyl |
| 2058 | N | C | C | C | 3-bromo-n-propyl | H | 26-dibromo-4-(heptafluoro-n-propylthio)phenyl |

TABLE 5-continued (1-E)

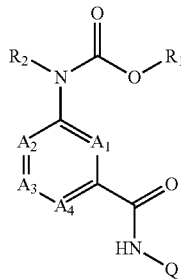

| Compound No. | A₁ | A₂ | A₃ | A₄ | R₁ | R₂ | Q |
|---|---|---|---|---|---|---|---|
| 2059 | N | C | C | C | 2-iodoethyl | H | 2,6-dibromo-4-(heptafluoro-n-propylthio)phenyl |
| 2060 | N | C | C | C | (6-chloropyridin-3-yl)methyl | H | 2,6-dibromo-4-(heptafluoro-n-propylthio)phenyl |
| 2061 | N-oxide | C | C | C | i-Pr | H | 2,6-dimethyl-4-heptafluoro-isopropylphenyl |
| 2062 | N-oxide | C | C | C | 2,2,2-trichloroethyl | H | 2,6-dimethyl-4-heptafluoro-isopropylphenyl |
| 2063 | N-oxide | C | C | C | Et | H | 2,6-dimethyl-4-heptafluoro-isopropylphenyl |
| 2064 | N-oxide | C | C | C | vinyl | H | 2,6-dimethyl-4-heptafluoro-isopropylphenyl |
| 2065 | N-oxide | C | C | C | cyclobutyl | H | 2,6-dimethyl-4-heptafluoro-isopropylphenyl |
| 2066 | N-oxide | C | C | C | cyclopentyl | H | 2,6-dimethyl-4-heptafluoro-isopropylphenyl |
| 2067 | N-oxide | C | C | C | 3-cyanobenzyl | H | 2,6-dimethyl-4-heptafluoro-isopropylphenyl |
| 2068 | N-oxide | C | C | C | 4-cyanobenzyl | H | 2,6-dimethyl-4-heptafluoro-isopropylphenyl |
| 2069 | N-oxide | C | C | C | 2-cyanoethyl | H | 2,6-dimethyl-4-heptafluoro-isopropylphenyl |
| 2070 | N-oxide | C | C | C | 2-(methylthio)ethyl | H | 2,6-dimethyl-4-heptafluoro-isopropylphenyl |
| 2071 | N-oxide | C | C | C | 2-(ethylthio)ethyl | H | 2,6-dimethyl-4-heptafluoro-isopropylphenyl |
| 2072 | N-oxide | C | C | C | 1-methyl-2-(methylthio)ethyl | H | 2,6-dimethyl-4-heptafluoro-isopropylphenyl |
| 2073 | N-oxide | C | C | C | 2-(ethylsulfinyl)ethyl | H | 2,6-dimethyl-4-heptafluoro-isopropylphenyl |
| 2074 | N-oxide | C | C | C | 2-fluoroethyl | H | 2,6-dimethyl-4-heptafluoro-isopropylphenyl |
| 2075 | N-oxide | C | C | C | 2,2-difluoroethyl | H | 2,6-dimethyl-4-heptafluoro-isopropylphenyl |
| 2076 | N-oxide | C | C | C | 2,2,2-trifluoroethyl | H | 2,6-dimethyl-4-heptafluoro-isopropylphenyl |
| 2077 | N-oxide | C | C | C | 1,3-difluoro-2-propyl | H | 2,6-dimethyl-4-heptafluoro-isopropylphenyl |
| 2078 | N-oxide | C | C | C | 1-chloro-3-fluoro-2-propyl | H | 2,6-dimethyl-4-heptafluoro-isopropylphenyl |
| 2079 | N-oxide | C | C | C | 1-methyl-2,2,2-trifluoroethyl | H | 2,6-dimethyl-4-heptafluoro-isopropylphenyl |
| 2080 | N-oxide | C | C | C | 3,3,3-trifluoro-n-propyl | H | 2,6-dimethyl-4-heptafluoro-isopropylphenyl |
| 2081 | N-oxide | C | C | C | 2,2,3,3,3-pentafluoro-n-propyl | H | 2,6-dimethyl-4-heptafluoro-isopropylphenyl |
| 2082 | N-oxide | C | C | C | 4,4,4-trifluoro-n-butyl | H | 2,6-dimethyl-4-heptafluoro-isopropylphenyl |
| 2083 | N-oxide | C | C | C | 2,2,3,3-tetrafluoro-cyclobutyl | H | 2,6-dimethyl-4-heptafluoro-isopropylphenyl |
| 2084 | N-oxide | C | C | C | 2-chloroethyl | H | 2,6-dimethyl-4-heptafluoro-isopropylphenyl |
| 2085 | N-oxide | C | C | C | 2,2-dichloroethyl | H | 2,6-dimethyl-4-heptafluoro-isopropylphenyl |
| 2086 | N-oxide | C | C | C | 1,3-dichloro-2-propyl | H | 2,6-dimethyl-4-heptafluoro-isopropylphenyl |
| 2087 | N-oxide | C | C | C | 3-chloro-n-propyl | H | 2,6-dimethyl-4-heptafluoro-isopropylphenyl |
| 2088 | N-oxide | C | C | C | 2-bromoethyl | H | 2,6-dimethyl-4-heptafluoro-isopropylphenyl |
| 2089 | N-oxide | C | C | C | 3-bromo-n-propyl | H | 2,6-dimethyl-4-heptafluoro-isopropylphenyl |

TABLE 5-continued (1-E)

| Compound No. | A₁ | A₂ | A₃ | A₄ | R₁ | R₂ | Q |
|---|---|---|---|---|---|---|---|
| 2090 | N-oxide | C | C | C | 2-iodoethyl | H | 2,6-dimethyl-4-heptafluoro-isopropylphenyl |
| 2091 | N-oxide | C | C | C | (6-chloropyridin-3-yl)methyl | H | 2,6-dimethyl-4-heptafluoro-isopropylphenyl |
| 2092 | N-oxide | C | C | C | Et | H | 2,6-dimethyl-4-(nonafluoro-2-butyl)phenyl |
| 2093 | N-oxide | C | C | C | i-Pr | H | 2,6-dimethyl-4-(nonafluoro-2-butyl)phenyl |
| 2094 | N-oxide | C | C | C | vinyl | H | 2,6-dimethyl-4-(nonafluoro-2-butyl)phenyl |
| 2095 | N-oxide | C | C | C | cyclobutyl | H | 2,6-dimethyl-4-(nonafluoro-2-butyl)phenyl |
| 2096 | N-oxide | C | C | C | cyclopentyl | H | 2,6-dimethyl-4-(nonafluoro-2-butyl)phenyl |
| 2097 | N-oxide | C | C | C | 3-cyanobenzyl | H | 2,6-dimethyl-4-(nonafluoro-2-butyl)phenyl |
| 2098 | N-oxide | C | C | C | 4-cyanobenzyl | H | 2,6-dimethyl-4-(nonafluoro-2-butyl)phenyl |
| 2099 | N-oxide | C | C | C | 2-cyanoethyl | H | 2,6-dimethyl-4-(nonafluoro-2-butyl)phenyl |
| 2100 | N-oxide | C | C | C | 2-(methylthio)ethyl | H | 2,6-dimethyl-4-(nonafluoro-2-butyl)phenyl |
| 2101 | N-oxide | C | C | C | 2-(ethylthio)ethyl | H | 2,6-dimethyl-4-(nonafluoro-2-butyl)phenyl |
| 2102 | N-oxide | C | C | C | 1-methyl-2-(methylthio)ethyl | H | 2,6-dimethyl-4-(nonafluoro-2-butyl)phenyl |
| 2103 | N-oxide | C | C | C | 2-(ethylsulfinyl)ethyl | H | 2,6-dimethyl-4-(nonafluoro-2-butyl)phenyl |
| 2104 | N-oxide | C | C | C | 2-fluoroethyl | H | 2,6-dimethyl-4-(nonafluoro-2-butyl)phenyl |
| 2105 | N-oxide | C | C | C | 2,2-difluoroethyl | H | 2,6-dimethyl-4-(nonafluoro-2-butyl)phenyl |
| 2106 | N-oxide | C | C | C | 2,2,2-trifluoroethyl | H | 2,6-dimethyl-4-(nonafluoro-2-butyl)phenyl |
| 2107 | N-oxide | C | C | C | 1,3-difluoro-2-propyl | H | 2,6-dimethyl-4-(nonafluoro-2-butyl)phenyl |
| 2108 | N-oxide | C | C | C | 1-chloro-3-fluoro-2-propyl | H | 2,6-dimethyl-4-(nonafluoro-2-butyl)phenyl |
| 2109 | N-oxide | C | C | C | 1-methyl-2,2,2-trifluoro-ethyl | H | 2,6-dimethyl-4-(nonafluoro-2-butyl)phenyl |
| 2110 | N-oxide | C | C | C | 3,3,3-trifluoro-n-propyl | H | 2,6-dimethyl-4-(nonafluoro-2-butyl)phenyl |
| 2111 | N-oxide | C | C | C | 2,2,3,3,3-pentafluoro-n-propyl | H | 2,6-dimethyl-4-(nonafluoro-2-butyl)phenyl |
| 2112 | N-oxide | C | C | C | 4,4,4-trifluoro-n-butyl | H | 2,6-dimethyl-4-(nonafluoro-2-butyl)phenyl |
| 2113 | N-oxide | C | C | C | 2,2,3,3-tetrafluoro-cyclobutyl | H | 2,6-dimethyl-4-(nonafluoro-2-butyl)phenyl |
| 2114 | N-oxide | C | C | C | 2-chloroethyl | H | 2,6-dimethyl-4-(nonafluoro-2-butyl)phenyl |
| 2115 | N-oxide | C | C | C | 2,2-dichloroethyl | H | 2,6-dimethyl-4-(nonafluoro-2-butyl)phenyl |
| 2116 | N-oxide | C | C | C | 2,2,2-trichloroethyl | H | 2,6-dimethyl-4-(nonafluoro-2-butyl)phenyl |
| 2117 | N-oxide | C | C | C | 1,3-dichloro-2-propyl | H | 2,6-dimethyl-4-(nonafluoro-2-butyl)phenyl |
| 2118 | N-oxide | C | C | C | 3-chloro-n-propyl | H | 2,6-dimethyl-4-(nonafluoro-2-butyl)phenyl |
| 2119 | N-oxide | C | C | C | 2-bromoethyl | H | 2,6-dimethyl-4-(nonafluoro-2-butyl)phenyl |
| 2120 | N-oxide | C | C | C | 3-bromo-n-propyl | H | 2,6-dimethyl-4-(nonafluoro-2-butyl)phenyl |

TABLE 5-continued

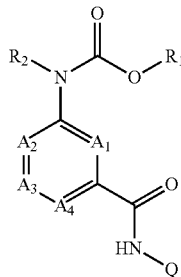

(1-E)

| Compound No. | A₁ | A₂ | A₃ | A₄ | R₁ | R₂ | Q |
|---|---|---|---|---|---|---|---|
| 2121 | N-oxide | C | C | C | 2-iodoethyl | H | 2,6-dimethyl-4-(nonafluoro-2-butyl)phenyl |
| 2122 | N-oxide | C | C | C | (6-chloropyridin-3-yl)methyl | H | 2,6-dimethyl-4-(nonafluoro-2-butyl)phenyl |
| 2123 | N-oxide | C | C | C | Et | H | 2,6-dibromo-4-(heptafluoro-n-propylthio)phenyl |
| 2124 | N-oxide | C | C | C | i-Pr | H | 2,6-dibromo-4-(heptafluoro-n-propylthio)phenyl |
| 2125 | N-oxide | C | C | C | vinyl | H | 2,6-dibromo-4-(heptafluoro-n-propylthio)phenyl |
| 2126 | N-oxide | C | C | C | cyclobutyl | H | 2,6-dibromo-4-(heptafluoro-n-propylthio)phenyl |
| 2127 | N-oxide | C | C | C | cyclopentyl | H | 2,6-dibromo-4-(heptafluoro-n-propylthio)phenyl |
| 2128 | N-oxide | C | C | C | 3-cyanobenzyl | H | 2,6-dibromo-4-(heptafluoro-n-propylthio)phenyl |
| 2129 | N-oxide | C | C | C | 4-cyanobenzyl | H | 2,6-dibromo-4-(heptafluoro-n-propylthio)phenyl |
| 2130 | N-oxide | C | C | C | 2-cyanoethyl | H | 2,6-dibromo-4-(heptafluoro-n-propylthio)phenyl |
| 2131 | N-oxide | C | C | C | 2-(methylthio)ethyl | H | 2,6-dibromo-4-(heptafluoro-n-propylthio)phenyl |
| 2132 | N-oxide | C | C | C | 2-(ethylthio)ethyl | H | 2,6-dibromo-4-(heptafluoro-n-propylthio)phenyl |
| 2133 | N-oxide | C | C | C | 1-methyl-2-(methylthio)ethyl | H | 2,6-dibromo-4-(heptafluoro-n-propylthio)phenyl |
| 2134 | N-oxide | C | C | C | 2-(ethylsulfinyl)ethyl | H | 2,6-dibromo-4-(heptafluoro-n-propylthio)phenyl |
| 2135 | N-oxide | C | C | C | 2-fluoroethyl | H | 2,6-dibromo-4-(heptafluoro-n-propylthio)phenyl |
| 2136 | N-oxide | C | C | C | 2,2-difluoroethyl | H | 2,6-dibromo-4-(heptafluoro-n-propylthio)phenyl |
| 2137 | N-oxide | C | C | C | 2,2,2-trifluoroethyl | H | 2,6-dibromo-4-(heptafluoro-n-propylthio)phenyl |
| 2138 | N-oxide | C | C | C | 1,3-difluoro-2-propyl | H | 2,6-dibromo-4-(heptafluoro-n-propylthio)phenyl |
| 2139 | N-oxide | C | C | C | 1-chloro-3-fluoro-2-propyl | H | 2,6-dibromo-4-(heptafluoro-n-propylthio)phenyl |
| 2140 | N-oxide | C | C | C | 1-methyl-2,2,2-trifluoroethyl | H | 2,6-dibromo-4-(heptafluoro-n-propylthio)phenyl |
| 2141 | N-oxide | C | C | C | 3,3,3-trifluoro-n-propyl | H | 2,6-dibromo-4-(heptafluoro-n-propylthio)phenyl |
| 2142 | N-oxide | C | C | C | 2,2,3,3,3-pentafluoro-n-propyl | H | 2,6-dibromo-4-(heptafluoro-n-propylthio)phenyl |
| 2143 | N-oxide | C | C | C | 4,4,4-trifluoro-n-butyl | H | 2,6-dibromo-4-(heptafluoro-n-propylthio)phenyl |
| 2144 | N-oxide | C | C | C | 2,2,3,3-tetrafluorocyclobutyl | H | 2,6-dibromo-4-(heptafluoro-n-propylthio)phenyl |
| 2145 | N-oxide | C | C | C | 2-chloroethyl | H | 2,6-dibromo-4-(heptafluoro-n-propylthio)phenyl |
| 2146 | N-oxide | C | C | C | 2,2-dichloroethyl | H | 2,6-dibromo-4-(heptafluoro-n-propylthio)phenyl |
| 2147 | N-oxide | C | C | C | 2,2,2-trichloroethyl | H | 2,6-dibromo-4-(heptafluoro-n-propylthio)phenyl |
| 2148 | N-oxide | C | C | C | 1,3-dichloro-2-propyl | H | 2,6-dibromo-4-(heptafluoro-n-propylthio)phenyl |
| 2149 | N-oxide | C | C | C | 3-chloro-n-propyl | H | 2,6-dibromo-4-(heptafluoro-n-propylthio)phenyl |
| 2150 | N-oxide | C | C | C | 2-bromoethyl | H | 2,6-dibromo-4-(heptafluoro-n-propylthio)phenyl |
| 2151 | N-oxide | C | C | C | 3-bromo-n-propyl | H | 2,6-dibromo-4-(heptafluoro-n-propylthio)phenyl |

TABLE 5-continued (1-E)

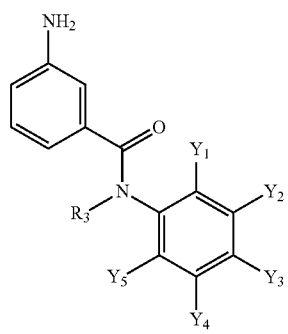

| Compound No. | A₁ | A₂ | A₃ | A₄ | R₁ | R₂ | Q |
|---|---|---|---|---|---|---|---|
| 2152 | N-oxide | C | C | C | 2-iodoethyl | H | 2,6-dibromo-4-(heptafluoro-n-propylthio)phenyl |
| 2153 | N-oxide | C | C | C | (6-chloropyridin-3-yl)methyl | H | 2,6-dibromo-4-(heptafluoro-n-propylthio)phenyl |
| 2154 | C | N | C | C | i-Pr | H | 2-methyl-4-heptafluoroisopropylphenyl |
| 2155 | C | N | C | C | 2,2,2-trichloroethyl | H | 2-methyl-4-heptafluoroisopropylphenyl |
| 2156 | C | N | C | C | i-Pr | H | 2,6-dimethyl-4-heptafluoro-isopropylphenyl |
| 2157 | C | N | C | C | 2,2,2-trichloroethyl | H | 2,6-dimethyl-4-heptafluoro-isopropylphenyl |
| 2158 | C | C | N | C | i-Pr | H | 2-methyl-4-heptafluoro-isopropylphenyl |
| 2159 | C | C | N | C | 2,2,2-trichloroethyl | H | 2-methyl-4-heptafluoro-isopropylphenyl |
| 2160 | C | C | N | C | i-Pr | H | 2,6-dimethyl-4-heptafluoro-isopropylphenyl |
| 2161 | C | C | N | C | 2,2,2-trichloroethyl | H | 2,6-dimethyl-4-heptafluoro-isopropylphenyl |
| 2162 | C | C | C | N | i-Pr | H | 2-methyl-4-heptafluoro-isopropylphenyl |
| 2163 | C | C | C | N | 2,2,2-trichloroethyl | H | 2-methyl-4-heptafluoro-isopropylphenyl |
| 2164 | C | C | C | N | i-Pr | H | 2,6-dimethyl-4-heptafluoro-isopropylphenyl |
| 2165 | C | C | C | N | 2,2,2-trichloroethyl | H | 2,6-dimethyl-4-heptafluoro-isopropylphenyl |
| 2166 | C | C | C | N-oxide | i-Pr | H | 2,6-dimethyl-4-heptafluoro-isopropylphenyl |
| 2167 | C | C | C | N-oxide | 2,2,2-trichloroethyl | H | 2,6-dimethyl-4-heptafluoro-isopropylphenyl |
| 2168 | N | C | C | C | 2,2,2-trichloroethyl | Me | 2,6-dimethyl-4-heptafluoro-isopropylphenyl |

TABLE 6

(4-A)

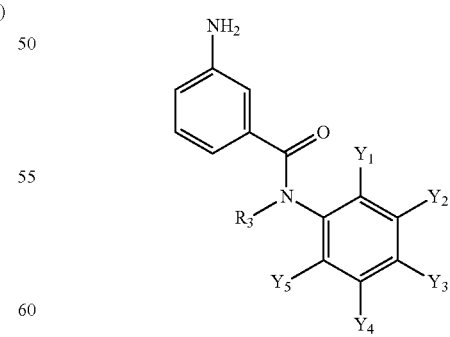

| Compound No. | R₃ | Y₁ | Y₂ | Y₃ | Y₄ | Y₅ |
|---|---|---|---|---|---|---|
| I-1 | H | Me | H | heptafluoro-n-propyl | H | Me |
| I-2 | H | H | H | heptafluoroisopropyl | H | H |
| I-3 | H | H | Me | heptafluoroisopropyl | H | H |
| I-4 | H | H | MeO | heptafluoroisopropyl | H | H |

TABLE 6-continued (4-A)

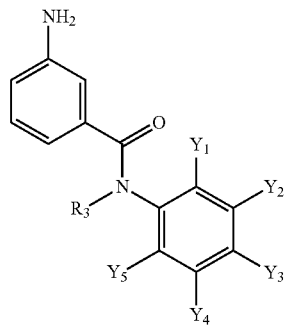

| Compound No. | R₃ | Y₁ | Y₂ | Y₃ | Y₄ | Y₅ |
|---|---|---|---|---|---|---|
| I-5 | H | H | Cl | heptafluoroisopropyl | H | H |
| I-6 | H | Me | H | heptafluoroisopropyl | H | H |
| I-7 | H | Me | H | heptafluoroisopropyl | H | Me |
| I-8 | H | Me | H | heptafluoroisopropyl | H | phenyl |
| I-9 | H | Me | H | heptafluoroisopropyl | Me | H |
| I-10 | H | Me | Me | heptafluoroisopropyl | H | H |
| I-11 | H | Me | Me | heptafluoroisopropyl | H | Cl |
| I-12 | H | Me | I | heptafluoroisopropyl | H | Cl |
| I-13 | Me | Me | H | heptafluoroisopropyl | H | Me |
| I-14 | i-Pr | Me | H | heptafluoroisopropyl | H | Me |
| I-15 | H | Et | H | heptafluoroisopropyl | H | H |
| I-16 | H | Et | H | heptafluoroisopropyl | H | Me |
| I-17 | H | Et | H | heptafluoroisopropyl | H | Et |
| I-18 | H | Et | H | heptafluoroisopropyl | H | I |
| I-19 | H | n-Pr | H | heptafluoroisopropyl | H | H |
| I-20 | H | i-Pr | H | heptafluoroisopropyl | H | Me |
| I-21 | H | MeO | H | heptafluoroisopropyl | H | Me |
| I-22 | H | Cl | H | heptafluoroisopropyl | H | Et |
| I-23 | H | Cl | H | heptafluoroisopropyl | Me | H |
| I-24 | H | Cl | H | heptafluoroisopropyl | MeO | H |
| I-25 | H | Cl | Me | heptafluoroisopropyl | H | Me |
| I-26 | H | Br | H | heptafluoroisopropyl | H | Me |
| I-27 | H | Br | H | heptafluoroisopropyl | H | Et |
| I-28 | H | Br | H | heptafluoroisopropyl | H | n-Pr |
| I-29 | H | Br | H | heptafluoroisopropyl | H | n-Bu |
| I-30 | H | Br | Me | heptafluoroisopropyl | H | Me |
| I-31 | H | I | H | heptafluoroisopropyl | H | Me |
| I-32 | H | I | H | heptafluoroisopropyl | H | n-Pr |
| I-33 | H | Me | H | nonafluoro-n-butyl | H | Me |
| I-34 | H | Me | H | nonafluoro-2-butyl | H | Me |
| I-35 | H | H | H | trifluoromethylthio | H | H |
| I-36 | H | Br | H | trifluoromethylthio | H | Br |
| I-37 | H | H | H | trifluoromethylsulfonyl | H | H |
| I-38 | H | Br | H | trifluoromethylsulfonyl | H | Br |
| I-39 | H | Me | H | 2,2,2-trifluoroethoxy | H | H |
| I-40 | H | H | H | heptafluoroisopropylthio | H | H |
| I-41 | H | Cl | H | heptafluoroisopropylthio | H | Cl |
| I-42 | H | Br | H | heptafluoroisopropylthio | H | Br |
| I-43 | H | Cl | H | heptafluoro-n-propylthio | H | Cl |
| I-44 | H | Br | H | heptafluoro-n-propylthio | H | Br |
| I-45 | H | Cl | H | heptafluoroisopropyl-sulfonyl | H | Cl |
| I-46 | H | Br | H | nonafluoro-n-butylthio | H | Br |
| I-47 | H | Br | H | pentafluoroethylthio | H | Br |
| I-48 | H | Br | H | heptafluoro-n-propyl-sulfinyl | H | Br |
| I-49 | Me | Me | H | heptafluoro-n-propylthio | H | Me |
| I-50 | Me | Br | H | heptafluoro-n-propylthio | H | Br |

TABLE 7

(4-B)

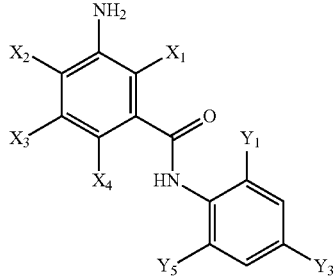

| Compound No. | X₁ | X₂ | X₃ | X₄ | Y₁ | Y₃ | Y₅ |
|---|---|---|---|---|---|---|---|
| I-51 | Me | H | H | H | Me | heptafluoroisopropyl | H |
| I-52 | Me | H | H | H | Me | heptafluoroisopropyl | Me |
| I-53 | H | Me | H | H | Me | heptafluoroisopropyl | H |
| I-54 | H | Me | H | H | Me | heptafluoroisopropyl | Me |
| I-55 | H | H | H | Me | Me | heptafluoroisopropyl | H |
| I-56 | H | H | H | Me | Me | heptafluoroisopropyl | Me |
| I-59 | F | H | H | H | Me | heptafluoroisopropyl | Me |
| I-60 | F | H | H | H | Me | heptafluoroisopropylthio | Me |
| I-61 | H | F | H | H | Me | heptafluoroisopropyl | Me |
| I-62 | H | H | H | F | Me | heptafluoroisopropyl | H |
| I-63 | H | H | H | F | Me | heptafluoroisopropyl | Me |
| I-64 | Cl | H | H | H | Me | heptafluoroisopropyl | H |
| I-65 | Cl | H | H | H | Me | heptafluoroisopropyl | Me |
| I-66 | H | Cl | H | H | Me | heptafluoroisopropyl | H |
| I-67 | H | Cl | H | H | Me | heptafluoroisopropyl | Me |
| I-68 | H | H | H | Cl | Me | heptafluoroisopropyl | H |
| I-69 | H | H | H | Cl | Me | heptafluoroisopropyl | Me |
| I-70 | Br | H | H | H | Me | heptafluoroisopropyl | Me |
| I-71 | H | H | H | Br | Me | heptafluoroisopropyl | H |
| I-72 | H | I | H | H | Me | heptafluoroisopropyl | H |
| I-73 | H | H | H | I | Me | heptafluoroisopropyl | H |
| I-74 | H | H | H | I | Me | heptafluoroisopropyl | Me |
| I-75 | H | H | CF₃ | H | Me | heptafluoroisopropyl | H |
| I-76 | H | H | CF₃ | H | Me | heptafluoroisopropyl | Me |
| I-77 | H | MeO | H | H | Me | heptafluoroisopropyl | H |
| I-78 | H | H | NH₂ | H | Me | heptafluoroisopropyl | H |
| I-79 | H | H | NH₂ | H | Me | heptafluoroisopropyl | Me |
| I-80 | Cl | Cl | H | Cl | Me | heptafluoroisopropyl | H |

TABLE 8

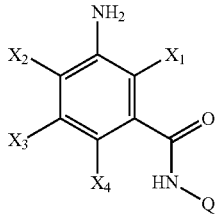

(4-C)

| Compound No. | $X_1$ | $X_2$ | $X_3$ | $X_4$ | Q |
|---|---|---|---|---|---|
| I-81 | H | H | H | H | 2-methyl-4-heptafluoroisopropyl-1-naphthyl |
| I-82 | H | H | H | H | 4-heptafluoroisopropyl-5,6,7,8-tetrahydro-1-naphthyl |
| I-83 | H | H | H | H | 2-chloro-4-heptafluoroisopropyl-5,6,7,8-tetrahydro-1-naphthyl |
| I-84 | H | H | H | H | 2-((1,1,1,3,3,3-hexafluoro2-propyloxy)pyridin-5-yl |
| I-85 | Cl | H | H | H | 2-(1,1,1,3,3,3-hexafluoro-2-propyloxy)-4-methylpyridin-5-yl |

TABLE 8-continued

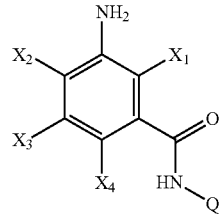

(4-C)

| Compound No. | $X_1$ | $X_2$ | $X_3$ | $X_4$ | Q |
|---|---|---|---|---|---|
| I-86 | H | H | H | H | 2-bromo-4-methyl-6-(1,1,1,3,3,3-hexafluoro-2-propyloxy)pyridin-3-yl |

Table 9 shows the physical properties of the compounds represented by formulae (1) and (4) of the present invention. This table also shows $^1$H-NMR shift values obtained by using tetramethylsilane as an internal reference material, and chloroform-d as a solvent.

TABLE 9

| Compound No. | $^1$H-NMR (CDCl$_3$, ppm) |
|---|---|
| 3 | δ 1.30 (6H, d, J = 6.3 Hz), 2.41 (3H, s), 5.00-5.05 (1H, m), 6.92 (1H, s), 7.40-7.61 (5H, m), 7.93 (1H, s), 8.01 (1H, s), 8.21 (1H, d, J = 8.8 Hz) |
| 4 | δ 0.96 (3H, t, J = 7.3 Hz), 1.38-1.47 (2H, m), 1.63-1.71 (2H, m), 2.41 (3H, s), 4.19 (2H, t, J = 6.6 Hz), 6.83 (1H, s), 7.42-7.62 (5H, m), 7.83 (1H, s), 8.00 (1H, s), 8.25 (1H, d, J = 8.5 Hz) |
| 5 | δ 0.98 (6H, d, J = 6.8 Hz), 1.94-2.05 (1H, m), 2.42 (3H, s), 3.98 (2H, d, J = 6.6 Hz), 6.81 (1H, s), 7.44-7.52 (3H, m), 7.55-7.61 (2H, m), 7.85 (1H, s), 8.01 (1H, s), 8.25 (1H, d, J = 8.6 Hz) |
| 6 | δ 0.96 (3H, t, J = 7.6 Hz), 1.29 (3H, d, J = 6.1 Hz), 1.58-1.73 (2H, m), 2.42 (3H, s), 4.83-4.92 (1H, m), 6.72 (1H, s), 7.42-7.61 (5H, m), 7.79 (1H, s), 8.01 (1H, s), 8.26 (1H, d, J = 8.5 Hz) |
| 7 | δ 1.53 (9H, s), 2.41 (3H, s), 6.66 (1H, s), 7.40-7.59 (5H, m), 7.80 (1H, s), 7.98 (1H, d, J = 1.7 Hz), 8.23 (1H, d, J = 8.8 Hz) |
| 8 | δ 0.98 (9H, s), 2.41 (3H, s), 3.89 (2H, s), 6.94 (1H, s), 7.41-7.50 (3H, m), 7.54-7.57 (1H, m), 7.62 (1H, d, J = 8.1 Hz), 7.86 (1H, s), 8.02 (1H, s), 8.24 (1H, d, J = 8.8 Hz) |
| 9 | δ 0.97 (9H, s), 1.62 (2H, t, J = 7.6 Hz), 2.41 (3H, s), 4.25 (2H, t, J = 7.6 Hz), 6.79 (1H, br), 7.42-7.51 (3H, m), 7.54-7.57 (1H, m), 7.61 (1H, d), 7.82 (1H, s), 7.99 (1H, s), 8.24 (1H, d, J = 8.5 Hz) |
| 10 | δ 0.90 (3H, t, J = 7.3 Hz), 0.91 (3H, t, J = 7.3 Hz), 1.26-1.41 (8H, m), 1.55-1.65 (1H, m), 2.40 (3H, s), 4.10 (2H, t, J = 5.4 Hz), 7.01 (1H, s), 7.40-7.50 (3H, m), 7.55 (1H, d, J = 7.8 Hz), 7.62 (1H, d, J = 7.8 Hz), 7.91 (1H, s), 8.01 (1H, s), 8.21 (1H, d, J = 8.5 Hz) |
| 11 | δ 2.42 (3H, s), 4.55 (1H, dd, J = 1.7 Hz, 6.3 Hz), 4.83 (1H, dd, J = 1.7 Hz, 13.9 Hz), 7.29 (1H, dd, J = 6.3 Hz, 13.9 Hz), 7.42-7.50 (3H, m), 7.61-7.63 (1H, m), 7.77 (1H, d, J = 7.8 Hz), 8.08 (1H, s), 8.15 (1H, d, J = 7.8 Hz), 8.30 (1H, s), 8.92 (1H, br-s) |
| 12 | δ 2.42 (3H, s), 4.68-4.70 (2H, m), 5.27-5.31 (1H, m), 5.35-5.41 (1H, m), 5.93-6.03 (1H, m), 6.83 (1H, br), 7.44-7.52 (3H, m), 7.55-7.63 (2H, m), 7.79 (1H, br), 8.00 (1H, s), 8.26 (1H, d, J = 8.8 Hz) |
| 13 | δ 0.82 (3H, d, J = 7.1 Hz), 0.84-0.99 (7H, m), 1.02-1.12 (2H, m), 1.36-1.42 (1H, m), 1.50-1.59 (1H, m), 1.68-1.72 (2H, m), 1.94-1.99 (1H, m), 2.11 (1H, d, J = 1.7 Hz), 2.42 (3H, s), 4.65-4.72 (1H, m), 6.74 (1H, s), 7.42-7.62 (5H, m), 7.80 (1H, s), 8.02 (1H, s), 8.25 (1H, d, J = 8.5 Hz) |
| 14 | δ 2.38 (3H, s), 5.19 (2H, s), 7.19 (1H, s), 7.32-7.61 (10H, m), 7.91 (1H, s), 8.00 (1H, s), 8.18 (1H, d, J = 8.5 Hz) |
| 16 | δ 2.34 (3H, s), 5.27 (2H, s), 6.96 (1H, br-s), 7.40-7.58 (6H, m), 7.63-7.69 (3H, m), 7.79 (1H, s), 8.00 (1H, s), 8.25 (1H, d, J = 8.8 Hz) |
| 17 | δ 2.33 (3H, s), 3.34 (3H, s), 3.57-3.61 (2H, m), 4.26-4.32 (2H, m), 7.13 (1H, s), 7.32-7.42 (3H, m), 7.46-7.53 (2H, m), 7.83 (1H, s), 7.91 (1H, d, J = 1.7 Hz), 8.13 (1H, d, J = 8.5 Hz) |
| 18 | δ 2.42 (3H, s), 5.83 (2H, s), 7.16 (1H, br-s), 7.43-7.52 (3H, m), 7.61 (1H, d, J = 8.1 Hz), 7.68 (1H, d, J = 8.1 Hz), 7.82 (1H, s), 8.03 (1H, s), 8.25 (1H, d, J = 8.5 Hz) |
| 18 | δ 2.42 (3H, s), 5.83 (2H, s), 7.16 (1H, br-s), 7.43-7.52 (3H, m), 7.61 (1H, d, J = 8.1 Hz), 7.68 (1H, d, J = 8.1 Hz), 7.82 (1H, s), 8.03 (1H, s), 8.25 (1H, d, J = 8.5 Hz) |

TABLE 9-continued

| Compound No. | $^1$H-NMR (CDCl$_3$, ppm) |
|---|---|
| 19 | δ 2.40 (3H, s), 3.74 (2H, t, J = 5.6 Hz), 4.44 (2H, t, J = 5.6 Hz), 7.19 (1H, s), 7.42-7.50 (3H, m), 7.55-7.58 (1H, m), 7.63 (1H, d, J = 7.6 Hz), 7.88 (1H, s), 8.01 (1H, s), 8.22 (1H, d, J = 8.8 Hz) |
| 20 | δ 2.40 (3H, s), 4.83 (2H, s), 7.42-7.49 (3H, m), 7.58-7.61 (1H, m), 7.67-7.69 (2H, m), 7.98 (1H, s), 8.06 (1H, s), 8.19 (1H, d, J = 8.5 Hz) |
| 21 | δ 2.43 (3H, s), 6.90 (1H, s), 7.22 (1H, br-s), 7.47-7.54 (3H, m), 7.64-7.68 (2H, m), 7.78 (1H, s), 8.06 (1H, s), 8.26 (1H, d, J = 8.8 Hz) |
| 22 | δ 2.01 (6H, s), 2.42 (3H, s), 6.95 (1H, br), 7.44-7.52 (3H, m), 7.57-7.62 (2H, m), 7.80 (1H, s), 8.02 (1H, s), 8.24 (1H, d, J = 8.5 Hz) |
| 23 | δ 2.41 (3H, s), 7.23-7.29 (1H, m), 7.40-7.55 (7H, m), 7.61-7.64 (1H, m), 7.72 (1H, d, J = 8.3 Hz), 7.78 (1H, s), 8.07 (1H, s), 8.26 (1H, d, J = 8.8 Hz) |
| 24 | δ 2.36 (3H, s), 2.40 (3H, s), 7.05-7.09 (2H, m), 7.15 (1H, s), 7.20 (2H, d, J = 8.1 Hz), 7.47-7.52 (3H, m), 7.60-7.63 (1H, m), 7.66-7.68 (1H, m), 7.79 (1H, s), 8.07 (1H, s), 8.25 (1H, d, J = 8.8 Hz) |
| 25 | δ 2.41 (3H, s), 7.12-7.17 (2H, m), 7.32-7.38 (2H, m), 7.42-7.48 (3H, m), 7.64 (1H, d, J = 7.8 Hz), 7.82 (1H, d, J = 7.8 Hz), 7.99 (1H, d, J = 8.5 Hz), 8.06 (1H, d, J = 8.5 Hz), 8.51 (1H, s), 9.52 (1H, s) |
| 59 | δ 2.32 (6H, s), 3.79 (3H, s), 6.92 (1H, br-s), 7.34 (2H, s), 7.43 (1H, t, J = 7.8 Hz), 7.52-7.62 (3H, m), 8.00 (1H, s) |
| 60 | δ 1.33 (3H, t, J = 7.1 Hz), 2.33 (6H, s), 4.24 (2H, q, J = 7.1 Hz), 6.80 (1H, s), 7.35 (2H, s), 7.44 (1H, t, J = 7.8 Hz), 7.46 (1H, s), 7.52-7.61 (2H, m), 8.02 (1H, s) |
| 61 | δ 0.99 (3H, t, J = 7.3 Hz), 1.71 (2H, m), 2.34 (6H, s), 4.14 (2H, t, J = 6.9 Hz), 6.79 (1H, s), 7.35 (2H, s), 7.41-7.47 (2H, m), 7.59-7.61 (2H, m), 8.02 (1H, s) |
| 62 | δ 1.31 (6H, d, J = 6.3 Hz), 2.33 (6H, s), 5.03 (1H, septet, J = 6.3 Hz), 6.74 (1H, s), 7.35 (2H, s), 7.43 (1H, t, J = 8.1 Hz), 7.52 (1H, s), 7.56-7.61 (2H, m), 8.03 (1H, s) |
| 63 | δ 0.96 (3H, t, J = 7.3 Hz), 1.38-1.48 (2H, m), 1.61-1.71 (2H, m), 2.34 (6H, s), 4.19 (2H, t, J = 6.9 Hz), 6.76 (1H, s), 7.35 (2H, s), 7.42-7.46 (2H, m), 7.58-7.61 (2H, m), 8.02 (1H, s) |
| 64 | δ 0.98 (6H, d, J = 6.8 Hz), 1.94-2.04 (1H, m), 2.34 (6H, s), 3.97 (2H, d, J = 6.6 Hz), 6.79 (1H, s), 7.35 (2H, s), 7.42-7.47 (2H, m), 7.59-7.61 (2H, m), 8.02 (1H, s) |
| 66 | δ 1.53 (9H, s), 2.34 (6H, s), 6.62 (1H, s), 7.35 (2H, s), 7.38-7.45 (2H, m), 7.51-7.60 (2H, m), 8.02 (1H, s) |
| 67 | δ 0.99 (9H, s), 2.34 (6H, s), 3.90 (2H, s), 6.79 (1H, s), 7.35 (2H, s), 7.43 (1H, br-s), 7.46 (1H, t, J = 8.1 Hz), 7.59-7.63 (2H, m), 8.03 (1H, s) |
| 68 | δ 0.95 (3H, d, J = 6.8 Hz), 0.96 (3H, d, J = 6.8 Hz), 1.24 (3H, d, J = 6.3 Hz), 1.81-1.89 (1H, m), 2.34 (6H, s), 4.75 (1H, quint, J = 6.3 Hz), 6.77 (1H, s), 7.35 (2H, s), 7.44 (1H, t, J = 8.1 Hz), 7.54-7.62 (3H, m), 8.05 (1H, s) |
| 69 | δ 0.94 (3H, t, J = 7.3 Hz), 1.29 (3H, d, J = 6.3 Hz), 1.32-1.45 (2H, m), 1.46-1.58 (1H, m), 1.61-1.70 (1H, m), 2.35 (6H, s), 4.93 (1H, sext., J = 6.3 Hz), 6.73 (1H, s), 7.35 (2H, s), 7.42-7.47 (1H, m), 7.51 (1H, s), 7.56-7.62 (2H, m), 8.05 (1H, s) |
| 70 | δ 0.93 (3H, d, J = 6.6 Hz), 0.94 (3H, d, J = 6.6 Hz), 1.29 (3H, d, J = 6.3 Hz), 1.31-1.37 (1H, m), 1.57-1.75 (2H, m), 2.34 (6H, s), 4.96-5.05 (1H, m), 6.70 (1H, s), 7.35 (2H, s), 7.42-7.46 (2H, m), 7.57-7.61 (2H, m), 8.04 (1H, s) |
| 71 | δ 0.97 (9H, s), 1.62 (2H, t, J = 7.6 Hz), 2.34 (6H, s), 4.25 (2H, t, J = 7.6 Hz), 6.73 (1H, s), 7.35 (2H, s), 7.43-7.47 (2H, m), 7.59-7.61 (2H, m), 8.02 (1H, s) |
| 72 | δ 1.27-1.34 (2H, m), 1.50-1.66 (4H, m), 1.74-1.83 (2H, m), 2.18-2.32 (1H, m), 2.34 (6H, s), 4.07 (2H, d, J = 7.1 Hz), 6.79 (1H, s), 7.35 (2H, s), 7.43-7.51 (2H, m), 7.58-7.62 (2H, m), 8.03 (1H, s) |
| 73 | δ 1.62 (3H, d, J = 6.6 Hz), 2.33 (6H, s), 5.90 (1H, q, J = 6.6 Hz), 6.82 (1H, br-s), 7.28-7.45 (9H, m), 7.56 (1H, d, J = 8.1 Hz), 7.60 (1H, d, J = 7.6 Hz), 8.02 (1H, br-s) |
| 74 | δ 2.34 (6H, s), 3.02 (2H, t, J = 7.1 Hz), 4.42 (2H, t, J = 7.1 Hz), 6.74 (1H, br-s), 7.23-7.27 (2H, m), 7.31-7.35 (5H, m), 7.41-7.47 (2H, m), 7.58-7.62 (2H, m), 7.99 (1H, br-s) |
| 75 | δ 2.34 (6H, s), 4.58 (1H, dd, J = 2.0 Hz, 6.3 Hz), 4.87 (1H, dd, J = 2.0 Hz, 13.9 Hz), 7.00 (1H, s), 7.25 (1H, dd, J = 6.3 Hz, 13.9 Hz), 7.35 (2H, s), 7.47 (1H, t, J = 7.8 Hz), 7.55 (1H, s), 7.63-7.65 (2H, m), 8.03 (1H, s) |
| 76 | δ 2.34 (6H, s), 4.68-4.70 (2H, m), 5.26-5.31 (1H, m), 5.35-5.41 (1H, m), 5.92-6.02 (1H, m), 6.84 (1H, s), 7.35 (2H, s), 7.42-7.47 (2H, m), 7.60-7.62 (2H, m), 8.02 (1H, s) |
| 77 | δ 2.33 (6H, s), 2.53 (1H, t, J = 1.4 Hz), 4.79 (2H, d, J = 1.4 Hz), 6.97 (1H, br-s), 7.35 (2H, s), 7.44 (1H, t, J = 8.1 Hz), 7.51 (1H, s), 7.59-7.63 (2H, m), 8.02 (1H, s) |
| 78 | δ 1.60-1.70 (1H, m), 1.78-1.86 (1H, m), 2.07-2.18 (2H, m), 2.33 (6H, s), 2.35-2.43 (2H, m), 5.00-5.08 (1H, m), 6.80 (1H, s), 7.35 (2H, s), 7.41-7.46 (1H, m), 7.53-7.62 (3H, m), 8.03 (1H, s) |
| 79 | δ 1.68-1.80 (6H, m), 1.86-1.94 (2H, m), 2.34 (6H, s), 5.20-5.23 (1H, m), 6.72 (1H, s), 7.35 (2H, s), 7.42-7.62 (4H, m), 8.04 (1H, s) |

TABLE 9-continued

| Compound No. | $^1$H-NMR (CDCl$_3$, ppm) |
|---|---|
| 81 | δ 2.32 (6H, s), 5.22 (2H, s), 6.87 (1H, s), 7.34 (2H, s), 7.36-7.45 (7H, m), 7.57-7.61 (2H, m), 8.01 (1H, s) |
| 82 | δ 2.33 (9H, s), 5.18 (2H, s), 6.83 (1H, br-s), 7.14-7.20 (3H, m), 7.31 (1H, d, J = 7.8 Hz), 7.35 (2H, s), 7.44 (2H, t, J = 7.8 Hz), 7.52-7.62 (2H, m), 8.01 (1H, br-s) |
| 83 | δ 2.34 (6H, s), 5.28 (2H, s), 6.90 (1H, br-s), 7.35 (2H, s), 7.43-7.54 (4H, m), 7.61-7.66 (4H, m), 8.01 (1H, s) |
| 84 | δ 2.34 (6H, s), 5.24 (2H, s), 6.92 (1H, br-s), 7.35-7.52 (4H, m), 7.63-7.81 (6H, m), 8.02 (1H, s) |
| 85 | δ 2.34 (6H, s), 5.27 (2H, s), 6.97 (1H, br-s), 7.35 (2H, s), 7.45-7.52 (4H, m), 7.61-7.69 (4H, m), 8.01 (1H, s) |
| 89 | δ 2.34 (6H, s), 5.34 (2H, s), 6.90 (1H, br), 7.28-7.30 (3H, m), 7.35 (2H, s), 7.39-7.49 (3H, m), 7.59-7.64 (2H, m), 8.04 (1H, m) |
| 90 | δ 2.33 (6H, s), 5.18 (2H, s), 6.92 (1H, s), 7.22-7.34 (5H, m), 7.40-7.47 (3H, m), 7.59-7.63 (2H, m), 8.02 (1H, s) |
| 91 | δ 2.33 (6H, s), 5.18 (2H, s), 6.86 (1H, s), 7.29-7.38 (6H, m), 7.43-7.47 (2H, m), 7.60-7.62 (2H, m), 8.01 (1H, s) |
| 92 | δ 2.34 (6H, s), 5.32 (2H, s), 6.92 (1H, br-s), 7.36 (2H, s), 7.42 (1H, s), 7.48 (1H, t, J = 7.8 Hz), 7.58 (2H, d, J = 9.0 Hz), 7.62-7.66 (2H, m), 8.01 (1H, s), 8.25 (2H, d, J = 9.0 Hz) |
| 93 | δ 2.35 (6H, s), 3.93 (3H, s), 5.28 (2H, s), 6.88 (1H, br-s), 7.36 (2H, s), 7.41 (1H, s), 7.45-7.49 (4H, m), 7.63 (2H, d, J = 6.8 Hz), 8.02 (1H, s), 8.05 (1H, d, J = 6.8 Hz) |
| 94 | δ 2.32 (6H, s), 2.62 (1H, br), 3.87 (2H, t, J = 4.4 Hz), 4.29-4.32 (2H, m), 7.26 (1H, s), 7.34 (2H, s), 7.42 (1H, t, J = 8.1 Hz), 7.54-7.61 (2H, m), 7.77 (1H, s), 8.00 (1H, s) |
| 95 | δ 2.31 (6H, s), 3.41 (3H, s), 3.64-3.66 (2H, m), 4.32-4.35 (2H, m), 7.14 (1H, s), 7.34 (2H, s), 7.40 (1H, t, J = 7.8 Hz), 7.55-7.60 (2H, m), 7.67 (1H, s), 8.00 (1H, s) |
| 96 | δ 1.23 (3H, t, J = 6.8 Hz), 2.29 (6H, s), 3.56 (2H, q, J = 6.8 Hz), 3.67-3.70 (2H, m), 4.31-4.34 (2H, m), 7.26 (1H, s), 7.33 (2H, s), 7.38-7.40 (1H, m), 7.52-7.60 (2H, m), 7.83 (1H, s), 8.00 (1H, s) |
| 97 | δ 1.18 (6H, d, J = 6.1 Hz), 2.29 (6H, s), 3.63-3.69 (3H, m), 4.30-4.32 (2H, m), 7.26 (1H, s), 7.33 (2H, s), 7.38 (1H, t, J = 7.8 Hz), 7.56-7.60 (2H, m), 7.82 (1H, s), 8.00 (1H, s) |
| 98 | δ 2.28 (6H, s), 3.70-3.73 (2H, m), 4.33-4.36 (2H, m), 4.57 (2H, s), 7.23-7.39 (9H, m), 7.53 (1H, d, J = 7.8 Hz), 7.58 (1H, d, J = 7.8 Hz), 7.87 (1H, s), 7.99 (1H, s) |
| 99 | δ 1.20 (3H, t, J = 8.1 Hz), 1.95-2.00 (2H, m), 2.35 (6H, s), 3.47-3.57 (4H, m), 4.30 (2H, t, J = 6.6 Hz), 6.78 (1H, s), 7.35 (2H, s), 7.46 (2H, t, J = 7.8 Hz), 7.61 (2H, d, J = 7.8 Hz), 8.02 (1H, s) |
| 100 | δ 1.30 (3H, t, J = 7.3 Hz), 2.34 (6H, s), 4.26 (2H, q, J = 7.3 Hz), 4.72 (2H, s), 7.35 (2H, s), 7.36-7.40 (1H, m), 7.52-7.60 (3H, m), 7.77-7.79 (1H, m), 7.90 (1H, br-s) |
| 101 | δ 1.56 (3H, d, J = 7.3 Hz), 2.33 (6H, s), 3.79 (3H, s), 5.18 (1H, q, J = 7.3 Hz), 7.21 (1H, br), 7.35 (2H, s), 7.41 (1H, t, J = 7.8 Hz), 7.55-7.62 (3H, m), 7.98 (1H, s) |
| 102 | δ 1.29 (3H, t, J = 6.8 Hz), 1.55 (3H, d, J = 6.8 Hz), 2.34 (6H, s), 4.23 (2H, q, J = 6.8 Hz), 5.16 (1H, q, J = 6.8 Hz), 7.24 (1H, br), 7.35 (2H, s), 7.41 (1H, t, J = 7.8 Hz), 7.55-7.62 (3H, m), 7.96 (1H, s) |
| 103 | δ 2.21 (3H, s), 2.34 (6H, s), 2.84 (2H, t, J = 6.1 Hz), 4.46 (2H, t, J = 6.1 Hz), 6.91 (1H, br-s), 7.35 (2H, s), 7.43 (1H, t, J = 7.8 Hz), 7.52-7.70 (3H, m), 8.01 (1H, s) |
| 104 | δ 2.10 (3H, s), 2.34 (6H, s), 4.33-4.42 (4H, m), 6.97 (1H, br-s), 7.35 (2H, s), 7.45 (1H, t, J = 7.8 Hz), 7.57-7.64 (3H, m), 8.01 (1H, s) |
| 106 | δ 2.33 (6H, s), 2.78 (2H, t, J = 6.3 Hz), 4.40 (2H, t, J = 6.3 Hz), 7.12 (1H, br), 7.35 (2H, s), 7.45 (1H, t, J = 7.8 Hz), 7.60-7.65 (3H, m), 8.01 (1H, s) |
| 108 | δ 2.17 (3H, s), 2.34 (6H, s), 2.80 (2H, t, J = 6.6 Hz), 4.37 (2H, t, J = 6.6 Hz), 6.84 (1H, br-s), 7.35 (2H, s), 7.43-7.52 (2H, m), 7.58-7.63 (2H, m), 8.02 (1H, s) |
| 109 | δ 1.25-1.31 (3H, m), 2.33 (6H, s), 2.57-2.64 (2H, m), 2.81-2.85 (2H, m), 4.32-4.38 (2H, m), 6.92 (1H, s), 7.35 (2H, s), 7.42-7.49 (1H, m), 7.58-7.63 (3H, m), 8.03 (1H, s) |
| 110 | δ 1.28 (6H, d, J = 6.6 Hz), 2.34 (6H, s), 2.84 (2H, t, J = 7.1 Hz), 2.94-3.04 (1H, m), 4.34 (2H, t, J = 7.1 Hz), 6.88 (1H, s), 7.35 (2H, s), 7.42-7.49 (1H, m), 7.52-7.64 (3H, m), 8.02 (1H, s) |
| 111 | δ 1.40 (3H, d, J = 6.1 Hz), 2.17 (3H, s), 2.34 (6H, s), 2.67 (1H, dd, J = 6.1 Hz, 13.7 Hz), 2.77 (1H, dd, J = 6.1 Hz, 13.7 Hz), 5.08 (1H, sextett., J = 6.1 Hz), 6.80 (1H, s), 7.35 (2H, s), 7.45 (1H, t, J = 7.8 Hz), 7.52 (1H, s), 7.57-7.63 (2H, m), 8.04 (1H, s) |
| 112 | δ 1.24-1.37 (3H, m), 2.35 (6H, s), 2.26-2.31 (2H, m), 2.98-3.06 (2H, m), 4.67-4.76 (2H, m), 7.35 (3H, s), 7.45 (2H, t, J = 7.8 Hz), 7.55-7.74 (2H, m), 8.08 (1H, br-s) |
| 113 | δ 1.36-1.43 (3H, m), 2.35 (6H, s), 3.04-3.10 (2H, m), 3.37 (2H, t, J = 5.9 Hz), 4.68-4.73 (2H, m), 7.00 (1H, br-s), 7.35 (2H, s), 7.46 (2H, t, J = 7.8 Hz), 7.55-7.70 (2H, m), 8.02-8.07 (1H, m) |

TABLE 9-continued

| Compound No. | ¹H-NMR (CDCl₃, ppm) |
|---|---|
| 116 | δ 2.35 (6H, s), 4.45 (2H, dt, J = 28.3 Hz, 4.0 Hz), 4.66 (2H, dt, J = 47.3 Hz, 4.0 Hz), 6.88 (1H, br-s), 7.36 (2H, s), 7.46-7.50 (2H, m), 7.59-7.65 (2H, m), 8.02 (1H, s) |
| 117 | δ 2.34 (6H, s), 4.38 (2H, dt, J = 3.9 Hz, 13.6 Hz), 6.00 (1H, tt, J = 3.9 Hz, 47.3 Hz), 7.05 (1H, br-s), 7.35 (2H, s), 7.47 (1H, t, J = 7.8 Hz), 7.57-7.66 (3H, m), 8.01 (1H, s) |
| 118 | δ 2.33 (6H, s), 4.57 (2H, q, J = 8.3 Hz), 7.09 (1H, br), 7.35 (2H, s), 7.45-7.50 (2H, m), 7.61-7.66 (2H, m), 8.01 (1H, s) |
| 119 | δ 2.35 (6H, s), 4.61-4.75 (4H, m), 5.18-5.31 (1H, m), 6.98 (1H, br-s), 7.36 (2H, s), 7.45-7.52 (2H, m), 7.58-7.66 (2H, m), 8.03 (1H, s) |
| 120 | δ 2.35 (6H, s), 3.75-3.83 (2H, m), 4.46-4.80 (2H, m), 5.19-5.24 (1H, m), 6.97 (1H, br-s), 7.36 (2H, s), 7.36-7.48 (2H, m), 7.60-7.66 (2H, m), 8.03 (1H, s) |
| 121 | (DMSO-d₆) δ 1.48 (3H, d, J = 6.6 Hz), 2.35 (6H, s), 5.35 (1H, septet, J = 6.6 Hz), 7.33 (2H, s), 7.42 (1H, t, J = 7.8 Hz), 7.68 (1H, d, J = 7.8 Hz), 7.76 (1H, d, J = 7.8 Hz), 8.11 (1H, s), 8.76 (1H, s), 9.26 (1H, s) |
| 122 | (CDCl₃ + DMSO-d₆) δ 2.35 (6H, s), 5.87 (1H, septet, J = 6.3 Hz), 7.33 (2H, s), 7.44 (1H, t, J = 8.1 Hz), 7.71-7.78 (2H, m), 8.17 (1H, s), 8.97 (1H, s), 10.19 (1H, s) |
| 123 | δ 2.34 (6H, s), 2.48-2.59 (2H, m), 4.42 (2H, t, J = 6.3 Hz), 6.93 (1H, br-s), 7.35 (2H, s), 7.46 (1H, t, J = 7.8 Hz), 7.57-7.64 (3H, m), 8.01 (1H, br-s) |
| 124 | δ 2.35 (6H, s), 4.67 (2H, t, J = 13.2 Hz), 6.98 (1H, br-s), 7.29 (2H, s), 7.36 (1H, s), 7.50 (1H, t, J = 7.8 Hz), 7.65-7.67 (2H, m), 8.01 (1H, s) |
| 125 | δ 1.51 (3H, d, J = 6.4 Hz), 2.35 (6H, s), 5.49-5.50 (1H, m), 6.90 (1H, br-s), 7.36 (2H, s), 7.44 (1H, br-s), 7.50 (1H, t, J = 7.8 Hz), 7.62-7.67 (2H, m), 8.02 (1H, s) |
| 126 | δ 1.95-2.05 (2H, m), 2.22-2.27 (2H, m), 2.35 (6H, s), 4.26 (2H, t, J = 6.4 Hz), 6.81 (1H, s), 7.36 (2H, s), 7.45-7.49 (2H, m), 7.61-7.63 (2H, m), 8.02 (1H, s) |
| 127 | δ 2.35 (6H, s), 2.61-2.65 (1H, m), 2.9-3.1 (1H, m), 5.2-5.3 (1H, m), 7.01 (1H, br-s), 7.36 (2H, s), 7.45-7.52 (2H, m), 7.62-7.68 (2H, m), 8.01 (1H, s) |
| 128 | δ 2.34 (6H, s), 5.84 (2H, s), 7.03 (1H, s), 7.36 (2H, s), 7.44-7.52 (2H, m), 7.65-7.67 (2H, m), 8.04 (1H, s) |
| 129 | δ 2.36 (6H, s), 7.33 (2H, s), 7.40-7.46 (1H, m), 7.65 (1H, d, J = 7.8 Hz), 7.90 (1H, d, J = 7.8 Hz), 7.95 (1H, d, J = 1.7 Hz), 8.55 (1H, s), 9.07 (1H, s) |
| 130 | δ 2.35 (6H, s), 3.74-3.77 (2H, m), 4.44-4.47 (2H, m), 6.87 (1H, br), 7.36 (2H, s), 7.43-7.52 (2H, m), 7.59-7.64 (2H, m), 8.02 (1H, s) |
| 131 | δ 2.32 (6H, s), 4.53 (2H, d, J = 5.9 Hz), 5.90 (1H, t, J = 5.9 Hz), 7.11 (1H, br-s), 7.35 (2H, s), 7.45 (1H, t, J = 8.1 Hz), 7.60-7.64 (3H, m), 8.01 (1H, br-s) |
| 132 | δ 2.33 (6H, s), 4.84 (2H, s), 7.29 (1H, br), 7.35 (2H, s), 7.47 (1H, t, J = 7.8 Hz), 7.58 (1H, s), 7.64-7.66 (2H, m), 8.04 (1H, s) |
| 133 | δ 2.35 (6H, s), 6.90 (1H, s), 7.17 (1H, br), 7.36 (2H, s), 7.42 (1H, s), 7.50-7.54 (1H, m), 7.66-7.71 (2H, m), 8.06 (1H, s) |
| 134 | δ 2.35 (6H, s), 3.83 (4H, d, J = 5.1 Hz), 5.22 (1H, quint, J = 5.1 Hz), 6.93 (1H, s), 7.36 (2H, s), 7.43 (1H, s), 7.48 (1H, t, J = 7.8 Hz), 7.60-7.66 (2H, m), 8.03 (1H, s) |
| 135 | δ 2.01 (6H, s), 2.35 (6H, s), 6.88 (1H, br), 7.36 (2H, s), 7.43-7.52 (2H, m), 7.58-7.65 (2H, m), 8.03 (1H, s) |
| 136 | δ 2.17 (2H, quint, J = 6.3 Hz), 2.34 (6H, s), 3.66 (2H, t, J = 6.3 Hz), 4.36 (2H, t, J = 6.3 Hz), 6.83 (1H, s), 7.35 (2H, s), 7.43-7.48 (1H, m), 7.52 (1H, s), 7.59-7.63 (2H, m), 8.02 (1H, s) |
| 137 | δ 2.35 (6H, s), 3.59 (2H, t, J = 5.9 Hz), 4.51 (2H, t, J = 5.9 Hz), 6.86 (1H, br), 7.36 (2H, s), 7.43-7.52 (2H, m), 7.60-7.64 (2H, m), 8.02 (1H, s) |
| 138 | δ 2.34 (6H, s), 5.03 (2H, s), 7.15 (1H, br), 7.35 (2H, s), 7.47-7.54 (2H, m), 7.64-7.69 (2H, m), 8.06 (1H, s) |
| 139 | δ 2.25 (2H, quint, J = 6.1 Hz), 2.34 (6H, s), 3.51 (2H, t, J = 6.1 Hz), 4.35 (2H, t, J = 6.1 Hz), 6.83 (1H, s), 7.35 (2H, s), 7.46 (1H, t, J = 8.1 Hz), 7.54 (1H, s), 7.58-7.64 (2H, m), 8.02 (1H, s) |
| 140 | δ 2.34 (6H, s), 3.34-3.39 (2H, m), 4.42-4.47 (2H, m), 6.91-6.99 (1H, br), 7.35 (2H, s), 7.43-7.49 (1H, m), 7.56-7.64 (3H, m), 8.03 (1H, s) |
| 141 | (DMSO-d₆) δ 1.82 (3H, s), 2.28 (6H, s), 3.33 (2H, q, J = 5.9 Hz), 4.11 (2H, t, J = 5.9 Hz), 7.44 (2H, s), 7.46 (1H, d, J = 7.8 Hz), 7.62-7.69 (2H, m), 8.04 (1H, t, J = 5.9 Hz), 8.09 (1H, s), 9.90 (1H, s), 9.93 (1H, s) |
| 146 | δ 2.34 (6H, s), 2.36 (3H, s), 7.05-7.08 (2H, m), 7.17-7.20 (2H, m), 7.33 (2H, s), 7.43 (1H, t, J = 7.8 Hz), 7.68 (1H, d, J = 7.8 Hz), 7.80 (1H, d, J = 7.8 Hz), 8.17 (1H, s), 8.67 (1H, s), 9.29 (1H, s) |
| 147 | δ 2.35 (6H, s), 7.33 (2H, s), 7.41-7.57 (5H, m), 7.72 (1H, d, J = 7.8 Hz), 7.82 (1H, d, J = 7.8 Hz), 8.18 (1H, s), 9.01 (1H, s), 9.73 (1H, s) |
| 148 | δ 2.35 (6H, s), 7.13-7.18 (2H, m), 7.32-7.37 (4H, m), 7.41-7.45 (1H, m), 7.70 (1H, d, J = 7.6 Hz), 7.81 (1H, d, J = 7.6 Hz), 8.16 (1H, s), 9.04 (1H, s), 9.69 (1H, s) |

TABLE 9-continued

| Compound No. | ¹H-NMR (CDCl₃, ppm) |
|---|---|
| 149 | δ 2.34 (6H, s), 7.32 (2H, s), 7.33-7.36 (1H, m), 7.42-7.52 (3H, m), 7.65 (1H, d, J = 2.4 Hz), 7.70 (1H, d, J = 7.8 Hz), 7.80-7.88 (4H, m), 8.20 (1H, s), 8.76 (1H, s), 9.48 (1H, s) |
| 154 | δ 2.08-2.14 (1H, m), 2.18-2.30 (1H, m), 2.35 (6H, s), 3.86-4.01 (4H, m), 5.37-5.39 (1H, m), 6.87 (1H, br-s), 7.35 (2H, s), 7.46 (2H, t, J = 7.6 Hz), 7.58-7.63 (2H, m), 8.01 (1H, s) |
| 155 | δ 2.34 (6H, s), 5.18 (2H, s), 6.38 (1H, d, J = 3.2 Hz), 6.48 (1H, d, J = 3.2 Hz), 6.83 (1H, br-s), 7.35 (2H, s), 7.43-7.47 (3H, m), 7.57-7.63 (2H, m), 8.01 (1H, s) |
| 156 | δ 2.34 (6H, s), 5.10 (2H, s), 6.48 (1H, s), 6.79 (1H, br-s), 7.35 (2H, s), 7.39-7.47 (3H, m), 7.53 (1H, s), 7.59-7.63 (2H, m), 8.01 (1H, br-s) |
| 157 | δ 1.58-1.67 (1H, m), 1.93-1.95 (2H, m), 2.01-2.09 (1H, m), 2.34 (6H, s), 3.78-3.93 (2H, m), 4.06-4.23 (2H, m), 4.31 (1H, dd, J = 3.2 Hz, 11.2 Hz), 6.95 (1H, br-s), 7.35 (2H, s), 7.45 (2H, t, J = 7.8 Hz), 7.50-7.56 (1H, m), 7.63 (1H, d, J = 7.1 Hz), 8.04 (1H, s) |
| 158 | δ 1.66-1.73 (1H, m), 2.05-2.13 (1H, m), 2.34 (6H, s), 2.60-2.70 (1H, m), 3.64-3.68 (1H, m), 3.73-3.79 (1H, m), 3.85-3.92 (2H, m), 4.09-4.15 (2H, m), 6.87 (1H, br-s), 7.35 (2H, s), 7.46 (2H, t, J = 7.8 Hz), 7.61-7.66 (2H, m), 8.01 (1H, br-s) |
| 159 | δ 2.34 (6H, s), 5.38 (2H, s), 6.83 (1H, br-s), 6.98-7.02 (1H, m), 7.16 (1H, d, J = 2.9 Hz), 7.34-7.36 (3H, m), 7.43-7.47 (2H, m), 7.59-7.63 (2H, m), 8.01 (1H, s) |
| 160 | δ 2.34 (6H, s), 5.23 (2H, s), 6.83 (1H, br-s), 7.14 (1H, d, J = 5.1 Hz), 7.33-7.37 (4H, m), 7.45 (2H, t, J = 7.8 Hz), 7.61-7.64 (2H, m), 8.02 (1H, s) |
| 161 | δ 2.32 (6H, s), 5.34 (2H, s), 7.24-7.28 (2H, m), 7.35 (2H, s), 7.39 (1H, d, J = 7.8 Hz), 7.43 (1H, d, J = 7.8 Hz), 7.55 (1H, s), 7.61 (2H, t, J = 7.8 Hz), 7.73 (1H, dt, J = 1.7 Hz, 7.8 Hz), 8.03 (1H, s), 8.61 (1H, br-s) |
| 162 | δ 2.36 (6H, s), 5.36 (2H, s), 6.37 (1H, br-s), 6.70 (1H, s), 7.31-7.39 (4H, m), 7.73-7.82 (4H, m), 8.58-8.61 (1H, m), 8.72 (1H, d, J = 2.0 Hz) |
| 163 | δ 2.34 (6H, s), 5.22 (2H, s), 6.89 (1H, br-s), 7.35-7.49 (5H, m), 7.62 (2H, d, J = 7.3 Hz), 7.72-7.77 (1H, m), 8.00 (1H, br-s), 8.45 (1H, d, J = 2.4 Hz) |
| 164 | δ 1.23 (6H, d, J = 6.8 Hz), 2.34 (3H, s), 3.18 (1H, septet, J = 6.8 Hz), 3.81 (3H, s), 6.84 (1H, s), 7.36 (1H, s), 7.42 (1H, s), 7.46 (1H, t, J = 7.8 Hz), 7.56-7.63 (3H, m), 8.01 (1H, s) |
| 165 | δ 1.22 (6H, d, J = 6.8 Hz), 1.33 (3H, t, J = 7.3 Hz), 2.33 (3H, s), 3.17 (1H, septet, J = 6.8 Hz), 4.24 (2H, q, J = 7.3 Hz), 6.80 (1H, s), 7.35 (1H, s), 7.41 (1H, s), 7.44 (1H, t, J = 7.8 Hz), 7.58-7.62 (3H, m), 8.02 (1H, s) |
| 166 | δ 1.32 (6H, d, J = 6.1 Hz), 5.03 (1H, septet, J = 6.1 Hz), 6.71 (1H, s), 7.40-7.44 (1H, m), 7.54 (1H, d, J = 2.0 Hz), 7.56 (1H, d, J = 2.0 Hz), 7.60 (2H, d, J = 8.8 Hz), 7.80 (2H, d, J = 8.8 Hz), 7.98 (1H, s), 8.03 (1H, s) |
| 167 | δ 1.32 (6H, d, J = 6.1 Hz), 2.53 (3H, d, J = 8.8 Hz), 5.04 (1H, septet, J = 6.1 Hz), 6.71 (1H, br s), 7.41-7.65 (6H, m), 7.95-7.97 (2H, m) |
| 168 | δ 1.32 (6H, d, J = 6.1 Hz), 1.33 (3H, t, J = 7.6 Hz), 2.74 (2H, q, J = 7.6 Hz), 5.04 (1H, septet, J = 6.1 Hz), 6.70 (1H, s), 7.43-7.56 (4H, m), 7.60 (1H, d, J = 8.1 Hz), 7.86 (1H, s), 8.00 (1H, s), 8.27 (1H, d, J = 8.5 Hz) |
| 169 | δ 1.02 (3H, t, J = 7.3 Hz), 1.32 (6H, d, J = 6.3 Hz), 1.67-1.77 (2H, m), 2.70 (2H, t, J = 7.3 Hz), 5.03 (1H, septet, J = 6.3 Hz), 6.72 (1H, s), 7.43-7.60 (5H, m), 7.89 (1H, s), 8.03 (1H, s), 8.29 (1H, d, J = 8.5 Hz) |
| 170 | δ 1.32 (6H, d, J = 6.4 Hz), 3.89 (3H, s), 5.04 (1H, septet, J = 6.4 Hz), 6.73 (1H, br s), 7.05-7.08 (1H, m), 7.42-7.46 (1H, m), 7.51-7.58 (3H, m), 7.80 (1H, s), 8.00 (1H, s), 8.15 (1H, s) |
| 171 | δ 1.32 (6H, d, J = 6.4 Hz), 5.03 (1H, septet, J = 6.4 Hz), 6.75 (1H, s), 7.28-7.47 (2H, m), 7.52-7.58 (2H, m), 7.72-7.75 (1H, m), 7.92 (1H, s), 8.00 (1H, s), 8.37 (1H, s) |
| 172 | δ 1.31 (6H, d, J = 6.3 Hz), 2.30 (3H, s), 2.47 (3H, d, J = 5.9 Hz), 5.01-5.09 (1H, m), 6.72 (1H, br-s), 7.40-7.47 (2H, m), 7.56-7.60 (2H, m), 7.77 (1H, d, J = 8.6 Hz), 7.83 (1H, br-s), 8.00 (1H, br-s) |
| 173 | δ 1.31 (6H, d, J = 6.1 Hz), 2.35 (3H, s), 2.52 (3H, d, J = 9.0 Hz), 4.99-5.09 (1H, m), 6.71 (1H, br-s), 7.30 (1H, br-s), 7.44 (1H, t, J = 7.8 Hz), 7.52-7.57 (1H, m), 7.61 (1H, d, J = 7.8 Hz), 7.72 (1H, s), 7.98 (1H, s), 8.06 (1H, s) |
| 174 | δ 1.23 (6H, t, J = 7.6 Hz), 1.32 (6H, d, J = 6.1 Hz), 2.69 (4H, q, J = 7.6 Hz), 5.03 (1H, septet, J = 6.1 Hz), 6.70 (1H, s), 7.38 (2H, s), 7.42-7.47 (2H, m), 7.58-7.62 (2H, m), 8.01 (1H, s) |
| 175 | δ 1.22 (3H, t, J = 7.6 Hz), 1.31 (6H, d, J = 6.3 Hz), 2.34 (3H, s), 2.69 (2H, q, J = 7.6 Hz), 5.03 (1H, septet, J = 6.3 Hz), 6.70 (1H, s), 7.37 (2H, s), 7.42-7.47 (2H, m), 7.58-7.61 (2H, m), 8.02 (1H, s) |
| 176 | δ 1.22 (6H, d, J = 6.8 Hz), 1.31 (6H, d, J = 6.3 Hz), 2.33 (3H, s), 3.17 (1H, septet, J = 6.8 Hz), 5.03 (1H, septet, J = 6.3 Hz), 6.76 (1H, s), 7.35 (1H, s), 7.41 (1H, s), 7.44 (1H, t, J = 8.1 Hz), 7.56-7.62 (3H, m), 8.03 (1H, s) |
| 177 | δ 1.32 (6H, d, J = 6.1 Hz), 2.35 (3H, s), 3.85 (3H, s), 5.04 (1H, septet, J = 6.1 Hz), 6.67 (1H, s), 6.96 (1H, s), 7.13 (1H, s), 7.44 (1H, t, J = 8.1 Hz), 7.59-7.65 (3H, m), 7.96 (1H, s) |
| 178 | δ 1.30 (6H, d, J = 6.1 Hz), 2.42 (3H, s), 5.00 (1H, septet, J = 6.1 Hz), 6.63 (1H, s), 7.27-7.41 (8H, m), 7.45 (1H, s), 7.53 (1H, s), 7.58 (1H, d, J = 7.8 Hz), 7.74 (1H, s) |

TABLE 9-continued

| Compound No. | ¹H-NMR (CDCl₃, ppm) |
|---|---|
| 179 | δ1.31 (6H, d, J = 6.1 Hz), 2.61 (3H, d, J = 6.3 Hz), 5.05 (1H, septet, J = 6.1 Hz), 6.76 (1H, br s), 7.45-7.58 (3H, m), 7.70 (1H, d, J = 8.1 Hz), 7.96 (1H, t, J = 1.8 Hz), 8.56-8.58 (1H, m), 8.70 (1H, br s) |
| 180 | δ 1.24 (3H, t, J = 7.6 Hz), 1.31 (6H, d, J = 6.3 Hz), 2.75 (2H, q, J = 7.6 Hz), 5.03 (1H, septet, J = 6.3 Hz), 6.74 (1H, s), 7.42-7.47 (2H, m), 7.57-7.67 (4H, m), 8.02 (1H, s) |
| 181 | δ 0.93 (3H, t, J = 7.3 Hz), 1.32 (6H, d, J = 6.1 Hz), 1.63-1.71 (2H, m), 2.70 (2H, t, J = 7.6 Hz), 5.04 (1H, septet, J = 6.1 Hz), 6.72 (1H, s), 7.44-7.48 (2H, m), 7.57-7.63 (3H, m), 7.68 (1H, s), 8.02 (1H, s) |
| 182 | δ1.32 (6H, d, J = 6.4 Hz), 3.92 (3H, s), 5.06 (1H, septet, J = 6.4 Hz), 6.73 (1H, s), 7.46-7.50 (1H, m), 7.55-7.60 (2H, m), 7.69 (1H, d, J = 7.8 Hz), 7.96 (1H, s), 8.48 (1H, d, J = 1.2 Hz), 8.58 (1H, s) |
| 183 | δ1.31 (6H, d, J = 6.2 Hz), 2.30 (3H, s), 2.44 (3H, d, J = 6.4 Hz), 5.01-5.05 (1H, m), 6.72 (1H, br-s), 7.44-7.48 (2H, m), 7.61-7.62 (2H, m), 7.78 (1H, s), 8.03 (1H, br-s) |
| 184 | δ 1.32 (6H, d, J = 6.1 Hz), 2.35 (3H, s), 2.58 (3H, d, J = 6.8 Hz), 5.01-5.07 (1H, m), 6.68 (1H, br-s), 7.35 (1H, s), 7.46 (1H, t, J = 7.8 Hz), 7.61-7.65 (2H, m), 7.72 (1H, s), 8.01 (1H, s) |
| 185 | δ1.31 (6H, d, J = 6.4 Hz), 2.49 (3H, s), 4.77 (2H, br-s), 5.06 (1H, sept, J = 6.4 Hz), 6.73 (1H, br-s), 7.44-7.49 (1H, m), 7.55 (1H, s), 7.61-7.63 (2H, m), 7.81 (1H, s), 8.05 (1H, br-s) |
| 186 | δ1.32 (6H, d, J = 6.4 Hz), 2.61 (3H, s), 5.05 (1H, septet), 6.73 (1H, br-s), 7.44-7.48 (2H, m), 7.57-7.64 (2H, m), 7.95 (1H, br-s), 8.06 (1H, br-s) |
| 187 | δ 4.84 (2H, s), 7.28 (1H, br), 7.45 (1H, t, J = 8.1 Hz), 7.59-7.65 (4H, m), 7.81 (2H, d, J = 8.5 Hz), 7.99 (1H, s), 8.17 (1H, s) |
| 188 | δ 2.53 (3H, d, J = 8.8 Hz), 4.85 (2H, s), 7.15 (1H, br s), 7.45-7.65 (6H, m), 8.00-8.02 (2H, m) |
| 189 | δ 1.34 (3H, t, J = 7.6 Hz), 2.75 (2H, q, J = 7.6 Hz), 4.85 (2H, s), 7.10 (1H, s), 7.47-7.52 (3H, m), 7.59-7.66 (2H, m), 7.87 (1H, s), 8.05 (1H, s), 8.27 (1H, d, J = 8.8 Hz) |
| 190 | δ 1.02 (3H, t, J = 7.3 Hz), 1.67-1.77 (2H, m), 2.70 (2H, t, J = 7.6 Hz), 4.85 (2H, s), 7.10 (1H, br-s), 7.44-7.52 (3H, m), 7.59-7.65 (2H, m), 7.88 (1H, s), 8.07 (1H, s), 8.30 (1H, d, J = 8.5 Hz) |
| 191 | δ3.89 (3H, s), 4.85 (2H, s), 7.06 (1H, dd, J = 8.5 Hz, 2.0 Hz), 7.18 (1H, br s), 7.46-7.54 (2H, m), 7.61-7.63 (2H, m), 7.79-7.80 (1H, m), 8.01 (1H, s), 8.10 (1H, s) |
| 192 | δ4.86 (2H, s), 7.09 (1H, br.), 7.43-7.79 (5H, m), 8.03 (1H, br.), 8.56 (1H, br) 8.76 (1H, d, J = 8.8 Hz) |
| 193 | δ4.86 (2H, s), 7.16 (1H, br s), 7.47-7.74 (5H, m), 7.93 (1H, s), 8.02 (1H, s), 8.23 (1H, s) |
| 194 | δ 2.30 (3H, s), 2.47 (3H, d, J = 6.0 Hz), 4.85 (2H, s), 7.12 (1H, br-s), 7.42 (1H, d, J = 9.0 Hz), 7.49 (1H, t, J = 8.1 Hz), 7.62-7.67 (2H, m), 7.78-7.81 (2H, m), 8.03 (1H, br-s) |
| 195 | δ 2.35 (3H, s), 2.52 (3H, d, J = 8.8 Hz), 4.86 (2H, s), 7.05 (1H, br-s), 7.31 (1H, s), 7.50 (1H, t, J = 7.8 Hz), 7.60-7.67 (2H, m), 7.71 (1H, s), 8.03 (1H, s), 8.07 (1H, s) |
| 196 | δ 1.23 (6H, t, J = 7.6 Hz), 2.70 (4H, q, J = 7.6 Hz), 4.85 (2H, s), 7.03 (1H, br), 7.39 (3H, s), 7.50 (1H, t, J = 8.1 Hz), 7.65 (1H, d, J = 8.1 Hz), 7.69 (1H, br-s), 8.04 (1H, s) |
| 197 | δ 1.23 (3H, t, J = 7.6 Hz), 2.35 (3H, s), 2.69 (2H, q, J = 7.6 Hz), 4.85 (2H, s), 7.05 (1H, br), 7.37 (2H, s), 7.42 (1H, s), 7.50 (1H, t, J = 7.8 Hz), 7.64-7.66 (2H, m), 8.04 (1H, s) |
| 198 | δ1.23 (6H, d, J = 6.8 Hz), 2.34 (3H, s), 3.17 (1H, septet, J = 6.8 Hz), 4.85 (2H, s), 7.18 (1H, br-s), 7.36 (1H, s), 7.42 (1H, s), 7.49 (1H, t, J = 8.1 Hz), 7.55 (1H, s), 7.65-7.67 (2H, m), 8.05 (1H, s) |
| 199 | δ 2.36 (3H, s), 3.86 (3H, s), 4.85 (2H, s), 6.96 (1H, s), 7.01 (1H, br), 7.14 (1H, s), 7.49 (1H, t, J = 8.1 Hz), 7.64-7.68 (3H, m), 7.99 (1H, s) |
| 200 | δ 2.43 (3H, s), 4.83 (2H, s), 6.99 (1H, br), 7.33-7.42 (8H, m), 7.45 (1H, s), 7.54 (1H, s), 7.64 (1H, d, J = 6.3 Hz), 7.78 (1H, s) |
| 201 | δ 2.47 (3H, s), 4.86 (2H, s), 7.06 (1H, s), 7.11 (1H, br.), 7.24-7.27 (1H, m), 7.53 (1H, t, J = 7.3 Hz), 7.66 (2H, t, J = 7.3 Hz), 7.95 (1H, s), 8.17 (1H, s), 8.85 (1H, s) |
| 202 | δ1.57 (3H, s), 4.86 (2H, s), 7.10 (1H, br s), 7.52 (2H, t, J = 7.8 Hz), 7.63-7.65 (1H, m), 7.72-7.74 (1H, m), 8.03 (1H, br-s), 8.57-8.59 (1H, m), 8.70 (1H, br s) |
| 203 | δ 2.10 (3H, s), 4.84 (2H, s), 7.11 (1H, d, J = 8.8 Hz), 7.18-7.22 (2H, m), 7.47 (1H, t, J = 7.8 Hz), 7.61 (1H, d, J = 7.8 Hz), 7.65 (1H, d, J = 7.8 Hz), 7.80 (1H, br-s), 8.00 (1H, br-s) |
| 204 | δ1.50 (9H, s), 2.29 (3H, s), 4.85 (2H, s), 6.46 (1H, br-s), 7.20 (1H, br-s), 7.45-7.49 (2H, m), 7.50 (1H, d, J = 7.3 Hz), 7.65 (1H, d, J = 7.3 Hz), 7.88 (1H, br-s), 7.99 (1H, br-s), 8.19 (1H, d, J = 8.8 Hz) |
| 205 | δ 1.26 (3H, t, J = 7.6 Hz), 2.76 (2H, q, J = 7.6 Hz), 4.85 (2H, s), 7.06 (1H, br), 7.47-7.53 (2H, m), 7.58-7.61 (2H, m), 7.67-7.69 (2H, m), 8.05 (1H, s) |
| 206 | δ 1.25 (3H, t, J = 7.3 Hz), 2.77 (2H, q, J = 7.3 Hz), 4.85 (2H, s), 7.06 (1H, br), 7.49-7.53 (2H, m), 7.62 (1H, s), 7.68-7.70 (2H, m), 7.74 (1H, s), 8.06 (1H, s) |

TABLE 9-continued

| Compound No. | ¹H-NMR (CDCl₃, ppm) |
|---|---|
| 207 | δ 1.24 (3H, t, J = 7.3 Hz), 2.77 (2H, q, J = 7.3 Hz), 4.86 (2H, s), 7.07 (1H, br), 7.50-7.58 (3H, m), 7.70-7.72 (2H, m), 7.96 (1H, s), 8.07 (1H, s) |
| 208 | δ 0.93 (3H, t, J = 7.3 Hz), 1.63-1.69 (2H, m), 2.70 (2H, t, J = 7.6 Hz), 4.85 (2H, s), 7.10 (1H, s), 7.45 (1H, s), 7.49-7.52 (1H, m), 7.53 (1H, s), 7.58-7.69 (3H, m), 8.04 (1H, s) |
| 209 | δ 0.93 (3H, t, J = 7.3 Hz), 1.61-1.70 (2H, m), 2.71 (2H, t, J = 7.3 Hz), 4.85 (2H, s), 7.10 (1H, br-s), 7.48-7.53 (2H, m), 7.63 (1H, s), 7.67-7.70 (2H, m), 7.74 (1H, d, J = 2.0 Hz), 8.05 (1H, s) |
| 210 | δ 0.90 (3H, t, J = 7.3 Hz), 1.28-1.38 (2H, m), 1.56-1.64 (2H, m), 2.73 (2H, t, J = 7.8 Hz), 4.85 (2H, s), 7.06 (1H, br-s), 7.49-7.53 (2H, m), 7.60 (1H, s), 7.67-7.74 (3H, m), 8.04 (1H, s) |
| 211 | δ 3.93 (3H, s), 4.86 (2H, s), 7.13 (1H, br s), 7.53 (1H, t, J = 8 Hz), 7.61-7.65 (2H, m), 7.71 (1H, d, J = 8 Hz), 8.04 (1H, s), 8.48 (1H, d, J = 1.2 Hz), 8.58 (1H, s) |
| 212 | δ 2.47 (3H, s), 4.85 (2H, s), 7.08 (1H, br-s), 7.40 (1H, s), 7.51 (1H, t, J = 7.8 Hz), 7.63 (1H, s), 7.67-7.71 (3H, m), 8.03 (1H, s) |
| 213 | δ 4.86 (2H, s), 7.06 (1H, br.), 7.52 (1H, t, J = 7.8 Hz), 7.67-7.71 (3H, m), 7.67 (2H, s), 8.05 (1H, s) |
| 214 | δ 2.26 (3H, s), 2.45 (3H, d, J = 6.4 Hz), 4.86 (2H, s), 7.08 (1H, br-s), 7.49-7.53 (2H, m), 7.69-7.75 (3H, m), 8.05 (1H, br-s) |
| 215 | δ 2.35 (3H, s), 2.58 (3H, d, J = 6.6 Hz), 4.85 (2H, s), 7.08 (1H, br-s), 7.35 (1H, s), 7.51 (1H, t, J = 8.1 Hz), 7.68 (2H, d, J = 8.1 Hz), 7.73 (1H, s), 8.04 (1H, s) |
| 216 | δ 2.50 (3H, s), 4.77 (2H, br-s), 4.86 (2H, s), 7.12 (1H, br-s), 7.51-7.56 (2H, m), 7.69 (2H, d, J = 7.3 Hz), 8.84 (1H, s), 8.08 (1H, br-s) |
| 217 | δ 2.43 (3H, s), 4.86 (2H, s), 7.12 (1H, br-s), 7.51 (1H, t, J = 7.9 Hz), 7.57 (1H, br-s), 7.69 (1H, d, J = 7.9 Hz), 7.76 (1H, br-s), 7.86 (1H, br-s), 8.08 (1H, br-s) |
| 218 | δ 2.51 (3H, s), 4.86 (2H, s), 7.00 (1H, br-s), 7.50-7.55 (2H, m), 7.68-7.70 (2H, m), 7.87 (1H, br-s), 8.08 (1H, br-s) |
| 219 | δ 2.62 (3H, s), 4.86 (2H, s), 7.00 (1H, br-s), 7.47 (1H, s), 7.52 (1H, t, J = 7.8 Hz), 7.68-7.70 (2H, m), 7.89 (1H, br-s), 8.07 (1H, br-s) |
| 220 | δ 2.12 (3H, s), 4.50 (2H, br-s), 4.86 (2H, s), 7.14 (1H, br-s), 7.29 (1H, br-s), 7.51 (1H, t, J = 7.8 Hz), 7.68-7.70 (2H, m), 7.77 (1H, br-s), 8.04 (1H, br-s) |
| 221 | δ 0.90 (3H, t, J = 7.3 Hz), 1.28-1.37 (2H, m), 1.55-1.63 (2H, m), 2.48-2.60 (2H, m), 2.73 (2H, t, J = 7.8 Hz), 4.43 (2H, t, J = 6.3 Hz), 6.85 (1H, s), 7.46-7.50 (2H, m), 7.60-7.68 (3H, m), 7.73 (1H, d, J = 1.5 Hz), 8.00 (1H, s) |
| 222 | δ 1.32 (6H, d, J = 6.3 Hz), 2.39 (3H, s), 5.04 (1H, septet, J = 6.3 Hz), 6.71 (1H, s), 7.43-7.47 (2H, m), 7.57-7.64 (3H, m), 7.73 (1H, s), 8.04 (1H, s) |
| 223 | δ 1.32 (6H, d, J = 6.3 Hz), 5.03 (1H, septet, J = 6.3 Hz), 7.41 (1H, t, J = 8.1 Hz), 7.63-7.68 (1H, m), 7.67 (2H, s), 7.75 (1H, d, J = 7.6 Hz), 8.00 (1H, s), 8.06 (1H, t, J = 1.7 Hz), 8.93 (1H, s) |
| 224 | (DMSO-d₆) δ 1.31 (6H, d, J = 6.3 Hz), 5.03 (1H, septet, J = 6.3 Hz), 7.41 (1H, t, J = 8.1 Hz), 7.64 (1H, d, J = 8.1 Hz), 7.79 (1H, d, J = 8.1 Hz), 7.93 (1H, s), 8.00 (1H, s), 8.15 (1H, s), 8.26 (1H, s), 9.36 (1H, s) |
| 225 | δ 1.31 (6H, d, J = 6.3 Hz), 2.34 (6H, s), 5.03 (1H, septet, J = 6.3 Hz), 6.73 (1H, s), 7.33 (2H, s), 7.44 (1H, t, J = 7.8 Hz), 7.53-7.62 (3H, m), 8.05 (1H, s) |
| 226 | δ 1.31 (6H, d, J = 6.3 Hz), 2.33 (6H, s), 5.02 (1H, septet, J = 6.3 Hz), 6.75 (1H, s), 7.33 (2H, s), 7.43 (1H, t, J = 7.8 Hz), 7.52-7.61 (3H, m), 8.04 (1H, s) |
| 227 | δ 4.84 (2H, s), 7.24 (1H, s), 7.45 (1H, t, J = 7.8 Hz), 7.59-7.62 (4H, m), 7.77 (2H, d, J = 8.8 Hz), 7.99 (1H, s), 8.16 (1H, s) |
| 228 | δ 2.39 (3H, s), 4.85 (2H, s), 7.11 (1H, br-s), 7.47-7.52 (2H, m), 7.58 (1H, s), 7.67-7.70 (2H, m), 7.73 (1H, s), 8.06 (1H, s) |
| 229 | (DMSO-d₆) δ 4.86 (2H, s), 7.45 (1H, t, J = 7.8 Hz), 7.72 (1H, s), 7.73 (1H, d, J = 7.8 Hz), 7.83-7.84 (2H, m), 8.14 (1H, s), 9.27 (1H, s), 9.34 (1H, s) |
| 230 | (DMSO-d6) δ 4.86 (2H, s), 7.44 (1H, t, J = 8.1 Hz), 7.67 (1H, s), 7.68 (1H, s), 7.71-7.74 (1H, m), 7.85 (1H, d, J = 7.3 Hz), 8.15 (1H, s), 9.31 (1H, s), 9.41 (1H, br-s) |
| 231 | (DMSO-d₆) δ 4.96 (2H, s), 7.51 (1H, t, J = 7.8 Hz), 7.65-7.73 (2H, m), 8.13 (1H, s), 8.15 (1H, s), 8.49 (1H, s), 10.41 (1H, s), 10.58 (1H, s) |
| 232 | (DMSO-d₆) δ 4.86 (2H, s), 7.45 (1H, t, J = 7.8 Hz), 7.70 (1H, d, J = 7.8 Hz), 7.88 (1H, d, J = 7.8 Hz), 7.94 (1H, s), 8.08 (1H, s), 8.16 (1H, s), 9.33 (1H, s), 9.42 (1H, s) |
| 233 | δ 2.34 (6H, s), 4.85 (2H, s), 7.10 (1H, br), 7.34 (2H, s), 7.47-7.51 (2H, m), 7.65-7.68 (2H, m), 8.06 (1H, s) |
| 234 | δ 2.34 (6H, s), 4.85 (2H, s), 7.10 (1H, br), 7.35 (2H, s), 7.47-7.52 (2H, m), 7.65-7.68 (2H, m), 8.05 (1H, s) |
| 235 | δ 4.84 (2H, s), 7.17 (1H, br-s), 7.49 (1H, t, J = 7.8 Hz), 7.63 (1H, d, J = 7.8 Hz), 7.67 (1H, d, J = 7.8 Hz), 7.94 (1H, s), 8.07 (1H, s) |

TABLE 9-continued

| Compound No. | ¹H-NMR (CDCl₃, ppm) |
|---|---|
| 236 | δ 4.85 (2H, s), 7.14 (1H, s), 7.51 (1H, t, J = 7.8 Hz), 7.68-7.73 (2H, m), 7.83 (1H, s), 7.86 (2H, s), 8.07 (1H, s) |
| 237 | δ 2.48-2.60 (2H, m), 4.43 (2H, t, J = 6.3 Hz), 6.90 (1H, s), 7.48 (1H, t, J = 7.8 Hz), 7.63-7.69 (2H, m), 7.86 (3H, s), 8.03 (1H, s) |
| 238 | (DMSO-d₆) δ 2.50-2.61 (2H, m), 4.41 (2H, t, J = 6.3 Hz), 7.43 (1H, t, J = 7.8 Hz), 7.70 (1H, d, J = 7.8 Hz), 7.71 (1H, s), 7.80-7.84 (2H, m), 8.06 (1H, s), 8.82 (1H, s), 9.26 (1H, s) |
| 239 | δ 1.34 (3H, t, J = 7.3 Hz), 4.26 (2H, q, J = 7.3 Hz), 6.77 (1H, br-s), 7.46-7.53 (2H, m), 7.70 (1H, brd, J = 7.3 Hz), 7.86-7.94 (3H, m), 8.39 (1H, s), 8.71 (1H, d, J = 8.8 Hz) |
| 240 | δ 1.32 (6H, d, J = 6.3 Hz), 5.06 (1H, septet, J = 6.3 Hz), 6.74 (1H, s), 7.45-7.52 (2H, m), 7.70 (1H, d, J = 7.3 Hz), 7.86-7.94 (3H, m), 8.40 (1H, s), 8.71 (1H, d, J = 8.8 Hz) |
| 241 | δ 4.58 (1H, dd, J = 2.0 Hz, 5.8 Hz), 4.85 (1H, dd, J = 2.0 Hz, 4.2 Hz), 7.06 (1H, br-s), 7.30 (1H, d, J = 6.4 Hz), 7.49-7.57 (2H, m), 7.74 (1H, d, J = 7.8 Hz), 7.87 (1H, d, J = 7.8 Hz), 7.91 (1H, s), 7.99 (1H, s), 8.40 (1H, s), 8.71 (1H, d, J = 8.8 Hz) |
| 242 | δ 1.62-1.70 (2H, m), 1.71-1.87 (4H, m), 1.89-1.96 (2H, m), 5.22-5.26 (1H, m), 6.72 (1H, s), 7.45-7.51 (2H, m), 7.70 (1H, brd, J = 7.3 Hz), 7.86-7.93 (3H, m), 8.34 (1H, s), 8.70 (1H, d, J = 8.8 Hz) |
| 243 | δ 3.76 (2H, t, J = 5.4 Hz), 4.47 (2H, t, J = 5.4 Hz), 6.97 (1H, br-s), 7.47-7.56 (2H, m), 7.69 (1H, d, J = 7.8 Hz), 7.86-7.91 (2H, m), 7.97 (1H, s), 8.39 (1H, s), 8.71 (1H, d, J = 8.8 Hz) |
| 244 | δ 2.82 (2H, t, J = 6.3 Hz), 4.41 (2H, t, J = 6.3 Hz), 7.46 (1H, t, J = 7.8 Hz), 7.54-7.57 (1H, m), 7.81 (1H, d, J = 8.3 Hz), 7.88 (1H, d, J = 8.8 Hz), 7.91 (1H, s), 8.10 (1H, s), 8.56-8.63 (2H, m), 9.55 (1H, br-s) |
| 245 | δ 4.40 (2H, dt, J = 3.9 Hz, 14.1 Hz), 6.04 (1H, tt, J = 3.9 Hz, 55.3 Hz), 7.43-7.48 (1H, m), 7.55 (1H, d, J = 7.8 Hz), 7.80 (1H, d, J = 7.3 Hz), 7.86 (1H, d, J = 8.8 Hz), 7.91 (1H, s), 8.07 (1H, s), 8.53 (1H, s), 8.64 (1H, d, J = 8.8 Hz), 9.42 (1H, s) |
| 246 | δ 4.56 (2H, d, J = 5.9 Hz), 5.92 (1H, t, J = 5.9 Hz), 6.97 (1H, br-s), 7.49-7.57 (2H, m), 7.69 (1H, d, J = 7.3 Hz), 7.87-7.92 (2H, m), 7.98 (1H, s), 8.39 (1H, s), 8.71 (1H, d, J = 8.8 Hz) |
| 247 | δ 4.86 (2H, s), 7.15 (1H, br-s), 7.50-7.59 (2H, m), 7.72 (1H, d, J = 7.8 Hz), 7.86-7.92 (2H, m), 8.02 (1H, s), 8.40 (1H, s), 8.71 (1H, d, J = 8.8 Hz) |
| 248 | δ 5.05 (2H, s), 7.09 (1H, br-s), 7.51-7.59 (2H, m), 7.73 (1H, d, J = 7.8 Hz), 7.88 (1H, d, J = 8.3 Hz), 7.92 (1H, s), 8.03 (1H, s), 8.39 (1H, s), 8.72 (1H, d, J = 8.8 Hz) |
| 249 | δ 2.49-2.60 (2H, m), 4.44 (2H, t, J = 6.3 Hz), 6.86 (1H, br-s), 7.48-7.56 (2H, m), 7.69 (1H, d, J = 6.3 Hz), 7.88 (1H, d, J = 8.8 Hz), 7.92 (1H, s), 7.96 (1H, s), 8.39 (1H, s), 8.71 (1H, d, J = 8.8 Hz) |
| 250 | δ 4.68 (2H, t, J = 13.2 Hz), 708 (1H, br-s), 7.50-7.59 (2H, m), 7.70 (1H, br-d, J = 7.3 Hz), 7.87-7.92 (2H, m), 8.00 (1H, s), 8.39 (1H, s), 8.71 (1H, d, J = 8.7 Hz) |
| 251 | δ 5.29 (2H, s), 6.92 (1H, br-s), 7.47-7.55 (4H, m), 7.65-7.70 (3H, m), 7.87 (1H, d, J = 8.8 Hz), 7.92 (1H, s), 7.97 (1H, s), 8.38 (1H, br-s), 8.71 (1H, d, J = 8.8 Hz) |
| 252 | δ 5.23 (2H, s), 6.82 (1H, br-s), 7.37 (1H, d, J = 8.3 Hz), 7.50-7.53 (2H, m), 7.6 (1H, m), 7.75 (1H, dd, J = 2.4 Hz, 8.3 Hz), 7.87-7.96 (3H, m), 8.38 (1H, br-s), 8.47 (1H, d, J = 2.4 Hz), 8.72 (1H, d, J = 8.3 Hz) |
| 253 | δ 1.31 (6H, d, J = 6.3 Hz), 2.33 (6H, s), 5.02 (1H, septet, J = 6.3 Hz), 6.75 (1H, br-s), 7.33 (2H, s), 7.43 (1H, t, J = 7.8 Hz), 7.54-7.61 (3H, m), 8.04 (1H, s) |
| 254 | δ 2.34 (6H, s), 4.39 (2H, dt, J = 3.9 Hz, 13.6 Hz), 6.01 (1H, tt, J = 3.9 Hz, 54.6 Hz), 6.98 (1H, s), 7.34 (2H, s), 7.46-7.50 (2H, m), 7.60-7.66 (2H, m), 8.02 (1H, s) |
| 255 | δ 2.34 (6H, s), 4.61-4.66 (2H, m), 4.71-4.77 (2H, m), 5.18-5.30 (1H, m), 7.12 (1H, s), 7.34 (2H, s), 7.45-7.50 (1H, m), 7.52-7.66 (2H, m), 7.76-7.84 (1H, m), 8.04 (1H, s) |
| 256 | δ 2.34 (6H, s), 4.58 (2H, q, J = 8.3 Hz), 7.02 (1H, s), 7.34 (2H, s), 7.45-7.51 (2H, m), 7.62-7.67 (2H, m), 8.02 (1H, s) |
| 257 | δ 2.34 (6H, s), 4.85 (2H, s), 7.10 (1H, br), 7.34 (2H, s), 7.47-7.51 (2H, m), 7.63-7.67 (2H, m), 8.05 (1H, s) |
| 258 | δ 1.48 (3H, d, J = 6.8 Hz), 2.34 (6H, s), 5.30-5.36 (1H, m), 6.95 (1H, br-s), 7.30 (2H, s), 7.46-7.51 (2H, m), 7.60-7.67 (2H, m), 8.03 (1H, br-s) |
| 259 | δ 2.35 (6H, s), 2.49-2.59 (2H, m), 4.42 (2H, t, J = 6.3 Hz), 6.85 (1H, br-s), 7.34 (2H, s), 7.45-7.49 (2H, m), 7.60-7.65 (2H, m), 8.02 (1H, br-s) |
| 300 | δ 4.85 (2H, s), 7.10 (1H, br), 7.50 (1H, t, J = 7.8 Hz), 7.68-7.71 (3H, m), 7.72 (2H, s), 8.04 (1H, s) |
| 301 | δ 4.85 (2H, s), 7.08 (1H, br), 7.51-7.55 (1H, m), 7.69-7.72 (2H, m), 7.84 (1H, s), 8.06 (2H, s), 8.10 (1H, s) |
| 331 | δ 2.29 (6H, s), 4.85 (2H, s), 7.11-7.19 (3H, m), 7.39 (1H, s), 7.49 (1H, t, J = 7.9 Hz), 7.66-7.73 (2H, m), 8.00 (1H, s) |
| 348 | δ 2.35 (6H, s), 3.81 (3H, s), 6.80 (1H, br), 7.36 (2H, s), 7.44-7.63 (4H, m), 8.02 (1H, s) |

TABLE 9-continued

| Compound No. | ¹H-NMR (CDCl₃, ppm) |
|---|---|
| 377 | δ 2.36 (6H, s), 4.85 (2H, s), 7.09 (1H, s), 7.37 (2H, s), 7.44 (1H, s), 7.50 (1H, t, J = 8.3 Hz), 7.67 (2H, d, J = 7.3 Hz), 8.05 (1H, s) |
| 424 | δ4.85 (2H, s), 7.10 (1H, s), 7.51 (1H, t, J = 7.8 Hz), 7.69-7.70 (3H, m), 7.73 (2H, s), 8.05 (1H, s) |
| 464 | δ 2.47-2.59 (2H, m), 4.41 (2H, t, J = 6.3 Hz), 6.96 (1H, br-s), 7.46 (1H, t, J = 7.8 Hz), 7.63-7.67 (2H, m), 7.83 (1H, s), 7.91 (2H, s), 8.00 (1H, s) |
| 471 | δ 4.85 (2H, s), 7.13 (1H, br-s), 7.50 (1H, t, J = 7.8 Hz), 7.68-7.74 (3H, m), 7.92 (2H, s), 8.04 (1H, s) |
| 511 | (DMSO-d₆) δ 2.67-2.78 (2H, m), 4.34 2H, t, J = 5.9 Hz), 7.50 (1H, t, J = 7.8 Hz), 7.68-7.73 (2H, m), 8.13 (1H, s), 8.52 (2H, s), 10.02 (1H, s), 10.77 (1H, s) |
| 518 | (DMSO-d₆) δ 4.96 (2H, s), 7.52 (1H, t, J = 7.8 Hz), 7.71-7.75 (2H, m), 8.16 (1H, s), 8.51 (2H, s), 10.42 (1H, s), 10.79 (1H, s) |
| 565 | δ4.86 (2H, s), 7.00 (1H, br-s), 7.52 (1H, t, J = 8.3 Hz), 7.70-7.73 (3H, m), 7.93 (2H, s), 8.06 (1H, s) |
| 605 | δ 2.49-2.60 (2H, m), 4.43 (2H, t, J = 6.3 Hz), 6.82 (1H, s), 7.49 (1H, t, J = 7.8 Hz), 7.66-7.68 (3H, m), 7.94 (2H, s), 8.01 (1H, s) |
| 612 | δ4.86 (2H, s), 7.45 (1H, t, J = 7.8 Hz), 7.72 (1H, d, J = 7.8 Hz), 7.94 (1H, br-s), 7.93 (2H, s), 8.13 (1H, s), 9.02 (1H, s), 9.17 (1H, s) |
| 659 | δ4.86 (2H, s), 7.06 (1H, s), 7.51 (1H, t, J = 7.8 Hz), 7.68-7.71 (3H, m), 7.93 (2H, s), 8.06 (1H, s) |
| 706 | δ4.84 (2H, s), 7.40 (1H, br-s), 7.48 (1H, t, J = 7.8 Hz), 7.67-7.75 (2H, m), 8.00 (1H, s), 8.09 (2H, s), 8.24 (1H, s) |
| 770 | δ 2.39 (3H, s), 4.86 (2H, s), 7.00 (1H, br-s), 7.48-7.67 (5H, m), 7.79 (1H, s), 8.04 (1H, s), 8.24 (1H, d, J = 8.8 Hz) |
| 800 | δ 2.31 (6H, s), 4.85 (2H, s), 7.11 (1H, br-s), 7.43 (2H, s), 7.47-7.53 (2H, m), 7.66 (1H, s), 7.67 (1H, s), 8.05 (1H, s) |
| 817 | δ0.89 (3H, t, J = 7.3 Hz), 1.24-1.37 (2H, m), 1.55-1.63 (2H, m), 2.47-2.59 (2H, m), 2.70 (2H, t, J = 7.8 Hz), 4.42 (2H, t, J = 5.9 Hz), 6.96 (1H, br-s), 7.43-7.47 (2H, m), 7.57 (1H, d, J = 1.5 Hz), 7.62-7.64 (2H, m), 7.74 (1H, s), 8.00 (1H, s) |
| 818 | δ0.86 (3H, t, J = 7.3 Hz), 1.24-1.33 (2H, m), 1.49-1.57 (2H, m), 2.45-2.56 (2H, m), 2.67 (2H, t, J = 7.8 Hz), 4.38 (2H, t, J = 6.3 Hz), 7.15 (1H, s), 7.39 (1H, t, J = 7.8 Hz), 7.48 (1H, s), 7.62-7.64 (2H, m), 7.88 (1H, s), 7.93 (1H, d, J = 2.0 Hz), 8.01 (1H, s) |
| 819 | δ 0.81 (3H, t, J = 7.3 Hz), 1.25 (3H, d, J = 6.8 Hz), 1.53-1.64 (2H, m), 2.49-2.60 (2H, m), 2.92-3.01 (1H, m), 4.43 (2H, t, J = 5.9 Hz), 6.87 (1H, br), 7.46-7.51 (2H, m), 7.62-7.67 (3H, m), 7.74 (1H, d, J = 1.5 Hz), 8.01 (1H, s) |
| 820 | δ1.32 (6H, d, J = 6.3 Hz), 2.36 (3H, s), 5.01-5.07 (1H, m), 6.69 (1H, s), 7.11-7.13 (2H, m), 7.44 (1H, t, J = 8.3 Hz), 7.55-7.59 (2H, m), 7.68 (1H, br-s), 7.95 (1H, d, J = 8.3 Hz), 7.99 (1H, s) |
| 821 | δ 1.27 (6H, d, J = 6.8 Hz), 1.31 (6H, d, J = 6.3 Hz), 2.96 (1H, septet, J = 6.8 Hz), 5.05 (1H, septet, J = 6.3 Hz), 6.79 (1H, s), 7.42-7.52 (4H, m), 7.72 (1H, d, J = 7.8 Hz), 7.86 (1H, t, J = 2.0 Hz), 8.14 (1H, s), 8.21 (1H, d, J = 8.3 Hz) |
| 822 | δ 1.33 (6H, d, J = 6.6 Hz), 5.01-5.09 (1H, m), 6.73 (1H, s), 7.41-7.52 (2H, m), 7.57-7.60 (1H, m), 7.65 (1H, s), 8.05 (1H, s), 8.20 (2H, s), 8.35 (1H, s) |
| 823 | δ 1.32 (6H, d, J = 6.3 Hz), 5.04 (1H, septet, J = 6.3 Hz), 6.70 (1H, br-s), 6.98-7.06 (1H, m), 7.45 (1H, t, J = 7.8 Hz), 7.53-7.55 (1H, m), 7.62 (1H, d, J = 8.8 Hz), 7.94 (2H, s), 8.07-8.14 (1H, m) |
| 824 | δ1.32 (6H, d, J = 6.1 Hz), 2.46 (3H, s), 2.54 (3H, d, J = 15 Hz), 5.04 (1H, septet, J = 6.1 Hz), 6.72 (1H, s), 7.40-7.44 (2H, m), 7.51-7.56 (3H, m), 7.94 (1H, s), 7.97 (1H, s) |
| 825 | δ 1.31 (6H, d, J = 6.3 Hz), 2.30 (3H, s), 5.03 (1H, septet, J = 6.3 Hz), 6.72 (1H, s), 7.20 (1H, d, J = 2.2 Hz), 7.32 (1H, d, J = 2.2 Hz), 7.43 (1H, t, J = 7.8 Hz), 7.59-7.62 (3H, m), 8.00 (1H, s) |
| 826 | δ1.31 (6H, d, J = 6.3 Hz), 2.28 (3H, s), 2.31 (3H, s), 5.03 (1H, septet, J = 6.3 Hz), 6.71 (1H, br-s), 7.01 (1H, s), 7.13 (1H, s), 7.43 (1H, t, J = 7.8 Hz), 7.61-7.63 (3H, m), 7.97 (1H, s) |
| 827 | δ 1.31 (6H, d, J = 6.1 Hz), 2.25 (6H, s), 5.03 (1H, septet, J = 6.1 Hz), 6.70 (1H, br-s), 7.26 (2H, s), 7.38 (1H, br-s), 7.43 (1H, t, J = 7.8 Hz), 7.55-7.61 (2H, m), 8.01 (1H, s) |
| 828 | δ 1.31 (6H, d, J = 6.3 Hz), 2.24 (6H, s), 5.02 (1H, septet, J = 6.3 Hz), 6.71 (1H, br-s), 7.26 (2H, s), 7.39-7.44 (2H, m), 7.55-7.60 (2H, m), 8.00 (1H, s) |
| 829 | δ1.31 (6H, d, J = 6.4 Hz), 2.23 (6H, s), 5.03 (1H, septet, J = 6.4 Hz), 6.69 (1H, br-s), 7.37 (1H, br-s), 7.43 (1H, t, J = 7.8 Hz), 7.48 (2H, s), 7.55-7.61 (2H, m), 8.01 (1H, br-s) |
| 830 | δ1.32 (6H, d, J = 6.3 Hz), 2.35 (6H, s), 5.04 (1H, septet, J = 6.3 Hz), 6.72 (1H, s), 7.32-7.36 (3H, m), 7.41-7.46 (4H, m), 7.56-7.63 (4H, m), 8.00 (1H, s) |
| 831 | δ1.32 (6H, d, J = 6 Hz), 2.30 (3H, s), 2.32 (6H, s), 5.04 (1H, septet, J = 6 Hz), 6.73 (1H, s), 7.08 (2H, s), 7.22-7.26 (4H, m), 7.43-7.48 (2H, m), 7.61-7.63 (2H, m), 8.01 (1H, s) |
| 832 | δ1.32 (6H, d, J = 6 Hz), 2.31 (6H, s), 2.42 (3H, s), 5.04 (1H, septet, J = 6 Hz), 6.71 (1H, s), 7.16 (1H, d, J = 8 Hz), 7.30-7.59 (7H, m), 7.62 (2H, t, J = 8 Hz), 8.01 (1H, s) |
| 833 | δ1.31 (6H, d, J = 6 Hz), 2.33 (6H, s), 2.49 (3H, s), 5.03 (1H, septet, J = 6 Hz), 6.73 (1H, s), 7.12-7.25 (2H, m), 7.32 (2H, s), 7.42-7.52 (4H, m), 7.59-7.63 (2H, m), 7.99 (1H, s) |

TABLE 9-continued

| Compound No. | $^1$H-NMR (CDCl$_3$, ppm) |
|---|---|
| 834 | δ1.32 (6H, d, J = 6 Hz), 2.32 (6H, s), 3.80 (3H, s), 5.04 (1H, septet, J = 6 Hz), 6.73 (1H, s), 6.97 (1H, d, J = 8 Hz), 7.02 (1H, t, J = 7 Hz), 7.27 (2H, s), 7.30 (2H, d, J = 7 Hz), 7.34-7.46 (2H, m), 7.60-7.63 (2H, m), 7.95 (1H, s) |
| 835 | δ1.32 (6H, d, J = 7 Hz), 2.34 (6H, s), 3.87 (3H, s), 5.04 (1H, septet, J = 7 Hz), 6.72 (1H, s), 6.88-6.91 (1H, m), 7.11 (1H, t, J = 2 Hz), 7.16 (1H, td, J = 8 Hz, 1 Hz), 7.33-7.37 (3H, m), 7.43-7.50 (2H, m), 7.59-7.64 (2H, m), 8.01 (1H, s) |
| 836 | δ1.32 (6H, d, J = 7 Hz), 2.33 (6H, s), 3.85 (3H, s), 5.04 (1H, septet, J = 7 Hz), 6.73 (1H, br-s), 6.96 (2H, d, J = 9 Hz), 7.29 (2H, s), 7.42-7.52 (4H, m), 7.60-7.63 (2H, m), 8.00 (1H, s) |
| 837 | δ1.32 (6H, d, J = 6 Hz), 1.44 (3H, t, J = 7 Hz), 2.33 (6H, s), 4.08 (2H, q, J = 7 Hz), 5.04 (1H, septet, J = 6 Hz), 6.72 (1H, s), 6.94-6.97 (2H, m), 7.29 (2H, s), 7.42-7.52 (4H, m), 7.61-7.63 (2H, m), 7.99 (1H, s) |
| 838 | δ1.31 (6H, d, J = 6 Hz), 2.34 (6H, s), 2.53 (3H, s), 5.04 (1H, septet, J = 6 Hz), 6.72 (1H, s), 7.31-7.65 (10H, m), 8.00 (1H, s). |
| 839 | δ1.31 (6H, d, J = 6.3 Hz), 2.34 (6H, s), 5.04 (1H, septet, J = 6.3 Hz), 6.72 (1H, s), 7.12-7.32 (5H, m), 7.41-7.48 (3H, m), 7.61-7.63 (2H, m), 7.99 (1H, s) |
| 840 | δ1.32 (6H, d, J = 7 Hz), 2.34 (6H, s), 5.03 (1H, septet, J = 7 Hz), 6.74 (1H, br s), 7.01-7.05 (1H, m), 7.28-7.64 (9H, m), 8.02 (1H, s) |
| 841 | δ1.31 (6H, d, J = 7 Hz), 2.34 (6H, s), 5.04 (1H, septet, J = 7 Hz), 6.73 (1H, s), 7.11 (2H, t, J = 9 Hz), 7.28 (2H, s), 7.42-7.63 (6H, m), 8.01 (1H, s) |
| 842 | δ1.24 (6H, d, J = 6.8 Hz), 1.31 (6H, d, J = 6.3 Hz), 2.32 (3H, s), 2.86 (1H, septet, J = 6.8 Hz), 5.03 (1H, septet, J = 6.3 Hz), 6.74 (1H, s), 7.08 (1H, s), 7.33 (1H, d, J = 2.0 Hz), 7.43 (1H, t, J = 7.8 Hz), 7.61-7.65 (3H, m), 7.96 (1H, s) |
| 843 | δ1.32 (6H, d, J = 6.3 Hz), 2.37 (3H, s), 5.03 (1H, septet, J = 6.3 Hz), 6.74 (1H, s), 7.46 (1H, t, J = 7.8 Hz), 7.51-7.57 (2H, m), 7.61-7.65 (2H, m), 7.90 (1H, s), 8.08 (1H, s) |
| 844 | δ 1.32 (6H, d, J = 6.3 Hz), 2.35 (3H, s), 5.03 (1H, septet, J = 6.3 Hz), 6.72 (1H, s), 7.09 (1H, s), 7.21 (1H, d, J = 2.2 Hz), 7.44 (1H, t, J = 8.1 Hz), 7.52-7.61 (3H, m), 8.02 (1H, s) |
| 845 | δ 1.29 (6H, d, J = 6.8 Hz), 1.31 (6H, d, J = 6.3 Hz), 2.98 (1H, septet, J = 6.8 Hz), 5.04 (1H, septet, J = 6.3 Hz), 6.70 (1H, s), 7.42-7.48 (2H, m), 7.56-7.67 (4H, m), 7.92 (1H, s) |
| 846 | δ 1.32 (6H, d, J = 6.3 Hz), 5.03 (1H, septet, J = 6.3 Hz), 6.75 (1H, br-s), 7.41-7.51 (2H, m), 7.62-7.65 (1H, m), 7.91 (1H, br-s), 8.08 (1H, s) |
| 847 | (DMSO-d$_6$) δ 1.24-1.44 (5H, m), 1.68-1.80 (5H, m), 2.46-2.50 (1H, m), 4.97 (1H, s), 7.19 (2H, d, J = 8.8 Hz), 7.47 (1H, t, J = 7.8 Hz), 7.60-7.70 (4H, m), 8.04 (1H, s), 10.19 (1H, s), 10.37 (1H, s) |
| 848 | δ 4.84 (2H, s), 7.29 (1H, d, J = 7.8 Hz), 7.35 (1H, br-s), 7.48 (1H, t, J = 7.8 Hz), 7.56-7.67 (3H, m), 7.75 (1H, d, J = 7.3 Hz), 7.97 (1H, s), 8.23 (1H, s), 8.37 (1H, d, J = 7.8 Hz) |
| 849 | δ 4.85 (2H, s), 7.12 (1H, br-s), 7.47 (1H, t, J = 7.8 Hz), 7.59-7.67 (4H, m), 7.72-7.75 (2H, m), 7.99 (1H, s), 8.03 (1H, s) |
| 850 | (DMSO-d$_6$) δ 4.87 (2H, s), 7.43 (1H, t, J = 7.8 Hz), 7.65 (1H, d, J = 7.8 Hz), 7.82 (1H, d, J = 7.8 Hz), 7.96 (2H, d, J = 8.8 Hz), 8.07 (1H, s), 8.18-8.22 (2H, m), 9.66 (1H, br), 10.51 (1H, s) |
| 851 | δ4.85 (2H, s), 6.67 (1H, br-s), 7.47 (1H, t, J = 7.8 Hz), 7.60-7.64 (2H, m), 7.65 (2H, d, J = 8.8 Hz), 7.74 (2H, d, J = 8.8 Hz), 7.98 (1H, s), 8.00 (1H, s) |
| 852 | δ4.86 (2H, s), 7.09 (1H, br-s), 7.48-7.53 (1H, m), 7.61-7.65 (2H, m), 7.81 (2H, d, J = 8.8 Hz), 7.95 (2H, d, J = 8.8 Hz), 7.95-8.04 (1H, m), 8.14 (1H, s) |
| 854 | δ0.90 (3H, t, J = 7.3 Hz), 1.28-1.38 (2H, m), 1.56-1.65 (2H, m), 2.72 (2H, t, J = 7.8 Hz), 4.85 (2H, s), 7.14 (1H, br-s), 7.45 (1H, s), 7.50 (1H, t, J = 7.8 Hz), 7.58 (1H, d, J = 1.5 Hz), 7.66-7.68 (3H, m), 8.04 (1H, s) |
| 855 | δ 0.88 (3H, t, J = 7.3 Hz), 1.24-1.35 (2H, m), 1.52-1.60 (2H, m), 2.70 (2H, t, J = 7.8 Hz), 4.84 (2H, s), 7.27 (1H, s), 7.46-7.50 (2H, m), 7.67-7.69 (2H, m), 7.76 (1H, s), 7.94 (1H, d, J = 1.5 Hz), 8.06 (1H, s) |
| 856 | δ 0.81 (3H, t, J = 7.3 Hz), 1.25 (3H, d, J = 5.9 Hz), 1.55-1.65 (2H, m), 2.91-3.01 (1H, m), 4.85 (2H, s), 7.14 (1H, br), 7.50-7.53 (2H, m), 7.61-7.77 (4H, m), 8.05 (1H, s) |
| 857 | δ0.90 (3H, t, J = 7.3 Hz), 1.31 (3H, d, J = 6.8 Hz), 1.63-1.74 (2H, m), 2.82-2.91 (1H, m), 4.85 (2H, s), 7.22 (1H, s), 7.47-7.53 (3H, m), 7.58-7.62 (1H, m), 7.66 (1H, d, J = 8.3 Hz), 7.93 (1H, s), 8.05 (1H, s), 8.13-8.15 (1H, m) |
| 858 | δ 2.36 (3H, s), 4.85 (2H, s), 7.11-7.14 (3H, m), 7.49 (1H, t, J = 8.3 Hz), 7.61-7.69 (3H, m), 7.95 (1H, d, J = 8.3 Hz), 8.02 (1H, s) |
| 859 | δ 2.31 (3H, s), 4.34 (2H, q, J = 7.8 Hz), 4.84 (2H, s), 6.80-6.86 (2H, m), 7.16 (1H, br-s), 7.47 (1H, t, J = 7.8 Hz), 7.60-7.72 (4H, m), 7.99 (1H, br-s) |
| 860 | δ 2.39 (3H, s), 4.85 (2H, s), 7.09-8.14 (9H, m) |
| 861 | δ 2.31 (3H, s), 4.84 (2H, s), 7.17 (1H, br), 7.20-7.23 (2H, m), 7.47 (1H, t, J = 8.1), 7.58-7.67 (3H, m), 7.84-7.87 (1H, m), 8.00 (1H, s) |
| 862 | δ 1.27 (6H, d, J = 6.8 Hz), 2.97 (1H, septet, J = 6.8 Hz), 4.85 (2H, s), 7.18 (1H, br), 7.46-7.51 (3H, m), 7.57 (1H, dd, J = 1.5 Hz, 7.8 Hz), 7.74 (1H, d, J = 7.8 Hz), 7.94 (1H, s), 8.14 (1H, s), 8.21 (1H, d, J = 8.3 Hz) |
| 863 | δ4.87 (2H, s), 7.51-8.01 (8H, m), 8.86 (1H, s) |

TABLE 9-continued

| Compound No. | $^1$H-NMR (CDCl$_3$, ppm) |
|---|---|
| 864 | δ 4.87 (2H, s), 7.08 (1H, br.), 7.49-7.58 (4H, m), 8.07 (1H, br.), 8.20 (3H, s) |
| 865 | δ 4.86 (2H, s), 7.08 (1H, br-s), 7.48-7.60 (3H, m), 7.64 (1H, d, J = 2.4 Hz), 7.72 (1H, d, J = 7.3 Hz), 7.98 (1H, s), 8.18 (1H, s), 8.39 (1H, d, J = 8.8 Hz) |
| 866 | δ 4.85 (2H, s), 7.06 (1H, br), 7.41-7.51 (2H, m), 7.60 (1H, s), 7.65-7.74 (4H, m), 7.97 (1H, s) |
| 867 | δ4.86 (2H, s), 7.10 (1H, br-s), 7.48-7.57 (2H, m), 7.71 (1H, d, J = 8.3 Hz), 7.90-7.97 (3H, m), 8.19 (1H, br-s), 8.22 (1H, d, J = 8.8 Hz) |
| 868 | δ 4.85 (2H, s), 7.12 (1H, br-s), 7.46-7.56 (4H, m), 7.71 (1H, d, J = 7.8 Hz), 7.99 (1H, s), 8.14 (1H, s), 8.48 (1H, d, J = 8.8 Hz) |
| 869 | δ 4.84 (2H, s), 6.97-7.05 (1H, m), 7.22 (1H, br-s), 7.48 (1H, t, J = 7.8 Hz), 7.59 (1H, d, J = 7.8 Hz), 7.69 (1H, d, J = 7.8 Hz), 7.96 (1H, s), 7.98 (1H, s), 8.05-8.12 (1H, m) |
| 870 | δ 2.46 (3H, s), 2.55 (3H, d, J = 14 Hz), 4.86 (2H, s), 7.13 (1H, br s), 7.40 (1H, s), 7.46-7.62 (4H, m), 7.88 (1H, s), 7.99 (1H, s) |
| 871 | δ 2.34 (3H, s), 2.38 (3H, s), 4.85 (2H, s), 6.97-8.03 (8H, m) |
| 872 | δ 2.31 (6H, s), 3.99 (1H, s), 4.85 (2H, s), 7.15 (1H, br-s), 7.45-7.51 (4H, m), 7.64-7.66 (2H, m), 8.01 (1H, s) |
| 873 | δ 2.34 (6H, s), 3.74 (1H, s), 4.85 (2H, s), 7.08 (1H, br-s), 7.48 (1H, s), 7.49 (2H, s), 7.52 (1H, s), 7.65-7.67 (2H, m), 8.04 (1H, s) |
| 874 | δ 2.30 (6H, s), 4.87 (2H, s), 7.08 (1H, br), 7.49-7.58 (4H, m), 8.07 (1H, br), 8.20 (3H, s) |
| 875 | δ 2.25 (6H, s), 4.85 (2H, s), 7.07 (1H, br), 7.12 (2H, s), 7.36 (1H, br-s), 7.48 (1H, t, J = 7.8 Hz), 7.64-7.66 (2H, m), 8.02 (1H, s) |
| 876 | δ 2.28 (3H, s), 2.31 (3H, s), 4.84 (2H, s), 7.00 (1H, s), 7.12 (1H, s), 7.18 (1H, br), 7.47 (1H, t, J = 7.8 Hz), 7.60 (1H, s), 7.66-7.68 (2H, m), 7.99 (1H, s) |
| 877 | δ 2.19 (6H, s), 4.82 (2H, s), 7.22 (2H, s), 7.41 (1H, t, J = 8.1 Hz), 7.48 (1H, br), 7.61-7.66 (3H, m), 7.99 (1H, s) |
| 878 | δ 2.22 (6H, s), 4.84 (2H, s), 7.13 (1H, br-s), 7.39 (1H, s), 7.45-7.49 (3H, m), 7.64-7.65 (2H, m), 8.01 (1H, br-s) |
| 879 | δ 2.35 (6H, s), 4.85 (2H, s), 7.09 (1H, s), 7.32-7.69 (11H, m), 8.02 (1H, s) |
| 880 | δ 2.30 (3H, s), 2.32 (6H, s), 4.85 (2H, s), 7.09 (2H, s), 7.13 (1H, s), 7.21-7.27 (4H, m), 7.46-7.51 (2H, m), 7.68 (2H, d, J = 7 Hz), 8.03 (1H, s) |
| 881 | δ 2.34 (6H, s), 2.42 (3H, s), 4.85 (2H, s), 7.12-7.23 (2H, m), 7.29-7.39 (4H, m), 7.47-7.52 (2H, m), 7.68 (2H, d, J = 7 Hz), 8.03 (1H, s) |
| 882 | δ 2.34 (6H, s), 2.40 (3H, s), 4.85 (2H, s), 7.13 (1H, d, J = 4 Hz), 7.23-7.26 (2H, m), 7.30 (2H, s), 7.33-7.50 (4H, m), 7.67 (2H, d, J = 8 Hz), 8.02 (1H, s) |
| 883 | δ 2.32 (6H, s), 3.81 (3H, s), 4.85 (2H, s), 6.97-7.04 (2H, m), 7.10 (1H, br s), 7.28 (2H, s), 7.30-7.34 (2H, m), 7.42 (1H, s), 7.49 (1H, t, J = 8 Hz), 7.66-7.70 (2H, m), 7.99 (1H, s) |
| 884 | δ 2.35 (6H, s), 3.88 (3H, s), 4.85 (2H, s), 6.89-6.91 (1H, m), 7.10-7.18 (3H, m), 7.33-7.37 (3H, m), 7.47-7.52 (2H, m), 7.68 (2H, d, J = 7 Hz), 8.03 (1H, s) |
| 885 | δ 2.33 (6H, s), 3.86 (3H, s), 4.85 (2H, s), 6.96 (2H, d, J = 9 Hz), 7.14 (1H, br s), 7.30 (2H, s), 7.47-7.53 (4H, m), 7.68 (2H, d, J = 7 Hz), 8.02 (1H, s) |
| 886 | δ1.44 (3H, t, J = 7 Hz), 2.33 (6H, s), 4.08 (2H, q, J = 7 Hz), 4.85 (2H, s), 6.95 (2H, d, J = 9 Hz), 7.13 (1H, s), 7.30 (2H, s), 7.45-7.52 (4H, m), 7.68 (2H, d, J = 7 Hz), 8.01 (1H, s) |
| 887 | δ 2.33 (6H, s), 2.53 (3H, s), 4.84 (2H, s), 7.14 (1H, s), 7.30-7.38 (4H, m), 7.46-7.57 (4H, m), 7.67 (2H, d, J = 6 Hz), 8.02 (1H, s) |
| 888 | δ 2.34 (6H, s), 4.85 (2H, s), 7.10-7.34 (6H, m), 7.41-7.52 (3H, m), 7.68 (2H, d, J = 8 Hz), 8.02 (1H, s) |
| 889 | δ 2.34 (6H, s), 4.85 (2H, s), 7.01-7.06 (1H, m), 7.16 (1H, br s), 7.25-7.50 (8H, m), 7.68 (1H, d, J = 8 Hz), 8.03 (1H, s) |
| 890 | δ 2.33 (6H, s), 4.85 (2H, s), 7.09-7.15 (3H, m), 7.29 (2H, s), 7.46-7.55 (4H, m), 7.67-7.69 (2H, m), 8.03 (1H, s) |
| 891 | δ 2.34 (6H, s), 4.85 (2H, s), 7.09 (1H, br s), 7.18-7.30 (4H, m), 7.34-7.51 (3H, m), 7.67-7.69 (2H, m), 8.04 (1H, s) |
| 892 | δ 2.30 (9H, s), 4.85 (2H, s), 7.05 (1H, t, J = 8.8 Hz), 7.14 (1H, br s), 7.28 (2H, s), 7.32-7.51 (4H, m), 7.67-7.69 (2H, m), 8.03 (1H, s) |
| 893 | δ 2.31 (6H, s), 4.85 (2H, s), 6.69 (1H, s), 7.09 (1H, br-s), 7.25 (2H, s), 7.41 (1H, s), 7.47-7.51 (2H, m), 7.66-7.68 (2H, m), 7.72 (1H, s), 8.02 (1H, s) |
| 894 | δ 2.30 (6H, s), 4.84 (2H, s), 7.07-7.09 (1H, m), 7.25 (1H), 7.27-7.29 (1H, m), 7.36 (2H, s), 7.36 (2H, s), 7.45-7.50 (2H, m), 7.65-7.67 (2H, m), 8.02 (1H, s) |
| 895 | δ 2.32 (6H, s), 4.85 (2H, s), 7.18 (1H, s), 7.35-7.50 (7H, m), 7.67 (2H, d, J = 6.8 Hz), 8.02 (1H, s) |
| 896 | δ 2.31 (3H, s), 4.85 (2H, s), 7.10 (1H, br), 7.20 (1H, d, J = 2.2 Hz), 7.32 (1H, d, J = 2.2 Hz), 7.49 (1H, t, J = 7.8 Hz), 7.57 (1H, s), 7.66-7.68 (2H, m), 8.02 (1H, s) |

TABLE 9-continued

| Compound No. | $^1$H-NMR (CDCl$_3$, ppm) |
|---|---|
| 897 | (DMSO-d$_6$) δ 4.85 (2H, s), 7.44 (1H, t, J = 7.8 Hz), 7.63-7.68 (2H, m), 7.72 (1H, d, J = 2.4 Hz), 7.84 (1H, s), 8.06 (1H, s), 8.80 (1H, s), 9.09 (1H, s) |
| 898 | δ4.85 (2H, s), 7.00 (1H, br-s), 7.51 (1H, t, J = 8.3 Hz), 7.69-7.72 (5H, m), 8.05 (1H, s) |
| 899 | δ4.86 (2H, s), 7.00 (1H, br-s), 7.53 (1H, t, J = 7.8 Hz), 7.67-7.73 (2H, m), 7.92 (1H, s), 8.05 (2H, s), 8.11 (1H, s) |
| 900 | (DMSO-d$_6$) δ 4.98 (2H, s), 7.52 (1H, t, J = 7.8 Hz), 7.70-7.75 (2H, m), 8.17 (1H, s), 8.31 (2H, s), 10.42 (1H, s), 10.63 (1H, s) |
| 901 | (DMSO-d$_6$) δ 1.24-1.47 (5H, m), 1.66-1.80 (5H, m), 2.54-2.60 (1H, m), 4.96 (2H, s), 7.48 (1H, t, J = 7.8 Hz), 7.60 (2H, s), 7.67-7.71 (2H, m), 8.11 (1H, s), 10.24 (1H, s), 10.37 (1H, s) |
| 902 | (DMSO-d$_6$) δ 4.86 (2H, s), 7.44 (1H, t, J = 7.8 Hz), 7.67 (1H, d, J = 7.8 Hz), 7.82 (1H, d, J = 2.0 Hz), 7.85 (1H, s), 8.05 (1H, d, J = 2.0 Hz), 8.06 (1H, d, J = 7.8 Hz), 9.04 (1H, s), 9.27 (1H, s) |
| 903 | δ4.86 (2H, s), 7.00 (1H, br-s), 7.51 (1H, t, J = 7.8 Hz), 7.70 (2H, d, J = 7.8 Hz), 7.75 (1H, s), 7.94 (2H, s), 8.06 (1H, s) |
| 904 | δ 2.20 (3H, s), 4.85 (2H, s), 6.60 (1H, d, J = 2.4 Hz), 7.17 (1H, br.), 7.50 (1H, t, J = 7.8 Hz), 7.54 (1H, s), 7.59 (1H, s), 7.69 (1H, d, J = 7.8 Hz), 7.72 (1H, br), 8.03 (1H, s) |
| 905 | δ 2.36 (3H, s), 4.85 (2H, s), 7.08 (1H, br-s), 7.10 (1H, s), 7.22-7.23 (1H, m), 7.50 (1H, t, J = 8.1 Hz), 7.59 (1H, s), 7.67-7.69 (2H, m), 8.04 (1H, s) |
| 906 | δ 2.36 (3H, s), 4.86 (2H, s), 4.88 (2H, s), 7.04 (1H, br.), 7.12 (1H, d, J = 2.4 Hz), 7.27 (1H, s), 7.50 (1H, t, J = 7.8 Hz), 7.56 (1H, s), 7.67-7.70 (2H, m), 8.02 (1H, s) |
| 907 | δ 2.38 (3H, s), 4.85 (2H, s), 7.14 (1H, br), 7.49-7.53 (2H, m), 7.62-7.70 (3H, m), 7.85 (1H, s), 8.09 (1H, s) |
| 908 | δ 2.28 (3H, s), 4.84 (2H, s), 7.11 (1H, br-s), 7.48 (1H, t, J = 7.8 Hz), 7.55 (1H, s), 7.59 (1H, s), 7.64-7.68 (3H, m), 8.01 (1H, br-s) |
| 909 | δ1.24 (6H, d, J = 6.8 Hz), 2.33 (3H, s), 2.86 (1H, septet, J = 6.8 Hz), 4.85 (2H, s), 7.09 (1H, s), 7.16 (1H, br), 7.33 (1H, d, J = 2.0 Hz), 7.48 (1H, t, J = 7.8 Hz), 7.60 (1H, s), 7.67-7.69 (2H, m), 8.00 (1H, s) |
| 910 | δ 2.23 (3H, s), 4.86 (2H, s), 6.51 (1H, s), 6.78 (1H, d, J = 2.4 Hz), 7.15 (1H, br.), 7.49 (1H, br.), 7.51 (1H, t, J = 7.8), 7.56 (1H, s), 7.71 (1H, d, J = 6.8 Hz), 8.05 (1H, s) |
| 911 | δ 1.29 (6H, d, J = 7.3 Hz), 2.98 (1H, septet, J = 7.3 Hz), 4.85 (2H, s), 7.10 (1H, br), 7.47-7.52 (2H, m), 7.56-7.58 (2H, m), 7.65 (1H, d, J = 7.3 Hz), 7.72 (1H, br), 7.96 (1H, s) |
| 912 | δ 2.37 (3H, s), 4.85 (2H, s), 4.88 (2H, s), 7.06 (1H, br), 7.16 (1H, d, J = 2.4 Hz), 7.43 (1H, d, J = 2.4 Hz), 7.50 (1H, t, J = 7.8 Hz), 7.56 (1H, s), 7.68 (1H, s), 7.70 (1H, s), 8.03 (1H, s) |
| 913 | (DMSO-d$_6$) δ 4.96 (2H, s), 7.49 (1H, t, J = 7.8 Hz), 7.64 (1H, d, J = 7.8 Hz), 7.71 (1H, d, J = 7.8 Hz), 8.02 (1H, d, J = 2.0 Hz), 8.10 (1H, s), 8.30 (1H, d, J = 2.0 Hz), 10.34 (1H, s), 10.38 (1H, s) |
| 914 | (DMSO-d$_6$) δ 1.29 (6H, d, J = 6.8 Hz), 2.99 (1H, septet, J = 6.8 Hz), 4.86 (2H, s), 7.42 (1H, t, J = 7.8 Hz), 7.52 (1H, d, J = 1.5 Hz), 7.68 (1H, d, J = 7.8 Hz), 7.74 (1H, d, J = 1.5 Hz), 7.85 (1H, d, J = 7.8 Hz), 8.09 (1H, s), 9.27 (1H, s), 9.66 (1H, s) |
| 915 | δ 4.85 (2H, s), 7.04 (1H, br), 7.47-7.55 (2H, m), 7.63-7.70 (3H, m), 7.90 (1H, d, J = 1.5 Hz), 7.99 (1H, s) |
| 916 | (DMSO-d6) δ 4.86 (2H, s), 7.43 (1H, t, J = 7.8 Hz), 7.70 (1H, d, J = 7.8 Hz), 7.84 (1H, d, J = 7.8 Hz), 8.10 (1H, s), 9.46 (1H, br-s), 9.73 (1H, br-s) |
| 917 | δ 2.22 (6H, s), 3.79 (2H, t, J = 5.4 Hz), 4.42 (2H, t, J = 5.4 Hz), 7.37 (1H, t, J = 7.8 Hz), 7.44 (2H, s), 7.63 (1H, d, J = 7.8 Hz), 7.71 (1H, d, J = 7.8 Hz), 8.12 (1H, br-s), 9.37 (1H, s), 9.60 (1H, br-s) |
| 918 | δ 2.34 (6H, s), 2.53-2.56 (2H, m), 4.43 (2H, t, J = 6.3 Hz), 6.80 (1H, br-s), 7.41 (1H, s), 7.47 (2H, s), 7.50 (1H, s), 7.62-7.64 (2H, m), 7.9 (1H, s) |
| 919 | (DMSO-d$_6$) δ 2.66-2.78 (2H, m), 4.34 (2H, t, J = 5.9 Hz), 7.49 (1H, t, J = 7.8 Hz), 7.66-7.72 (2H, m), 8.12 (1H, s), 8.30 (2H, s), 10.00 (1H, s), 10.60 (1H, s) |
| 920 | δ 1.32 (6H, d, J = 6.1 Hz), 2.51 (3H, s), 5.01-5.07 (1H, m), 6.72 (1H, br-s), 7.50 (1H, t, J = 7.8 Hz), 7.54-7.57 (2H, m), 7.64 (1H, d, J = 8.1 Hz), 7.71 (2H, d, J = 7.3 Hz), 7.85 (1H, s), 8.01-8.03 (1H, m), 8.13 (1H, s), 8.45-8.48 (1H, m) |
| 921 | δ1.32 (6H, d, J = 6.1 Hz), 1.74-1.77 (2H, m), 1.84-1.87 (2H, m), 2.74 (2H, t, J = 6.4 Hz), 3.02 (2H, q, J = 6.4 Hz), 5.04 (1H, septet, J = 6.1 Hz), 6.73 (1H, br s), 7.42-7.46 (2H, m), 7.52-7.55 (1H, m), 7.62 (1H, br s, J = 8 Hz), 7.76 (1H, br s), 7.96 (1H, br s), 8.03-8.06 (1H, m) |
| 922 | δ1.31 (6H, d, J = 6.4 Hz), 1.68-1.76 (4H, m), 2.81 (2H, t, J = 5.7 Hz), 2.99 (2H, q, J = 6.1 Hz), 5.03 (1H, septet, J = 6.4 Hz), 6.73 (1H, br-s), 7.43-7.47 (2H, m), 7.59-7.64 (3H, m), 8.03 (1H, s) |
| 923 | δ1.31 (6H, d, J = 6.4 Hz), 3.83 (3H, s), 5.02 (1H, septet, J = 6.4 Hz), 6.55 (1H, s), 6.78 (1H, br-s), 7.41-7.50 (2H, m), 7.57 (1H, d, J = 7.8 Hz), 8.03 (1H, br-s), 8.08 (1H, br-s) |
| 924 | δ1.32 (6H, d, J = 6.3 Hz), 3.86 (3H, s), 5.04 (1H, septet, J = 6.3 Hz), 6.72 (1H, br-s), 7.45-7.53 (2H, m), 7.63 (1H, d, J = 7.3 Hz), 7.80 (1H, br-s), 8.14 (1H, br-s) |
| 925 | δ1.32 (6H, d, J = 5.9 Hz), 3.89 (3H, s), 5.04 (1H, septet, J = 5.9 Hz), 6.72 (1H, s), 7.47-7.50 (2H, m), 7.70 (1H, d, J = 8.3 Hz), 7.90 (1H, br-s), 8.14 (1H, br-s) |
| 926 | δ1.32 (6H, d, J = 6.1 Hz), 3.88 (3H, s), 3.93 (3H, s), 5.04 (1H, septet), 6.78 (1H, br-s), 7.47 (1H, br-s), 7.64-7.68 (2H, m), 8.05 (1H, br-s), 9.40 (1H, br-s) |

TABLE 9-continued

| Compound No. | $^1$H-NMR (CDCl$_3$, ppm) |
|---|---|
| 927 | δ1.33 (6H, d, J = 5.9 Hz), 2.34 (3H, s), 5.02 (1H, septet, J = 5.9 Hz), 6.74 (1H, br-s), 7.24 (1H, s), 7.44 (1H, t, J = 7.8 Hz), 7.49-7.52 (1H, m), 7.58-7.60 (1H, m), 7.82 (1H, br-s), 8.07 (1H, br-s), 8.71 (1H, s) |
| 928 | δ1.31 (6H, d, J = 6.4 Hz), 2.35 (3H, s), 5.01-5.07 (1H, m), 6.74 (1H, br-s), 7.25 (1H, s), 7.46 (1H, t, J = 7.8 Hz), 7.58-7.63 (2H, m), 7.68 (1H, br-s), 8.07 (1H, br-s) |
| 929 | δ1.32 (6H, d, J = 5.9 Hz), 5.03 (1H, septet, J = 5.9 Hz), 6.52 (1H, septet, J = 6.3 Hz), 6.71 (1H, br-s), 6.99 (1H, d, J = 8.8 Hz), 7.43 (1H, t, J = 7.8 Hz), 7.51-7.58 (2H, m), 7.92 (1H, br-s), 8.01 (1H, br-s), 8.14 (1H, dd, J = 8.8 Hz, 2.4 Hz), 8.34 (1H, d, J = 2.4 Hz) |
| 930 | δ1.32 (6H, d, J = 5.9 Hz), 2.33 (3H, s), 5.50 (1H, septet, J = 5.9 Hz), 6.53 (1H, septet, J = 6.4 Hz), 6.74 (1H, br-s), 6.87 (1H, s), 7.43 (1H, t, J = 7.8 Hz), 7.54-7.58 (2H, m), 7.64 (1H, br-s), 8.04 (1H, br-s), 8.37 (1H, s) |
| 931 | δ1.32 (6H, d, J = 6.3 Hz), 5.05 (1H, septet, J = 6.3 Hz), 6.30 (1H, septet, J = 6.3 Hz), 6.69 (1H, br-s), 7.01 (1H, d, J = 8.8 Hz), 7.47 (1H, t, J = 7.8 Hz), 7.56 (1H, dd, J = 7.8 Hz, 1.5 Hz), 7.68 (1H, d, J = 7.8 Hz), 7.98 (1H, br-s), 8.27 (1H, br-s), 8.82 (1H, d, J = 8.8 Hz) |
| 932 | δ1.32 (6H, d, J = 6.4 Hz), 2.29 (3H, s), 2.41 (3H, s), 5.04 (1H, septet, J = 6.4 Hz), 6.58 (1H, septet, J = 6.4 Hz), 6.72 (2H, s), 7.37-7.46 (2H, m), 7.53-7.57 (1H, m), 7.60 (1H, d, J = 7.8 Hz), 8.05 (1H, br-s) |
| 933 | δ 2.49 (3H, s), 4.85 (2H, s), 7.16 (1H, br-s), 7.48-7.57 (3H, s), 7.70 (2H, s), 7.76 (1H, d, J = 7.6 Hz), 7.92 (1H, s), 8.00 (1H, dd, J = 3.4 Hz, 6.8 Hz), 8.13 (1H, s), 8.47 (1H, dd, J = 3.4 Hz, 6.8 Hz) |
| 934 | δ1.75-1.79 (2H, m), 1.84-1.87 (2H, m), 2.74 (2H, t, J = 6.4 Hz), 3.02 (2H, q, J = 6.4 Hz), 4.85 (2H, s), 7.13 (1H, br s), 7.41-7.51 (2H, m), 7.59-7.69 (2H, m), 7.76 (1H, br s), 8.00 (1H, br s), 8.06 (1H, br d, J = 8.5 Hz) |
| 935 | δ1.65-1.76 (4H, m), 2.81 (2H, t, J = 6.1 Hz), 2.99 (2H, q, J = 6.4 Hz), 4.85 (2H, s), 7.10 (1H, br-s), 7.48-7.52 (2H, m), 7.59 (1H, s), 7.67-7.69 (2H, m), 8.04 (1H, s) |
| 936 | δ3.86 (3H, s), 4.85 (2H, s), 6.58 (1H, s), 7.10 (1H, br-s), 7.51 (1H, t, J = 7.8 Hz), 7.60 (1H, d, J = 7.8 Hz), 7.65 (1H, d, J = 7.8 Hz), 7.84 (1H, br-s), 8.10 (1H, br-s) |
| 937 | δ3.85 (3H, s), 4.85 (2H, s), 7.16 (1H, br-s), 7.51 (1H, t, J = 7.9 Hz), 7.62 (1H, d, J = 7.9 Hz), 7.68 (1H, d, J = 7.9 Hz), 7.85 (1H, br-s), 8.12 (1H, br-s) |
| 938 | δ3.87 (3H, s), 4.85 (2H, s), 7.21 (1H, br-s), 7.51 (1H, t, J = 8.3 Hz), 7.61 (1H, d, J = 8.3 Hz), 7.68 (1H, d, J = 8.3 Hz), 7.92 (1H, br-s), 8.13 (1H, br-s) |
| 939 | δ3.89 (3H, s), 3.94 (3H, s), 4.86 (2H, s), 7.20 (1H, br-s), 7.52 (1H, t, J = 7.8 Hz), 7.70-7.73 (2H, m), 8.09 (1H, br-s), 9.44 (1H, s) |
| 940 | δ4.87 (2H, s), 7.07-7.11 (2H, m), 7.31-7.34 (1H, m), 7.47-7.52 (2H, m), 7.67-7.69 (1H, m), 8.01 (1H, dd, J = 8.0 Hz, 1.4 Hz), 8.19 (1H, br-s), 8.58-8.60 (1H, m), 11.3 (1H, br-s) |
| 941 | δ4.84 (2H, s), 7.19 (1H, br-s), 7.33 (1H, dd, J = 8.3 Hz, 4.8 Hz), 7.44 (1H, t, J = 8.3 Hz), 7.58-7.59 (2H, m), 7.94-7.97 (2H, m), 8.44 (1H, dd, J = 4.8 Hz, 1.4 Hz), 9.14 (1H, br-s) |
| 942 | δ 2.44 (3H, s), 4.86 (2H, s), 7.11 (1H, br-s), 7.52 (1H, t, J = 7.8 Hz), 7.59 (1H, d, J = 2.9 Hz), 7.63-7.65 (2H, m), 7.76 (1H, s), 8.09 (1H, s), 9.23 (1H, s) |
| 943 | δ4.85 (2H, s), 6.52 (1H, septet, J = 6.3 Hz), 6.99 (1H, d, J = 8.8 Hz), 7.07 (1H, br-s), 7.48 (1H, t, J = 8.3 Hz), 7.61-7.62 (2H, m), 7.86 (1H, s), 8.02 (1H, s), 8.15 (1H, dd, J = 8.8 Hz, 2.5 Hz), 8.33 (1H, d, J = 2.5 Hz) |
| 944 | δ 2.35 (3H, s), 4.85 (2H, s), 6.55 (1H, septet, J = 6.4 Hz), 6.89 (1H, s), 7.08 (1H, br-s), 7.49 (1H, t, J = 7.8 Hz), 7.59 (1H, s), 7.63 (2H, d, J = 8.3 Hz), 8.05 (1H, s), 8.40 (1H, s) |
| 945 | δ 2.34 (3H, s), 4.85 (2H, s), 7.17 (1H, br-s), 7.22-7.26 (1H, m), 7.49 (1H, t, J = 7.8 Hz), 7.60-7.66 (2H, m), 7.75 (1H, br-s), 8.07 (1H, br-s), 8.73 (1H, br-s) |
| 946 | δ4.86 (2H, s), 7.13 (1H, br-s), 7.52 (1H, t, J = 8.3 Hz), 7.67 (1H, d, J = 8.3 Hz), 7.74 (1H, d, J = 8.3 Hz), 8.02 (1H, s), 8.05 (1H, s), 8.66 (1H, s), 8.70 (1H, br-s) |
| 947 | δ 2.36 (3H, s), 5.05 (2H, s), 7.16 (1H, br-s), 7.25 (1H, s), 7.51 (1H, t, J = 7.8 Hz), 7.68-7.70 (3H, m), 8.08 (1H, br-s) |
| 948 | δ4.86 (2H, s), 6.30 (1H, septet, J = 6.4 Hz), 7.00 (1H, d, J = 8.8 Hz), 7.04 (1H, br-s), 7.52 (1H, t, J = 7.8 Hz), 7.63 (1H, dd, J = 7.8 Hz, 1.5 Hz), 7.70 (1H, d, J = 7.8 Hz), 8.04 (1H, br-s), 8.27 (1H, br-s), 8.83 (1H, d, J = 8.8 Hz) |
| 992 | δ 2.37 (3H, s), 4.85 (2H, s), 6.33 (1H, septet, J = 5.8 Hz), 6.87 (1H, s), 7.05 (1H, br-s), 7.49-7.53 (2H, m), 7.66-7.68 (2H, m), 8.05 (1H, s) |
| 1010 | δ1.33 (6H, d, J = 6.4 Hz), 2.37 (3H, s), 5.04 (1H, septet, J = 6.4 Hz), 6.34 (1H, septet, J = 6.4 Hz), 6.72 (1H, br-s), 6.88 (1H, s), 7.45 (1H, t, J = 7.8 Hz), 7.58-7.64 (3H, m), 8.05 (1H, s) |
| 1039 | δ 2.38 (3H, s), 4.86 (2H, s), 6.34 (1H, septet), 6.89 (1H, s), 7.09 (1H, br-s), 7.51 (1H, t, J = 7.8 Hz), 7.57 (1H, br-s), 7.66 (1H, br-s), 7.68 (1H, d, J = 7.8 Hz), 8.07 (1H, s) |
| 1086 | δ 2.37 (3H, s), 4.85 (2H, s), 6.33 (1H, septet, J = 5.8 Hz), 6.87 (1H, s), 7.05 (1H, br-s), 7.49-7.53 (2H, m), 7.66-7.68 (2H, m), 8.05 (1H, s) |
| 1104 | δ1.32 (6H, d, J = 6.4 Hz), 2.29 (3H, s), 2.41 (3H, s), 5.04 (1H, septet, J = 6.4 Hz), 6.58 (1H, septet, J = 6.4 Hz), 6.72 (2H, s), 7.37-7.46 (2H, m), 7.53-7.57 (1H, m), 7.60 (1H, d, J = 7.8 Hz), 8.05 (1H, br-s) |
| 1180 | δ 2.46 (3H, s), 4.86 (2H, s), 7.11 (1H, s), 7.51-7.86 (5H, m), 8.10 (1H, br-s) |

TABLE 9-continued

| Compound No. | $^1$H-NMR (CDCl$_3$, ppm) |
|---|---|
| 1198 | δ 1.31 (6H, d, J = 6.3 Hz), 2.40 (3H, s), 5.03 (1H, septet, J = 6.3 Hz), 6.72 (1H, s), 7.42-7.47 (2H, m), 7.56 (1H, s), 7.60-7.63 (2H, m), 7.74 (1H, s), 8.03 (1H, s) |
| 1227 | δ 2.41 (3H, s), 4.85 (2H, s), 7.05 (1H, br), 7.44 (1H, s), 7.51 (1H, t, J = 8.1 Hz), 7.57 (1H, s), 7.67-7.70 (3H, m), 8.05 (1H, s) |
| 1245 | δ 1.31 (6H, d, J = 6.1 Hz), 2.42 (3H, s), 5.04 (1H, septet, J = 6.1 Hz), 6.71 (1H, s), 7.45 (1H, d, J = 8.1 Hz), 7.48 (1H, s), 7.61-7.64 (2H, m), 7.72-7.74 (2H, m), 8.04 (1H, s) |
| 1274 | δ 2.43 (3H, s), 4.86 (2H, s), 7.08 (1H, br), 7.48-7.53 (2H, m), 7.68-7.73 (4H, m), 8.06 (1H, s) |
| 1292 | δ 1.32 (6H, d, J = 6.3 Hz), 2.42 (3H, s), 5.04 (1H, septet, J = 6.3 Hz), 6.72 (1H, s), 7.44-7.52 (2H, m), 7.62-7.66 (3H, m), 7.93 (1H, s), 8.04 (1H, s) |
| 1321 | δ 2.43 (3H, s), 4.86 (2H, s), 7.08 (1H, br), 7.50-7.54 (2H, m), 7.63 (1H, s), 7.70-7.72 (2H, m), 7.94 (1H, s), 8.08 (1H, s) |
| 1361 | δ 0.87 (3H, t, J = 7.3 Hz), 1.53-1.63 (2H, m), 2.44-2.56 (2H, m), 2.64 (2H, t, J = 7.8 Hz), 4.38 (2H, t, J = 6.3 Hz), 7.16 (1H, s), 7.38 (1H, t, J = 7.8 Hz), 7.48 (1H, s), 7.61-7.64 (2H, m), 7.91-7.94 (2H, m), 8.00 (1H, s) |
| 1368 | δ 0.93 (3H, t, J = 7.3 Hz), 1.59-1.69 (2H, m), 2.71 (2H, t, J = 7.8 Hz), 4.86 (2H, s), 7.11 (1H, br), 7.49-7.54 (2H, m), 7.62 (1H, s), 7.69-7.72 (2H, m), 7.96 (1H, d, J = 1.5 Hz), 8.07 (1H, s) |
| 1385 | δ 2.35 (3H, s), 2.44 (3H, s), 4.86 (2H, s), 6.74 (1H, s), 7.34-7.38 (3H, m), 7.46 (1H, s), 7.52 (1H, d, J = 8.8 Hz), 7.89 (1H, s), 8.35 (1H, d, J = 8.8 Hz) |
| 1386 | δ 1.32 (6H, d, J = 6.3 Hz), 2.40 (6H, s), 2.41 (3H, s), 5.03 (1H, septet, J = 6.3 Hz), 6.46 (1H, br-s), 7.15 (1H, s), 7.28-7.37 (4H, m), 7.95 (1H, d, J = 8.3 Hz) |
| 1387 | δ 2.40 (6H, s), 2.45 (3H, s), 4.86 (2H, s), 6.80 (1H, br), 7.16 (1H, s), 7.32-7.42 (4H, m), 7.85 (1H, br) |
| 1388 | δ 1.35 (3H, t, J = 7.3 Hz), 2.36 (6H, s), 4.28 (2H, q, J = 7.3 Hz), 6.91 (1H, s), 7.29 (1H, t, J = 8.3 Hz), 7.37 (2H, s), 7.74-7.79 (2H, m), 8.32 (1H, br-d, J = 5.9 Hz) |
| 1389 | δ 1.34 (6H, d, J = 6.3 Hz), 2.36 (6H, s), 5.07 (1H, septet, J = 6.3 Hz), 6.86 (1H, br-s), 7.30 (1H, t, J = 8.1 Hz), 7.37 (2H, s), 7.72-7.79 (2H, m), 8.32 (1H, br) |
| 1408 | δ 2.37 (6H, s), 4.70 (4H, dt, J = 2.0 Hz, 46.8 Hz), 5.28 (1H, tt, J = 4.4 Hz, 24.9 Hz), 7.08 (1H, br-s), 7.33 (1H, t, J = 8.3 Hz), 7.37 (2H, s), 7.76 (1H, d, J = 12.2 Hz), 7.81 (1H, dt, J = 1.4 Hz, 7.8 Hz), 8.29 (1H, br-s) |
| 1411 | δ 2.37 (6H, s), 2.51-2.62 (2H, m), 4.46 (2H, t, J = 6.4 Hz), 6.97 (1H, br-s), 7.32 (1H, t, J = 8.3 Hz), 7.37 (2H, s), 7.74-7.82 (2H, m), 8.28 (1H, br-s) |
| 1416 | δ 2.37 (6H, s), 3.76-3.79 (2H, m), 4.49 (2H, t, J = 5.4 Hz), 7.02 (1H, br), 7.32 (1H, t, J = 7.8 Hz), 7.37 (2H, s), 7.74-7.81 (2H, m), 8.30 (1H, br) |
| 1418 | δ 2.37 (6H, s), 4.88 (2H, s), 7.21 (1H, br), 7.32-7.37 (3H, m), 7.76-7.85 (2H, m), 8.31 (1H, br) |
| 1421 | δ 2.36 (6H, s), 3.60 (2H, t, J = 5.9 Hz), 4.54 (2H, t, J = 5.9 Hz), 7.03 (1H, br), 7.32 (1H, t, J = 7.8 Hz), 7.37 (2H, s), 7.76-7.81 (2H, m), 8.29 (1H, br) |
| 1435 | δ 1.35 (3H, t, J = 7.3 Hz), 2.36 (6H, s), 4.29 (2H, q, J = 7.3 Hz), 6.89 (1H, br-s), 7.30 (1H, t, J = 7.8 Hz), 7.35 (2H, s), 7.74-7.78 (2H, m), 8.32 (1H, br-s) |
| 1455 | δ 2.33 (6H, s), 4.70 (4H, ddd, J = 48.8 Hz, 2.4 Hz, 4.3 Hz), 5.28 (1H, tt, J = 20.0, 4.3 Hz), 7.08 (1H, br-s), 7.32 (1H, d, J = 8.3 Hz), 7.35 (2H, s), 7.75-7.83 (2H, m), 8.29 (1H, br-s) |
| 1458 | δ 2.36 (6H, s), 2.51-2.62 (2H, m), 4.47 (2H, t, J = 6.3 Hz), 6.95 (1H, br-s), 7.32 (1H, t, J = 7.3 Hz), 7.35 (2H, s), 7.74-7.82 (2H, m), 8.29 (1H, br-s) |
| 1463 | δ 2.36 (6H, s), 3.77 (2H, t, J = 5.4 Hz), 4.49 (2H, t, J = 5.4 Hz), 7.03 (1H, br), 7.31 (1H, t, J = 8.3 Hz), 7.35 (2H, s), 7.76-7.80 (2H, m), 8.29 (1H, br) |
| 1465 | δ 2.36 (6H, s), 4.88 (2H, s), 7.18 (1H, br), 7.35 (1H, t, J = 8.3 Hz), 7.36 (2H, s), 7.75-7.85 (2H, m), 8.31 (1H, br) |
| 1898 | δ 1.33 (6H, d, J = 6.3 Hz), 2.37 (3H, s), 5.05 (1H, septet, J = 6.3 Hz), 7.21 (1H, br-s), 7.32 (1H, d, J = 6.6 Hz), 7.39 (1H, t, J = 8.1 Hz), 7.46 (1H, s), 7.50-7.53 (2H, m), 8.30-8.36 (2H, m) |
| 1899 | δ 2.38 (3H, s), 4.87 (2H, s), 7.40-7.51 (5H, m), 7.62 (1H, s), 8.27-8.30 (2H, m) |
| 1900 | δ 1.34 (6H, d, J = 6.1 Hz), 2.41 (6H, s), 5.05 (1H, septet, J = 6.1 Hz), 7.22-7.26 (2H, m), 7.31-7.40 (4H, m), 8.33 (1H, dd, J = 1.5 Hz, 8.1 Hz) |
| 1901 | δ 2.40 (6H, s), 4.88 (2H, s), 7.29 (1H, s), 7.37 (2H, s), 7.38-7.43 (2H, m), 7.50 (1H, s), 8.28 (1H, d, J = 6.8 Hz) |
| 1902 | δ 4.88 (2H, s), 7.39 (1H, dd, J = 1.5 Hz, 7.3 Hz), 7.44-7.51 (2H, m), 7.88-7.92 (2H, m), 8.03 (1H, s), 8.36 (1H, d, J = 8.3 Hz), 8.70 (1H, d, J = 8.3 Hz) |
| 1903 | δ 2.37 (3H, s), 4.88 (2H, s), 6.55 (1H, septet, J = 6.3 Hz), 6.90 (1H, s), 7.32 (1H, s), 7.41-7.48 (3H, m), 8.31 (1H, br-s), 8.49 (1H, s) |

TABLE 9-continued

| Compound No. | $^1$H-NMR (CDCl$_3$, ppm) |
|---|---|
| 1904 | δ 1.34 (6H, d, J = 6.3 Hz), 2.44 (6H, s), 5.05 (1H, septet, J = 6.3 Hz), 7.13 (1H, s), 7.25-7.28 (2H, m), 7.37 (2H, s), 7.41 (1H, t, J = 8.3 Hz), 8.31 (1H, dd, J = 1.5 Hz, 8.3 Hz) |
| 1905 | δ 2.44 (6H, s), 4.88 (2H, s), 7.15 (1H, br), 7.33-7.37 (3H, m), 7.43-7.53 (2H, m), 8.25 (1H, d, J = 8.3 Hz) |
| 1906 | δ 2.40 (3H, s), 4.86 (2H, s), 7.05-7.10 (2H, m), 7.47 (1H, s), 7.53 (1H, d, J = 8.8 Hz), 7.58 (1H, br), 8.22 (1H, br), 8.28 (1H, d, J = 8.8 Hz). |
| 1907 | δ 2.40 (6H, s), 4.86 (2H, s), 7.00-7.11 (3H, m), 7.37 (2H, s), 8.18 (1H, br) |
| 1908 | δ 1.33 (6H, d, J = 6.3 Hz), 2.39 (6H, s), 5.04 (1H, septet, J = 6.3 Hz), 6.81 (1H, br), 7.30 (1H, br), 7.37 (2H, s), 8.23 (1H, br) |
| 1909 | δ 1.33 (6H, d, J = 6.1 Hz), 2.34 (3H, s), 2.42 (3H, s), 5.05 (1H, septet, J = 6.1 Hz), 6.46 (1H, br), 7.30 (1H, d, J = 8.1 Hz), 7.45 (1H, s), 7.49 (1H, d, J = 8.5 Hz), 7.60 (1H, dd, J = 1.7 Hz, 8.1 Hz), 7.83 (1H, s), 8.27 (1H, d, J = 8.5 Hz), 8.46 (1H, br) |
| 1910 | δ 2.39 (3H, s), 2.42 (3H, s), 4.86 (2H, s), 6.77 (1H, br), 7.35 (1H, d, J = 8.1 Hz), 7.46 (1H, s), 7.50 (1H, d, J = 8.8 Hz), 7.65 (1H, dd, J = 2.0 Hz, 8.1 Hz), 7.80 (1H, s), 8.27 (1H, d, J = 8.8 Hz), 8.36 (1H, br) |
| 1911 | δ 1.33 (6H, d, J = 6.3 Hz), 2.34 (9H, s), 5.04 (1H, septet, J = 6.3 Hz), 6.48 (1H, br-s), 7.31 (1H, d, J = 7.8 Hz), 7.34 (2H, s), 7.55 (1H, s), 7.64 (1H, dd, J = 1.5 Hz, 7.8 Hz), 8.46 (1H, s) |
| 1912 | δ 2.34 (6H, s), 2.40 (3H, s), 4.86 (2H, s), 6.78 (1H, br), 7.34-7.36 (3H, m), 7.50 (1H, s), 7.69 (1H, dd, J = 1.5 Hz, 7.8 Hz), 8.36 (1H, s) |
| 1913 | δ1.32 (6H, d, J = 6.3 Hz), 2.43 (3H, s), 3.96 (3H, s), 5.05 (1H, sept., J = 6.3 Hz), 6.98 (1H, d, J = 8.5 Hz), 7.24 (1H, s), 7.44 (1H, s), 7.49 (1H, d, J = 8.5 Hz), 7.71 (1H, dd, J = 2.2 Hz, 8.5 Hz), 7.82 (1H, s), 8.25 (1H, d, J = 8.5 Hz), 8.68 (1H, s) |
| 1914 | δ 2.43 (3H, s), 4.00 (3H, s), 4.87 (2H, s), 7.02 (1H, d, J = 8.5 Hz), 7.45 (1H, s), 7.50 (1H, d, J = 8.5 Hz), 7.54 (1H, s), 7.74-7.79 (2H, m), 8.28 (1H, d, J = 8.5 Hz), 8.66 (1H, s) |
| 1915 | δ 1.33 (6H, d, J = 6.3 Hz), 2.42 (3H, s), 5.00-5.10 (1H, m), 6.91 (1H, br), 7.20 (1H, dd, J = 8.5 Hz, 10.5 Hz), 7.46 (1H, s), 7.49 (1H, d, J = 8.8 Hz), 7.62-7.66 (1H, m), 7.82 (1H, s), 8.20 (1H, d, J = 8.8 Hz), 8.71 (1H, d, J = 6.1 Hz) |
| 1916 | δ 2.46 (3H, s), 4.87 (2H, s), 7.23-7.29 (2H, m), 7.47 (1H, s), 7.51 (1H, d, J = 8.8 Hz), 7.68-7.73 (1H, m), 7.78 (1H, s), 8.23 (1H, d, J = 8.5 Hz), 8.68 (1H, d, J = 6.1 Hz) |
| 1917 | δ 1.33 (6H, d, J = 6.3 Hz), 2.34 (6H, s), 5.04 (1H, septet, J = 6.3 Hz), 6.91 (1H, s), 7.20 (1H, dd, J = 8.5 Hz, 10.5 Hz), 7.35 (2H, s), 7.56 (1H, s), 7.66-7.70 (1H, m), 8.71 (1H, br-d, J = 6.6 Hz) |
| 1918 | δ 2.34 (6H, s), 4.87 (2H, s), 7.22 (1H, dd, J = 8.8 Hz, 10.5 Hz), 7.32 (2H, s), 7.75-7.79 (1H, m), 7.87 (1H, s), 8.56 (1H, s), 8.63 (1H, br) |
| 1919 | δ1.34 (6H, d, J = 6.3 Hz), 2.43 (3H, s), 5.06 (1H, septet, J = 6.3 Hz), 7.21 (1H, s), 7.46 (1H, s), 7.49-7.52 (2H, m), 7.61 (1H, dd, J = 2.2 Hz, 8.5 Hz), 7.82 (1H, s), 8.24 (1H, d, J = 8.5 Hz), 8.78 (1H, d, J = 2.2 Hz) |
| 1920 | δ 2.43 (3H, s), 4.88 (2H, s), 7.47 (1H, s), 7.50-7.57 (3H, m), 7.66 (1H, dd, J = 2.0 Hz, 8.3 Hz), 7.78 (1H, s), 8.26 (1H, d, J = 8.3 Hz), 8.72 (1H, s) |
| 1921 | δ 1.34 (6H, d, J = 6.1 Hz), 2.34 (6H, s), 5.05 (1H, septet, J = 6.1 Hz), 7.23 (1H, s), 7.35 (2H, s), 7.51 (1H, d, J = 8.3 Hz), 7.63-7.69 (2H, m), 8.76 (1H, s) |
| 1922 | δ 2.35 (6H, s), 4.88 (2H, s), 7.36 (2H, s), 7.50 (1H, br), 7.53-7.59 (2H, m), 7.70 (1H, dd, J = 2.0 Hz, 8.3 Hz), 8.72 (1H, s) |
| 1923 | δ 2.35 (6H, s), 2.45 (3H, s), 4.84 (2H, s), 7.00 (1H, br), 7.36 (2H, s), 7.41 (1H, s), 7.48 (2H, s), 7.83 (1H, s) |
| 1924 | δ 1.33 (6H, d, J = 6.1 Hz), 2.46 (3H, s), 5.05 (1H, septet, J = 6.1 Hz), 6.89 (1H, br-s), 7.48 (1H, s), 7.51 (1H, d, J = 9.1 Hz), 7.79 (2H, s), 7.89 (1H, s), 8.18 (1H, d, J = 9.1 Hz), 8.19 (1H, s) |
| 1925 | δ 2.43 (3H, s), 4.86 (2H, s), 7.31 (1H, br-s), 7.49 (1H, s), 7.52 (1H, d, J = 8.8 Hz), 7.78 (1H, s), 7.85 (1H, s), 7.94 (1H, s), 8.18 (1H, d, J = 8.8 Hz), 8.24 (1H, s) |
| 1926 | δ 1.32 (6H, d, J = 6.1 Hz), 2.34 (6H, s), 5.04 (1H, septet, J = 6.1 Hz), 6.87 (1H, s), 7.36 (2H, s), 7.50 (1H, s), 7.83 (1H, s), 7.90 (1H, s), 8.20 (1H, s) |
| 1927 | δ 2.35 (6H, s), 4.86 (2H, s), 7.26 (1H, s), 7.37 (2H, s), 7.48 (1H, s), 7.89 (1H, s), 7.97 (1H, s), 8.24 (1H, s) |
| 1928 | δ1.31 (6H, d, J = 6.3 Hz), 2.33 (6H, s), 3.89 (2H, br.), 4.97-5.04 (1H, m), 6.59 (1H, s), 6.92 (1H, s), 7.02 (1H, s), 7.23-7.26 (1H, m), 7.34 (2H, s), 7.39 (1H, br) |
| 1929 | δ 2.35 (6H, s), 3.04 (6H, s), 4.84 (2H, s), 6.94 (2H, br), 7.04 (1H, s), 7.30 (1H, s), 7.349 (2H, s), 7.404 (1H, s) |
| 1930 | δ 1.30 (6H, d, J = 6.3 Hz), 2.37 (3H, s), 2.48 (3H, s), 5.02 (1H, septet, J = 6.3 Hz), 6.57 (1H, s), 7.20-7.28 (2H, m), 7.44 (2H, s), 7.50 (1H, d, J = 8.3 Hz), 7.76 (1H, s), 8.28 (1H, d, J = 9.1 Hz) |
| 1931 | δ 2.39 (3H, s), 2.48 (3H, s), 4.84 (2H, s), 7.22 (1H, d, J = 8.3 Hz), 7.44-7.54 (3H, m), 7.80 (1H, s), 8.13 (1H, d, J = 8.1 Hz), 8.20 (1H, s), 9.04 (1H, s) |

TABLE 9-continued

| Compound No. | ¹H-NMR (CDCl₃, ppm) |
|---|---|
| 1932 | δ 1.30 (6H, d, J = 6.1 Hz), 2.39 (6H, s), 2.48 (3H, s), 5.02 (1H, septet, J = 6.1 Hz), 6.63 (1H, s), 7.19-7.25 (3H, m), 7.36 (2H, s), 7.81 (1H, s) |
| 1933 | δ 2.40 (6H, s), 2.50 (3H, s), 4.84 (2H, s), 7.01 (1H, br-s), 7.18 (1H, s), 7.24-7.27 (1H, m), 7.31-7.34 (1H, m), 7.37 (2H, s), 7.82 (1H, s) |
| 1934 | δ 1.31 (6H, d, J = 6.1 Hz), 2.41 (3H, s), 5.04 (1H, septet, J = 6.1 Hz), 6.69 (1H, s), 7.16-7.21 (1H, m), 7.46 (1H, s), 7.5 (1H, d, J = 8.8 Hz), 7.88 (1H, dd, J = 2.9 Hz, 6.6 Hz), 7.96 (1H, br), 8.40 (1H, d, J = 8.8 Hz), 8.57 (1H, d, J = 17.6 Hz) |
| 1935 | δ 2.42 (3H, s), 4.84 (2H, s), 7.04 (1H, br), 7.20-7.27 (1H, m), 7.46 (1H, s), 7.51 (1H, d, J = 8.5 Hz), 7.94 (1H, br), 8.01 (1H, dd, J = 2.9 Hz, 6.6 Hz), 8.40 (1H, d, J = 8.5 Hz), 8.57 (1H, br-d, J = 17.6 Hz) |
| 1936 | δ 1.31 (6H, d, J = 6.3 Hz), 2.35 (6H, s), 5.02 (1H, septet, J = 6.3 Hz), 6.70 (1H, s), 7.19 (1H, dd, J = 9.0 Hz, 11.2 Hz), 7.36 (2H, s), 7.83 (1H, dd, J = 2.9 Hz, 6.6 Hz), 7.99 (1H, br), 8.01 (1H, d, J = 5.1 Hz) |
| 1937 | δ 2.36 (6H, s), 4.84 (2H, s), 7.10 (1H, br-s), 7.21-7.26 (1H, m), 7.36 (2H, s), 7.94-8.03 (3H, m) |
| 1938 | δ 1.31 (6H, d, J = 6.3 Hz), 2.41 (3H, s), 5.03 (1H, septet, J = 6.3 Hz), 6.68 (1H, s), 7.40 (1H, d, J = 8.8 Hz), 7.46 (1H, s), 7.51 (1H, d, J = 8.5 Hz), 7.67 (1H, d, J = 8.5 Hz), 7.78 (1H, d, J = 2.7 Hz), 8.06 (1H, s), 8.32 (1H, d, J = 8.8 Hz) |
| 1939 | δ 2.42 (3H, s), 4.84 (2H, s), 7.38 (1H, d, J = 8.8 Hz), 7.45-7.49 (2H, m), 7.72 (1H, d, J = 7.3 Hz), 7.93 (1H, s), 8.17 (1H, d, J = 8.5 Hz), 8.52 (1H, s), 9.43 (1H, s) |
| 1940 | δ 1.31 (6H, d, J = 6.1 Hz), 2.40 (6H, s), 5.03 (1H, septet, J = 6.1 Hz), 6.70 (1H, s), 7.36 (2H, s), 7.41 (1H, d, J = 8.8 Hz), 7.63-7.66 (2H, m), 7.75 (1H, d, J = 2.7 Hz) |
| 1941 | δ 2.40 (6H, s), 4.84 (2H, s), 7.08 (1H, br), 7.37 (2H, s), 7.46 (1H, d, J = 8.8 Hz), 7.64-7.70 (2H, m), 7.82 (1H, d, J = 2.7 Hz) |
| 1942 | δ1.31 (6H, d, J = 6.3 Hz), 2.41 (3H, s), 4.97-5.07 (1H, m), 6.70 (1H, s), 7.45-7.58 (4H, m), 7.72-7.75 (2H, m), 8.30 (1H, d, J = 8.8 Hz) |
| 1943 | δ 2.44 (3H, s), 4.85 (2H, s), 7.43-7.47 (2H, m), 7.54 (1H, d, J = 8.5 Hz), 7.61 (1H, d, J = 8.5 Hz), 7.86 (1H, s), 7.99 (1H, d, J = 8.1 Hz), 9.09 (1H, s), 9.89 (1H, s) |
| 1944 | δ 2.43 (3H, s), 4.84 (2H, s), 7.36 (1H, s), 7.44 (1H, s), 7.47 (1H, d, J = 8.5 Hz), 7.79 (2H, d, J = 8.5 Hz), 8.08 (1H, d, J = 8.5 Hz), 8.62 (1H, s), 9.65 (1H, s) |
| 1945 | δ 1.31 (6H, d, J = 6.3 Hz), 2.45 (6H, s), 5.03 (1H, septet, J = 6.3 Hz), 6.66 (1H, s), 7.16-7.21 (2H, m), 7.36 (2H, s), 7.76 (1H, s), 7.82 (1H, dd, J = 2.7 Hz, 8.8 Hz) |
| 1946 | δ1.52 (9H, s), 2.41 (3H, s), 6.58 (1H, s), 7.19 (1H, dd, J = 2.7 Hz, 8.5 Hz), 7.41 (1H, s), 7.45 (1H, s), 7.51 (1H, d, J = 7.1 Hz), 7.69 (1H, s), 7.79 (1H, d, J = 8.5 Hz), 8.30 (1H, d, J = 8.5 Hz) |
| 1947 | δ 2.44 (3H, s), 2.45 (3H, s), 4.83 (2H, d, J = 1.7 Hz), 7.00 (1H, br), 7.07-7.27 (2H, m), 7.36 (2H, s), 7.74-7.77 (1H, d, J = 10.3 Hz), 7.86 (1H, dd, J = 8.5 Hz, 10.3 Hz) |
| 1948 | δ3.45 (3H, s), 4.80 (2H, s), 7.53-7.57 (2H, m), 7.68 (1H, s), 7.82 (1H, d, J = 7.8 Hz), 7.93-7.95 (3H, m) |
| 1949 | δ 2.30 (3H, s), 3.41 (3H, s), 4.77 (2H, s), 6.77 (1H, s), 6.95-7.00 (1H, m), 7.07-7.16 (2H, m), 7.29-7.41 (4H, m) |
| 1950 | δ 1.26 (6H, d, J = 5.9 Hz), 2.28 (6H, s), 3.33 (3H, s), 4.96 (1H, septet, J = 5.9 Hz), 6.47 (1H, s), 6.88 (1H, d, J = 7.8 Hz), 7.04 (1H, t, J = 7.8 Hz), 7.21 (2H, s), 7.23-7.47 (2H, m) |
| 1951 | δ 2.29 (6H, s), 3.34 (3H, s), 4.77 (2H, s), 6.81 (1H, br), 6.99 (1H, d, J = 7.8 Hz), 7.10 (1H, t, J = 7.8 Hz), 7.22 (2H, s), 7.24-7.26 (1H, m), 7.42 (1H, s) |
| 1954 | δ 1.26 (6H, d, J = 6.3 Hz), 2.34 (3H, s), 3.34 (3H, s), 4.97 (1H, septet, J = 6.3 Hz), 6.46 (1H, s), 6.99 (1H, d, J = 7.8 Hz), 7.07 (1H, t, J = 7.8 Hz), 7.28-7.31 (2H, m), 7.40-7.44 (1H, m), 7.62 (1H, s) |
| 1955 | δ 2.35 (3H, s), 3.36 (3H, s), 4.77 (2H, s), 7.02-7.13 (3H, m), 7.29-7.37 (2H, m), 7.44-7.52 (1H, m), 7.62 (1H, s) |
| 1956 | δ 1.26 (3H, t, J = 7.3 Hz), 2.29 (6H, s), 3.86 (2H, q, J = 7.3 Hz), 4.76 (2H, s), 6.86 (1H, br), 6.92-6.95 (1H, m), 7.08 (1H, t, J = 8.1 Hz), 7.22 (2H, s), 7.23-7.30 (1H, m), 7.38 (1H, t, J = 2.0 Hz) |
| 1957 | δ 1.46 (6H, d, J = 6.3 Hz), 2.07 (6H, s), 4.77 (2H, s), 5.40 (1H, septet, J = 6.3 Hz), 6.78 (1H, br), 6.98 (1H, d, J = 7.8 Hz), 7.14-7.19 (1H, m), 7.17 (2H, s), 7.29 (1H, s), 7.46 (1H, d, J = 7.8 Hz) |
| 1958 | δ 2.34 (6H, s), 3.45 (3H, s), 4.80 (2H, s), 7.36 (2H, s), 7.50-7.56 (3H, m), 7.78 (1H, d, J = 6.1 Hz), 7.90 (1H, s) |
| 1959 | (DMSO-d₆) δ 2.32 (6H, s), 3.30 (3H, s), 4.86 (2H, s), 6.83 (1H, t, J = 7.4 Hz), 7.40 (1H, t, J = 7.4 Hz), 7.44 (2H, s), 7.67 (1H, t, J = 7.4 Hz), 10.05 (1H, s) |
| 1960 | δ1.29 (6H, d, J = 6.3 Hz), 2.35 (6H, s), 3.35 (3H, s), 3.38 (3H, s), 4.97-5.03 (1H, m), 7.36 (2H, s), 7.58 (1H, s), 7.76 (1H, s), 7.84 (1H, s), 8.56 (1H, s) |
| 1961 | (DMSO-d₆) δ 2.28 (6H, s), 2.33 (3H, s), 7.44 (2H, s), 7.48 (1H, t, J = 7.8 Hz), 7.66-7.75 (2H, m), 8.11 (1H, t, J = 2.0 Hz), 9.96 (1H, s), 10.56 (1H, s) |

TABLE 9-continued

| Compound No. | ¹H-NMR (CDCl₃, ppm) |
|---|---|
| 1962 | (DMSO-d₆) δ 1.34 (3H, t, J = 7.3 Hz), 2.34 (6H, s), 2.96 (2H, q, J = 7.3 Hz), 7.33 (2H, s), 7.41 (1H, t, J = 7.8 Hz), 7.67 (1H, d, J = 7.8 Hz), 7.83-7.85 (1H, m), 8.11 (1H, d, J = 2.0 Hz), 8.79 (1H, s), 9.58 (1H, s) |
| 1963 | δ 1.32 (6H, d, J = 6.6 Hz), 2.37 (6H, s), 5.00-5.06 (1H, m), 6.69 (1H, s), 7.35-7.65 (5H, m), 8.09 (1H, s), 8.72 (1H, s) |
| 1964 | δ 2.37 (6H, s), 4.85 (2H, s), 7.07 (1H, br.), 7.39 (2H, s), 7.45 (1H, t, J = 8.1 Hz), 7.61-7.68 (2H, m), 8.11 (1H, s), 8.69 (1H, s) |
| 1967 | δ 1.34 (6H, d, J = 6.3 Hz), 2.34 (6H, s), 5.09 (1H, septet, J = 6.3 Hz), 7.29 (1H, br-s), 7.35 (2H, s), 7.91 (1H, t, J = 7.8 Hz), 7.97 (1H, d, J = 7.8 Hz), 8.21 (1H, d, J = 7.8 Hz), 9.19 (1H, br-s) |
| 1968 | δ 2.35 (6H, s), 4.89 (2H, s), 7.36 (2H, s), 7.63 (1H, br-s), 7.97 (1H, dd, J = 8.3 Hz, 7.6 Hz), 8.05 (1H, d, J = 7.6 Hz), 8.21 (1H, d, J = 8.3 Hz), 9.17 (1H, br-s) |
| 1969 | δ 2.35 (6H, s), 3.77-3.80 (2H, m), 4.48-4.52 (2H, m), 7.36 (2H, s), 7.46 (1H, br-s), 7.94 (1H, t, J = 7.8 Hz), 8.02 (1H, dd, J = 7.8 Hz, 1.0 Hz), 8.19 (1H, dd, J = 7.8 Hz, 1.0 Hz), 9.17 (1H, br-s) |
| 2061 | δ 1.36 (6H, d, J = 6.4 Hz), 2.52 (6H, s), 5.07-5.14 (1H, m), 7.36 (2H, s), 7.56 (1H, t, J = 8.2 Hz), 8.15 (1H, dd, J = 8.2 Hz, 1.9 Hz), 8.44 (1H, dd, J = 8.2 Hz, 1.9 Hz), 9.45 (1H, br-s), 12.9 (1H, br-s) |
| 2062 | δ 2.37 (6H, s), 4.91 (2H, s), 7.36 (2H, s), 7.61 (1H, t, J = 8.3 Hz), 8.23 (1H, dd, J = 8.3 Hz, 1.9 Hz), 8.45 (1H, dd, J = 8.3 Hz, 1.9 Hz), 9.81 (1H, br-s), 12.7 (1H, br-s) |
| 2157 | δ 2.36 (6H, s), 4.90 (2H, s), 7.38 (2H, s), 7.52-7.60 (2H, m), 8.44 (1H, s), 8.56 (1H, d, J = 5.4 Hz), 8.58 (1H, br-s) |
| 2164 | δ 1.33 (6H, d, J = 5.8 Hz), 2.35 (6H, s), 5.03-5.07 (1H, m), 7.06 (1H, s), 7.35 (2H, s), 7.93 (1H, d, J = 2.4 Hz), 7.95 (1H, d, J = 5.9 Hz, 2.4 Hz), 8.49 (1H, d, J = 5.9 Hz), 9.58 (1H, br-s) |
| 2165 | (DMSO-d₆) δ 2.26 (6H, s), 5.02 (2H, s), 7.43 (2H, s), 7.75 (1H, dd, J = 5.4 Hz, 2.0 Hz), 8.31 (1H, d, J = 2.0 Hz), 8.60 (1H, d, J = 5.4 Hz), 10.41 (1H, br-s), 10.92 (1H, br-s) |
| 2167 | (DMSO-d₆) δ 2.36 (6H, s), 4.90 (2H, s), 7.34 (2H, s), 7.94 (1H, dd, J = 7.3 Hz, 3.4 Hz), 8.31 (1H, d, J = 7.3 Hz), 8.60 (1H, d, J = 3.4 Hz), 10.90 (1H, br-s), 13.65 (1H, br-s) |
| 2168 | (DMSO-d₆) δ 2.30 (6H, s), 3.61 (3H, s), 5.03 (2H, s), 7.47 (2H, s), 7.92 (1H, d, J = 7.6 Hz), 7.98 (1H, d, J = 7.6 Hz), 8.08 (1H, t, J = 7.6 Hz), 10.18 (1H, s) |
| I-1 | δ 2.34 (6H, s), 3.87 (2H, br-s), 6.86-6.89 (1H, m), 7.21-7.30 (3H, m), 7.33 (2H, s), 7.39 (1H, s) |
| I-2 | δ 3.87 (2H, br), 6.84-7.00 (1H, m), 7.14-7.17 (1H, m), 7.20 (1H, t, J = 2.0 Hz), 7.24-7.28 (1H, m), 7.60 (2H, d, J = 8.8 Hz), 7.78 (2H, d, J = 8.8 Hz), 7.90 (1H, br-s) |
| I-3 | δ 2.51 (3H, d, J = 8.8 Hz), 3.86 (2H, br-s), 6.83-8.68 (1H, m), 7.13-7.25 (3H, m), 7.26-7.63 (3H, m), 7.90 (1H, br-s) |
| I-4 | δ 3.87 (2H, br-s), 3.89 (3H, s), 6.86-6.88 (1H, m), 6.99 (1H, dd, J = 8.6 Hz, 2.0 Hz), 7.15-7.20 (2H, m), 7.27 (1H, t, J = 7.8 Hz), 7.51 (1H, d, J = 8.6 Hz), 7.83 (1H, s), 7.93 (1H, s) |
| I-5 | δ 3.89 (2H, br-s), 6.86-6.89 (1H, m), 7.12-7.30 (3H, m), 7.52-7.59 (2H, m), 7.76-7.93 (2H, m) |
| I-6 | δ 2.43 (3H, s), 3.83 (2H, br), 6.85-6.88 (1H, m), 7.14-7.17 (1H, m), 7.21-7.29 (2H, m), 7.45 (1H, s), 7.49 (1H, d, J = 8.8 Hz), 7.76 (1H, br), 8.27 (1H, d, J = 8.8 Hz) |
| I-7 | δ 2.34 (6H, s), 3.87 (2H, br), 6.86-6.89 (1H, m), 7.20-7.35 (6H, m) |
| I-8 | δ 2.42 (3H, s), 3.79 (2H, br-s), 6.80 (1H, dd, J = 2.2 Hz, 7.8 Hz), 6.90 (1H, d, J = 7.8 Hz), 7.05 (1H, s), 7.15 (1H, t, J = 7.8 Hz), 7.26-7.44 (7H, m), 7.53 (1H, s) |
| I-9 | δ 2.33 (3H, s), 2.52 (3H, d, J = 8.8 Hz), 3.89 (2H, br-s), 6.86-6.89 (1H, m), 7.14-7.16 (1H, m), 7.22 (1H, s), 7.28-7.30 (2H, m), 7.65 (1H, br-s), 8.11 (1H, s) |
| I-10 | δ 2.28 (3H, s), 2.46 (3H, d, J = 6.1 Hz), 3.88 (2H, br-s), 6.84-6.89 (1H, m), 7.15-7.19 (1H, m), 7.23-7.29 (2H, m), 7.41 (1H, d, J = 9.1 Hz), 7.73 (1H, br-s), 7.81 (1H, d, J = 9.1 Hz) |
| I-12 | δ 2.60 (3H, s), 3.92 (2H, br-s), 6.89-6.92 (1H, m), 7.24-7.32 (3H, m), 7.46 (1H, s), 7.76 (1H, br-s) |
| I-13 | δ 2.27 (6H, s), 3.31 (3H, s), 6.40-6.43 (1H, m), 6.54-6.58 (1H, m), 6.71 (1H, t, J = 2.0 Hz), 6.76-6.86 (1H, m), 7.22 (2H, s) |
| I-14 | δ 1.45 (6H, d, J = 6.3 Hz), 2.07 (6H, s), 3.53 (2H, br), 5.37 (1H, septet, J = 6.3 Hz), 6.56-6.63 (3H, m), 6.96 (1H, t, J = 7.8 Hz), 7.16 (2H, s) |
| I-15 | δ 1.32 (3H, t, J = 7.6 Hz), 2.72 (2H, q, J = 7.6 Hz), 3.88 (2H, br), 6.85-6.89 (1H, m), 7.13-7.14 (1H, m), 7.22-7.30 (2H, m), 7.46 (1H, s), 7.50 (1H, d, J = 8.8 Hz), 7.80 (1H, br-s), 8.29 (1H, d, J = 8.8 Hz) |
| I-16 | δ 1.17 (3H, t, J = 7.6 Hz), 2.28 (3H, s), 2.65 (2H, q, J = 7.6 Hz), 3.85 (2H, br-s), 6.82-6.85 (1H, m), 7.21-7.23 (3H, m), 7.34 (2H, s), 7.64 (1H, s) |
| I-17 | δ 1.22 (6H, t, J = 7.6 Hz), 2.69 (4H, q, J = 7.6 Hz), 3.86 (2H, br-s), 6.86-6.89 (1H, m), 7.15-7.36 (4H, m), 7.38 (2H, s) |

TABLE 9-continued

| Compound No. | ¹H-NMR (CDCl₃, ppm) |
|---|---|
| I-18 | δ 1.23 (3H, t, J = 7.3 Hz), 2.76 (2H, q, J = 7.3 Hz), 3.88 (2H, br-s), 6.88-6.91 (1H, m), 7.26-7.32 (3H, m), 7.50 (1H, s), 7.53 (1H, s), 7.95 (1H, d, J = 1.5 Hz) |
| I-19 | δ 1.00 (3H, t, J = 7.3 Hz), 1.65-1.75 (2H, m), 2.67 (2H, t, J = 7.3 Hz), 3.89 (2H, br), 6.84-6.88 (1H, m), 7.11-7.29 (3H, m), 7.43 (1H, s), 7.49 (1H, d, J = 8.5 Hz), 7.85 (1H, br-s), 8.27 (1H, d, J = 7.8 Hz) |
| I-20 | δ1.22 (6H, d, J = 6.8 Hz), 2.32 (3H, s), 3.17 (1H, septet, J = 6.8 Hz), 3.87 (2H, br-s), 6.85-6.93 (1H, m), 7.20-7.29 (3H, m), 7.35 (1H, s), 7.40-7.45 (2H, m). |
| I-21 | δ 2.35 (3H, s), 3.85 (5H, s), 6.85-6.89 (1H, m), 6.95 (1H, s), 7.13 (1H, s), 7.23-7.30 (3H, m), 7.62 (1H, s) |
| I-22 | δ 1.25 (3H, t, J = 7.6 Hz), 2.76 (2H, q, J = 7.6 Hz), 3.88 (2H, br-s), 6.87-6.91 (1H, m), 7.24-7.31 (3H, m), 7.47 (1H, s), 7.55 (1H, s), 7.57 (1H, s) |
| I-23 | δ 2.62 (3H, d, J = 6.4 Hz), 3.91 (2H, br-s), 6.89 (1H, d, J = 8.0 Hz), 7.20-7.32 (4H, m), 7.49 (1H, d, J = 9.0 Hz), 8.58-8.60 (1H, m) |
| I-24 | δ3.91 (2H, br-s), 3.92 (3H, s), 6.89-6.92 (1H, m), 7.21-7.33 (3H, m), 7.59 (1H, d, J = 1.2 Hz), 8.50 (1H, s), 8.54 (1H, s) |
| I-25 | δ 2.35 (3H, s), 2.57 (3H, d, J = 6.8 Hz), 3.88 (2H, br-s), 6.88-6.91 (1H, m), 7.25-7.34 (4H, m), 7.67 (1H, s) |
| I-26 | δ 2.41 (3H, s), 3.88 (2H, br-s), 6.87-6.91 (1H, m), 7.25-7.31 (3H, m), 7.47 (1H, s), 7.65 (1H, s), 7.72 (1H, s) |
| I-27 | δ 1.23 (3H, t, J = 7.3 Hz), 2.74 (2H, q, J = 7.3 Hz), 3.87 (2H, br-s), 6.86-6.91 (1H, m), 7.25-7.31 (3H, m), 7.50 (1H, s), 7.59 (1H, s), 7.73 (1H, d, J = 1.5 Hz) |
| I-28 | (DMSO-d₆) δ 0.84 (3H, t, J = 7.3 Hz), 1.48-1.58 (2H, m), 2.66 (2H, t, J = 7.3 Hz), 5.36 (2H, br-s), 6.77 (1H, dd, J = 1.0 Hz, 7.8 Hz), 7.10-7.19 (3H, m), 7.59 (1H, s), 7.80 (1H, s), 10.03 (1H, s) |
| I-29 | δ 0.90 (3H, t, J = 7.3 Hz), 1.25-1.37 (2H, m), 1.55-1.63 (2H, m), 2.72 (2H, t, J = 7.8 Hz), 3.89 (2H, br), 6.87-6.91 (1H, m), 7.24-7.31 (3H, m), 7.48 (1H, s), 7.55 (1H, s), 7.73 (1H, d, J = 1.5 Hz) |
| I-30 | δ 2.39 (3H, s), 2.66 (3H, d, J = 6.9 Hz), 7.43 (1H, s), 7.75-7.79 (2H, m), 8.33 (1H, d, J = 8.3 Hz), 8.48 (1H, d, J = 8.3 Hz), 8.80 (1H, s) |
| I-31 | δ 2.41 (3H, s), 3.88 (2H, s), 6.86-6.91 (1H, m), 7.28-7.32 (3H, m), 7.49 (1H, s), 7.58 (1H, s), 7.93 (1H, d, J = 1.2 Hz) |
| I-32 | δ 0.91 (3H, t, J = 7.3 Hz), 1.58-1.67 (2H, m), 2.69 (2H, t, J = 7.8 Hz), 3.88 (2H, br-s), 6.87-6.90 (1H, m), 7.26-7.31 (3H, m), 7.50 (1H, s), 7.54 (1H, s), 7.95 (1H, d, J = 2.0 Hz) |
| I-33 | δ 2.33 (6H, s), 3.87 (2H, br-s), 6.86-6.89 (1H, m), 7.21-7.29 (3H, m), 7.34 (2H, s), 7.52 (1H, s) |
| I-34 | δ 2.32 (6H, s), 3.86 (2H, br-s), 6.85-6.88 (1H, m), 7.20-7.28 (3H, m), 7.33 (2H, s), 7.60 (1H, s) |
| I-35 | δ 3.86 (2H, br), 6.84-6.87 (1H, m), 7.13-7.28 (3H, m), 7.63-7.64 (2H, m), 7.70-7.74 (2H, m), 7.91 (1H, br-s) |
| I-36 | δ 3.99 (2H, br-s), 6.85-6.88 (1H, m), 7.23-7.34 (3H, m), 7.91 (2H, s), 8.69 (1H, s) |
| I-37 | δ 3.91 (2H, br), 6.88-6.91 (1H, m), 7.15-7.21 (2H, m), 7.29 (1H, t, J = 7.8 Hz), 7.94-7.98 (2H, m), 8.03 (2H, d, J = 8.8 Hz), 8.11 (1H, s) |
| I-38 | (DMSO-d₆) δ 5.39 (2H, br-s), 6.77-6.80 (1H, m), 7.12-7.19 (3H, m), 8.49 (2H, s), 10.53 (1H, s) |
| I-39 | (DMSO-d₆) δ 2.30 (3H, s), 4.32 (2H, br-s), 4.39 (2H, q, J = 8.3 Hz), 6.79-6.86 (3H, m), 7.18-7.27 (2H, m), 7.45 (1H, d, J = 8.8 Hz), 7.56 (1H, s), 8.91 (1H, br-s) |
| I-40 | δ3.87 (2H, br-s), 6.85-6.88 (1H, m), 7.14 (1H, dd, J = 9.3 Hz, 1.0 Hz), 7.19 (1H, t, J = 2.0 Hz), 7.27 (1H, t, J = 7.9 Hz), 7.64 (2H, d, J = 8.7 Hz), 7.71 (2H, d, J = 8.7 Hz), 7.86 (1H, s) |
| I-42 | δ3.88 (2H, s), 6.90 (1H, d, J = 6.8 Hz), 7.23-7.32 (3H, m), 7.60 (1H, s), 7.92 (2H, s) |
| I-43 | δ3.89 (2H, br-s), 6.90 (1H, dt, J = 2.5 Hz, 6.3 Hz), 7.25-7.32 (3H, m), 7.59 (1H, s), 7.72 (2H, s) |
| I-44 | δ3.89 (2H, br-s), 6.90 (1H, dt, J = 2.5 Hz, 6.4 Hz), 7.28-7.30 (3H, m), 7.60 (1H, s), 7.93 (2H, s) |
| I-45 | δ3.92 (2H, s), 6.92 (1H, dt, J = 1.5 Hz, 7.3 Hz), 7.23-7.30 (3H, m), 7.79 (1H, s), 8.04 (2H, s) |
| I-46 | δ3.89 (2H, br-s), 6.90 (1H, dd, J = 2.4 Hz, 4.9 Hz), 7.23-7.32 (3H, m), 7.61 (1H, s), 7.93 (2H, s) |
| I-47 | δ3.88 (2H, br-s), 6.90 (1H, d, J = 6.3 Hz), 7.23-7.32 (3H, m), 7.62 (1H, s), 7.92 (2H, s) |
| I-48 | δ6.90-6.94 (1H, m), 7.28-7.33 (3H, m), 7.73 (1H, s), 8.02 (1H, s), 8.25 (1H, s) |
| I-49 | δ 2.31 (6H, s), 2.90 (3H, s), 6.81 (1H, dd, J = 1.9 Hz, 7.8 Hz), 7.15-7.18 (2H, m), 7.30 (1H, t, J = 7.8 Hz), 7.42 (1H, s), 7.52 (2H, s) |
| I-50 | δ 2.91 (3H, s), 6.82-6.85 (1H, m), 7.21-7.23 (2H, m), 7.32 (1H, t, J = 7.8 Hz), 7.64 (1H, s), 7.93 (2H, s) |
| I-51 | δ 2.29 (3H, s), 2.34 (3H, s), 3.82 (2H, br), 6.81 (1H, d, J = 8.1 Hz), 6.92 (1H, d, J = 8.1 Hz), 7.11 (1H, t, J = 7.8 Hz), 7.41-7.44 (2H, m), 7.50 (1H, d, J = 8.3 Hz), 8.36 (1H, d, J = 8.3 Hz) |

TABLE 9-continued

| Compound No. | $^1$H-NMR (CDCl$_3$, ppm) |
|---|---|
| I-53 | δ 2.23 (3H, s), 2.39 (3H, s), 3.82 (2H, br), 7.10-7.16 (2H, m), 7.24 (1H, d, J = 1.7 Hz), 7.44 (1H, s), 7.49 (1H, d, J = 8.1 Hz), 7.73 (1H, s), 8.30 (1H, d, J = 8.8 Hz) |
| I-55 | δ 2.34 (3H, s), 2.40 (3H, s), 3.70 (2H, br), 6.72 (1H, dd, J = 2.4 Hz, 8.1 Hz), 6.83 (1H, d, J = 2.4 Hz), 7.07 (1H, d, J = 8.1 Hz), 7.36 (1H, s), 7.44 (1H, s), 7.50 (1H, d, J = 8.5 Hz), 8.30 (1H, d, J = 8.5 Hz) |
| I-56 | δ 2.38 (6H, s), 2.42 (3H, s), 3.70 (2H, br), 6.72 (1H, dd, J = 2.4 Hz, 8.1 Hz), 6.89 (1H, d, J = 2.4 Hz), 7.05 (1H, s), 7.07 (1H, d, J = 8.1 Hz), 7.36 (2H, s) |
| I-59 | δ 2.37 (6H, s), 3.90 (2H, br-s), 6.96-7.01 (1H, m), 7.10 (1H, t, J = 7.8 Hz), 7.36 (2H, s), 7.43-7.47 (1H, m), 7.86 (1H, d, J = 13.2 Hz) |
| I-60 | δ 2.33 (6H, s), 6.99 (1H, dt, J = 1.5 Hz, 7.8 Hz), 7.10 (1H, t, J = 7.8 Hz), 7.43 (2H, s), 7.46 (1H, d, J = 7.8 Hz), 7.84 (1H, d, J = 13.2 Hz) |
| I-61 | δ 2.33 (6H, s), 3.93 (2H, s), 7.05-7.14 (1H, m), 7.17-7.21 (1H, m), 7.31 (1H, s), 7.35 (2H, s), 7.37-7.40 (1H, m) |
| I-62 | δ 2.40 (3H, s), 3.77 (2H, br), 6.79-6.83 (1H, m), 6.97-7.03 (1H, m), 7.44-7.51 (3H, m), 8.42 (1H, d, J = 8.8 Hz), 8.60 (1H, br-d, J = 18.8 Hz) |
| I-63 | δ 2.35 (6H, s), 3.74 (2H, br-s), 6.77-6.83 (1H, m), 7.01 (1H, dd, J = 8.8 Hz, 11.7 Hz), 7.35 (2H, s), 7.42 (1H, dd, J = 2.9 Hz, 6.6 Hz), 8.01 (1H, d, J = 15.6 Hz) |
| I-64 | δ 2.38 (3H, s), 4.27 (2H, br), 6.89 (1H, dd, J = 1.5 Hz, 8.1 Hz), 7.05 (1H, d, J = 8.8 Hz), 7.18 (1H, t, J = 8.1 Hz), 7.45 (1H, s), 7.51 (1H, d, J = 8.1 Hz), 7.60 (1H, s), 8.34 (1H, d, J = 8.8 Hz) |
| I-65 | δ 2.40 (6H, s), 4.27 (2H, br-s), 6.88 (1H, dd, J = 1.5 Hz, 7.8 Hz), 7.03 (1H, dd, J = 1.5 Hz, 7.8 Hz), 7.16 (1H, t, J = 7.8 Hz), 7.29 (1H, s), 7.36 (2H, s) |
| I-66 | δ 2.39 (3H, s), 4.27 (2H, br), 7.08 (1H, dd, J = 2.2 Hz, 8.3 Hz), 7.32-7.36 (2H, m), 7.45 (1H, s), 7.50 (1H, d, J = 8.5 Hz), 7.68 (1H, s), 8.24 (1H, d, J = 8.5 Hz) |
| I-67 | δ 2.33 (6H, s), 4.27 (2H, br-s), 7.15 (1H, d, J = 8.1 Hz), 7.35-7.38 (5H, m) |
| I-68 | δ 2.41 (3H, s), 3.87 (2H, br), 6.73 (1H, dd, J = 2.9 Hz, 8.5 Hz), 7.18 (1H, d, J = 2.9 Hz), 7.21 (1H, d, J = 8.8 Hz), 7.45 (1H, s), 7.50 (1H, d, J = 8.8 Hz), 8.12 (1H, s), 8.34 (1H, d, J = 8.5 Hz) |
| I-69 | δ 2.39 (6H, s), 3.85 (2H, br-s), 6.72 (1H, dd, J = 2.7 Hz, 8.5 Hz), 7.15 (1H, d, J = 2.7 Hz), 7.22 (1H, d, J = 8.5 Hz), 7.36 (2H, s), 7.66 (1H, s) |
| I-70 | δ 2.43 (6H, s), 4.34 (2H, br), 6.86 (1H, dd, J = 1.5 Hz, 8.3 Hz), 6.96 (1H, dd, J = 1.5 Hz, 8.3 Hz), 7.13 (1H, s), 7.19 (1H, t, J = 8.3 Hz), 7.36 (2H, s) |
| I-71 | δ 2.41 (3H, s), 3.87 (2H, br), 6.66 (1H, dd, J = 2.9 Hz, 8.5 Hz), 7.03 (1H, d, J = 2.9 Hz), 7.38 (1H, d, J = 8.5 Hz), 7.45 (1H, s), 7.50 (1H, d, J = 8.5 Hz), 7.75 (1H, br-s), 8.33 (1H, d, J = 8.5 Hz) |
| I-72 | δ 2.40 (3H, s), 3.94 (2H, br), 7.05-7.16 (2H, m), 7.36 (1H, dd, J = 2.2 Hz, 8.5 Hz), 7.45 (1H, s), 7.50 (1H, d, J = 9.0 Hz), 7.66 (1H, s), 8.24 (1H, d, J = 9.0 Hz) |
| I-73 | δ 2.41 (3H, s), 3.88 (2H, br-s), 6.54 (1H, dd, J = 2.9 Hz, 8.5 Hz), 6.88 (1H, d, J = 2.9 Hz), 7.37 (1H, s), 7.45 (1H, s), 7.52 (1H, d, J = 8.3 Hz), 7.61 (1H, d, J = 8.3 Hz), 8.32 (1H, d, J = 8.5 Hz) |
| I-74 | δ 2.44 (6H, s), 3.86 (2H, br-s), 6.52 (1H, dd, J = 2.9 Hz, 8.5 Hz), 6.91 (1H, d, J = 2.9 Hz), 7.12 (1H, s), 7.35 (2H, s), 7.62 (1H, d, J = 8.5 Hz) |
| I-75 | δ 2.38 (3H, s), 4.39 (2H, s), 7.06 (1H, s), 7.40 (1H, d, J = 1.7 Hz), 7.43-7.50 (3H, m), 7.90 (1H, d, J = 9.1 Hz), 8.73 (1H, s) |
| I-76 | δ 2.27 (6H, s), 4.09 (2H, br-s), 7.08 (1H, s), 7.33 (2H, s), 7.37 (1H, s), 7.43 (1H, s), 7.83 (1H, s) |
| I-77 | δ 2.39 (3H, s), 2.93 (3H, s), 3.95 (2H, br), 6.84 (1H, d, J = 8.3 Hz), 7.21-7.27 (2H, m), 7.44 (1H, s), 7.48 (1H, d, J = 8.5 Hz), 7.69 (1H, s), 8.28 (1H, d, J = 8.5 Hz) |
| I-79 | δ 2.33 (6H, s), 3.76 (4H, br), 6.19 (1H, d, J = 2.0 Hz), 6.60 (2H, d, J = 2.0 Hz), 7.34 (1H, br), 7.52 (2H, s) |
| I-80 | δ 2.38 (3H, s), 4.65 (2H, s), 7.26 (1H, s), 7.34 (1H, s), 7.47 (1H, s), 7.52 (1H, d, J = 8.5 Hz), 8.20 (1H, d, J = 8.5 Hz) |
| I-81 | δ 2.50 (3H, s), 3.90 (2H, s), 6.91-6.94 (1H, m), 7.27-7.35 (3H, m), 7.48-7.57 (2H, m), 7.70 (1H, s), 7.75 (1H, s), 8.01-8.04 (1H, m), 8.45-8.48 (1H, m) |
| I-82 | δ 1.74-1.78 (2H, m), 1.82-1.88 (2H, m), 2.72 (2H, t, J = 6.0 Hz), 3.01 (2H, q, J = 6.0 Hz), 3.88 (2H, br-s), 6.85-6.88 (1H, m), 7.14-7.16 (1H, m), 7.22-7.29 (2H, m), 7.42 (1H, d, J = 8.6 Hz), 7.70 (1H, br-s), 8.10 (1H, d, J = 9.0 Hz) |
| I-83 | δ 1.71-1.79 (4H, m), 2.81 (2H, t, J = 6.1 Hz), 2.99 (2H, q, J = 6.3 Hz), 3.87 (2H, br-s), 6.87-6.90 (1H, m), 7.24-7.29 (3H, m), 7.47-7.52 (2H, m) |
| I-84 | δ 3.87 (2H, br-s), 6.51 (1H, septet, J = 6.3 Hz), 6.85-6.88 (1H, m), 6.99 (1H, d, J = 8.7 Hz), 7.15 (1H, d, J = 7.3 Hz), 7.20 (1H, t, J = 2.0 Hz), 7.25-7.29 (1H, m), 7.75 (1H, br-s), 8.15 (1H, dd, J = 8.7 Hz, 2.4 Hz), 8.30 (1H, d, J = 2.4 Hz) |
| I-85 | δ 2.37 (3H, s), 4.27 (2H, br-s), 6.55 (1H, septet, J = 6.3 Hz), 6.88-6.91 (2H, m), 7.06 (1H, dd, J = 7.3 Hz, 1.5 Hz), 7.18 (1H, t, J = 7.3 Hz), 7.37 (1H, br-s), 8.50 (1H, br-s) |

TABLE 9-continued

| Compound No. | $^1$H-NMR (CDCl$_3$, ppm) |
|---|---|
| I-86 | δ 2.37 (3H, s), 3.88 (2H, br-s), 6.34 (1H, septet, J = 6.3 Hz), 6.88 (1H, s), 6.89-6.91 (1H, m), 7.23-7.31 (3H, m), 7.47 (1H, br-s) |

The insecticides containing the compounds represented by formula (1) of the present invention as active ingredients are suitable for preventing insect pests such as agricultural, horticultural and stored grain insect pests which are noxious to paddy rice, fruit trees, vegetables, other crops and flowing plants, sanitary pests, or nematodes. For example, the insecticides have strong insecticidal activity on the following insect pests: Lepidoptera such as cotton caterpillar (*Diaphania indica*), oriental tea tortrix (*Homona magnanima*), cabbage webworm (*Hellulla undalis*), summer fruit tortrix (*Adoxophyes orana fasciata*), smaller tea tortrix (*Adoxophyes* sp.), apple tortrix (*Archips fuscocupreanus*), peach fruit moth (*Carposina niponensis*), Manchurian fruit moth (*Grapholita inopinata*), oriental fruit moth (*Grapholita molesta*), soybean pod borer (*Leguminivora glycinivorella*), mulberry leafroller (*Olethreutes mori*), citrus leafminer (*Phyllocnistis citrella*), persimmon fruit moth (*Stathmopoda masinissa*), tea leafroller (*Caloptilia theivora*), *Caloptilia* sp. (*Caloptilia zachrysa*), apple leafminer (*Phyllonorycter ringoniella*), pear barkminer (*Spulerrina astaurota*), small citrus dog (*Papilio xuthus*), common cabbage worm (*Pieris rapae crucivora*), tabacco budworm (*Heliothis armigera*), codling moth (*Lapsey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), paddy borer (*Scirpophaga incertulas*), rice skipper (*Parnara guttata*), rice armyworm (*Pseudaletia separata*), pink borer (*Sesamia inferens*), cabbage armyworm (*Mamestra brassicae*), common cutworm (*Spodoptera litura*), beet armyworm (*Spodoptera exigua*), black cutworm (*Agrotis ipsilon*), turnip moth (*Agrotis segetum*), beet semi-looper (*Autographa nigrisigna*), and cabbage looper (*Trichoplusia ni*); hemiptera such as aster leafHopper (*Macrosteles fascifrons*), green rice leafHopper (*Nephotettix cincticeps*), brown rice planthopper (*Nilaparvata lugens*), small brown planthopper (*Laodelphax striatellus*), whitebacked rice planthopper (*Sogatella furcifera*), citrus psylla (*Diaphorina citri*), grape whitefly (*Aleurolobus taonabae*), silverleaf whitefly (*Bermisia argentifolii*), sweetpotato whitefly (*Bemisia tabaci*), greenHouse whitefly (*Trialeurodes vaporariorum*), turnip aphid (*Lipaphis erysimi*), cotton aphid (*Aphis gossypii*), apple aphid (*Aphis Citricola*), green peach aphid (*Myzus persicae*), Indian wax scale (*Ceroplastes ceriferus*), Comstock mealybug (*Pseudococcus Comstocki*), Japanese mealybug (*Planococcus kraunhiae*), cottony citrus scale (*Pulvinaria aurantii*), camphor scale (*Pseudaonidia duplex*), San Jose scale (*Comstockaspis perniciosa*), arrowHead scale (*Unaspis yanonensis*), brownwinged green bug (*Plautia Stali*), and brown marmorated stink bug (*Halyomorpha mista*); Coleoptera such as soybean beetle (*Anomala rufocuprea*), Japanese beetle (*Popillia japonica*), cigarette beetle (*Lasioderma serricorne*), powderpost beetle (*Lyctus brunneus*), twenty-eight-spotted ladybird (*Epilachna vigintioctopunctata*), adzuki been weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), yellowspotted longicorn beetle (*Psacothea hilaris*), and whitespotted longicorn beetle (*Anoplophora malasiaca*); Diptera such as melon fly (*Dacus (Bactrocera) dorsalis*), rice leafminer (*Agromyza oryzae*), onion maggot (*Delia antiqua*), seedcorn maggot (*Delia platura*), soybean pod gall midge (*Asphondylia* sp.), house fly (*Musca domestica*), garden pea leafminer (*Chromatomyia horticola*), legume leafminer (*Liriomyza trifolii*), bryony leafminer (*Liriomyza bryoniae*), and common house mosquito (*Culex pipiens pallens*); Nematoda such as coffee root-lesion nematode (*Pratylenchus coffeae*), root-lesion nematode (*Pratylenchus* sp.), potato cyst nematode (*Globodera rostochiensis*), root-knot nematode (*Meloidogyne* sp.), citrus nematode (*Tylenchulus semipenetrans*), nematode (*Aphelenchus avenae*), and chrysanthemum foliar nematode (*Aphelenchoides ritzemabosi*); Thysanoptera such as melon thrips (*Thrips palmi*), western flower thrips (*Frankliniella occidentalis*), yellow tea thrips (*Scirtothrips dorsalis*), honeysuckle thrips (*Thrips flavus*), and onion thrips (*Thrips tabaci*); Orthoptera such as German cockroach (*Blattella germanica*), American cockroach (*Periplaneta americana*), and rice grasshopper (*Oxya yezoensis*).

The insecticides containing the compounds represented by formula (1) of the present invention as active ingredients have a significant preventive effect on the above-described insect pests noxious to lowland crops, dry field crops, fruit trees, vegetables, other crops, and flowering plants. The effect as the insecticides of the present invention can be achieved by treating paddy water, foliages or soil of paddy fields, dry fields, fruit trees, vegetables, other crops, or flowering plants before the breeding of noxious insects or at the time of observation of the breeding of noxious insects at the predicted breeding season of noxious insects.

The insecticides of the present invention are generally formed into formulations suitable for use according to a normal method for formulating agricultural/Horticultural pesticides. Namely, a compound represented by formula (1) may be mixed with an appropriate inert carrier, and if required, an auxiliary at a proper proportion, and the resultant mixture is subjected to dissolution, separation, suspension, mixing, impregnation, adsorption or adhesion to form a suitable formulation such as a suspension, an emulsion, a liquid drug, a wettable powder, a granule, a dusting powder, or a tablet. As the inert carrier used in the present invention, either a solid or a liquid may be used. Examples of a material usable as the solid carrier include soybean flour, grain flour, wood flour, bark flour, sawing flour, tobacco stalk flour, walnut shell flour, bran, cellulose powder, a residue after plant extraction, a synthetic polymer such as a synthetic resin powder, clay (for example, kaoline, bentonite, or acid white clay), talc (for example, talc or pyrophyllite), silica (for example, diatomite, silica powder, mica, white carbon (synthetic high-dispersion silicate referred to as "hydrous silicate fine powder" or "hydrous silicate", some products containing calcium silicate as main components)), activated carbon, sulfur powder, pumice, calcined diatomite, brick powder, fly ash, sand, inorganic mineral powders such as calcium carbonate and calcium phosphate, chemical fertilizers such as ammonium sulfate, ammonium phosphate, ammonium nitrate, urea, and ammonium chloride, and compost. These carriers are used alone or in a mixture of at least two kinds.

As a material usable as the liquid carrier, a material having a solvent ability or a material having no solvent ability but having an ability to disperse an active ingredient compound with the aid of an auxiliary is selected. Typical examples of the liquid carrier are given below, and these examples can be used alone or in a mixture of two more kinds. Examples of the liquid carrier include water, alcohols (for example, methanol, ethanol, isopropanol, butanol, and ethylene glycol); ketones (for example, acetone, methylethyl ketone, methyl isobutyl ketone, diisobutyl ketone, and cyclohexanone); ethers (for example, diethyl ether, dioxane, cellosolve, diisopropyl ether, and tetrahydrofuran); aliphatic hydrocarbons (for example, kerosine and mineral oil); aromatic hydrocarbons (for example, benzene, toluene, xylene, solvent naphtha, and alkylnaphthalene); halogenated hydrocarbons (for example, dichloromethane, chloroform, carbon tetrachloride, and chlorobenzene); esters (for example, ethyl acetate, butyl acetate, ethyl propionate, diisobutyl phthalate, dibutyl phthalate, and dioctyl phthalate); amides (for example, dimethylformamide, diethylformamide, and dimethylacetamide); and nitriles (for example, acetonitrile).

Typical examples of other auxiliaries are given below, and these examples are used alone or in combination according to purposes. The auxiliary is not necessarily used. For example, a surfactant is used for emulsifying, dispersing, solubilizing and/or wetting the active ingredient compound. Examples of the surfactant include polyoxyethylene alkyl ether, polyoxyethylene alkyl aryl ether, polyoxyethylene higher fatty acid esters, polyoxyethylene resin acid esters, polyoxyethylene sorbitan monolaurate, polyoxyethylene sorbitan monooleate, alkylaryl sulfonate, naphthalenesulfonate, lignin-sulfonate, higher alcohol sulfates. Examples of other auxiliaries used for stabilizing dispersion of the active ingredient compound, and tackifying and/or bonding the active ingredient compound are given below. Examples of such auxiliaries include casein, gelatin, starch, methyl cellulose, carboxymethyl cellulose, gum arabic, polyvinyl alcohol, wood turpentine, bran oil, bentonite, xanthan gum, and lignin-sulfonate.

Another auxiliary for improving fluidity of a solid product can also be used. Examples of such an auxiliary include wax, stearates, and alkyl phosphates. Also, an auxiliary such as a naphthalenesulfonic acid condensate or condensed phosphate, can be used as a deflocculant for a suspending product. Furthermore, an auxiliary such as silicone oil can be used as a defoaming agent.

The compounds represented by formula (1) of the present invention are stable to light, heat and oxidation. However, an appropriate amount of an antioxidant or an ultraviolet absorber, for example, a phenol derivative such as BHT (2,6-di-t-butyl-4-methyl phenol) or BHA (butylated hydroxyanisole), a bisphenol derivative, an arylamine such as phenyl-α-naphthylamine, phenyl-β-naphthylamine, or a condensate of phenetidine and acetone, or a benzophenone compound, may be added as a stabilizer to produce compositions having a stable effect.

When a compound represented by formula (1) of the present invention is used as an active ingredient, generally, the amount thereof used in a dust is 0.5% by weight to 20% by weight, the amount in an emulsion is 5% by weight to 50% by weight, the amount in a wettable powder is 10% by weight to 90% by weight, the amount in a granule is 0.1% by weight to 20% by weight, and the amount in a flowable formulation is 10% by weight to 90% by weight. With respect to the amount of the carrier in a formulation, the amount in a dust is 60% by weight to 99% by weight, the amount in an emulsion is 40% by weight to 95% by weight, the amount in a wettable powder is 10% by weight to 90% by weight, the amount in a granule is 80% by weight to 99% by weight, and the amount in a flowable formulation is 10% by weight to 90% by weight. With respect to the amount of the auxiliary in a formulation, the amount in a dust is 0.1% by weight to 20% by weight, the amount in an emulsion is 1% by weight to 20% by weight, the amount in a wettable powder is 0.1% by weight to 20% by weight, the amount in a granule is 0.1% by weight to 20% by weight, and the amount in a flowable formulation is 0.1% by weight to 20% by weight.

In order to prevent various noxious insects, the compound of the present invention is directly used or properly diluted with water or suspended in water, and an effective amount thereof for preventing pests is applied to crops in which the breeding of the noxious insects is predicted, or a place where the breeding of the noxious insects is undesirable. The amount of the compound used depends upon the various factors, for example, the purpose, the object insects, the growth conditions of crops, the breeding tendency of insects, weather, environmental conditions, formulations, application methods, application places, and application times. However, the content of the active ingredient used is generally 0.0001 ppm to 5000 ppm, and preferably 0.01 ppm to 1000 ppm. The amount of the active ingredient per 10a is generally 1 g to 300 g.

An insecticide containing as an active ingredient the compounds represented by formula (1) of the present invention may be singly used for preventing insect pests such as agricultural, horticultural or stored grain insect pests which are noxious to paddy rice, fruit trees, vegetables, other crops and flowering plants, sanitary pests, or nematodes. In order to further obtain an excellent preventive effect on various noxious insects which simultaneously occur, at least one of other insecticides and/or fungicides may be combined with the compounds represented by formula (1) of the present invention.

Examples of such insecticides which can be combined with the compounds represented by formula (1) of the present invention include synthetic pyrethroid insecticides such as allethrin, tetramethrin, resmethrin, phenothrin, furamethrin, permethrin, cypermethrin, deltamethrin, cyhalothrin, cyfluthrin, fenpropathrin, tralomethrin, cycloprothrin, flucythrinate, fluvalinate, acrinathrin, tefluthrin, bifenthrin, empenthrin, beta-cyfluthrin, zeta-cypermethrin, and fenvalerate, and various isomers thereof and pyrethrum extracts; organophosphate insecticides such as DDVP, cyanophos, fenthion, fenitrothion, tetrachlorvinphos, dimethylvinphos, propaphos, methylparathion, temephos, phoxim, acephate, isofenphos, salithion, DEP, EPN, ethion, mecarbam, pyridafenthion, diazinon, pirimiphos-methyl, etrimfos, isoxathion, quinalphos, chlorpyrifos-methyl, chlorpyrifos, phosalone, phosmet, methidathion, oxydeprofos, vamidothion, malathion, phenthoate, dimethoate, formothion, thiometon, ethylthiometon, phorate, terbufos, profenofos, prothiofos, sulprofos, pyraclofos, monocrotophos, naled, fosthiazate, and cadusafos; carbamate insecticides such as NAC, MTMC, MIPC, BPMC, XMC, PHC, MPMC, ethiofencarb, bendiocarb, pirimicarb, carbosulfan, benfuracarb, methomyl, oxamyl, and aldicarb; arylpropylether insecticides such as etofenprox and halfenprox; silylether insecticides such as silafluofen; insecticidal natural products such as nicotine-sulfate, polynactin complex, abamectin, milbemectin, and BT agents; insecticides such as, cartap, thiocyclam, bensultap, diflubenzuron, chlorfluazuron, teflubenzuron, triflumuron, flufenoxuron, flucycloxuron, hexaflumuron, fluazuron, imidacloprid, nitenpyram, acetamiprid, dinotefuran, pymetrozine, fipronil, buprofezin, fenoxycarb, pyriproxyfen, methoprene, hydroprene, kinoprene, diafenthiuron, triazamate, tebufenozide, and endosulfan; acaricides such as dicofol, chlorobenzilate, bromopropylate, tetradifon, CPCBS, BPPS, chinomethionate, amitraz, benzoximate, hexythiazox, fenbutatin oxide, cyhexatin, dienochlor, clofentezine, pyridaben, fenpyroximate, fenazaquin, and tebufenpyrad; and other insecticides such as novaluron, noviflumuron, emamectin benzoate, clothianidin, thiacloprid, thiamethoxam, flupyrazofos, acequinocyl, bifenazate, chromafenozide, etoxazole, fluacrypyrim, flufenzine, halofenozide, indoxacarb, methoxyfenozide, spirodiclofen, tolfenpyrad, gamma-cyhalothrin, ethiprole, amidoflumet, bistrifluoron, flonicamid, flubrocythrinate, flufenerim, pyridalyl, pyrimidifen, spinosad, and spiromesifen.

Examples of fungicides which can be combined with the compounds represented by formula (1) of the present invention include azole fungicides such as triadimefon, hexaconazole, propiconazole, ipconazole, prochloraz, and triflumizole; pyrimidine fungicides such as pyrifenox and fenarimol; anilinopyrimidine fungicides such as mepanipyrim and cyprodinil; acylalanine fungicides such as metalaxyl, oxadixyl, and benalaxyl; benzimidazole fungicides such as thiophanate-methyl and benomyl; dithiocarbamate fungicids such as mancozeb, propineb, zineb, and metiram; organochlorine fungicides such as tetrachloroisophthalonitrile; carboxamide fungicides such as carpropamid and ethaboxam; morpholine fungicides such as dimethomorph; strobilurin fungicides such as azoxystrobin, kresoxim-methyl, metominostrobin, orysastrobin, fluoxastrobin, trifloxystrobin, dimoxystrobin, pyraclostrobin, and picoxystrobin; dicarboxylmide fungicides such as iprodione and procymidone; soil-applied fungicides such as flusulfamide, dazomet, methyl isothiocyanate, and chloropicrin; copper fungicides such as basic copper chloride, basic copper sulfate, copper nonylphenol sulfonate, oxine-copper, and DBEDC; inorganic fungicides such as sulfur and zinc sulfate; organophosphate fungicides such as edifenphos, tolclofos-methyl, and fosetyl-aluminum; melanin biosynthesis inhibitors such as phthalide, tricyclazole, pyroquilon, and diclocymet; antibiotics such as kasugamycin, validamycin, and polyoxins; fungicidal natural products such as repe seed oil; and other fungicides such as benthiavalicarb-isopropyl, iprovalicarb, cyflufenamid, fenhexamid, quinoxyfen, spiroxamine, diflumetorim, metrafenone, picobenzamid, proquinazid, silthiofam, oxyporconazole, famoxadone, cyazofamid, fenamidone, furametpyr, zoxamide, boscalid, tiadinil, simeconazole, chlorothalonil, cymoxanil, captan, dithianon, fluazinam, folpet, dichlofluanid, (RS)—N-[2-(1,3-dimethylbutyl)thiophen-3-yl]-1-methyl-3-trifluoromethyl-1H-pyrazole-4-carboxamide (penthiopyrad; ISO proposed), oxycarboxin, mepronil, flutolanil, triforine, oxolinic acid, probenazole, acibenzolar-S-methyl, isoprothiolane, ferimzone, diclomezine, pencycuron, fluoroimide, chinomethionate, iminoctadine-triacetate, and iminoctadine-albesilate.

When the compounds represented by formula (1) of the present invention are combined with at least one type of other insecticide and/or fungicide, mixed compositions of the compounds represented by formula (1) and other insecticides and/or fungicides may be used, or the compounds represented by formula (1) may be mixed with other insecticides and/or fungicides during agricultural treatment.

Besides the above-described insecticides and fungicides, the compounds represented by formula (1) may be mixed with a herbicide, a fertilizer, an ameliorant, a plant protective such as a plant growth regulator, or resources to form multipurpose compositions having superior efficiency or compositions from which an additive effect or a synergistic effect can be expected.

Although representative examples of the present invention will be described below, the present invention is not limited to these examples.

EXAMPLE 1

(1-1) Production of N-(2,6-dimethyl-4-heptafluoroisopropyl)phenyl 3-nitrobenzamide To a solution prepared by adding 20.0 g of 2,6-dimethyl-4-heptafluoroisopropylaniline and 11.0 g of pyridine to 100 ml of tetrahydrofuran and then stirring the resultant mixture at room temperature was dropwise added a solution of 13.0 g of 3-nitrobenzoyl chloride in 20 ml of tetrahydrofuran. After the resultant mixture was stirred at room temperature for 10 hours, ethyl acetate and water were added to the reaction solution. Then, a separating operation was performed, and an organic layer was separated and then dried with anhydrous magnesium sulfate. The solution was filtered, and then the filtrate was collected, and the solvent of the filtrate was distilled off under reduced pressure. The residue was washed with a n-hexane-diisopropyl ether solvent mixture to obtain 26.0 g (yield 85%) of the title compound as a white solid.

$^1$H-NMR (CDCl$_3$, ppm) δ 2.33 (6H, s), 7.37 (2H, s), 7.68 (1H, s), 7.72 (1H, t, J=8.1 Hz), 8.28 (1H, d, J=8.1 Hz), 8.44 (1H, dd, J=1.2 Hz, 8.1 Hz), 8.75 (1H, t, J=1.2 Hz)

(1-2) Production of N-(2,6-dimethyl-4-heptafluoroisopropyl)phenyl 3-aminobenzamide To a solution prepared by adding 0.90 g of N-(2,6-dimethyl-4-heptafluoroisopropyl)phenyl 3-nitrobenzamide and 1.56 g of tin chloride anhydride to 25 ml of ethanol and stirring the resultant mixture at room temperature was added 2 ml of conc. hydrochloric acid. The resultant mixture was then stirred under heating at 60° C. for 1 hour. After the temperature was returned to room temperature, the reaction solution was poured into water and then neutralized with potassium carbonate. Then, ethyl acetate was added to the reaction solution, and insoluble materials were filtered off. Then, an organic layer was separated and then dried with anhydrous magnesium sulfate. The solution was filtered, and then the filtrate was collected, and the solvent of the filtrate was distilled off under reduced pressure. The residue was washed with hexane to obtain 0.44 g (yield 53%) of the title compound as a white solid.

$^1$H-NMR (CDCl$_3$, ppm) δ 2.34 (6H, s), 3.87 (2H, broad), 6.86-6.89 (1H, m), 7.20-7.35 (6H, m)

(1-3) Production of N-(2,6-dimethyl-4-heptafluoroisopropyl)phenyl 3-(2-chloroethoxycarbonylamino) benzamide (Compound No. 130)

To a solution prepared by adding 0.20 g of N-(2,6-dimethyl-4-heptafluoroisopropyl)phenyl 3-aminobenzamide and 0.08 g of pyridine to 5 ml of tetrahydrofuran and stirring the resultant mixture at room temperature was dropwise added a solution of 0.07 g of 2-chloroethyl chloroformate in 1 ml of tetrahydrofuran. After the resultant mixture was stirred for 2 hours, ethyl acetate and water were added to the reaction solution. Then, a separating operation was performed, and an organic layer was separated and then dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.23 g (yield 91%) of the title compound as a white solid.

$^1$H-NMR (CDCl$_3$, ppm) δ 2.35 (6H, s), 3.74-3.77 (2H, m), 4.44-4.47 (2H, m), 6.87 (1H, broad), 7.36 (2H, s), 7.43-7.52 (2H, m), 7.59-7.64 (2H, m), 8.02 (1H, s)

The compounds shown in Table 6 can be produced as production intermediates useful for producing the compounds represented by formula (1) of the present invention according to the processes described in Examples 1-1 and 1-2.

EXAMPLE 2

Production of N-(2,6-dimethyl-4-heptafluoroisopropyl)phenyl 3-(ethylthiocarbonylamino)benzamide (Compound No. 1962)

To a solution prepared by adding 0.25 g of N-(2,6-dimethyl-4-heptafluoroisopropyl)phenyl 3-aminobenzamide produced in (1-2) of Example 1 and 0.06 g of pyridine to 5 ml of tetrahydrofuran and then stirring the resultant mixture at room temperature was dropwise added a solution of 0.08 g of ethyl chlorothioformate in 1 ml of tetrahydrofuran. After the resultant mixture was stirred for 2 hours, ethyl acetate and water were added to the reaction solution. Then, a separating operation was performed, and an organic layer was separated and then dried with anhydrous magnesium sulfate. The solution was filtered, and then the filtrate was collected, and the solvent of the filtrate was distilled off under reduced pressure. The residue was washed with hexane to obtain 0.27 g (yield 89%) of the title compound as a white solid.

$^1$H-NMR (CDCl$_3$+DMSO-d$_6$, ppm) δ 1.34 (3H, t, J=7.3 Hz), 2.34 (6H, s), 2.96 (2H, q, J=7.3 Hz), 7.33 (2H, s), 7.41 (1H, t, J=7.8 Hz), 7.67 (1H, d, J=7.8 Hz), 7.83-7.85 (1H, m), 8.11 (1H, d, J=2.0 Hz), 8.79 (1H, s), 9.58 (1H, s)

EXAMPLE 3

Production of N-(2,6-dimethyl-4-heptafluoroisopropyl)phenyl 3-[(4-cyanobenzyl)oxycarbonylamino]benzamide (Compound No. 85)

To a solution prepared by adding 0.30 g 3-isocyanatobenzoyl chloride to 10 ml of ether and then stirring the resultant mixture at 2° C. was dropwise added, over 5 minutes at a temperature kept at 2° C., a solution of 0.23 g of 4-cyanobenzyl alcohol and 0.32 g of tri-n-butylamine in 5 ml of ether. After the resultant mixture was stirred at 2° C. for 2 hours, the temperature was returned to room temperature, and then a solution of 0.49 g of 2,6-dimethyl-4-heptafluoroisopropylaniline in 5 ml of ether was dropwise added to the mixture, followed by stirring at room temperature for 8 hours. Then, ethyl acetate was added to the reaction solution, and the reaction solution was washed with water twice. Then, an organic layer was dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=2:1 to 1:1) to obtain 0.50 g (yield 40%) of the title compound as an oily material.

$^1$H-NMR (CDCl, ppm) δ 2.34 (6H, s), 5.27 (2H, s), 6.97 (1H, broad-s), 7.35 (2H, s), 7.45-7.52 (4H, m), 7.61-7.69 (4H, m), 8.01 (1H, s)

Similarly, N-(2,6-dimethyl-4-heptafluoroisopropyl)phenyl 3-[(6-chloropyridine-3-yl)methoxycarbonylamino]benzamide (Compound No. 163) was produced by using 2-chloro-5-hydroxymethylpyridine.

$^1$H-NMR (CDCl$_3$, ppm) δ 2.34 (6H, s), 5.22 (2H, s), 6.89 (1H, broad-s), 7.35-7.49 (5H, m), 7.62 (2H, d, J=7.3 Hz), 7.72-7.77 (1H, m), 8.00 (1H, broad-s), 8.45 (1H, d, J=2.4 Hz)

N-(2,6-dimethyl-4-heptafluoroisopropyl)phenyl 3-[(tetrahydrofuran-3-yl)methoxycarbonylamino]benzamide (Compound No. 158) was produced by the same process as described above using 3-hydroxymethyltetrahydrofuran except that the solvent was changed to tetrahydrofuran.

$^1$H-NMR (CDCl$_3$, ppm) δ 1.66-1.73 (1H, m), 2.05-2.13 (1H, m), 2.34 (6H, s), 2.60-2.70 (1H, m), 3.64-3.68 (1H, m), 3.73-3.79 (1H, m), 3.85-3.92 (2H, m), 4.09-4.15 (2H, m), 6.87 (1H, broad-s), 7.35 (2H, s), 7.46 (2H, t, J=7.8 Hz), 7.61-7.66 (2H, m), 8.01 (1H, broad-s)

EXAMPLE 4

(4-1) Production of N-(2,6-dimethyl-4-heptafluoroisopropyl)phenyl 3-aminobenzthioamide To 10 ml of toluene were added 0.35 g of N-(2,6-dimethyl-4-heptafluoroisopropyl)phenyl 3-aminobenzamide produced in Example (1-2) and 0.19 g of Lawesson's reagent. Then, the resultant mixture was stirred under heating at a reflux temperature for 6 hours. The reaction solution was concentrated under reduced pressure, and the solvent was distilled off. The residue was purified by silica gel column chromatography (eluent; hexane:ethyl acetate=3:1) to obtain 0.07 g (yield 20%) of the title compound.

$^1$H-NMR (CDCl$_3$, ppm) δ 2.36 (6H, s), 3.87 (2H, broad-s), 6.84-6.87 (1H, m), 7.18-7.24 (2H, m), 7.33 (1H, s), 7.39 (2H, s), 8.56 (1H, broad-s)

(4-2) Production of N-(2,6-dimethyl-4-heptafluoroisopropyl)phenyl 3-(2,2,2-trichloroethoxycarbonylamino)benzthioamide (Compound No. 1964)

To a solution prepared by adding 0.07 g of N-(2,6-dimethyl-4-heptafluoroisopropyl)phenyl 3-aminobenzthioamide and 0.03 g of pyridine to 5 ml of tetrahydrofuran and then stirring the resultant mixture at room temperature was dropwise added a solution of 0.05 g of 2,2,2-trichloroethyl chloroformate in 1 ml of tetrahydrofuran. After the resultant mixture was stirred 2 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.09 g (yield 90%) of the title compound as a white solid.

$^1$H-NMR (CDCl$_3$, ppm) δ 2.37 (6H, s), 4.85 (2H, s), 7.07 (1H, broad), 7.39 (2H, s), 7.45 (1H, t, J=8.1 Hz), 7.61-7.68 (2H, m), 8.11 (1H, s), 8.69 (1H, s)

EXAMPLE 5

(5-1) Production of N-(2,6-dimethyl-4-heptafluoroisopropyl)phenyl 6-chloropyridine-2-carboxamide First, to a solution prepared by adding 2.36 g of 6-chloropyridine-2-carboxylic acid and 5 droplets of N,N-dimethylformamide to 30 ml of toluene was added 2.14 g of thionyl chloride, and then the resultant mixture was stirred under heating at 80° C. for 2 hours. Then, the solvent was distilled off under reduced pressure, and the residue was dissolved in 10 ml of tetrahydrofuran. The resultant solution was added dropwise, at room temperature, to a solution obtained by adding 3.83 g of 2,6-dimethyl-4-heptafluoroisopropylaniline and 1.28 g of pyridine to 20 ml of tetrahydrofuran, followed by stirring for 5 hours. Then, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 3.90 g (yield 67%) of the title compound as a solid.

$^1$H-NMR (CDCl$_3$, ppm) δ 2.36 (6H, s), 7.36 (2H, s), 7.56 (1H, dd, J=1.0 Hz, 8.1 Hz), 7.88 (1H, dd, J=7.6 Hz, 8.1 Hz), 8.23 (1H, dd, J=1.0 Hz, 7.6 Hz), 9.27 (1H, broad-s)

(5-2) Production of N-(2,6-dimethyl-4-heptafluoroisopropyl)phenyl 6-aminopyridine-2-carboxamide In a 200 ml autoclave were charged 3.08 g of N-(2,6-dimethyl-4-heptafluoroisopropyl)phenyl 6-chloropyridine-2-carboxamide, 30 ml of 28% ammonia water, 0.20 g of cupper sulfate, and 70 ml of methanol, and the resultant mixture was stirred under heating at 150° C. for 2 hours. After the mixture was cooled to room temperature, ammonia was distilled off at 60° C. under atmospheric pressure, and methanol was distilled off under reduced pressure. Then, ethyl acetate and water were added to the reaction solution, and a separating operation was performed. Then, an organic layer was separated and dried with anhydrous sodium sulfate. The solution was filtered, and then the filtrate was collected, and the solvent of the filtrate was distilled off under reduced pressure. The residue was purified by silica gel column chromatography (eluent; hexane:ethyl acetate=3:2 to 2:3) to obtain 2.90 g (yield 98%) of the title compound as a oily material.

$^1$H-NMR (CDCl$_3$, ppm) δ 2.35 (6H, s), 4.57 (2H, broad-s), 6.69-6.74 (1H, m), 7.34 (2H, s), 7.62-7.66 (2H, m), 9.39 (1H, broad-s)

(5-3) Production of N-(2,6-dimethyl-4-heptafluoroisopropyl)phenyl 6-(2,2,2-trichloroethoxycarbonylamino)pyridine-2-carboxamide (Compound No. 1968)

To a solution prepared by adding 0.15 g of N-(2,6-dimethyl-4-heptafluoroisopropyl)phenyl 6-aminopyridine-2-carboxamide and 0.06 g of pyridine to 5 ml of tetrahydrofuran and stirring the resultant mixture at room temperature was dropwise added a solution of 0.085 g of 2,2,2-trichloroethyl chloroformate in 1 ml of tetrahydrofuran. After the resultant mixture was stirred for 2 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=10:1) to obtain 0.13 g (yield 61%) of the title compound as a white solid.

$^1$H-NMR (CDCl$_3$, ppm) δ 2.35 (6H, s), 4.89 (2H, s), 7.36 (2H, s), 7.63 (1H, broad-s), 7.97 (1H, dd, J=7.6 Hz, 8.3 Hz), 8.05 (1H, d, J=7.6 Hz), 8.21 (1H, d, J=8.3 Hz), 9.17 (1H, broad-s)

(5-4) Production of N-(2,6-dimethyl-4-heptafluoroisopropyl)phenyl 6-(2,2,2-trichloroethoxycarbonylamino)pyridine-N-oxide-2-carboxamide (Compound No. 2062)

To 10 ml of benzene was added 0.26 g of N-(2,6-dimethyl-4-heptafluoroisopropyl)phenyl 6-(2,2,2-trichloroethoxycarbonylamino)pyridine-2-carboxamide produced in Example 5-3, and then the resultant mixture was stirred. Then, 0.08 g of m-chloroperbenzoic acid was added to the mixture at room temperature. After the resultant mixture was stirred at 70° C. for 1 hour, 0.2 g of m-chloroperbenzoic acid was further added to the mixture, followed by stirring at 70° C. for 7 hours. Then, the mixture was diluted with ethyl acetate, and an organic layer was washed with a saturated aqueous solution of sodium hydrogen carbonate three times and dried with anhydrous magnesium sulfate. Then, the solvent was distilled off under reduced pressure. The residue was purified by silica gel column chromatography (eluent; hexane:ethyl acetate=10:1) to obtain 0.11 g (yield 41%) of the title compound as an amorphous material.

$^1$H-NMR (CDCl$_3$, ppm) δ 2.37 (6H, s), 4.91 (2H, s), 7.36 (2H, s), 7.61 (1H, t, J=8.3 Hz), 8.23 (1H, dd, J=8.3 Hz, 1.9 Hz), 8.45 (1H, dd, J=8.3 Hz, 1.9 Hz), 9.81 (1H, broad-s), 12.70 (1H, broad-s)

(5-5) Production of N-(2,6-dimethyl-4-heptafluoroisopropyl)phenyl 6-(methylamino)pyridine-2-carboxamide N-(2,6-dimethyl-4-heptafluoroisopropyl)phenyl 6-(methylamino)pyridine-2-carboxamide was produced by using N-(2,6-dimethyl-4-heptafluoroisopropyl)phenyl 6-chloropyridine-2-carboxamide produced in Example 5-1 and a methylamine aqueous solution as reaction materials according to the process described in Example 5-2.

$^1$H-NMR (DMSO-d$_6$, ppm) δ 2.30 (6H, s), 2.92 (3H, s), 6.71 (1H, d, J=8.3 Hz), 6.85 (1H, d, J=4.9 Hz), 7.22 (1H, d, J=7.0 Hz), 7.44 (2H, s), 7.55 (1H, dd, J=7.0 Hz, 8.3 Hz), 10.05 (1H, s)

(5-6) Production of N-(2,6-dimethyl-4-heptafluoroisopropyl)phenyl 6-[N-(2,2,2-trichloroethoxycarbonyl)-N-methylamino]pyridine-2-carboxamide (Compound No. 2168)

N-(2,6-dimethyl-4-heptafluoroisopropyl)phenyl 6-[N-(2,2,2-trichloroethoxycarbonyl)-N-methylamino]pyridine-2-carboxamide was produced by using N-(2,6-dimethyl-4-heptafluoroisopropyl)phenyl 6-(methylamino)pyridine-2-carboxamide produced in Example 5-5 as a starting material according to the process described in Example 5-3.

$^1$H-NMR (DMSO-d$_6$, ppm) δ 2.30 (6H, s), 3.61 (3H, s), 5.03 (2H, s), 7.47 (2H, s), 7.92 (1H, d, J=7.6 Hz), 7.98 (1H, d, J=7.6 Hz), 8.08 (1H, t, J=7.6 Hz), 10.18 (1H, s)

EXAMPLE 6

(6-1) Production of ethyl 3-(2,2,2-trichloroethoxycarbonylamino)benzoate

To a solution prepared by adding 1.0 g of ethyl m-aminobenzoate and 0.72 g of pyridine to 10 ml of tetrahydrofuran and stirring the resultant mixture at room temperature was dropwise added a solution of 1.55 g of 2,2,2-trichloroethyl chloroformate in 5 ml of tetrahydrofuran. After the resultant mixture was stirred for 2 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was washed with hexane to obtain 1.89 g (yield 91%) of the title compound.

$^1$H-NMR (CDCl$_3$, ppm) δ 1.40 (3H, t, J=7.3 Hz), 4.38 (2H, q, J=7.3 Hz), 4.84 (2H, s), 6.96 (1H, broad-s), 7.43 (1H, t, J=7.8 Hz), 7.76-7.82 (2H, m), 7.99 (1H, t, J=2.0 Hz)

(6-2) Production of ethyl 3-[N-methyl-N-(2,2,2-trichloroethoxycarbonyl)amino]benzoate To a suspension of 0.14 g of 60% sodium hydride in 5 ml of tetrahydrofuran was dropwise added a solution of 1.0 g of ethyl 3-(2,2,2-trichloroethoxycarbonylamino)benzoate in 5 ml of tetrahydrofuran, and the resultant mixture was stirred at room temperature. Then, a solution of 0.45 g of dimethyl sulfate in 5 ml of tetrahydrofuran was dropwise added, and the resultant mixture was stirred at room temperature for 3 hours. After water was added to the mixture, the mixture was subjected to extraction with ethyl acetate, and an organic layer was washed twice with water and dried with anhydrous magnesium sulfate. Then, the solvent was distilled off under reduced pressure. The residue was purified by silica gel column chromatography (eluent; hexane:ethyl acetate=4:1) to obtain 0.84 g (yield 79%) of the title compound as an oily material.

$^1$H-NMR (CDCl$_3$, ppm) δ 1.40 (3H, t, J=7.1 Hz), 3.41 (3H, s), 4.39 (2H, q, J=7.1 Hz), 4.77 (2H, s), 7.43-7.52 (2H, m), 7.93-8.01 (2H, m)

(6-3) Production of 3-[N-methyl-N-(2,2,2-trichloroethoxycarbonyl)amino]benzoic acid To 5 ml of ethanol were added 0.5 g of ethyl 3-[N-methyl-N-(2,2,2-trichloroethoxycarbonyl)amino]benzoate and a 1N sodium hydroxide aqueous solution, and the resultant mixture was stirred at room temperature for 1.5 hours. After the reaction solution was controlled to pH 3 by dropwise adding 1N hydrochloric acid, ethyl acetate was added to the reaction solution, and an organic layer was separated. The organic layer was washed with water twice and washed with a saturated saline solution once, and then dried with anhydrous magnesium sulfate. The solvent was distilled off under reduced pressure to obtain 0.45 g (yield 98%) of the title compound as a solid.

$^1$H-NMR (CDCl$_3$, ppm) δ 3.43 (3H, s), 4.79 (2H, s), 7.41-7.60 (2H, m), 7.93-8.05 (2H, m)

(6-4) Production of N-(2,6-dimethyl-4-heptafluoroisopropyl)phenyl 3-[N'-methyl-N'-(2,2,2-trichloroethoxycarbonyl)amino]benzamide (Compound No. 1958)

A solution of 0.30 g of 3-[N-methyl-N-(2,2,2-trichloroethoxycarbonyl)amino]benzoic acid and 0.07 g of N-methylmorpholine in 5 ml of tetrahydrofuran was stirred under cooling at −15° C. A solution of 0.09 g of isopropyl chloroformate in 5 ml of tetrahydrofuran was dropwise added to the solution, and then a solution of 0.20 g of 2,6-dimethyl-4-heptafluoroisopropylaniline in 5 ml of tetrahydrofuran was dropwise added to the resultant mixture. Then, the resultant mixture was stirred at −15° C. for 1 hour and at room temperature for 24 hours. After the temperature was returned to room temperature, ethyl acetate and water were added to the reaction solution, and a separating operation was performed. Then, an organic layer was washed with water twice and dried with anhydrous magnesium sulfate. The solvent was distilled off under reduced pressure. The residue was purified by silica gel column chromatography (eluent; hexane:ethyl acetate=4:1 to 2:1) to obtain 0.05 g (yield 5%) of the title compound as an oily material.

$^1$H-NMR (CDCl$_3$, ppm) δ 2.34 (6H, s), 3.45 (3H, s), 4.80 (2H, s), 7.36 (2H, s), 7.50-7.56 (3H, m), 7.78 (1H, d, J=6.1 Hz), 7.90 (1H, s)

EXAMPLE 7

(7-1) Production of N-(2,6-dimethyl-4-heptafluoroisopropyl)phenyl 2-iodo-5-aminobenzamide To a solution prepared by adding 0.70 g of N-(2,6-dimethyl-4-heptafluoroisopropyl)phenyl 3-aminobenzamide produced in Example 1-2 to 8 ml of N,N-dimethylformamide and then stirring the resultant mixture in an iced water bath was dropwise added a solution of 0.39 g of N-iodosuccinimide in 2 ml of N,N-dimethylformamide. After the dropwise addition, the temperature was returned to room temperature, and then mixture was further stirred for 3 hours. Then, ethyl acetate and water were added to the reaction solution, and a separating operation was performed. Then, an organic layer was separated and dried with anhydrous magnesium sulfate. The solvent was distilled off under reduced pressure. The residue was purified by silica gel column chromatography (eluent; hexane:ethyl acetate=3:2) to obtain 0.67 g (yield 73%) of the title compound as a solid.

$^1$H-NMR (CDCl$_3$, ppm) δ 2.44 (6H, s), 3.86 (2H, broad-s), 6.52 (1H, dd, J=2.9 Hz, 8.5 Hz), 6.91 (1H, d, J=2.9 Hz), 7.12 (1H, s), 7.35 (2H, s), 7.62 (1H, d, J=8.5 Hz)

(7-2) Production of N-(2,6-dimethyl-4-heptafluoroisopropyl)phenyl 2-iodo-5-(isopropyloxycarbonylamino)benzamide (Compound No. 1945)

To a solution obtained by adding 0.20 g of N-(2,6-dimethyl-4-heptafluoroisopropyl)phenyl 2-iodo-5-aminobenzamide and 0.06 g of pyridine to 5 ml of tetrahydrofuran and then stirring the mixture at room temperature was dropwise added a solution of 0.05 g of isopropyl chloroformate in 1 ml of tetrahydrofuran. After reaction for 2 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.22 g (yield 96%) of the title compound as a solid.

$^1$H-NMR (CDCl$_3$, ppm) δ 1.31 (6H, d, J=6.3 Hz), 2.45 (6H, s), 5.03 (1H, septet, J=6.3 Hz), 6.66 (1H, s), 7.16-7.21 (2H, m), 7.36 (2H, s), 7.76 (1H, s), 7.82 (1H, dd, J=2.7 Hz, 8.8 Hz)

EXAMPLE 8

(8-1) Production of N-(2,6-dimethyl-4-heptafluoroisopropyl)phenyl 2-chloro-3-nitrobenzamide First, to a solution prepared by adding 2.50 g of 2-chloro-3-nitrobenzoic acid and 5 droplets of N,N-dimethylformamide to 30 ml of toluene was added 1.62 g of thionyl chloride, and the resultant mixture was stirred under heating at 80° C. for 2 hours. Then, the solvent was distilled off under reduced pressure, and the residue was dissolved in 10 ml of tetrahydrofuran. The resultant solution was dropwise added to a solution of 3.24 g of 2,6-dimethyl-4-heptafluoroisopropylaniline and 1.77 g of pyridine in 20 ml of tetrahydrofuran at room temperature, and the mixture was stirred for 5 hours. Then, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 3.38 g (yield 64%) of the title compound as a solid.

$^1$H-NMR (CDCl$_3$, ppm) δ 2.42 (6H, s), 7.34 (1H, s), 7.37 (1H, s), 7.55 (1H, t, J=7.8 Hz), 7.80 (1H, dd, J=1.5 Hz, 7.8 Hz), 7.86 (1H, dd, J=1.5 Hz, 7.8 Hz), 9.58 (1H, s)

(8-2) Production of N-(2,6-dimethyl-4-heptafluoroisopropyl)phenyl 2-fluoro-3-nitrobenzamide To 25 ml of N,N-dimethylformamide dried with molecular sieve were added 2.35 g of N-(2,6-dimethyl-4-heptafluoroisopropyl)phenyl 2-chloro-3-nitrobenzamide and 0.87 g of potassium fluoride (spray-dried), and the resultant mixture was stirred under heating at 150° C. for 3 hours. After the temperature was returned to room temperature, ethyl acetate and water were added to the reaction solution, and a separating operation was performed. Then, an organic layer was separated, washed with water twice, and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 1.02 g (yield 45%) of the title compound as a solid.

$^1$H-NMR (CDCl$_3$, ppm) δ 2.37 (6H, s), 7.39 (2H, s), 7.48-7.53 (1H, m), 7.87 (1H, d, J=11.5 Hz), 8.23-8.28 (1H, m), 8.42-8.46 (1H, m)

(8-3) Production of N-(2,6-dimethyl-4-heptafluoroisopropyl)phenyl 2-fluoro-3-aminobenzamide The title compound was produced by using N-(2,6-dimethyl-4-heptafluoroisopropyl)phenyl 2-fluoro-3-nitrobenzamide produced in Example 8-2 as a starting material according to the same process as in Example 1-2 (yield 72%).

$^1$H-NMR (CDCl$_3$, ppm) δ 2.37 (6H, s), 3.90 (2H, broad-s), 6.96-7.01 (1H, m), 7.10 (1H, t, J=7.8 Hz), 7.36 (2H, s), 7.43-7.47 (1H, m), 7.86 (1H, d, J=13.2 Hz)

(8-4) Production of N-(2,6-dimethyl-4-heptafluoroisopropyl)phenyl 2-fluoro-3-(isopropyloxycarbonylamino)benzamide (Compound No. 1389)

The title compound was produced by using N-(2,6-dimethyl-4-heptafluoroisopropyl)phenyl 2-fluoro-3-aminobenzamide produced in Example 8-3 as a starting material according to the same process as in Example 7-2 (yield 72%).

$^1$H-NMR (CDCl$_3$, ppm) δ 1.34 (6H, d, J=6.3 Hz), 2.36 (6H, s), 5.07 (1H, septet, J=6.3 Hz), 6.86 (1H, broad-s), 7.30 (1H, t, J=8.1 Hz), 7.37 (2H, s), 7.72-7.79 (2H, m), 8.32 (1H, broad)

EXAMPLE 9

(9-1) Production of 3-[(2,2,2-trichloroethoxy)carbonylamino]benzoic acid

To an aqueous solution (200 ml) of 8.22 g of m-aminobenzoic acid and 4.8 g of sodium hydroxide was dropwise added 25.0 g of 2,2,2-trichloroethyl chloroformate at room temperature. During the dropwise addition, the reaction solution was controlled to pH 10 or more by appropriately adding a 1N sodium hydroxide aqueous solution. After the reaction, the solution was controlled to pH 1 by adding 1N hydrochloric acid, and the precipitates were collected by filtration. The resultant crude crystals were dried and then washed with a ethyl acetate/n-hexane mixed solvent to obtain 16.2 g (yield 87%) of the title compound as a solid.

$^1$H-NMR (DMSO-d$_6$, ppm) δ 4.85 (2H, s), 7.38 (1H, d, J=7.8 Hz), 7.75 (1H, d, J=7.8 Hz), 7.79-7.80 (1H, m), 8.14 (1H, s), 9.02 (1H, s)

(9-2) Production of 3-[(2,2,2-trichloroethoxy)carbonylamino]benzoyl chloride To a toluene solution (10 ml) of 1.0 g of 3-[(2,2,2-trichloroethoxy)carbonylamino]benzoic acid produced in Example 9-1 was added 2 ml of thionyl chloride, and the resultant mixture was stirred at 100° C. The solvent was distilled off under reduced pressure, and the residue was dissolved in toluene. The solvent was again distilled off under reduced pressure to obtain 1.0 g (yield 95%) of the title compound as a solid.

$^1$H-NMR (CDCl$_3$, ppm) δ 4.86 (2H, s), 7.00 (1H, broad-s), 7.51 (1H, t, J=7.8 Hz), 7.84 (1H, d, J=7.8 Hz), 7.88 (1H, d, J=7.8 Hz), 8.16 (1H, s)

(9-3) Production of N-(2,6-dimethyl-4-(nonafluoro-2-butyl)phenyl 3-[(2,2,2-trichloroethoxy)carbonylamino]benzamide (Compound No. 257)

First, to a solution prepared by adding 0.34 g of 2,6-dimethyl-4-(nonafluoro-2-butyl)aniline and 0.09 g of pyridine to 5 ml of tetrahydrofuran and stirring the resultant mixture at room temperature was added 0.33 g of 3-[(2,2,2-trichloroethoxy)carbonylamino]benzoyl chloride produced in Example 9-2. After reaction for 5 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.45 g (yield 71%) of the title compound as a solid.

$^1$H-NMR (CDCl$_3$, ppm) δ 2.34 (6H, s), 4.85 (2H, s), 7.10 (1H, s), 7.34 (2H, s), 7.47-7.51 (2H, m), 7.63-7.67 (2H, m), 8.05 (1H, s)

The following compounds were produced according to the processes described in Examples 9-1 and 9-2.
3-(ethoxycarbonylamino)benzoyl chloride
3-(isopropylpropyloxycarbonylamino)benzoyl chloride
3-[(cyclobutyloxy)carbonylamino]benzoyl chloride
3-[(cyclopentyloxy)carbonylamino]benzoyl chloride 3-[(3-cyanobenzyloxy)carbonylamino]benzoyl chloride
3-[(4-cyanobenzyloxy)carbonylamino]benzoyl chloride
3-[(2-cyanoethoxy)carbonylamino]benzoyl chloride
3-[(2-methylthioethoxy)carbonylamino]benzoyl chloride
3-[(2-ethylthioethoxy)carbonylamino]benzoyl chloride
3-[(2-ethylsulfinylethoxy)carbonylamino]benzoyl chloride
3-[(2-fluoroethoxy)carbonylamino]benzoyl chloride
3-[(2,2-difluoroethoxy)carbonylamino]benzoyl chloride
3-[(2,2,2-trifluoroethoxy)carbonylamino]benzoyl chloride
3-[(1,3-difluoro-2-propyloxy)carbonylamino]benzoyl chloride
3-[(1-chloro-3-fluoro-2-propyloxy)carbonylamino]benzoyl chloride
3-[(3,3,3-trifluoro-n-propyloxy)carbonylamino]benzoyl chloride
3-[(2,2,3,3,3-pentafluoro-n-propyloxy)carbonylamino]benzoyl chloride
3-[(4,4,4-trifluoro-n-butyloxy)carbonylamino]benzoyl chloride
3-[(2,2,3,3-tetrafluorocyclobutyloxy)carbonylamino]benzoyl chloride
3-[(2-chloroethoxy)carbonylamino]benzoyl chloride
3-[(2,2-dichloroethoxy)carbonylamino]benzoyl chloride
3-[(1,3-dichloro-2-propyloxy)carbonylamino]benzoyl chloride
3-[(3-chloro-n-propyloxy)carbonylamino]benzoyl chloride
3-[(2-bromoethoxy)carbonylamino]benzoyl chloride
3-[(3-bromo-n-propyloxy)carbonylamino]benzoyl chloride
3-[(2-iodoethoxy)carbonylamino]benzoyl chloride
3-[(6-chloropyridine-3-yl)methoxycarbonylamino]benzoyl chloride

EXAMPLE 10

(10-1) Production of N-(2,4-bistrifluoromethylphenyl) 3-isocyanatobenzamide

To a 1,4-dioxane solution (20 ml) of 0.57 g of phosgene dimmer was added a 1,4-dioxane solution (5 ml) of 2.0 g of N-(2,4-bistrifluoromethylphenyl) 3-aminobenzamide (produced by using 2,4-bistrifluoromethylaniline as a starting material according to the process described in Example 1-2), and the resultant mixture was stirred at 60° C. for 3 hours. Then, the solvent was distilled off under reduced pressure, and the residue was dissolved in 10 ml of 1,4-dioxane. Then, the solvent was again distilled off under reduced pressure. The product was washed with n-hexane and filtered off to obtain 1.54 g (yield 72%) of the title compound.
$^1$H-NMR (CDCl$_3$, ppm) δ 7.33-7.36 (1H, m), 7.51 (1H, t, J=7.8 Hz), 7.62-7.65 (2H, m), 7.88-7.92 (2H, m), 8.31 (1H, broad-s), 8.70 (1H, d, J=8.8 Hz)

(10-2) Production of N-(2,4-bistrifluoromethylphenyl) 3-[(2,2,3,3,3-pentafluoro-n-propyloxy)carbonylamino]benzamide (Compound No. 250)

First, to an anhydrous tetrahydrofuran solution (15 ml) of 0.5 g of N-(2,4-bistrifluoromethylphenyl) 3-isocyanatobenzamide produced in Example 10-1 were added 0.40 g of 2,2,3,3,3-pentafluoro-n-propanol and 0.13 g of triethylamine, and the resultant mixture was stirred at room temperature for 5 hours. The mixture was diluted with ethyl acetate (20 ml), and an organic layer was washed with a 1N sodium hydroxide aqueous solution and 1N hydrochloric acid. The solvent was distilled off under reduced pressure. The residue was purified by silica gel column chromatography (eluent; hexane:ethyl acetate=4:1) to obtain 0.49 g (yield 70%) of the title compound.
$^1$H-NMR (CDCl$_3$, ppm) δ 4.68 (2H, t, J=13.2 Hz), 7.08 (1H, broad-s), 7.50-7.59 (2H, m), 7.70 (1H, broad-s), 7.87-7.92 (2H, m), 8.00 (1H, s), 8.39 (1H, s), 8.71 (1H, d, J=8.8 Hz)

EXAMPLE 11

(11-1) Production of N-(2,6-dimethyl-4-heptafluoroisopropyl)phenyl 3-(benzyloxycarbonyl)benzamide A mixture of 3.24 g of benzyl alcohol and 2.85 g of pyridine was dropwise added to a tetrahydrofuran solution (60 ml) of 6.09 g of isophthaloyl chloride at room temperature. After the resultant mixture was stirred for 2 hours, a tetrahydrofuran solution (10 ml) of 2,6-dimethyl-4-heptafluoroisopropylaniline was added to the mixture in an ice bath, followed by stirring at room temperature for 2 hours. The reaction solution was diluted with ethyl acetate (50 ml), and an organic layer was washed with 1N hydrochloric acid. The solvent was distilled off under reduced pressure. The residue was purified by silica gel column chromatography (eluent; hexane:ethyl acetate=9:1) to obtain 9.5 g (yield 60%) of the title compound as an amorphous material.
$^1$H-NMR (CDCl$_3$, ppm) δ 2.33 (6H, s), 5.41 (2H, s), 7.34-7.48 (7H, m), 7.56 (1H, s), 7.61 (1H, t, J=7.8 Hz), 8.17 (1H, t, J=7.8 Hz), 8.28 (1H, d, J=7.8 Hz), 8.57 (1H, s)

(11-2) Production of 3-[(2,6-dimethyl-4-heptafluoroisopropylphenyl)aminocarbonyl]benzoic acid Catalytic hydrogen reduction was performed at normal pressure by using a methanol solution (20 ml) of 2.0 g of N-(2,6-dimethyl-4-heptafluoroisopropyl)phenyl 3-(benzyloxycarbonyl)benzamide produced in Example 11-1 and 0.2 g of 10% palladium-carbon (wet, 50% product) to produce 1.59 g (yield 96%) of the title compound as a solid.
$^1$H-NMR (CDCl$_3$, ppm) δ 2.36 (6H, s), 7.37 (2H, s), 7.59 (1H, s), 7.67 (1H, t, J=7.8 Hz), 8.23 (1H, d, J=7.8 Hz), 8.32 (1H, d, J=7.8 Hz), 8.62 (1H, s)

(11-3) Production of N-(2,6-dimethyl-4-heptafluoroisopropylphenyl) 3-isocyanatobenzamide First, to an acetone solution (25 ml) of 1.4 g of 3-[(2,6-dimethyl-4-heptafluoroisopropylphenyl)aminocarbonyl] benzoic acid produced in Example 11-2 and 0.38 g of triethylamine was added 0.44 g of ethyl chloroformate in an iced water bath, and the resultant mixture was stirred at room temperature for 1 hour. Then, an aqueous solution (10 ml) of 0.32 g of sodium azide was added to the mixture, followed by stirring at room temperature for 2 hours. The reaction solution was poured into iced water (150 ml), and the precipitates were extracted with ethyl acetate (50 ml) and then dried with anhydrous magnesium sulfate. After anhydrous magnesium sulfate was filtered off, toluene (50 ml) was added to the filtrate, and the low-boiling-point solvent was distilled off by heating to 110° C. using a Dean and Stark tube. After the end of gas generation was confirmed, the temperature was returned to room temperature, and then the residual solvent was distilled off under reduced pressure to obtain 1.23 g (yield 88%) of the title compound as a solid.
$^1$H-NMR (CDCl$_3$, ppm) δ 2.35 (6H, s), 7.32 (1H, d, J=7.8Hz), 7.37 (2H,s), 7.39 (1H,s), 7.49 (1H, t, J=7.8Hz), 7.67 (1H,s), 7.72 (1H, d, J=7.8Hz)

(11-4) Production of N-(2,6-dimethyl-4-heptafluoroisopropylphenyl) 3-[(1-chloro-3-trifluoromethyl-2-propyl)oxycarbonylamino]benzamide (Compound No. 120)

The title compound was produced by using N-(2,6-dimethyl-4-heptafluoroisopropylphenyl) 3-isocyanatobenzamide produced in Example 11-3 according to the process described in Example 10-2.

$^1$H-NMR (CDCl$_3$, ppm) δ 2.35 (6H, s), 3.75-3.83 (2H, m), 4.46-4.80 (2H, m), 5.19-5.24 (1H, m), 6.97 (1H, broad-s), 7.36 (2H, s), 7.36-7.48 (2H, m), 7.60-7.66 (2H, m), 8.03 (1H, s)

The following compounds were produced according to the processes described in Examples 10 and 11.

N-2,6-dimethyl-4-(nonafluoro-2-butyl)phenyl 3-isocyanatobenzamide
N-2,6-dimethyl-4-[(heptafluoro-n-propyl)thio]phenyl 3-isocyanatobenzamide
N-2,6-dibromo-4-[(heptafluoro-n-propyl)thio]phenyl 3-isocyanatobenzamide
N-2,6-dichloro-4-[(heptafluoro-n-propyl)thio]phenyl 3-isocyanatobenzamide
N-2,6-dimethyl-4-[(heptafluoroisopropyl)thio]phenyl 3-isocyanatobenzamide
N-2,6-dibromo-4-[(heptafluoroisopropyl)thio]phenyl 3-isocyanatobenzamide
N-2,6-dichloro-4-[(heptafluoroisopropyl)thio]phenyl 3-isocyanatobenzamide
N-2,6-dimethyl-4-[(nonafluoro-2-butyl)thio]phenyl 3-isocyanatobenzamide
N-2,6-dibromo-4-[(nonafluoro-2-butyl)thio]phenyl 3-isocyanatobenzamide
N-2,6-dichloro-4-[(nonafluoro-2-butyl)thio]phenyl 3-isocyanatobenzamide
N-2,6-dimethyl-4-[(heptafluoro-n-propyl)sulfinyl]phenyl 3-isocyanatobenzamide
N-2,6-dibromo-4-[(heptafluoro-n-propyl)sulfinyl]phenyl 3-isocyanatobenzamide
N-2,6-dichloro-4-[(heptafluoro-n-propyl)sulfinyl]phenyl 3-isocyanatobenzamide
N-2,6-dimethyl-4-[(heptafluoro-n-propyl)sulfonyl]phenyl 3-isocyanatobenzamide
N-2,6-dibromo-4-[(heptafluoro-n-propyl)sulfonyl]phenyl 3-isocyanatobenzamide
N-2,6-dichloro-4-[(heptafluoro-n-propyl)sulfonyl]phenyl 3-isocyanatobenzamide

EXAMPLE 12

(12-1) Production of 4-(heptafluoro-n-propylthio)aniline

To an acetonitrile solution (20 ml) of 4-aminothiophenol (1.25 g, 9.98 mmol) and triethylamine (1.11 g, 11.0 mmol) was added 1-iodoheptafluoro-n-propane (5.91 g, 19.9 mmol), and the resultant mixture was stirred at room temperature for 3 hours. The mixture was diluted with ether, and washed with a 1N sodium hydroxide aqueous solution. Then, the product was purified by silica gel column chromatography (eluent; hexane:ethyl acetate=4:1) to obtain 1.85 g (yield 63%) of the title compound.

$^1$H-NMR (CDCl$_3$, ppm) δ 3.95 (2H, s), 6.66 (2H, d, J=8.8 Hz), 7.40 (2H, d, J=8.8 Hz)

(12-2) Production of 2,6-dibromo-4-(heptafluoro-n-propylthio)aniline

First, to a solution of 0.77 g of 4-(heptafluoro-n-propylthio)aniline produced in Example 12-1 in 15 ml of N,N-dimethylformamide was added 0.98 g of N-bromosuccinimide. After the resultant mixture was stirred at 60° C. for 2 hours, ether and water were added to the mixture. Then, an organic layer was separated, washed with water twice and dried with anhydrous magnesium sulfate. The solvent was distilled off under reduced pressure. The residue was purified by silica gel column chromatography (eluent; hexane:ethyl acetate=9:1) to obtain 1.19 g (yield 100%) of the title compound as a red oily material.

$^1$H-NMR (CDCl$_3$, ppm) δ 4.98 (2H, broad-s), 7.66 (2H, s)

(12-3) Production of N-{2,6-dibromo-4-(heptafluoro-n-propylthio)}phenyl 3-nitrobenzamide To a solution prepared by adding 1.08 g of 2,6-dibromo-4-(heptafluoro-n-propylthio)aniline produced in Example 12-2 and 0.4 g of pyridine to 20 ml of tetrahydrofuran and stirring the resultant mixture at room temperature was dropwise added a solution of 0.55 g of 3-nitrobenzoyl chloride in 20 ml of tetrahydrofuran. After the resultant mixture was stirred at room temperature for 10 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.86 g (yield 48%) of the title compound as a white solid.

$^1$H-NMR (CDCl$_3$, ppm) δ 7.73 (1H, s, J=7.8 Hz, 7.77 (1H, t, J=7.8 Hz), 7.96 (2H, s), 8.31 (1H, s), 8.47-8.50 (1H, m), 8.79 (1H, t, J=2.0 Hz)

(12-4) Production of N-{2,6-dibromo-4-(heptafluoro-n-propylthio)}phenyl 3-aminobenzamide To a solution prepared by adding 0.97 g of N-{2,6-dibromo-4-(heptafluoro-n-propylthio)}phenyl 3-nitrobenzamide produced in Example 12-3 and 0.95 g of tin(II) chloride (anhydrous) to 20 ml of ethanol and stirring the resultant mixture at room temperature was added 2 ml of conc. hydrochloric acid, and the resultant mixture was stirred under heating at 60° C. for 1 hour. After the temperature was returned to room temperature, the reaction solution was poured into water, and the solution was neutralized with potassium carbonate. Then, ethyl acetate was added to the solution, and insoluble materials were filtered off. Then, an organic layer was separated and dried with anhydrous magnesium sulfate. The solution was filtered, and then the filtrate was collected, and the solvent of the filtrate was distilled off under reduced pressure. The residue was washed with hexane to obtain 0.75 g (yield 81%) of the title compound as a white solid.

$^1$H-NMR (CDCl$_3$, ppm) δ 3.89 (2H, broad-s), 6.90 (1H, dt, J=2.5 Hz, 6.4 Hz), 7.28-7.30 (3H, m), 7.60 (1H, s), 7.93 (2H, s)

(12-5) Production of N-{2,6-dibromo-4-(heptafluoro-n-propylthio)}phenyl 3-(2,2,2-trichloroethoxycarbonylamino)benzamide (Compound No. 612)

To a solution prepared by adding 0.10 g of N-{2,6-dibromo-4-(heptafluoro-n-propylthio)}phenyl 3-aminobenzamide and 0.02 g of pyridine to 5 ml of tetrahydrofuran and stirring the resultant mixture at room temperature was dropwise added a solution of 0.04 g of 2,2,2-trichloroethyl chloroformate in 1 ml of tetrahydrofuran. After reaction for 2 hours, ethyl acetate and water were added to the reaction solution, and a separating operation was performed. Then, an organic layer was separated and dried with anhydrous magnesium sulfate. The solution was filtered, and then the filtrate was collected, and the solvent of the filtrate was distilled off under reduced pressure. The residue was purified by silica gel column chromatography (eluent; hexane:ethyl acetate=4:1) to obtain 0.11 g (yield 84%) of the title compound as a solid.

$^1$H-NMR (CDCl$_3$, ppm) δ 4.86 (2H, s), 7.45 (1H, t, J=7.8 Hz), 7.72 (1H, d, J=7.8 Hz), 7.93 (2H, s), 7.94 (1H, broad-s), 8.13 (1H, s), 9.02 (1H, s), 9.17 (1H, s)

(12-6) Production of N-{2,6-dibromo-4-(heptafluoro-n-propylsulfinyl)}phenyl 3-nitrobenzamide and N-{2,6-dibromo-4-(heptafluoro-n-propylsulfonyl)}phenyl 3-nitrobenzamide A solution prepared by adding 0.5 g of N-{2,6-dibromo-4-(heptafluoro-n-propylthio)}phenyl 3-nitrobenzamide to 15 ml of chloroform was stirred at room temperature, and 0.5 g of m-chloroperbenzoic acid was added to the mixture. After the resultant mixture was stirred at room temperature for 1 week, an aqueous solution of sodium hydrogen sulfite was added to the mixture, followed by stirring. Then, an organic layer was separated and washed with a 1N sodium hydroxide aqueous solution and saturated saline water. Then, the solvent was distilled off under reduced pressure. The residue was purified by silica gel column chromatography (eluent; hexane:ethyl acetate=4:1) to obtain 0.21 g of N-({2,6-dibromo-4-(heptafluoro-n-propylsulfinyl)}phenyl 3-nitrobenzamide and 0.12 g of N-{2,6-dibromo-4-(heptafluoro-n-propylsulfonyl)}phenyl 3-nitrobenzamide as solids.

(sulfinyl compound) $^1$H-NMR (CDCl$_3$, ppm) δ 7.76-7.82 (2H, m), 8.06 (1H, s), 8.29 (1H, s), 8.33-8.35 (1H, m), 8.49-8.53 (1H, m), 8.81 (1H, s)

(12-7) Production of 2,6-dimethyl-4-(heptafluoro-n-propylthio)aniline

To 20 ml of DMF were added 3.0 g (1.3 mmol) of 2,6-dibromo-4-heptafluoro-n-propylthioaniline, 3.0 g (21.9 mmol) of potassium carbonate, 0.75 g (0.65 mmol) of tetrakis (triphenylphosphine) palladium, and 0.17 g (1.3 mmol) of trimethylboroxine, and the resultant mixture was stirred at 135° C. for 6 hours. After the reaction solution was cooled to room temperature, insoluble materials were filtered off with cerite. The filtrate was concentrated under reduced pressure. The residue was purified by silica gel column chromatography (eluent; n-hexane:ethyl acetate=12:1 to 4:1) to obtain 1.17 g (yield 55%) of the title compound as an oily material.

$^1$H-NMR (CDCl$_3$, ppm) δ 2.17 (6H, s), 3.86 (2H, broad-s), 7.22 (2H, s)

The following aniline derivatives can be produced according to the processes described in Examples 12-1, 12-2, 12-6, and 12-7.

2-methyl-4-(pentafluoroethylthio)aniline
2-methyl-4-(heptafluoro-n-propylthio)aniline
$^1$H-NMR (CDCl$_3$, ppm) δ 2.16 (3H, s), 3.90 (2H, broad-s), 6.65 (1H, d, J=8.3 Hz), 7.28-7.31 (2H, m)
2-bromo-4-(heptafluoro-n-propylthio)aniline
$^1$H-NMR (CDCl$_3$, ppm) δ 4.44 (2H, broad-s), 6.75 (1H, d, J=8.8 Hz), 7.36 (1H, dd, J=2.0 Hz, 8.8 Hz), 7.69 (1H, d, J=2.0 Hz)
2-methyl-4-(heptafluoroisopropylthio)aniline
2-methyl-4-(nonafluoro-n-butylthio)aniline
2-methyl-4-(pentafluoroethylsulfinyl)aniline
2-methyl-4-(heptafluoro-n-propylsulfinyl)aniline
2-methyl-4-(heptafluoroisopropylsulfinyl)aniline
2-methyl-4-(nonafluoro-n-butylsulfinyl)aniline
2-methyl-4-(pentafluoroethylsulfonyl)aniline
2-methyl-4-(heptafluoro-n-propylsulfonyl)aniline
2-methyl-4-(heptafluoroisopropylsulfonyl)aniline
2-methyl-4-(nonafluoro-n-butylsulfonyl)aniline
2,6-dichloro-4-(pentafluoroethylthio)aniline
2,6-dibromo-4-(pentafluoroethylthio)aniline
N-{2,6-dibromo-4-(pentafluoroethylthio)}phenyl 3-nitrobenzamide
$^1$H-NMR (CDCl$_3$, ppm) δ 7.73 (1H, s), 7.77 (1H, t, J=7.8 Hz), 7.96 (2H, s), 8.32 (1H, d, J=7.8 Hz), 8.47-8.50 (1H, m), 8.80 (1H, t, J=2.0 Hz)
2,6-dimethyl-4-(pentafluoroethylthio)aniline
2,6-dichloro-4-(heptafluoro-n-propylthio)aniline
$^1$H-NMR (CDCl$_3$, ppm) δ 4.82 (2H, broad-s), 7.48 (2H, s)
N-{2,6-dichloro-4-(heptafluoro-n-propylthio)}phenyl 3-nitrobenzamide
$^1$H-NMR (CDCl$_3$, ppm) δ 7.70 (1H, s), 7.76 (2H, s), 7.77 (1H, t, J=7.8 Hz), 8.31 (1H, d, J=7.8 Hz), 8.48 (1H, d, J=7.8 Hz), 8.78 (1H, t, J=2.0 Hz)
2,6-dibromo-4-(heptafluoro-n-propylthio)aniline
$^1$H-NMR (CDCl$_3$, ppm) δ 4.93 (2H, broad-s), 7.66 (2H, s)
2,6-dimethyl-4-(heptafluoro-n-propylthio)aniline
$^1$H-NMR (CDCl$_3$, ppm) δ 2.17 (6H, s), 3.86 (2H, broad-s), 7.22 (2H, s)
N-{2,6-dichloro-4-(heptafluoro-n-propylthio)}phenyl 2-chloro-3-nitrobenzamide
$^1$H-NMR (CDCl$_3$, ppm) δ 2.39 (6H, s), 7.30 (1H, s), 7.46 (2H, s), 7.57 (1H, t, J=7.8 Hz), 7.90 (1H, d, J=7.8 Hz), 7.91 (1H, d, J=7.8 Hz)
2-bromo-4-(heptafluoro-n-propyl)thio-6-methylaniline
$^1$H-NMR (CDCl$_3$, ppm) δ 2.22 (3H, s), 4.40 (2H, broad-s), 7.27 (1H, s), 7.60 (1H, d, J=2.0 Hz)
2,6-dichloro-4-(heptafluoroisopropylthio)aniline
$^1$H-NMR (CDCl$_3$, ppm) δ 6.40 (2H, s), 7.52 (2H, s)
2,6-dibromo-4-(heptafluoroisopropylthio)aniline
N-{2,6-dichloro-4-(heptafluoroisopropylthio)}phenyl 3-nitrobenzamide
$^1$H-NMR (CDCl$_3$, ppm) δ 7.73 (1H, s), 7.76 (1H, t, J=7.8 Hz), 7.95 (2H, s), 8.31 (1H, d, J=7.8 Hz), 8.48 (1H, d, J=7.8 Hz), 8.79 (1H, t, J=1.5 Hz)
2,6-dimethyl-4-(heptafluoroisopropylthio)aniline
2,6-dichloro-4-(nonafluoro-n-butylthio)aniline
2,6-dibromo-4-(nonafluoro-n-butylthio)aniline
N-{2,6-dichloro-4-(nonafluoro-n-butylthio)}phenyl 3-nitrobenzamide
$^1$H-NMR (CDCl$_3$, ppm) δ 7.76 (1H, s), 7.77 (1H, t, J=8.3 Hz), 7.96 (2H, s), 8.32 (1H, d, J=8.3 Hz), 8.48 (1H, d, J=8.3 Hz), 8.80 (1H, t, J=2.0 Hz)
2,6-dimethyl-4-(nonafluoro-n-butylthio)aniline
2,6-dichloro-4-(pentafluoroethylsulfinyl)aniline
2,6-dibromo-4-(pentafluoroethylsulfinyl)aniline
2,6-dimethyl-4-(pentafluoroethylsulfinyl)aniline
2,6-dichloro-4-(heptafluoro-n-propylsulfinyl)aniline
2,6-dibromo-4-(heptafluoro-n-propylsulfinyl)aniline
N-{2,6-dichloro-4-(heptafluoro-n-propylsulfinyl)}phenyl 3-nitrobenzamide
$^1$H-NMR (CDCl$_3$, ppm) δ 7.76-7.82 (2H, m), 8.06 (1H, s), 8.29 (1H, s), 8.33-8.35 (1H, m), 8.49-8.53 (1H, m), 8.81 (1H, s)
2,6-dimethyl-4-(heptafluoro-n-propylsulfinyl)aniline
2,6-dichloro-4-(heptafluoroisopropylsulfinyl)aniline
2,6-dibromo-4-(heptafluoroisopropylsulfinyl)aniline
2,6-dimethyl-4-(heptafluoroisopropylsulfinyl)aniline
2,6-dichloro-4-(nonafluoro-n-butylsulfinyl)aniline
2,6-dibromo-4-(nonafluoro-n-butylsulfinyl)aniline 2,6-dimethyl-4-(nonafluoro-n-butylsulfinyl)aniline
2,6-dichloro-4-(pentafluoroethylsulfonyl)aniline
2,6-dibromo-4-(pentafluoroethylsulfonyl)aniline
2,6-dimethyl-4-(pentafluoroethylsulfonyl)aniline
2,6-dichloro-4-(heptafluoro-n-propylsulfonyl)aniline
2,6-dibromo-4-(heptafluoro-n-propylsulfonyl)aniline
2,6-dimethyl-4-(heptafluoro-n-propylsulfonyl)aniline
2,6-dichloro-4-(heptafluoroisopropylsulfonyl)aniline
N-{2,6-dichloro-4-(heptafluoroisopropylsulfonyl)}phenyl 3-nitrobenzamide
$^1$H-NMR (CDCl$_3$, ppm) δ 7.79 (1H, t, J=7.8 Hz), 7.98 (1H, s), 8.07 (2H, s), 8.33 (1H, d, J=7.8 Hz), 8.51 (1H, d, J=7.8 Hz), 8.81 (1H, t, J=2.0 Hz)
2,6-dibromo-4-(heptafluoroisopropylsulfonyl)aniline
2,6-dimethyl-4-(heptafluoroisopropylsulfonyl)aniline
2,6-dichloro-4-(nonafluoro-n-butylsulfonyl)aniline
2,6-dibromo-4-(nonafluoro-n-butylsulfonyl)aniline
2,6-dimethyl-4-(nonafluoro-n-butylsulfonyl)aniline

EXAMPLE 13

(13-1) Production of 2,6-dimethyl-4-(1,1,1,3,3,3-hexafluoro-2-hydroxy-2-propyl)aniline A mixture of 2.42 g of 2,6-dimethylaniline, 7.35 g of hexafluoroacetone hydrate, and 0.04 g of p-toluenesulfonic acid monohydrate was stirred under heating at 100° C. for 5 hours. After the temperature was returned to room temperature, the mixture was diluted with ethyl acetate and washed with a 1N sodium hydroxide aqueous solution. Then, the solvent was distilled off under reduced pressure, and the precipitated crude crystals were washed with a n-hexane-ethyl acetate mixed solvent to obtain 4.47 g (yield 78%) of the title compound as a solid.
$^1$H-NMR (CDCl$_3$, ppm) δ 2.20 (6H, s), 3.26 (1H, broad-s), 3.76 (2H, broad-s), 7.25 (2H, s)

(13-2) Production of N-[2,6-dimethyl-4-(1,1,1,3,3,3-hexafluoro-2-hydroxy-2-propyl)]phenyl 3-(2,2,2-trichloroethoxycarbonylamino)benzamide (Compound No. 872)

The title compound was produced as an amorphous material by using 2,6-dimethyl-4-(1,1,1,3,3,3-hexafluoro-2-hydroxy-2-propyl)aniline produced in Example 13-1 as a starting material according to the process described in Example 9-3 (yield 92%).
$^1$H-NMR (CDCl$_3$, ppm) δ 2.31 (6H, s), 3.99 (1H, s), 4.85 (2H, s), 7.15 (1H, broad-s), 7.45-7.51 (4H, m), 7.64-7.66 (2H, m), 8.01 (1H, s)

Formulation examples containing the compounds represented by formula (1) of the present invention as active ingredients are shown below, however the present invention is not limited to these examples. In each of the formulation examples, "part(s)" represents "part(s) by weight".

FORMULATION EXAMPLE 1

A mixture of 20 parts of a compound represented by formula (1) of the present invention, 10 parts of Sorpol 355S (surfactant produced by Toho CHemical Industry Co., Ltd.), and 70 parts of xylene was uniformly stirred to produce an emulsion.

FORMULATION EXAMPLE 2

A mixture of 10 parts of a compound represented by formula (1) of the present invention, 2 parts of sodium alkylnaphthalenesulfonate, 1 part of sodium lignin-sulfonate, 5 parts of white carbon, and 82 parts of diatomite was uniformly stirred to produce a wettable powder.

FORMULATION EXAMPLE 3

A mixture of 0.3 parts of a compound represented by formula (1) of the present invention and 0.3 parts of white carbon was uniformly stirred, and 99.2 parts of clay and 0.2 parts of Driless A (produced by Sankyo Co., Ltd.) were added to the mixture. The resultant mixture was uniformly ground to produce a dust.

FORMULATION EXAMPLE 4

A mixture of 2 parts of a compound represented by formula (1) of the present invention, 2 parts of white carbon, 2 parts of sodium lignin-sulfonate, and 94 parts of bentonite was uniformly ground, and then water was added to the mixture. The resultant mixture was kneaded, granulated and then dried to produce granules.

FORMULATION EXAMPLE 5

A mixture of 20 parts of a compound represented by formula (1) of the present invention and 5 parts of a 20% aqueous solution of polyvinyl alcohol was sufficiently stirred, and then 75 parts of a 0.8% aqueous solution of xanthane gum was added to the mixture. Then, the resultant mixture was again stirred to produce a flowable agent.

Test examples for making clear that the compounds represented by formula (1) of the present invention have excellent insecticidal activity are shown below, however the present invention is not limited to these examples.

TEST EXAMPLE 1

Insecticidal Test for Common Cutworm (*Spodoptera litura*)

A cabbage leaf piece was immersed in a solution prepared by diluting a test compound to a predetermined concentration for 30 seconds, and then dried in air. Then, the cabbage leaf piece was placed in a polyethylene cup of 7 cm-size in which 2nd-instar larvae of common cutworm were placed. The cup was allowed to stand in a thermostatic chamber at 25° C. Three days after, the numbers of living and dead larvae were counted. The test was carried out in two replications each containing five larvae.

As a result, at a concentration of 1000 ppm, a mortality of 70% or more was exhibited by Compounds Nos. 20, 59, 60, 62, 64, 66, 75, 78, 79, 81, 83, 84, 85, 90, 91, 92, 106, 108, 109, 111, 112, 116, 117, 118, 119, 120, 121, 123, 124, 125, 126, 127, 130, 131, 132, 134, 135, 136, 137, 138, 139, 140, 155, 156, 161, 163, 165, 174, 175, 176, 180, 181, 184, 186, 189, 190, 192, 196, 197, 198, 205, 206, 207, 208, 209, 210, 212, 213, 215, 216, 217, 218, 219, 220, 221, 224, 225, 228, 229, 230, 231, 232, 233, 234, 235, 236, 237, 241, 246, 247, 248, 250, 251, 252, 253, 254, 255, 256, 257, 258, 259, 300, 301, 348, 377, 424, 464, 471, 511, 518, 565, 605, 612, 659, 706, 770, 800, 817, 818, 819, 854, 855, 856, 857, 843, 844, 846, 847, 864, 867, 872, 873, 878, 890, 891, 892, 898, 899, 900, 902, 903, 905, 913, 915, 916, 919, 920, 922, 932, 933, 944, 948, 992, 1010, 1039, 1086, 1104, 1180, 1198, 1227, 1245, 1274, 1292, 1321, 1361, 1368, 1388, 1389, 1408, 1411, 1416, 1418, 1421, 1435, 1455, 1458, 1463, 1465, 1903, 1906, 1907, 1922, 1923, 1924, 1925, 1926, 1929, 1931, 1932, 1935, 1939, 1941, 1942, 1943, 1944, 1945, 1947, 1948, 1950, 1951, 1952, 1953, 1954, 1955, 1956, 1958, 1959, 1963, 1964, 1967, 1968, 1969, 2061, 2062, 2164, 2165, and 2168.

TEST EXAMPLE 2

Insecticidal Test for Diamondback Moth (*Plutella xylostella*)

A cabbage leaf pieces was immersed in a solution prepared by diluting a test compound to a predetermined concentration for 30 seconds, and then dried in air. Then, the leaf piece was placed in a polyethylene cup of 7 cm-size in which 2nd-instar larvae of common cutworm were placed. The cup was allowed to stand in a thermostatic chamber at 25° C. Three days after, the numbers of living and dead larvae were counted. The test was carried out in two replications each containing five larvae.

As a result, at a concentration of 1000 ppm, a mortality of 70% or more was exhibited by Compounds Nos. 3, 5, 7, 8, 20, 59, 60, 62, 66, 75, 77, 78, 79, 80, 84, 85, 92, 94, 95, 96, 99, 101, 103, 104, 106, 108, 109, 110, 111, 112, 113, 116, 117, 118, 119, 120, 121, 123, 126, 127, 130, 131, 132, 134, 136, 137, 138, 139, 140, 141, 154, 155, 156, 157, 158, 159, 160, 161, 162, 163, 168, 171, 174, 175, 176, 180, 181, 183, 184, 186, 190, 192, 196, 197, 198, 201, 203, 204, 205, 206, 207, 208, 209, 212, 213, 214, 215, 217, 218, 219, 220, 221, 223, 224, 228, 229, 230, 231, 232, 233, 234, 235, 236, 237, 238, 246, 247, 248, 249, 250, 252, 253, 254, 255, 256, 257, 258, 259, 300, 301, 348, 377, 424, 464, 471, 511, 518, 565, 605, 612, 659, 706, 800, 817, 818, 819, 820, 829, 858, 863, 865, 867, 868, 871, 872, 873, 878, 896, 897, 898, 899, 900, 902, 908, 913, 915, 919, 920, 922, 930, 932, 933, 936, 939, 941, 942, 943, 944, 945, 947, 948, 992, 1010, 1039, 1086, 1104, 1180, 1227, 1245, 1274, 1292, 1321, 1361, 1368, 1388, 1389, 1408, 1411, 1416, 1418, 1421, 1435, 1455, 1458, 1463, 1465, 1903, 1906, 1907, 1916, 1923, 1926, 1928, 1929, 1931, 1933, 1939, 1945, 1947, 1950, 1951, 1952, 1953, 1954, 1955, 1956, 1958, 1959, 1963, 1964, 1967, 1968, 1969, 2061, 2062, 2164, 2165, 2167, and 2168.

TEST EXAMPLE 3

Insecticidal Test for Small Brown Planthopper
(*Laodelphax striatellus*)

An acetone solution prepared by diluting a test compound to a predetermined concentration was sprayed on rice seedlings, and the rice seedlings were dried in air. Ten small brown planthoppers and an original chemical were used for the test. The rice seedlings were allowed to stand in a thermostatic chamber at 25° C. Six days after, the number of living insects was examined, and three days after, the number of dead insects was examined. The test was carried out one replication containing ten insects.

As a result, at a concentration of 1000 ppm, a mortality of 70% or more was exhibited by Compounds Nos. 108, 127, 184, 196, 197, 205, 209, 212, 215, 1321, 1361, 1368, 1408, 1411, 1416, 1435, 1455, 1458, 1463, 1958, 1959, and 1968.

The invention claimed is:
1. An aniline derivative represented by formula (9):

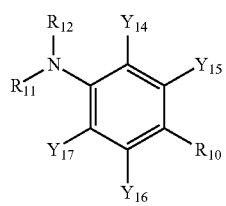

(9)

wherein (a) in the case of $R_{10}$ represents a C1-C6 haloalkyl group which may be substituted by at least one hydroxyl group, $R_{11}$ represents a m-nitrobenzoyl group or a substituted m-nitrobenzoyl group and $R_{12}$ represents a C1-C4 alkyl group, $Y_{14}$, $Y_{15}$, $Y_{16}$, and $Y_{17}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group;

(b) in the case of $R_{10}$ represents a C2-C6 haloalkyl group which may be substituted by at least one hydroxyl group, $R_{11}$ and $R_{12}$ represent a hydrogen atom, $Y_{14}$ represents a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group or a pentafluorosulfanyl group, $Y_{15}$ and $Y_{16}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, $Y_{17}$ represents a C1-5 haloalkyl group, a C2-C6 alkoxy group, a C1-C6 haloalkoxy group, a C2-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group or a pentafluorosulfanyl group, when $Y_{14}$ represents a hydrogen atom, $Y_{17}$ represents a C2-5 haloalkyl group, a C1-C6 haloalkoxy group, a C2-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group or a pentafluorosulfanyl group;

(c) in the case of $R_{10}$ represents a C2-C6 haloalkyl group which may be substituted by at least one hydroxyl group, $R_{11}$ represents a hydrogen atom, a m-nitrobenzoyl group, or a substituted m-nitrobenzoyl group and $R_{12}$ represents a m-nitrobenzoyl group or a halogen-substituted m-nitrobenzoyl group, $Y_{14}$, $Y_{15}$, $Y_{16}$ and $Y_{17}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, or a cyano group, (d) in the case of $R_{10}$ represents a C2-C6 haloalkyl group which may be substituted by at least one hydroxyl group, $R_{11}$ represents a hydrogen atom and $R_{12}$ represents a C1-C4 alkyl group, $Y_{14}$ and $Y_{17}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, when either $Y_{14}$ or $Y_{17}$ represents a C1 alkyl group, the other represents a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, when either $Y_{14}$ or $Y_{17}$ represents a hydrogen atom, the other represents a halogen atom, a C2-C6 alkyl group, a C1-C6 haloalkyl group, a C1-C6 alkoxy group, a 1l-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group, and $Y_{15}$ and $Y_{16}$ may be the same or different and each represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a cyano group, or a nitro group.

2. The aniline derivative according to claim 1, wherein in formula (9), $R_{11}$ represents a hydrogen atom, a C1-C4 alkyl group, a m-nitrobenzoyl group or a substituted m-nitrobenzoyl group, and $R_{12}$ represents a m-nitrobenzoyl group or a substituted m-nitrobenzoyl group.

* * * * *

UNITED STATES PATENT AND TRADEMARK OFFICE
CERTIFICATE OF CORRECTION

PATENT NO. : 9,089,133 B2  Page 1 of 1
APPLICATION NO. : 13/419063
DATED : July 28, 2015
INVENTOR(S) : Kei Yoshida et al.

It is certified that error appears in the above-identified patent and that said Letters Patent is hereby corrected as shown below:

In the Claims

Column 200, Line 28, (Claim 1), delete "C1-5" and insert --C1-C5--.

Column 200, Line 35, (Claim 1), delete "C2-5" and insert --C2-C5--.

Column 201, Line 9, (Claim 1), delete "1I-C6" and insert --C1-C6--.

Signed and Sealed this
Ninth Day of February, 2016

Michelle K. Lee
*Director of the United States Patent and Trademark Office*